United States Patent
Chhun et al.

(10) Patent No.: US 9,353,173 B2
(45) Date of Patent: May 31, 2016

(54) FUNCTIONAL ENHANCEMENT OF MICROORGANISMS TO MINIMIZE PRODUCTION OF ACRYLAMIDE

(75) Inventors: Aline Chhun, Toronto (CA); John Ivan Husnik, Charlottetown (CA)

(73) Assignee: Renaissance BioScience Corp., Vancouver (CA)

( * ) Notice: Subject to any disclaimer, the term of this patent is extended or adjusted under 35 U.S.C. 154(b) by 565 days.

(21) Appl. No.: 13/581,087

(22) PCT Filed: Mar. 1, 2011

(86) PCT No.: PCT/CA2011/000222
§ 371 (c)(1),
(2), (4) Date: Aug. 24, 2012

(87) PCT Pub. No.: WO2011/106874
PCT Pub. Date: Sep. 9, 2011

(65) Prior Publication Data
US 2012/0321744 A1    Dec. 20, 2012

Related U.S. Application Data

(60) Provisional application No. 61/309,623, filed on Mar. 2, 2010, provisional application No. 61/316,634, filed on Mar. 23, 2010.

(51) Int. Cl.
*C12N 9/82*    (2006.01)
*C12N 15/81*    (2006.01)
(Continued)

(52) U.S. Cl.
CPC ............ *C07K 14/705* (2013.01); *A23L 1/0158* (2013.01); *C12N 9/82* (2013.01); *C12N 15/81* (2013.01)

(58) Field of Classification Search
None
See application file for complete search history.

(56) References Cited

U.S. PATENT DOCUMENTS

| | | | |
|---|---|---|---|
| 7,396,670 B2 | 7/2008 | Budolfsen et al. | |
| 7,666,652 B2 | 2/2010 | Matsui et al. | |

(Continued)

FOREIGN PATENT DOCUMENTS

| | | |
|---|---|---|
| CN | 101473865 | 7/2009 |
| EP | 2156750 A1 | 2/2010 |

(Continued)

OTHER PUBLICATIONS

Hendriksen, H.V. et al. "Evaluating the Potential for Enzymatic Acrylamide Mitigation in a Range of Food Products Using as Asparaginase from Aspergillus oryzae", Journal of Agriculture and Food Chemistry, May 27, 2009, 57(10): 4168-4176.

(Continued)

*Primary Examiner* — Nancy T Vogel
(74) *Attorney, Agent, or Firm* — Bereskin & Parr LLP; Melanie Szweras

(57) ABSTRACT

The present disclosure provides yeast transformed with a nucleic acid molecule (GAT1) to reduce nitrogen catabolite repression of asparagine transport/degradation and/or overexpress genes (ASP1 or ASP3) encoding cell-wall or extracellular proteins involved in asparagine degradation and/or genes (AGP1 or GNP1 or GAP1) encoding proteins involved in asparagine transport under food preparation/processing conditions. The genetically modified yeast has enhanced ability to reduce acnlamide concentration in foods prepared by heating. Also provided are methods and uses of the transgenic yeast for reducing acnlamide in a food product and food products having reduced acrylamide content prepared using the transgenic yeast.

22 Claims, 15 Drawing Sheets

(51) Int. Cl.
*C07K 14/705* (2006.01)
*A23L 1/015* (2006.01)

(56) References Cited

U.S. PATENT DOCUMENTS

| 8,124,396 B2 | 2/2012 | Budolfsen |
|---|---|---|
| 2004/0086597 A1 | 5/2004 | Awad et al. |
| 2005/0214411 A1 | 9/2005 | Lindsay et al. |
| 2009/0170157 A1 | 7/2009 | Matsui et al. |
| 2010/0080868 A1 | 4/2010 | Crosby et al. |
| 2010/0143540 A1 | 6/2010 | Bhaskar et al. |

FOREIGN PATENT DOCUMENTS

| EP | 2767586 A1 | 8/2014 |
|---|---|---|
| JP | 2006510354 | 4/2004 |
| WO | WO2004/030468 A2 | 4/2004 |
| WO | WO2007073945 A1 | 7/2007 |
| WO | WO 2008/110513 A1 | 9/2008 |
| WO | WO2014037837 A1 | 3/2014 |

OTHER PUBLICATIONS

Friedman, M. and Levin, C.E. "Review of Methods for the Reduction of Dietary Content and Toxicity of Acrylamide". Journal of Agriculture and Food Chemistry, Aug. 13, 2008, 56(15): 6113-6140.

Rommens, C.M. et al. "Low-Acrylamide French Fries and Potato Chips". Plant Biotechnology Journal, 2008, 6:843-853.

Chhun, Aline and John Husnik: "Using Baker's Yeast to Reduce Acrylamide Formation in Foods". Retrieved from the Internet: URL: http//www.fei-online.com/index.php?id=2918 [posted Oct. 18, 2010].

Company News Release: Jun. 30, 2010, "Functional Technologies' Yeast Tests Demonstrate Reduction in Acrylamide Formation in Foods". Retrieved from the Internet: URL: http//www.functionaltechcorp.com/s/NewReleases.asp?ReportID=407476.

Chhun, Aline and John Husnik. Snack Food and Wholesale Bakery, "Using Baker's Yeast to Reduct Acrylamide Formation in Foods". Retrieved from the Internet: URL: http//www.snackandbakery.com/Articles/White_Papers/BNP_GUID_9-5-2006_A_10000000000000922526.

Chhun, Aline and John Husnik. "Using Baker's Yeast to Reduce Acrylamide Formation in Foods". Food Engineering and Ingredients, Nov. 2010, vol. 35: 38-40.

Fredriksson, H. et al. "Fermentation reduces free asparagine in dough and acrylamide content in bread." Cereal Chemistry, Sep. 2004, vol. 81: 650-653.

Ferrara, M. A. et al. "Kinetics of asparaginase II fermentation in *Saccharomyces cerevisiae* ure2dal80 mutant: effect of nitrogen nutrition and pH." Applied Biochemistry and Biotechnology, Spring 2004, vol. 113-116: 299-305.

Ferrara, M. A. et al. "Asparaginase production by a recombinant Pichia pastoris strain harbouring *Saccharomyces cerevisiae* ASP3 gene." Enzyme and Microbial Technology, Nov. 2006, vol. 39: 1457-1463.

Zhao, X. et. al. "Metabolic Engineering of the Regulators in Nitrogen Catabolite Repression to Reduce the Production of Ethyl Carbamate in a Model Rice Wine System." Applied and Environmental Microbiology, Jan. 2014, vol. 80: 392-398.

Kamkar, A. et al. "The inhibitory role of autolysed yeast of *Saccharomyces cerevisiae*,vitamins B3 and B6 on acrylamide formation in potato chips." Toxin Reviews, Mar. 2015, vol. 34: 1-5.

Il-Sup et al., "Elucidation of Copper and Asparagine Transport Systems in *Saccharomyces cerevisiae* KNU5377 Through Genome-Wide Transcription Analysis", J. Microbiol. Biotechnol., (2005), vol. 15, No. 6, pp. 1240-1249.

Schreve et al., "The *Saccharomyces cerevisiae* YCC5 (YCL025c) Gene Encodes an Amino Acid Permease, Agp1, Which Transports Asparagine and Glutamine", J. Bacteriology, (1998) vol. 180, No. 9, pp. 2556-2559.

FUNCTIONAL ENHANCEMENT OF MICROORGANISMS TO MINIMIZE PRODUCTION OF ACRYLAMIDE

CROSS REFERENCE TO RELATED APPLICATIONS

This application is a national phase entry of PCT/CA2011/000222, filed Mar. 1, 2011, which claims priority from U.S. Provisional Patent Application Nos. 61/309,623 and 61/316,634, filed Mar. 2, 2010 and Mar. 23, 2010, respectively, all of which are incorporated herein by reference in their entirety.

INCORPORATION OF SEQUENCE LISTING

A computer readable form of the Sequence Listing "20363-20_SequenceListing.txt" (163,840 bytes), submitted via EFS-WEB and created on Aug. 23, 2012, is herein incorporated by reference.

FIELD

The disclosure relates to products and methods for reducing acrylamide concentration in food as well as to food products having a reduced acrylamide content. In particular, the disclosure relates to genetically modifying microorganisms to enhance their ability to reduce acrylamide.

BACKGROUND

Acrylamide is a colourless and odourless crystalline solid that is an important industrial monomer commonly used as a cement binder and in the synthesis of polymers and gels. Based on various in vivo and in vitro studies there is clear evidence on the carcinogenic and genotoxic effects of acrylamide and its metabolite glycidamide (Wilson et al, 2006; Rice, 2005). Acrylamide was evaluated by the International Agency for Research on Cancer (IARC) in 1994 and it was classified as "probably carcinogenic to humans" on the basis of the positive bioassays completed in mice and rats, supported by evidence that acrylamide is bio-transformed in mammalian tissues to the genotoxic glycidamide metabolite (IARC, 1994). The biotransformation of acrylamide to glycidamide is known to occur efficiently in both human and rodent tissues (Rice, 2005). In addition to the IARC classification, 'The Scientific Committee on Toxicity, Ecotoxicity and the Environment' of the European Union and the independent 'Committee on Carcinogenicity of Chemicals in Food, Consumer Products and the Environment' in the UK, both advised that the exposure of acrylamide to humans should be controlled to a level as low as possible due to its inherently toxic properties including neurotoxicity and genotoxicity to both somatic and germ cells, carcinogenicity and reproductive toxicity.

With respect to human epidemiological studies on dietary acrylamide exposure, there is no evidence for any carcinogenic effect of this chemical; however, it is also recognized that these epidemiological studies on acrylamide may not be sufficiently sensitive to reveal potential tumours in humans exposed to acrylamide (Rice, 2005; Wilson et al, 2006).

In 2002, the Swedish National Food Authority published a report detailing the concentrations of acrylamide found in a number of common foods, specifically heat-treated carbohydrate-rich foods such as French fries and potato chips. The list has now been expanded to include grain-based foods, vegetable-based foods, legume-based foods, beverages such as coffee or coffee substitutes; Table 1 shows FDA data on acrylamide concentrations in a variety of Foods.

It is now established that acrylamide is formed during the cooking of foods principally by the Maillard reaction between the amino acid asparagine and reducing sugars such as glucose, with asparagine being the limiting precursor (Amrein et al, 2004; Becalski et al 2003; Mustafa et al 2005; Surdyk et al, 2004; Yaylayan et al 2003).

There have also been a number of approaches attempted to reduce acrylamide content in food including the addition of commercial preparations of the enzyme asparaginase (Acrylaway®, Novozymes, Denmark and PreventASe, DSM, Netherlands), extensive yeast fermentation for 6 hours (Fredriksson et al, 2004), applying glycine to dough prior to fermentation (Brathen et al, 2005; Fink et al 2006), dipping potatoes into calcium chloride prior to frying (Gokmen and Senyuva, 2007), replacing reducing sugars with sucrose (Amrein et al, 2004), general optimization of the processing conditions such as temperature, pH and water content (Claus et al, 2007; Gokmen et al, 2007) and studies regarding different choices of raw materials (Claus et al, 2006). All of these listed approaches are inadequate to some degree or have inherent issues that make them impractical during the manufacture of food products including cost, effect on organoleptic properties of the food and/or ineffective acrylamide reduction under food processing conditions.

Like many microorganisms, *Saccharomyces cerevisiae* is capable of naturally consuming/degrading the acrylamide precursors asparagine and reducing sugars. This may be the reason for an observed reduction of acrylamide content in bread after an extensive fermentation time of 6 hours (Fredriksson et al, 2004). However, such an extensive fermentation time to effectively reduce acrylamide is impractical in modern food production processes.

In *S. cerevisiae*, the genes responsible for asparagine degradation are ASP1 and ASP3 that encode for a cytosolic asparaginase and a cell-wall asparaginase, respectively. There are also at least 41 genes in *S. cerevisiae* annotated to the term 'amino acid transport' and six of these transporters are known to be capable of transporting asparagine into the cell ["*Saccharomyces* Genome Database" http://www.yeastgenome.org/(Oct. 1, 2009)]. The gene names for these six asparagine transporters in *S. cerevisiae* are GAP1, AGP1, GNP1, DIP5, AGP2 and AGP3. It is also well established that *S. cerevisiae* is able to use a wide variety of nitrogen sources for growth and that in mixed substrate cultures it will sequentially select good to poor nitrogen sources (Cooper, 1982). This sequential use is controlled by molecular mechanisms consisting of a sensing system and a transcriptional regulatory mechanism known as nitrogen catabolite repression (NCR). In general, NCR refers to the difference in gene expression of permeases and catabolic enzymes required to degrade nitrogen sources. The expression of nitrogen catabolite pathways are regulated by four regulators known as Gln3p, Gat1p, Dal80p and Gzf3p that bind to the upstream activating consensus sequence 5'-GATAA-3'. Gln3p and Gat1p act positively on gene expression whereas Dal80p and Gzf3p act negatively. In the presence of a good nitrogen source, Gln3p and Gat1p are phosphorylated by the TOR kinases Tor1p and Tor2p; then form cytosolic complexes with Ure2p and are thereby inhibited from activating NCR-sensitive transcription. In the presence of poor nitrogen sources or nitrogen starvation Gln3p and Gat1p become dephosphorylated, dissociate from Ure2p, accumulate in the nucleus and activate NCR-sensitive transcription.

It is also well documented that a particular mutation of URE2 yields a dominant mutation referred to as [URE3].

[URE3] is a yeast prion that is formed by the autocatalytic conversion of Ure2p into infectious, protease-resistant amyloid fibrils (Wickner, 1994). The phenotypes of S. cerevisiae cells lacking a functional Ure2p and [URE3] infected cells are similar as they no longer respond to NCR (Wickner, 1994; Wickner et al, 1995). As noted above, in response to a good nitrogen source, Ure2p is involved in the down-regulation of Gln3p and Gat1p activity.

SUMMARY

The present disclosure provides a microorganism transformed with at least one nucleic acid molecule to reduce nitrogen catabolite repression under food preparation/processing conditions. The present disclosure also provides a microorganism transformed with at least one nucleic acid molecule to overexpress a gene encoding an extracellular protein involved in asparagine degradation and/or a gene encoding a protein involved in asparagine transport under food preparation/processing conditions. The present disclosure also provides a microorganism transformed with at least one nucleic acid molecule to reduce nitrogen catabolite repression and/or to overexpress a gene encoding an extracellular protein involved in asparagine degradation and/or a gene encoding a protein involved in asparagine transport under food preparation/processing conditions.

In one embodiment, the microorganism is transformed with a nucleic acid molecule encoding an extracellular asparaginase, such as the cell-wall associated asparaginase, Asp3p. In another embodiment, the microorganism is transformed with a nucleic acid molecule encoding an amino acid transporter, such as an asparagine amino acid transporter, for example, Gap1p, Agp1p, Gnp1p, Dip5p Agp2p and/or Agp3p.

In another embodiment, the microorganism is transformed with a nucleic acid molecule encoding both Asp3p and Gap1p or Asp3p and Gat1p. In another embodiment, the microorganism is transformed with a first and second nucleic acid molecule, wherein the first nucleic acid molecule encodes Asp3p and the second nucleic acid molecule encodes Gap1p or Gat1p.

In yet another embodiment, the microorganism is transformed with a nucleic acid molecule that modifies the activity of a regulatory factor of nitrogen catabolite repression of asparagine transport/degradation, such as Ure2p, Dal80p, Gzf3p, Gln3p, Gat1p, Tor1p and/or Tor2p. In another embodiment, the microorganism is transformed with a nucleic acid molecule that modifies the activity of both nitrogen catabolite repression regulatory factors Gln3p and Ure2p. In yet another embodiment, the microorganism is transformed with a first and second nucleic acid molecule that modify nitrogen catabolite repression, wherein the first nucleic acid molecule encodes Gln3p and the second nucleic acid molecule modifies the expression of Ure2p.

In an embodiment, the microorganism is a fungus or bacteria. The fungus can be any fungus, including yeast, such as *Saccharomyces cerevisiae, Saccharomyces bayanus, Saccharomyces carlsbergensis, Candida albicans, Candida kefyr, Candida tropicalis, Cryptococcus laurentii, Cryptotoccous neoformans, Hansenula anomala, Hansenula polymorpha, Kluyveromyces fragilis, Kluyveromyces lactis, Kluyveromyces marxianus* var *lactis, Pichia pastoris, Rhodotorula rubra, Schizosaccharomyces pombe, Yarrowia lipolyitca* or any yeast species belonging to the Fungi Kingdom. Other fungi that can be used include, but are not limited to, species from the genera *Aspergillus, Penicillium, Rhizopus* and *Mucor*. The bacteria can be any bacteria, including *Erwinia* sp., *Lactobacillus* sp., *Lactococcus* sp., *Bacillus* sp., *Pediococcus* sp., *Pseudomonas* sp., *Brevibacterium* sp., and *Leuconostoc* sp. In one embodiment, the microorganism is inactive, such as inactive yeast.

In one embodiment, the at least one nucleic acid molecule is operatively linked to a constitutively active promoter. In another embodiment, the at least one nucleic acid molecule is operatively linked to a promoter that is not subject to nitrogen catabolite repression.

Also provided herein is a method for reducing acrylamide in a food product comprising adding the microorganism disclosed herein to food under preparation or processing conditions; wherein the microorganism reduces nitrogen catabolite repression or overexpresses a gene involved in asparagine transport and/or degradation under preparation or processing conditions; thereby reducing acrylamide in the food product.

Further provided herein is a method for reducing acrylamide in a food product comprising (a) transforming a microorganism with at least one nucleic acid molecule to reduce nitrogen catabolite repression or to overexpress a gene encoding an extracellular protein involved in asparagine degradation and/or a gene encoding a protein involved in asparagine transport; (b) adding the microorganism to food under preparation or processing conditions; wherein the microorganism reduces nitrogen catabolite repression or overexpresses the gene encoding the extracellular protein involved in asparagine degradation and/or a gene encoding a protein involved in asparagine transport thereby reducing acrylamide in the food product.

In another embodiment, there is provided a food product having a reduced acrylamide concentration produced using the transformed microorganism disclosed herein. In yet another embodiment, there is provided a food product having a reduced acrylamide concentration produced using the method disclosed herein.

In one embodiment, the food product is a grain-based food product, including without limitation, biscuits, bread and crackers, a vegetable-based food product including, without limitation, potato products, a beverage including, without limitation, coffee and coffee substitutes, a fruit, legume, dairy or meat product.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
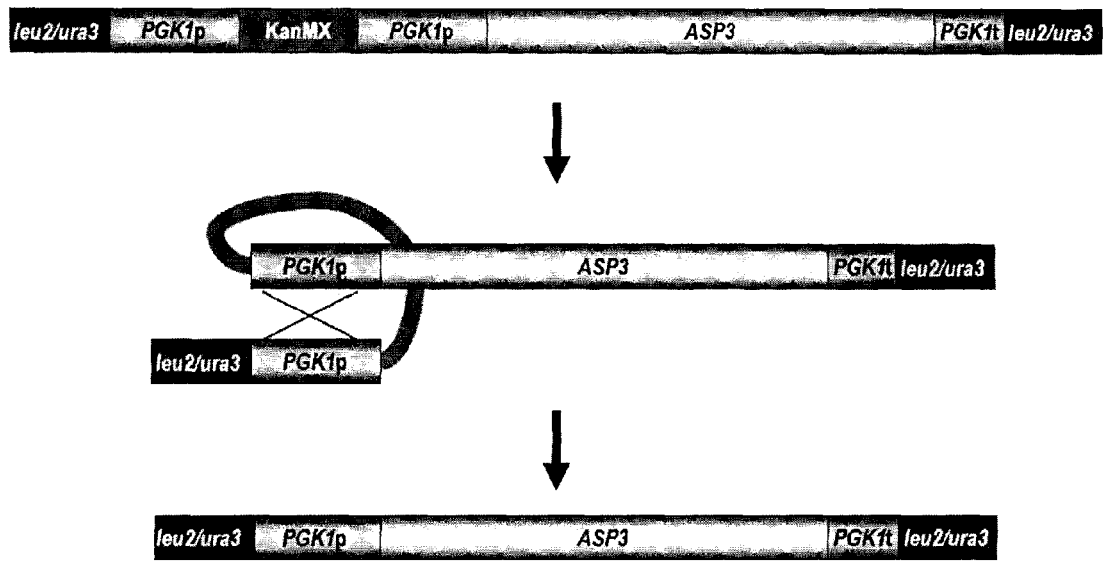
FIG. 1 is a schematic representation of the constructed ASP3 genetic cassette and the subsequent steps to lose the kanMX marker after integration into the LEU2 or URA3 locus of S. cerevisiae strains. The kanMX marker is removed by recombination of the PGK1 promoter direct repeats yielding a self-cloning strain containing only native DNA sequences.

The present inventors have produced yeast strains having increased ability to consume and/or degrade asparagine, which is a limiting precursor produced during food processing or preparation that results in the production of acrylamide.

Microorganisms

In one embodiment, there is provided a microorganism transformed with at least one nucleic acid molecule to reduce nitrogen catabolite repression and/or to overexpress a gene encoding an extracellular protein involved in asparagine degradation and/or a gene encoding a protein involved in asparagine transport under food preparation/processing conditions.

In another embodiment, the microorganism is transformed with at least two, at least 3, at least 4, at least 5 or more of the nucleic acid molecules.

The phrase "overexpress a gene encoding an extracellular protein involved in asparagine degradation and/or a gene encoding a protein involved in asparagine transport" as used herein refers to increased expression of mRNA or proteins that are transported to the cell membrane or secreted to the cell wall and that are involved in the transport and/or degradation of the amino acid asparagine compared to a control that has not been transformed with the nucleic acid molecule.

The nucleic acid molecule may be any nucleic acid molecule that encodes a protein involved, directly or indirectly, in asparagine transport and/or an extracellular protein involved directly or indirectly in asparagine degradation. In an embodiment, the nucleic acid molecule encodes a cell-wall asparaginase or fragment thereof that has asparagine-degrading activity. Extracellular asparaginases are enzymes known in the art and include, without limitation, extracellular, such as cell wall, asparaginases from any source that are able to convert asparagine to aspartate, such as yeast Asp3p, or homologs thereof and may be encoded by any asparaginase genes that encode cell-wall asparaginases, including without limitation, ASP3 or homologs thereof. In one embodiment, the cell wall asparaginase is encoded by the nucleic acid molecule ASP3 as shown in SEQ ID NO:2 or a homolog or fragment thereof or comprises the amino acid sequence Asp3p as shown in SEQ ID NO:1 or a homolog or fragment thereof. Microorganisms comprising nucleic acid molecules encoding extracellular asparaginases would be able to degrade asparagine under food preparation and processing conditions.

In another embodiment, the nucleic acid molecule encodes an amino acid transporter or fragment thereof that has the ability to transport asparagine into the cell. Amino acid transporters are known in the art and include, without limitation, amino acid transporters from any source that are able to actively transport asparagine into the microorganism, such as yeast Gap1p, Agp1p, Gnp1p, Dip5p Agp2p and Agp3p (NP_012965, NP_009905, NP_010796, NP_015058, NP_009690, and NP_116600) or a homolog thereof and may be encoded by any amino acid transporter gene including, without limitation, GAP1, AGP1, GNP1, DIP5, AGP2 and AGP3 (SGD:S000001747, SGD:S000000530, SGD: S000002916, SGD:S000006186, SGD:S000000336 and SGD:S000001839) or a homolog thereof. Accordingly, in one embodiment, the amino acid transporter is encoded by the nucleic acid molecule GAP1, AGP3, AGP2, GNP1, AGP1 or DIP5 as shown in SEQ ID NO:4, 6, 8, 10, 12, or 30 respectively, or a homolog or fragment thereof or comprises the amino acid sequence of Gap1p, Agp3p, Agp2p, Gnp1p, Agp1p or Dip5p as shown in SEQ ID NO:3, 5, 7, 9, 11, or 29 respectively, or a homolog or fragment thereof. Microorganisms comprising nucleic acid molecules encoding amino acid transporters would be able to consume or uptake asparagine under food preparation and processing conditions.

In another embodiment, the microorganism is transformed with a nucleic acid encoding a cell-wall asparaginase and a nucleic acid encoding an amino acid transporter. In such an embodiment, the microorganism is able to consume and degrade asparagine.

The phrase "reduce nitrogen catabolite repression (NCR)" of asparagine transport/degradation as used herein refers to actual reduction in gene repression of NCR-sensitive genes or refers to increased endogenous expression or heterologous expression of NCR-sensitive genes. For example, the nucleic acid molecule to reduce NCR can be a regulatory factor that modifies expression of nitrogen catabolite repression or can be overexpression of an NCR-sensitive gene.

In yet another embodiment, the nucleic acid molecule modifies the activity of a regulatory factor of nitrogen catabolite repression. Regulatory factors for nitrogen catabolite repression are known in the art and include, without limitation, regulatory factors from any source, such as yeast Gat1p, Ure2p, Tor1p, Dal80p, Gzf3p, Tor2p, or Gln3p as shown in SEQ ID NO:13, 15, 17, 19, 21, 33 or 31 or a homolog or fragment thereof and may be encoded by any gene encoding a regulatory factor, such as GAT1, URE2, TOR1, DAL80, GZF3, TOR2, or GLN3 as shown in SEQ ID NO:14, 16, 18, 20, 22, 34 or 32. For example, a microorganism can be produced that no longer has a functional negative regulator, such as Ure2p, Tor1p, Tor2p Dal80p or Gzf3p. This can be accomplished, for example, by a nucleic acid molecule that results in deletion of the URE2 gene, isolation and expression of an ure2 mutant phenotype so that it no longer down regulates the activities of Gln3p and Gat1p, by mating a wild type strain with a [URE3] strain, or inducing a [URE3] phenotype by any molecular biology means including cytoduction and overexpression of URE2. The consequence of cells lacking a functional Ure2p would result in NCR sensitive genes, such as those involved in asparagine transport and utilization (i.e. ASP3, AGP1, GAP1, GAT1, DAL80 and GZF3), to no longer be repressed in the presence of a good nitrogen source such as ammonia or glutamine. Accordingly, in one embodiment, the nucleic acid molecule comprises a URE2, TOR1, TOR2, DAL80 and/or GZF3 deletion cassette. Microorganisms lacking a functional Ure2p, Tor1p, Dal80p and/or Gzf3p would be able to consume and degrade asparagine under food preparation and processing conditions. Alternatively, this can be accomplished by a nucleic acid molecule that results in the overexpression of a functional positive regulator, such as Gat1p and/or Gln3p.

The term "gene" as used herein is in accordance with its usual definition, to mean an operatively linked group of nucleic acid sequences. The modification of a gene in the context of the present disclosure may include the modification of any one of the various sequences that are operatively linked in the gene. By "operatively linked" it is meant that the particular sequences interact either directly or indirectly to carry out their intended function, such as mediation or modulation of gene expression. The interaction of operatively linked sequences may for example be mediated by proteins that in turn interact with the nucleic acid sequences.

Various genes and nucleic acid sequences of the disclosure may be recombinant sequences. The term "recombinant" as used herein refers to something that has been recombined, so that with reference to a nucleic acid construct the term refers to a molecule that is comprised of nucleic acid sequences that have at some point been joined together or produced by means of molecular biological techniques. The term "recombinant" when made with reference to a protein or a polypeptide refers to a protein or polypeptide molecule which is expressed using a recombinant nucleic acid construct created by means of molecular biological techniques. The term "recombinant" when made in reference to a genetic composition refers to a gamete or progeny or cell or genome with new combinations of alleles that did not occur in the naturally-occurring parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated by human intervention using genetic engineering.

Nucleic acid molecules may be chemically synthesized using techniques such as are disclosed, for example, in Itakura et al. U.S. Pat. No. 4,598,049; Caruthers et al. U.S. Pat. No. 4,458,066; and Itakura U.S. Pat. Nos. 4,401,796 and 4,373,071. Such synthetic nucleic acids are by their nature "recombinant" as that term is used herein (being the product of successive steps of combining the constituent parts of the molecule).

The degree of homology between sequences (such as native Asp3p, Gap1p, Dip5p Gnp1p, Agp1p, Agp2p, Agp3p, Tor1p, Tor2p, Gat1p, Gln3p, Dal80p, Gzf3p or Ure2p amino acid sequences or native ASP3, GAP1, DIP5, GNP1, AGP1, AGP2, AGP3, TOR1, TOR2, GAT1, GLN3, DAL80, GZF3 or URE2 nucleic acid sequences and the sequence of a homolog) may be expressed as a percentage of identity when the sequences are optimally aligned, meaning the occurrence of exact matches between the sequences. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, J. Mol. Biol. 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST programs may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both strands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs). The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (9,1,0.87); PAM70 (10,1,0.87) BLOSUM80 (10,1,0.87); BLOSUM62 (11,1,0.82) and BLOSUM45 (14,2,0.87). One measure of the statistical similarity between two sequences using the BLAST algorithm is the smallest sum probability (P(N)), which provides an indication of the probability by which a match between two nucleotide or amino acid sequences would occur by chance. In alternative embodiments, nucleotide or amino acid sequences are considered substantially identical if the smallest sum probability in a comparison of the test sequences is less than about 1, less than about 0.1, less than about 0.01, or less than about 0.001. The similarity between sequences can also be expressed as percent identity.

Nucleic acid and protein sequences described herein may in some embodiments be substantially identical, such as substantially identical to Asp3p, Gap1p, Gnp1p, Agp1p, Agp2p, Agp3p, Gat1p, Tor1p, Tor2p, Dip5p Gln3p, Dal80p, Gzf3p, or Ure2p amino acid sequences or ASP3, GAP1, GNP1, AGP1, AGP2, AGP3, TOR1, TOR2, DIP5, GLN3, GAT1, DAL80, GZF3 or URE2 nucleic acid sequences. The substantial identity of such sequences may be reflected in percentage of identity when optimally aligned that may for example be greater than 50%, 80% to 100%, at least 80%, at least 90% or at least 95%, which in the case of gene targeting substrates may refer to the identity of a portion of the gene targeting substrate with a portion of the target sequence, wherein the degree of identity may facilitate homologous pairing and recombination and/or repair. An alternative indication that two nucleic acid sequences are substantially identical is that the two sequences hybridize to each other under moderately stringent, or highly stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under highly stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH. Washes for stringent hybridization may for example be of at least 15 minutes, 30 minutes, 45 minutes, 60 minutes, 75 minutes, 90 minutes, 105 minutes or 120 minutes.

It is well known in the art that some modifications and changes can be made in the structure of a polypeptide, such as Asp3p, Gap1p, Gnp1p, Agp1p, Agp2p, Agp3p, Gat1p, Tor1p, Tor2p, Dip5p Gln3p, Dal80p, Gzf3p, or Ure2p without substantially altering the biological function of that peptide, to obtain a biologically equivalent polypeptide. In one aspect, proteins having asparagine transport activity may include proteins that differ from the native Gap1p, Gnp1p, Dip5p Agp1p, Agp2p, Agp3p or other amino acid transporter sequences by conservative amino acid substitutions. Similarly, proteins having asparaginase activity may include proteins that differ from the native Asp3p, or other cell-wall asparaginase sequences by conservative amino acid substitutions. As used herein, the term "conserved or conservative amino acid substitutions" refers to the substitution of one amino acid for another at a given location in the protein, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the protein by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125-142, 184). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR, etc., where R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C5-C20) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids.

The microorganism can be any microorganism that is suitable for addition into food products, including without limitation, fungi and/or bacteria. Fungi useful in the present disclosure include, without limitation, *Aspergillus niger, Aspergillus oryzae, Neurospora crassa, Neurospora intermedia* var. *oncomensis, Penicillium camemberti, Penicillium candidum, Penicillium roqueforti, Rhizopus oligosporus, Rhizopus oryzae*. In another embodiment, the fungi is yeast, such as, *Saccharomyces cerevisiae, Saccharomyces bayanus, Saccharomyces carlsbergensis, Candida albicans, Candida kefyr, Candida tropicalis, Cryptococcus laurentii, Cryptotoccous neoformans, Hansenula anomala, Hansenula polymorpha, Kluyveromyces fragilis, Kluyveromyces lactis, Kluyveromyces marxianus* var *lactis, Pichia pastoris, Rhodotorula rubra, Schizosaccharomyces pombe, Yarrowia lipolyitca* or any strain belonging to the Fungi Kingdom. There are a variety of commercial sources for yeast strains, such as Lallemand Inc. (Canada), AB Mauri (Australia) and Lesaffre (France). In another embodiment the bacteria can be any bacteria, including *Erwinia* sp., *Lactobacillus* sp., *Lactococcus* sp., *Bacillus* sp., *Pediococcus* sp., *Pseudomonas* sp., *Brevibacterium* sp., and *Leuconostoc* sp.

In an embodiment, the microorganism is inactive, such as inactive yeast. The term "inactive" as used herein refers to a composition of inactive, inviable and/or dead microorganisms that still retain their nutritional content and other properties. For example, yeast may be grown under conditions that allow overexpression of the desired protein or proteins. The yeast can then be used to produce the inactive yeast, for example, through a variety of pasteurization methods including, without limitation, high-temperature and short-time pasteurization, a variety of sterilization methods including, without limitation, moist heat and irradiation, a variety of inactivation methods including, without limitation, high pressure, photocatalytic and pulsed-light, photosensitization, electric fields including RF and pulsed, cellular disruption, sonication, homogenization, autolysis, and chemical based inactivation including, without limitation, formaldehyde, thimerosol, chloramines, chlorine dioxide, iodine, silver, copper, antibiotics, and ozone.

Recombinant nucleic acid constructs may for example be introduced into a microorganism host cell by transformation. Such recombinant nucleic acid constructs may include sequences derived from the same host cell species or from different host cell species, which have been isolated and reintroduced into cells of the host species.

Recombinant nucleic acid sequences may become integrated into a host cell genome, either as a result of the original transformation of the host cells, or as the result of subsequent recombination and/or repair events. Alternatively, recombinant sequences may be maintained as extra-chromosomal elements. Such sequences may be reproduced, for example by using an organism such as a transformed yeast strain as a starting strain for strain improvement procedures implemented by mutation, mass mating or protoplast fusion. The resulting strains that preserve the recombinant sequence of the invention are themselves considered "recombinant" as that term is used herein.

Transformation is the process by which the genetic material carried by a cell is altered by incorporation of one or more exogenous nucleic acids into the cell. For example, yeast may be transformed using a variety of protocols (Gietz et al., 1995). Such transformation may occur by incorporation of the exogenous nucleic acid into the genetic material of the cell, or by virtue of an alteration in the endogenous genetic material of the cell that results from exposure of the cell to the exogenous nucleic acid. Transformants or transformed cells are cells, or descendants of cells, that have been functionally enhanced through the uptake of an exogenous nucleic acid. As these terms are used herein, they apply to descendants of transformed cells where the desired genetic alteration has been preserved through subsequent cellular generations, irrespective of other mutations or alterations that may also be present in the cells of the subsequent generations.

In one embodiment, a vector may be provided comprising a recombinant nucleic acid molecule having the asparaginase or amino acid transporter or positive NCR regulatory factor or mutant negative NCR regulatory factor coding sequence, or homologues thereof, under the control of a heterologous promoter sequence that mediates regulated expression of the polypeptide. To provide such vectors, the open reading frame (ORF), for example, one derived from the host microorganism, may be inserted into a plasmid containing an expression cassette that will regulate expression of the recombinant gene. Alternatively, the nucleic acid molecule may be a deletion cassette for deleting a negative NCR regulatory factor. The recombinant molecule may be introduced into a selected microorganism to provide a transformed strain having altered asparagine transport and degrading activity. In alternative embodiments, expression of a native asparaginase or amino acid transporter or NCR regulatory factor coding sequence or homologue in a host may also be effected by replacing the native promoter with another promoter. Additional regulatory elements may also be used to construct recombinant expression cassettes utilizing an endogenous coding sequence. Recombinant genes or expression cassettes may be integrated into the chromosomal DNA of a host.

In one embodiment, the microorganisms are transformed to continually degrade and/or uptake asparagines under food preparation/processing conditions. For example, the nucleic acid molecule may be operatively linked to a constitutively active promoter. Constitutively active promoters are known in the art and include, without limitation, PGK1 promoter, TEF promoter, truncated HXT7 promoter. Alternatively, the nucleic acid molecule may be operatively linked to a promoter that is not subject to nitrogen catabolite repression, such as ADH1, GAL1, CUP1, PYK1, or CaMV 35S.

The term "promoter" as used herein refers to a nucleotide sequence capable of mediating or modulating transcription of a nucleotide sequence of interest in the desired spatial or temporal pattern and to the desired extent, when the transcriptional regulatory region is operably linked to the sequence of interest. A transcriptional regulatory region and a sequence of interest are "operably or operatively linked" when the sequences are functionally connected so as to permit transcription of the sequence of interest to be mediated or modulated by the transcriptional regulatory region. In some embodiments, to be operably linked, a transcriptional regulatory region may be located on the same strand as the sequence of interest. The transcriptional regulatory region may in some embodiments be located 5' of the sequence of interest. In such embodiments, the transcriptional regulatory region may be directly 5' of the sequence of interest or there may be intervening sequences between these regions. Transcriptional regulatory sequences may in some embodiments be located 3' of the sequence of interest. The operable linkage of the transcriptional regulatory region and the sequence of interest may require appropriate molecules (such as transcriptional activator proteins) to be bound to the transcriptional regulatory region, the disclosure therefore encompasses embodiments in which such molecules are provided, either in vitro or in vivo.

Promoters for use include, without limitation, those selected from suitable native *S. cerevisiae* promoters, such as the PGK1 promoter. Such promoters may be used with additional regulator elements, such as the PGK1 terminator. A variety of native or recombinant promoters may be used, where the promoters are selected or constructed to mediate expression of asparagine degrading activities, such as Asp3p activities, under selected conditions, such as food preparation processing conditions. A variety of constitutive promoters may for example be operatively linked to the coding sequence.

Figure 2:
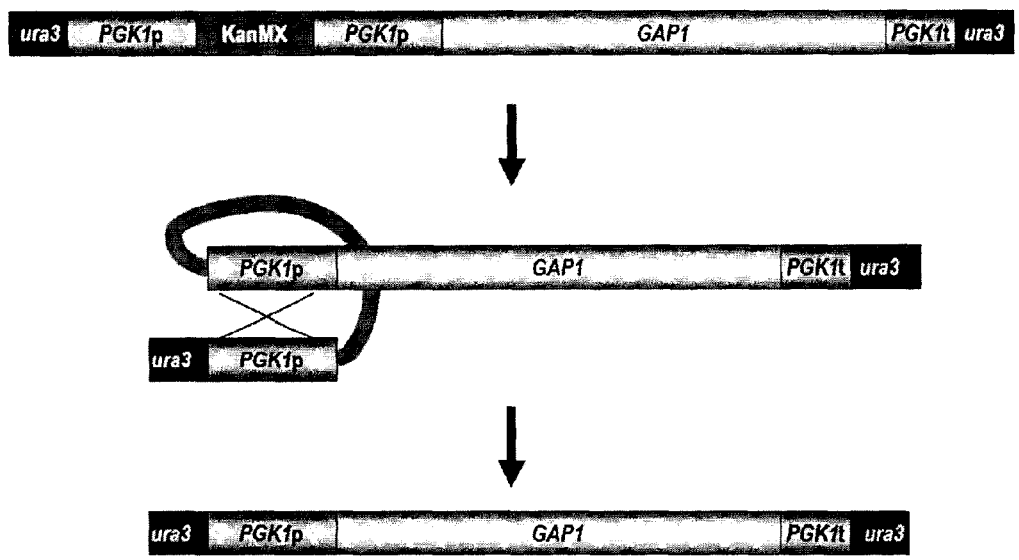
FIG. 2 is a schematic representation of the constructed GAP1 genetic cassette and the subsequent steps to lose the kanMX marker after integration into the URA3 locus of S. cerevisiae strains. The kanMX marker is removed by recombination of the PGK1 promoter direct repeats yielding a self-cloning strain containing only native DNA sequences.
Figure 3:
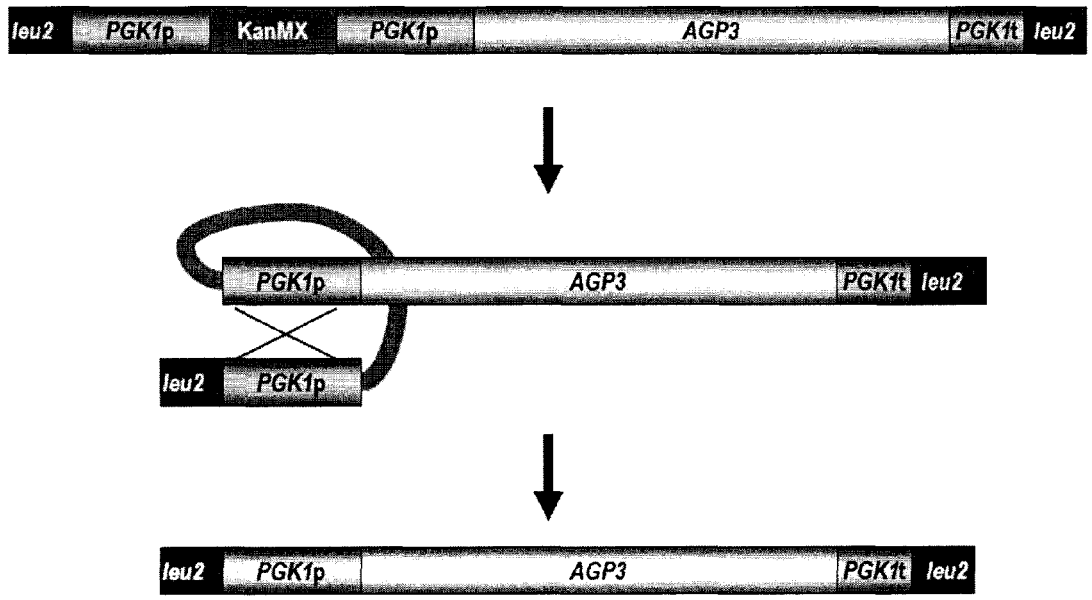
FIG. 3 is a schematic representation of the constructed AGP3 genetic cassette and the subsequent steps to lose the kanMX marker after integration into the LEU2 locus of *S. cerevisiae* strains. The kanMX marker is removed by recombination of the PGK1 promoter direct repeats yielding a self-cloning strain containing only native DNA sequences.
Figure 4:
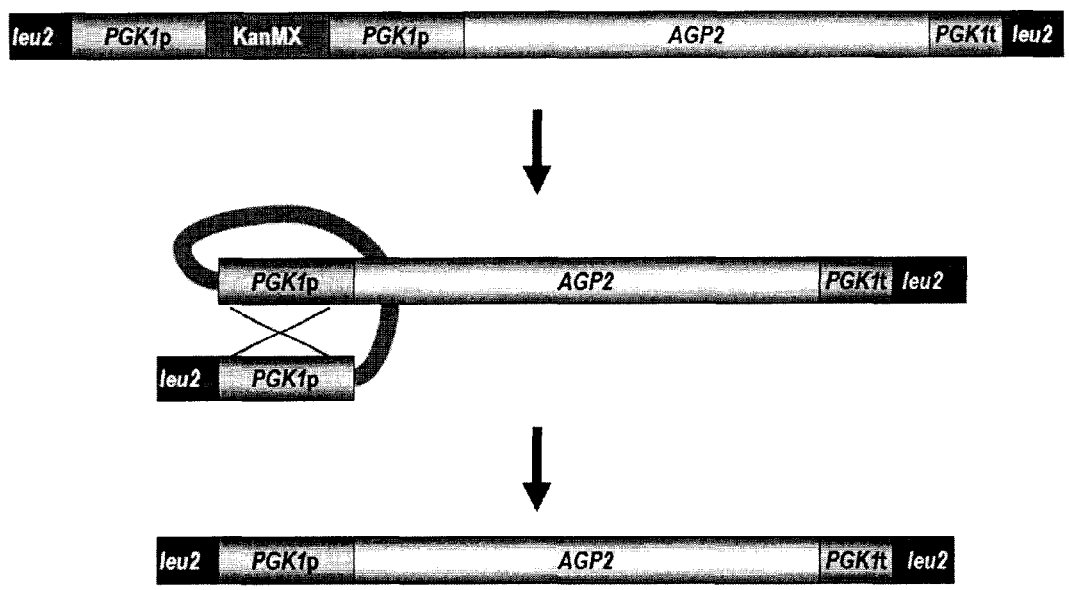
FIG. 4 is a schematic representation of the constructed AGP2 genetic cassette and the subsequent steps to lose the kanMX marker after integration into the LEU2 locus of *S. cerevisiae* strains. The kanMX marker is removed by recombination of the PGK1 promoter direct repeats yielding a self-cloning strain containing only native DNA sequences.
Figure 5:
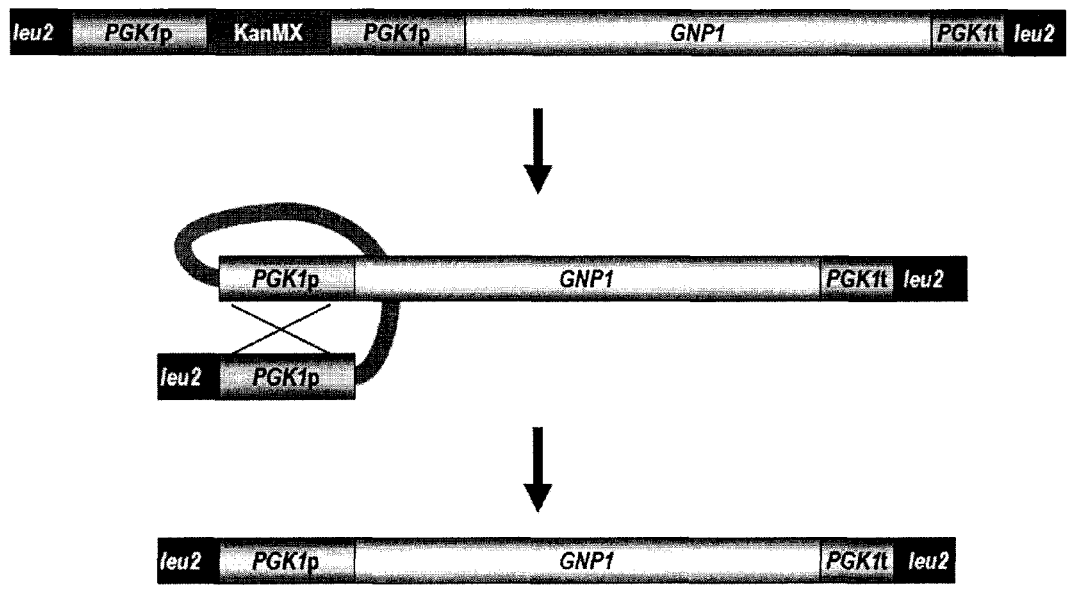
FIG. 5 is a schematic representation of the constructed GNP1 genetic cassette and the subsequent steps to lose the kanMX marker after integration into the LEU2 locus of *S. cerevisiae* strains. The kanMX marker is removed by recombination of the PGK1 promoter direct repeats yielding a self-cloning strain containing only native DNA sequences.
Figure 6:
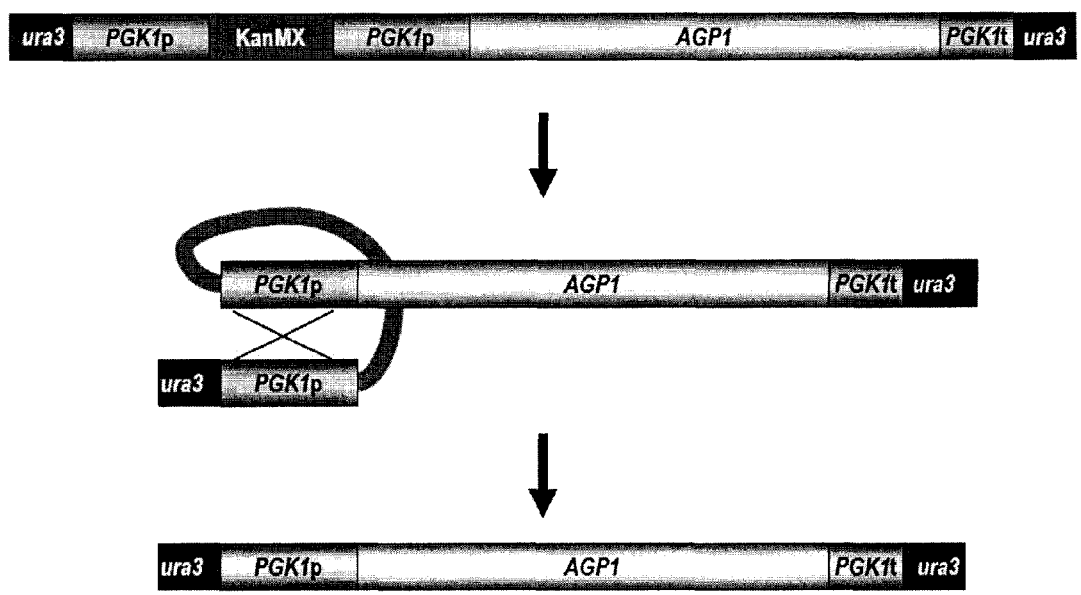
FIG. 6 is a schematic representation of the constructed AGP1 genetic cassette and the subsequent steps to lose the kanMX marker after integration into the URA3 locus of *S. cerevisiae* strains. The kanMX marker is removed by recombination of the PGK1 promoter direct repeats yielding a self-cloning strain containing only native DNA sequences.
Figure 7:
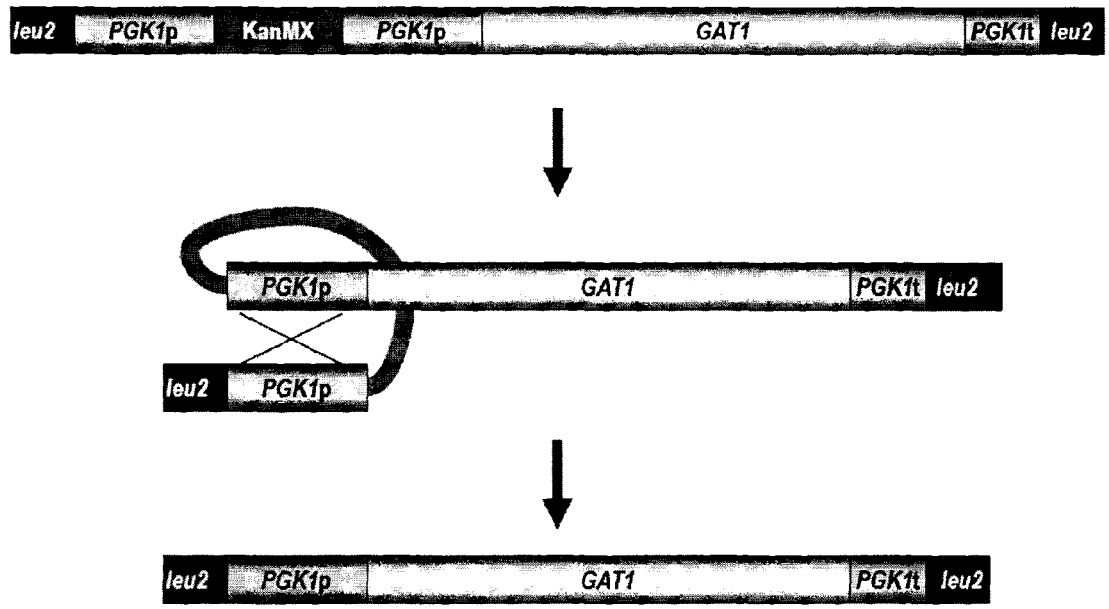
FIG. 7 is a schematic representation of the constructed GAT1 genetic cassette and the subsequent steps to lose the kanMX marker after integration into the LEU2 locus of *S. cerevisiae* strains. The kanMX marker is removed by recombination of the PGK1 promoter direct repeats yielding a self-cloning strain containing only native DNA sequences.
Figure 8:
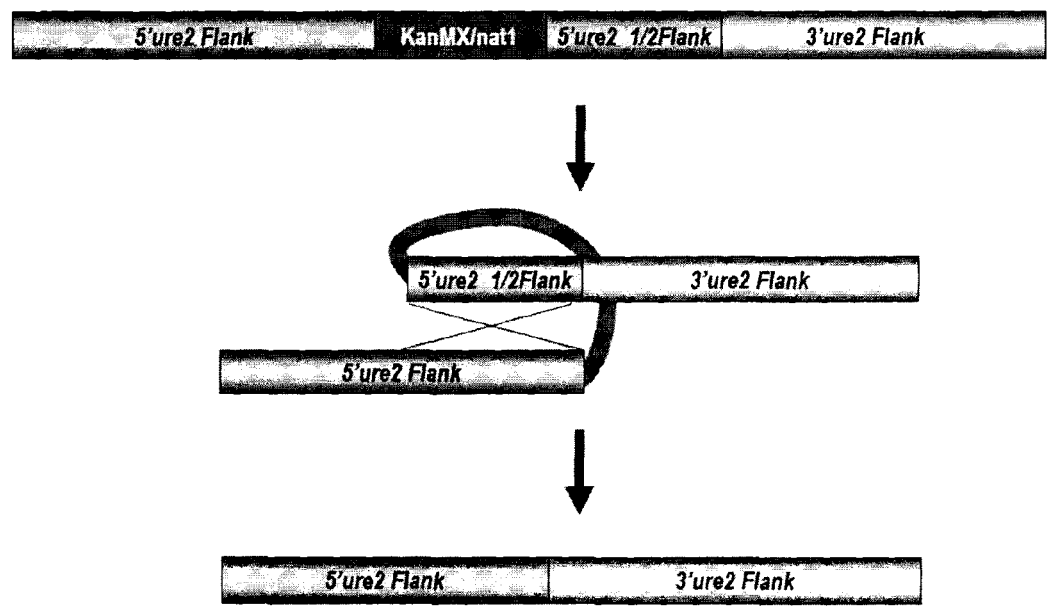
FIG. 8 is a schematic representation of the integration of the self-cloning ure2Δ cassette into the URE2 locus of *S. cerevisiae* strains using a kanMX marker and subsequent loss of the marker by recombination of part of the 5'URE2 flanking sequences acting as direct repeats. The resulting transformation deletes the URE2 gene from the genome.

In one embodiment, the nucleic acid molecule comprises the ASP3 or GNP1, or AGP2, or AGP3, or GAT1 genetic cassette (FIG. 1, 3, 4, 5 or 7), which is inserted into the LEU2 locus. In another embodiment, the nucleic acid molecule comprises the GAP1 or AGP1 or ASP3 cassette, which is inserted into the URA3 locus (FIGS. 1, 2 and 6). In another embodiment, the nucleic acid molecule comprises the ure2Δ cassette, which is inserted into the URE2 locus (FIG. 8).

Methods

In another aspect, there is provided a method for reducing asparagine during food preparation or processing comprising adding the microorganism described herein to food under preparation or processing conditions; wherein the microorganism reduces nitrogen catabolite repression and/or overexpresses the gene encoding the extracellular protein involved in asparagine degradation and/or the gene encoding the protein involved in asparagine transport thereby reducing asparagine in the food product. Also provided herein is use of the microorganisms disclosed herein for reducing asparagine during food preparation or processing conditions.

In another embodiment, there is provided a method for reducing asparagine during food preparation or processing comprising a) transforming a microorganism with at least one nucleic acid molecule to reduce nitrogen catabolite repression and/or to overexpress a gene encoding an extracellular protein involved in asparagine degradation and/or a gene encoding a protein involved in asparagine transport;

b) adding the microorganism to food under food preparation or processing conditions;

wherein the microorganism reduces nitrogen catabolite repression and/or overexpresses the gene encoding the extracellular protein involved in asparagine degradation and/or a gene encoding a protein involved in asparagine transport thereby reducing asparagine.

Asparagine is a limiting precursor in the reaction that produces acrylamide during food preparation or processing. Accordingly, in another embodiment, there is provided a method for reducing acrylamide in a food product comprising adding the microorganism described herein to food under preparation or processing conditions; wherein the microorganism reduces nitrogen catabolite repression and/or overexpresses the gene encoding the extracellular protein involved in asparagine degradation and/or the gene encoding the protein involved in asparagine transport thereby reducing acrylamide in the food product. Also provided herein is use of the microorganisms disclosed herein for reducing acrylamide concentration during food preparation or processing conditions.

In another embodiment, there is provided a method for reducing acrylamide in a food product comprising
a) transforming a microorganism with at least one nucleic acid molecule to reduce nitrogen catabolite repression and/or to overexpress a gene encoding an extracellular protein involved in asparagine degradation and/or a gene encoding a protein involved in asparagine transport;
b) adding the microorganism to food under food preparation or processing conditions;
wherein the microorganism reduces nitrogen catabolite repression and/or overexpresses the gene encoding the extracellular protein involved in asparagine degradation and/or the gene encoding the protein involved in asparagine transport thereby reducing acrylamide in the food product.

In one embodiment, the nucleic acid molecule encodes a cell wall asparaginase as described herein and under food preparation or processing conditions the microorganism expresses the asparaginase, for example, by constitutive expression. In another embodiment, the nucleic acid molecule encodes an amino acid transporter as described herein and under food preparation or processing conditions expresses the amino acid transporter, for example, by constitutive expression. In another embodiment, the nucleic acid molecule encodes both a cell-wall asparaginase and an amino acid transporter. In yet another embodiment, the nucleic acid modifies a regulatory factor of nitrogen catabolite repression as described herein and under food preparation or processing conditions does not express the regulatory factor, such that NCR-sensitive genes are expressed in the presence of good nitrogen sources. In yet another embodiment, after transformation, the microorganism is grown under conditions allowing overexpression of the desired proteins and then the microorganism is inactivated and processed for addition to food under food preparation or processing conditions. In such an embodiment, the proteins in the inactive microorganism have asparagine degradation activity thereby reducing acrylamide in the food product.

In one embodiment, the food preparation or processing conditions comprise fermentation. For example, the methods and uses herein are useful in fermenting of a food product, including without limitation, carbohydrate during breadmaking, potato processing, biscuit production, coffee production, or snack food manufacturing.

In another embodiment, the disclosure provides a method for selecting natural mutants of a fermenting organism having a desired level of asparagine degrading activity under food preparation and processing conditions. For example, strains may be selected that lack NCR of an amino acid transporter or cell-wall asparaginase, such as ASP3, GAP1, GNP1, AGP1, AGP2, AGP3, TOR1, TOR2, DIP5, GLN3, GAT1, DAL80, GZF3 or URE2. For an example of mutation and selection protocols for yeast, see U.S. Pat. No. 6,140,108 issued to Mortimer et al. Oct. 31, 2000, incorporated herein by reference. In such methods, a yeast strain may be treated with a mutagen, such as ethylmethane sulfonate, nitrous acid, or hydroxylamine, which produce mutants with base-pair substitutions. Mutants with altered asparagine degrading activity may be screened for example by plating on an appropriate medium.

In another embodiment, site directed mutagenesis may be employed to alter the level of asparagine transport or asparagine degrading activity in a host. For example, site directed mutagenesis may be employed to remove NCR mediating elements from a promoter, such as the yeast AGP1, ASP3, GAP1, DIP5, GAT1, TOR2, DAL80 or GZF3 promoter. For example, the GATAA(G) boxes in the native AGP1, ASP3, GAP1, DIP5, GAT1, TOR2, DAL80 or GZF3 promoter sequences, as shown in SEQ ID NOS: 23-28, 35 and 36 respectively, may be deleted or modified by substitution. In one embodiment, for example, one or all of the GATAA boxes may be modified by substituting a T for the G, so that the sequence becomes TATAA. Methods of site directed mutagenesis are for example disclosed in: Rothstein, 1991; Simon and Moore, 1987; Winzeler et al., 1999; and, Negritto et al., 1997. Selected or engineered promoters lacking NCR may then be operatively linked to the asparaginase or amino acid transporter coding sequence, to mediate expression of the protein under food preparation and processing conditions. In alternative embodiments, the genes encoding for Gln3p, Gat1p, Ure2p, Tor1/2p, Dal80p or Gzf3p that mediate NCR in *S. cerevisiae* may also be mutated to modulate NCR.

The relative asparagine transport or degrading enzymatic activity of a microbial strain may be measured relative to an untransformed parent strain. For example, transformed strains may be selected to have greater asparagine transport or degrading activity than a parent strain under food preparation and processing conditions, or an activity that is some greater proportion of the parent strain activity under the same fermenting conditions, such as at least 150%, 200%, 250%, 300%, 400% or 500% of the parent strain activity. Similarly, the activity of enzymes expressed or encoded by recombinant nucleic acids of the disclosure may be determined relative to the non-recombinant sequences from which they are derived, using similar multiples of activity.

In an embodiment of the methods and uses described herein, the microorganism is any active or inactive microorganism suitable for addition into food products, including without limitation, fungi and/or bacteria. As described herein, fungi useful in the present methods and uses include, without limitation, *Aspergillus niger, Aspergillus oryzae, Neurospora crassa, Neurospora intermedia* var. *oncomensis, Penicillium camemberti, Penicillium candidum, Penicillium roqueforti, Rhizopus oligosporus, Rhizopus oryzae*. In another embodiment, the fungi is yeast, such as *Saccharomyces cerevisiae, Saccharomyces bayanus, Saccharomyces carlsbergensis, Candida albicans, Candida kefyr, Candida tropicalis, Cryptococcus laurentii, Cryptotoccous neoformans, Hansenula anomala, Hansenula polymorpha, Kluyveromyces fragilis, Kluyveromyces lactis, Kluyveromyces marxianus* var *lactis, Pichia pastoris, Rhodotorula rubra, Schizosaccharomyces pombe, Yarrowia lipolyitca* or any strain belonging to the Fungi Kingdom. The bacteria can be any bacteria, including *Erwinia* sp., *Lactobacillus* sp., *Lactococcus* sp., *Bacillus* sp., *Pediococcus* sp., *Pseudomonas* sp., *Brevibacterium* sp., and *Leuconostoc* sp.

Food Products

In yet another aspect, the present disclosure provides a food product having a reduced acrylamide concentration produced using the transformed microorganism disclosed herein.

In another embodiment, the present disclosure provides a food product having a reduced acrylamide concentration produced using the methods disclosed herein.

The food product can be any food product that is produced under preparation or processing conditions that result in asparagine production and ultimately acrylamide production. Typical preparation and processing conditions that result in acrylamide production include preparation involving high cooking temperatures (greater than 120° C.) and includes, without limitation, frying and baking, toasting, roasting, grilling, braising and broiling. Acrylamide is typically found in high concentration in potato products, bakery products and any cereal or grain product (see also Table 1). Accordingly, in an embodiment, the food product is a vegetable, such as a potato, taro, or olive product, a bakery product or a cereal or grain product. Potato products include, without limitation, French fries, potato chips, fried/baked potato snacks and formed potato products. Bakery products include, without limitation, biscuits, cookies, crackers, breads, non-leavened bread products, battered products, corn and flour tortillas, pastries, pie crusts, cake and muffin mixes, and pastry dough. For example, breads can include, without limitation, fresh and frozen bread and doughs, sourdough, pizza dough, buns and rolls and variety breads, as well as related bread products such as fried or baked snacks or bread crumbs; and pastries can include, without limitation, sweet buns, donuts, and cakes. Cereal or grain products include, without limitation, typical breakfast cereals, beer malt and whey products, corn chips and pretzels, Other foods that are processed in high temperatures, include, without limitation, coffee, roasted nuts, roasted asparagus, beer, malt and whey drinks, chocolate powder, fish products, meat and poultry products, onion soup and dip mix, nut butter, coated peanuts, roasted soybeans, roasted sunflower seeds, fried or baked foods such as falafels and kobbeh, and chocolate bars.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Cloning and Constitutive Expression of the ASP3, ASP1, GAP1, GNP1, AGP1, AGP2, AGP3 and GAT1 Gene in a Strain of *Saccharomyces cerevisiae* and the Deletion of URE2, TOR1, DAL80, and GZF3

For clone selection the antibiotic resistance marker kanMX was used. An industrial/commercial bread yeast or laboratory strain was transformed to constitutively express ASP3, ASP1, GAP1, GNP1, AGP1, AGP2, AGP3 or GAT1, or a combination of ASP3 and GAP1 or a combination of ASP3 and GAT1, or have the URE2, TOR1, DAL80, or GZF3 gene deleted or a combination of tor1Δ and overexpression of ASP3. The only genetic and metabolic modifications were the intended constitutive expression of ASP3, ASP1, GAP1, GNP1, AGP1, AGP2, AGP3 or GAT1, or a combination of ASP3 and GAP1 or a combination of ASP3 and GAT1, or have the URE2 TOR1, DAL80, and GZF3 gene deleted or a combination of tor1Δ and overexpression of ASP3.

Example 2

Transformation of Yeast with the ASP3, ASP1, GAP1, GNP1, AGP1, AGP2, AGP3 or GAT1 Gene Cassette or URE2 Deletion Gene Cassette Yeast were transformed with recombinant nucleic acid containing the ASP3, ASP1, GAP1, GNP1, AGP1, AGP2, AGP3 or GAT1 gene under control of the PGK1 promoter and terminator signal. The PGK1 promoter is not subject to NCR. The URE2 deletion cassette contained 5' and 3' URE2 flanking sequences for targeted gene deletion.

Example 3

Self-Cloning Cassette Allowing Removal of Selectable Marker

FIGS. 1-8 illustrate how the designed genetic cassettes allow for selection of transformed yeast and subsequent removal of an antibiotic resistance marker via recombination of direct repeats, used in this example as described below. The ASP1 self-cloning cassette was constructed in a similar manner, transformed and antibiotic resistance marker removed as illustrated for other examples.

Example 4

Figure 11:
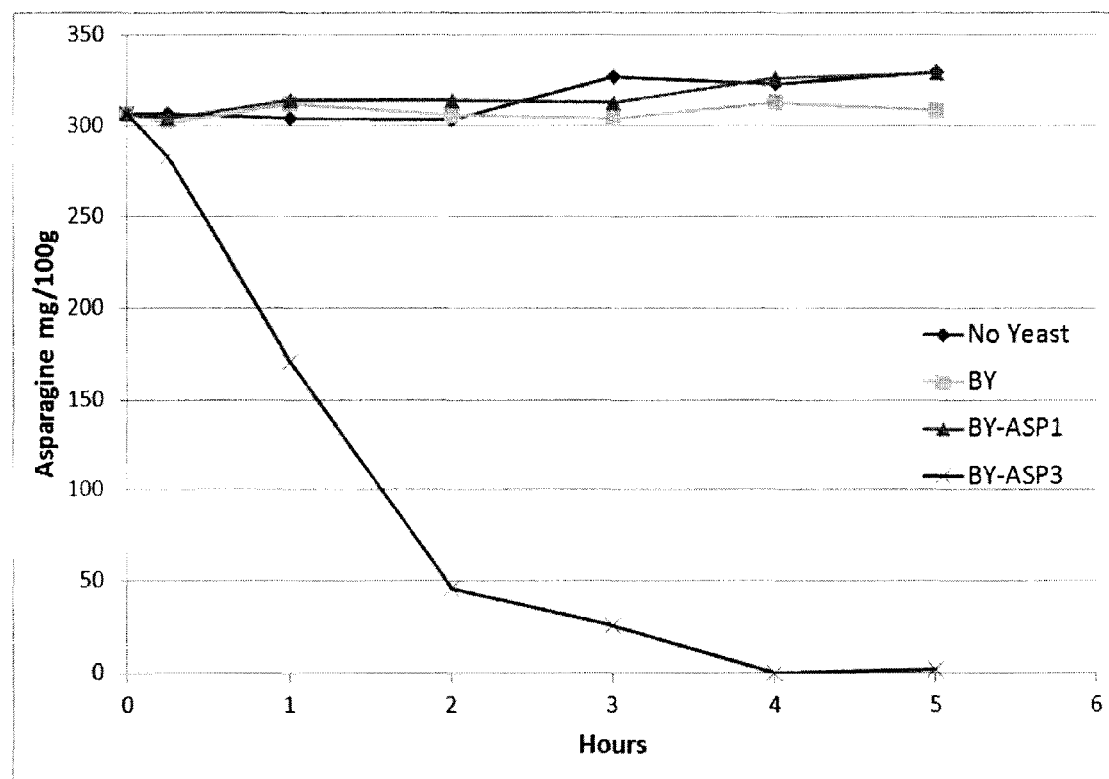
FIG. 11 shows the consumption of asparagine in bread dough using a commercial bread yeast (BY) overexpressing the gene ASP1 or ASP3.

Asparagine and Acrylamide Reduction Studies with the Self-Cloning Yeast to Establish the Occurrence of Reduced Acrylamide or the Limiting Precursor Asparagine FIGS. 11-20 show significant reductions of asparagine and/or acrylamide for yeast transformed with ASP3, GAP1, GNP1, AGP1, AGP2, AGP3 or GAT1, or a combination of ASP3 and GAP1 or a combination of ASP3 and GAT1, or have the URE2, TOR1, DAL80 or GZF3 gene deleted or a combination of tor1Δ and overexpression of ASP3. FIG. 11 also clearly shows that overexpression of cytosolic ASP1 does not work as compared to overexpression of ASP3 that encodes for a cell-wall associated asparaginase.

Figure 12:
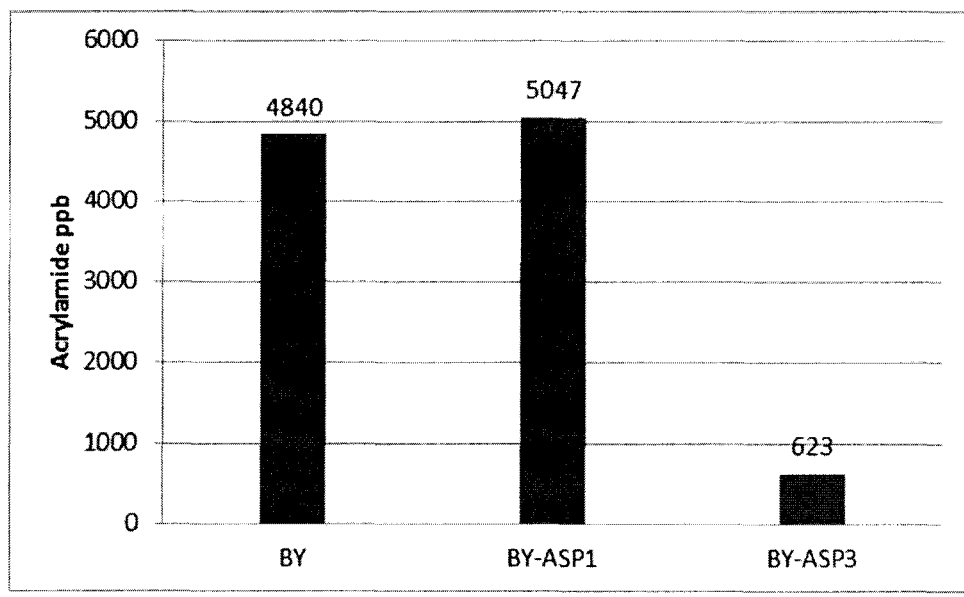
FIG. 12 shows acrylamide concentrations in a baked dough sample taken at timepoint 5 h taken from the experiment outlined in FIG. 11.
Figure 13:
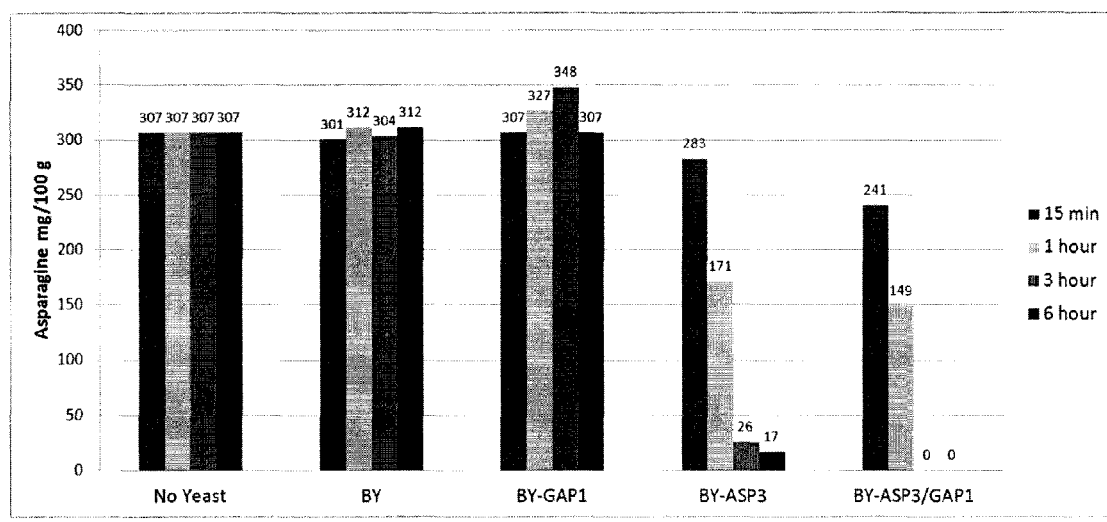
FIG. 13 shows consumption of asparagine in bread dough using a commercial bread yeast (BY) overexpressing ASP3 or GAP1 and a ASP3/GAP1 combination.
Figure 14:
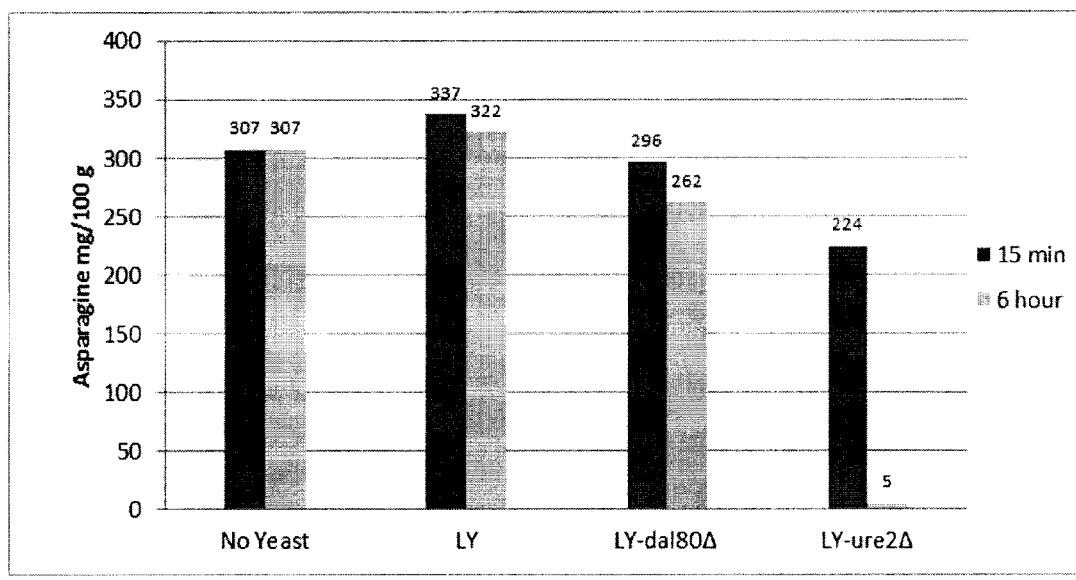
FIG. 14 shows consumption of asparagine in bread dough using a laboratory yeast (LY) with either DAL80 or the URE2 gene knocked-out.
Figure 15:
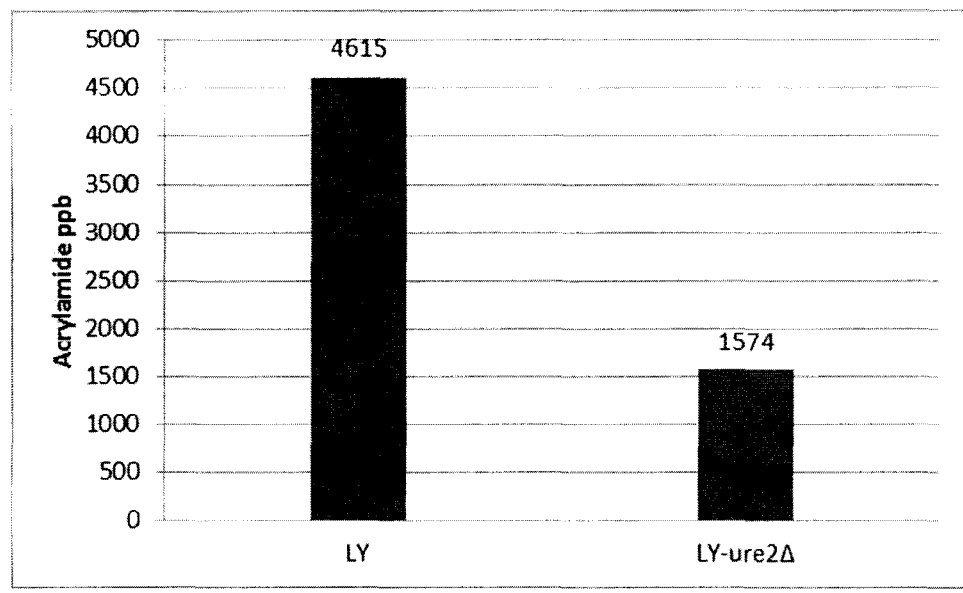
FIG. 15 shows acrylamide concentrations in a baked dough sample taken at timepoint 5 h, taken from the experiment outlined in FIG. 14.
Figure 16:
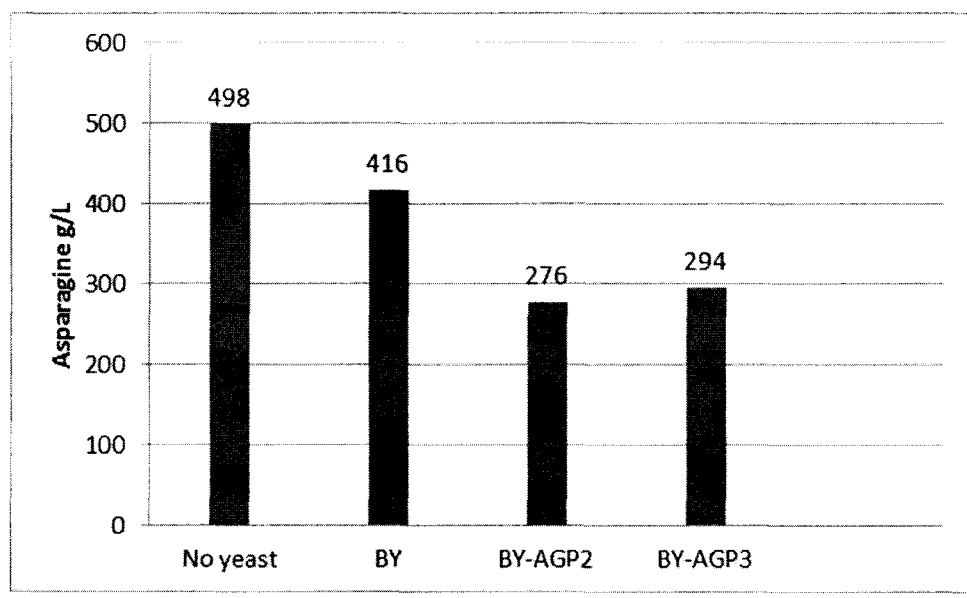
FIG. 16 shows consumption of asparagine in complex media using a commercial bread yeast (BY) overexpressing either AGP2 or AGP3 after 5 hours of growth.
Figure 17:
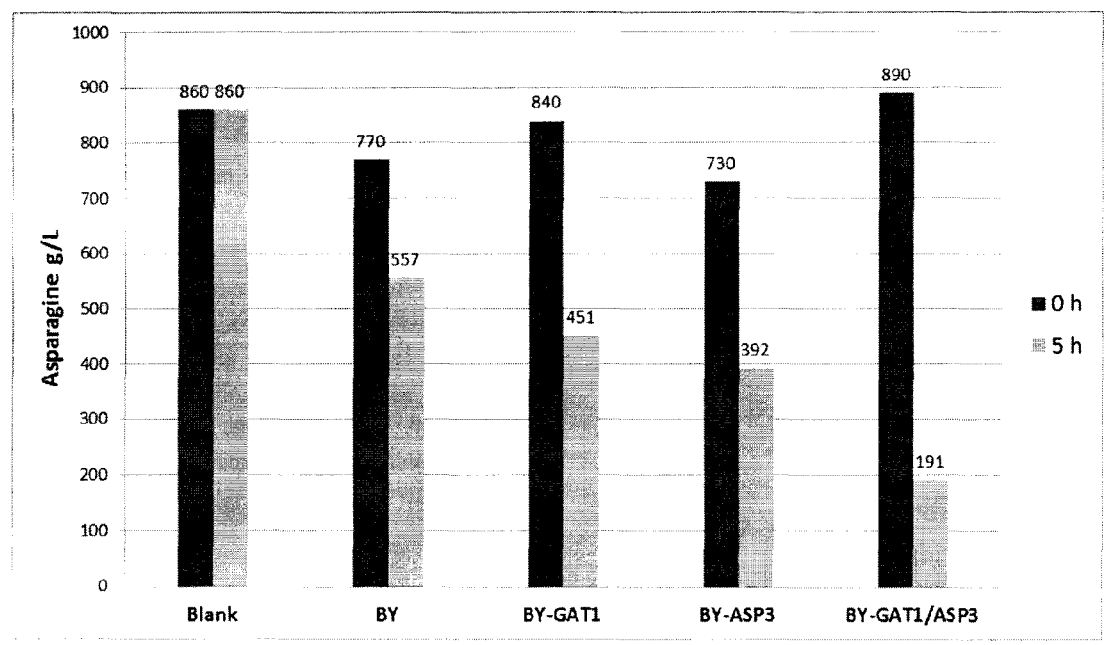
FIG. 17 shows consumption of asparagine in synthetic media containing asparagine and ammonia using a commercial bread yeast (BY) overexpressing either GAT1 or ASP3 and a GAT1/ASP3 combination.
Figure 18:
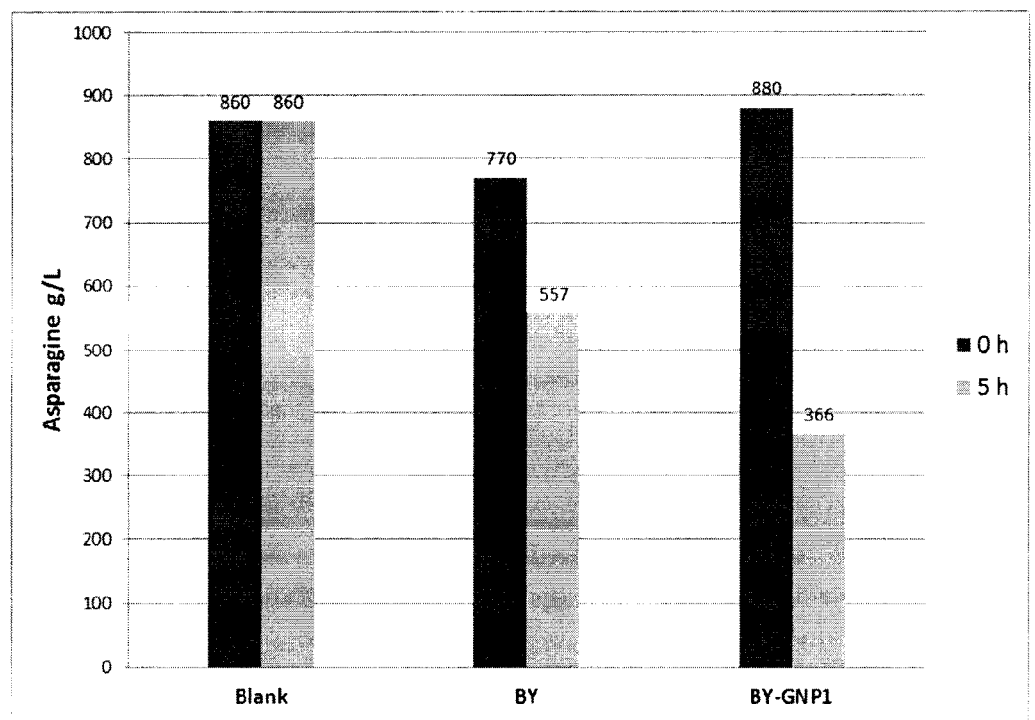
FIG. 18 shows consumption of asparagine in synthetic media containing asparagine and ammonia using a commercial bread yeast (BY) overexpressing GNP1.
Figure 19:
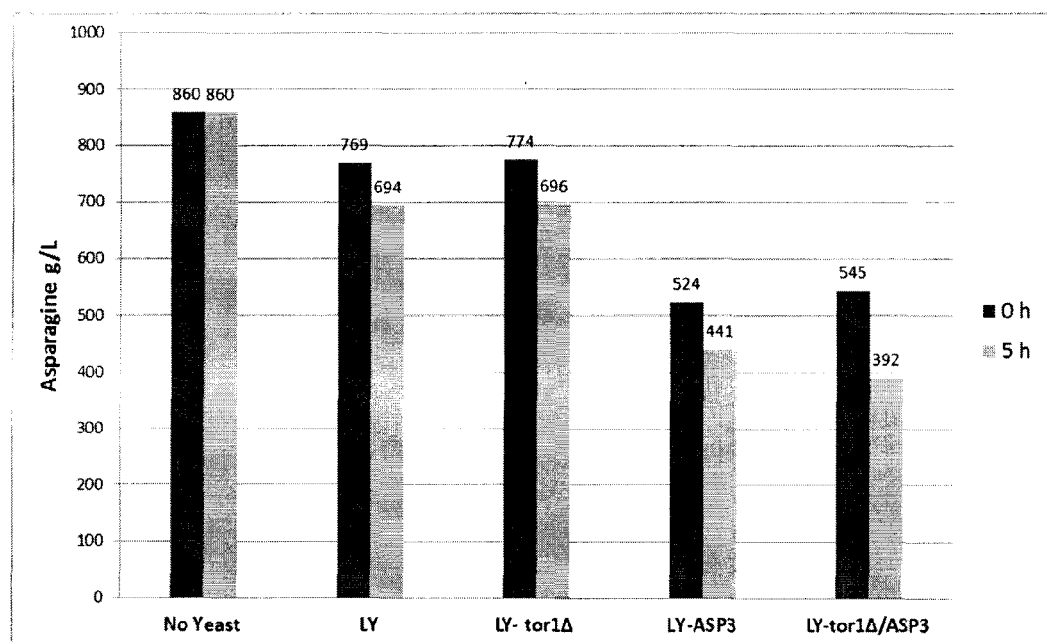
FIG. 19 shows consumption of asparagine in synthetic media containing asparagine and ammonia using a laboratory yeast (LY) overexpressing ASP3 or TOR1 deleted and a tor1Δ/ASP3 combination.
Figure 20:
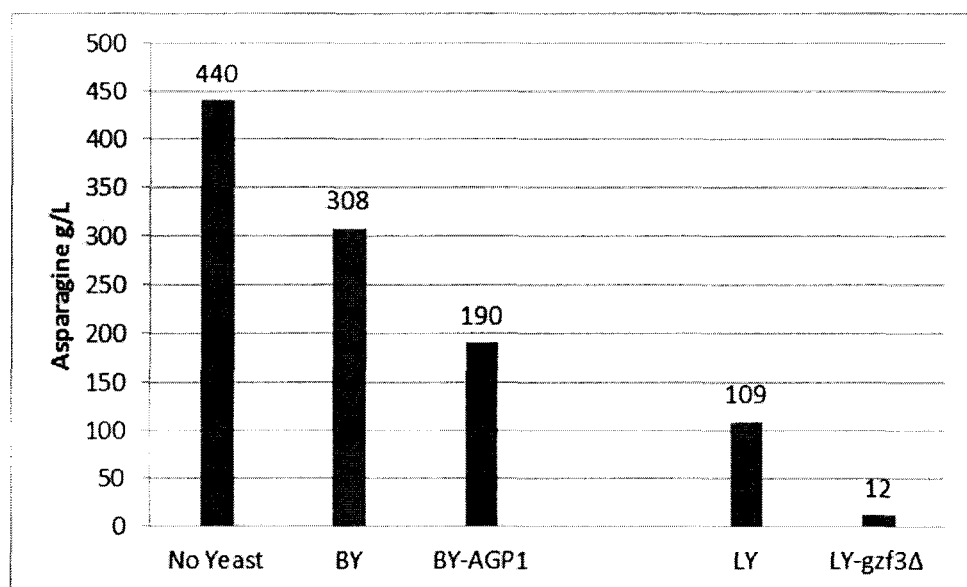
FIG. 20 shows consumption of asparagine in synthetic media containing asparagine using a commercial bread yeast (BY) overexpressing AGP1 and a laboratory yeast (LY) with GZF3 knocked out after 5 hours of growth.

Some of the transformed strains were tested in bread dough such as ASP3, GAP1/ASP3 and ure2Δ (FIGS. 11, 13 and 14). Both the transformed and commercial bread-yeast control strains were grown up simultaneously in two separate fermenters, and the cells were harvested the following day for dough trials. Asparagine was added to the dough in order to monitor asparagine consumption using enzymatic analysis. Once the transformed yeast was mixed into the dough, it was noted that asparagine levels immediately began to decrease; in contrast, no noticeable decline in asparagine was measured using the control strain. After the dough was formed, samples were taken periodically from the addition of yeast in order to be tested for asparagine concentration. The dough from some of these experiments (which contained higher levels of asparagine) was also used to prepare a baked sample in order to determine the acrylamide concentration in the final bread product. Acrylamide results from this experiment are shown in FIGS. 12 and 14 and reveal that the transformed yeast strains reduce acrylamide significantly more than the control yeast samples. This result is consistent with the asparagine reduction found in the dough analysis.

Transformed yeast were also tested in liquid media in order to simulate industrial processing conditions where the environmental conditions for yeast could have a higher moisture content (i.e. potato, cereal and coffee production). Equal cell numbers of each strain were inoculated into separate test tubes containing complex media or synthetic laboratory media spiked with various levels of asparagine. Samples were taken periodically and asparagine concentration was determined using an enzymatic kit or by LC-MS/MS. FIGS. 16-20 show transformed yeast strains with enhanced asparagine degradation.

To reduce acrylamide in food, manufacturers face the challenge of changing their processes and/or product parameters without compromising the taste, texture and appearance of their products. As an example various breads were made using the transformed yeast and the commercial bread yeast control. The final products showed no differences in colour, size or texture. Importantly, no changes were required in the baking process to achieve these significant reductions in acrylamide formation in bread.

Experimental Procedures Employed for the Above Examples

1. Construction of pAC1-ASP3, pAC1-AGP1, pAC1-AGP3, pAC1-GNP1, and pAC1-GAT1

Figure 9:
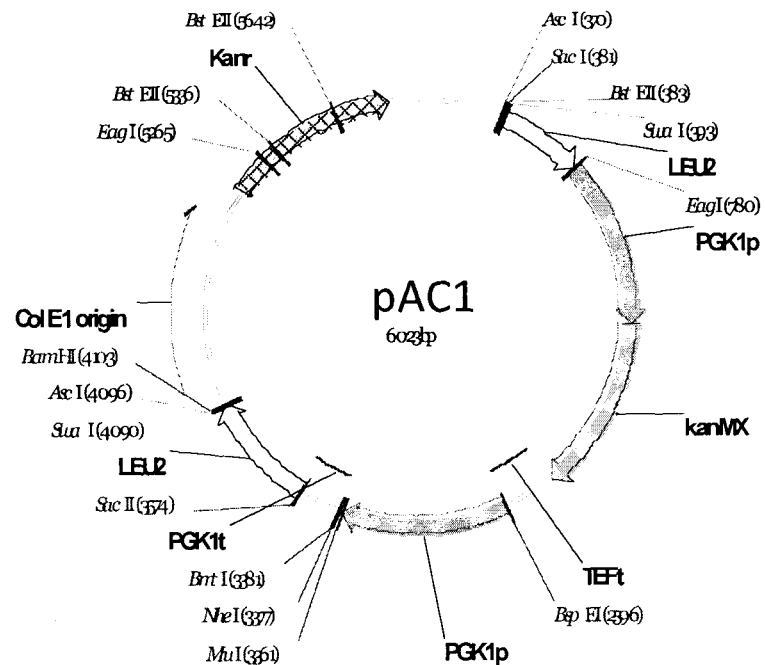
FIG. 9 shows the plasmid maps of constructed pAC1 used in the cloning genetic cassettes for integration into the LEU2 locus.

In order to place ASP3, AGP1, GNP1 and GAT1 under the control of the constitutive PGK1 promoter and terminator signals, each of the ORFs were cloned into pAC1 (FIG. 9). Each ORF from start to stop codon was amplified from $S.$ $cerevisiae$ genomic DNA using primers which contained Mlu1 and Bmt1 restriction enzyme sites built into their 5' ends.

Following PCR, 0.8% agarose gel visualization, and PCR cleanup (Qiagen, USA—PCR Purification Kit), both the PCR product (insert) and pAC1 (vector) were digested with Mlu1 and Bmt1 (Fermentas, Canada). After the digested vector was treated with rAPiD Alkaline Phosphatase (Roche, USA) to prevent re-circularization, the insert and dephosphorylated vector were ligated at room temperature (T4 DNA Ligase—Roche, USA); the ligation mixture (2 µL) was used to transform DH5α™ competent cells (Invitrogen, USA) that were subsequently grown on 100 µg/mL Ampicillin (Sigma-Aldrich, USA) supplemented LB (Difco, USA) plates. Plasmids from a random selection of transformed colonies were harvested (Qiagen, USA—QIAprep Spin Miniprep kit) and digested with Mlu1 and Bmt1 (Fermentas, Canada) to identify plasmids with the correct size insert; sequencing confirmed that the insert corresponded to AGP1, AGP3, GNP1 or GAT1.

2. Construction of pAC2-GAP1, pAC2-AGP1 and pAC2-ASP3

Figure 10:
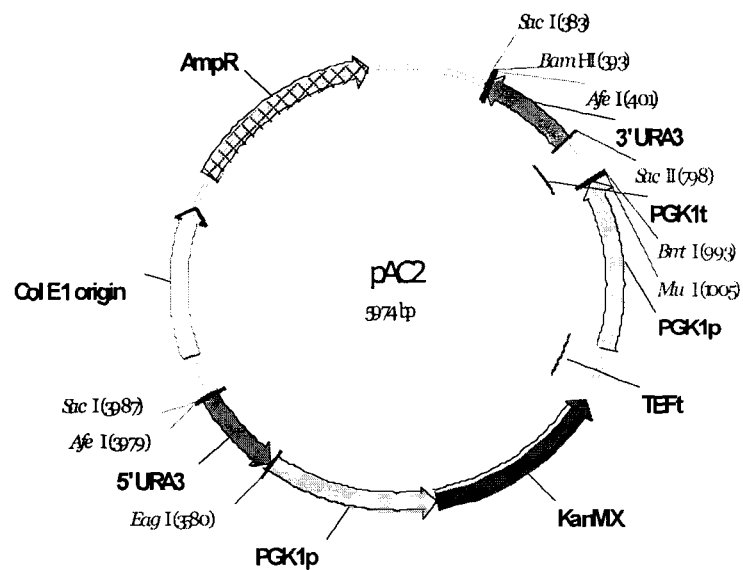
FIG. 10 shows the plasmid maps of pAC2 used in the cloning of genetic cassettes for integration into the URA3 locus.

In order to place GAP1, AGP1 and ASP3 under the control of the constitutive PGK1 promoter and terminator signals, each ORF was cloned into pAC2 (FIG. 10). Each ORF from start to stop codon was amplified from $S.$ $cerevisiae$ genomic DNA using primers which contained Mlu1 and Bmt1 restriction enzyme sites built into their 5' ends.

Following PCR, 0.8% agarose gel visualization, and PCR cleanup (Qiagen, USA—PCR Purification Kit), both the PCR product (insert) and pAC2 (vector) were digested with Mlu1 and Bmt1 (Fermentas, Canada). After the digested vector was treated with rAPiD Alkaline Phosphatase (Roche, USA) to prevent re-circularization, the insert and dephosphorylated vector were ligated at room temperature (T4 DNA Ligase—Roche, USA); the ligation mixture (2 µL) was used to transform DH5α™ competent cells (Invitrogen, USA) that were subsequently grown on 100 µg/mL Ampicillin (Sigma-Aldrich, USA) supplemented LB (Difco, USA) plates. Plasmids from a random selection of transformed colonies were harvested (Qiagen, USA—QIAprep Spin Miniprep kit) and digested with Mlu1 and Bmt1 (Fermentas, Canada) to identify plasmids with the correct size insert; sequencing confirmed that the insert corresponded to GAP1, AGP1 or ASP3.

3. Construction of ure2Δ Cassette

The ure2Δ cassette was completed by DNA synthesis (MrGene, Germany).

4. Transformation of the Linear Cassettes into $S.$ $cerevisiae$ and Selection of Transformants Each cassette was cut from the appropriate plasmid using Swa1 (Fermentas, Canada) and visualized on a 0.8% agarose gel. From the gel, the expected band size was resolved and extracted (Qiagen, USA—Gel extraction kit). After extraction, clean up, and quantification, 500 ng of linear cassette was used to transform $S.$ $cerevisiae$ strains. Yeast strains were transformed using the lithium acetate/polyethylene glycol/ssDNA method. Following transformation, cells were left to recover in YEG at 30° C. for 3 hours before plating on to YPD plates supplemented with 500 µg/mL G418 (Sigma, USA). Plates were incubated at 30° C. until colonies appeared.

5. Transformation of the Linear Ure2Δ Cassette into $S.$ $cerevisiae$ and Selection of Transformants The 3149 bp ure2Δ cassette was cut from pMrG-ure2Δ using Pme1 (Fermentas, Canada) and visualized on a 0.8% agarose gel. From the gel, the expected 3149 bp band was resolved and extracted (Qiagen, USA—Gel extraction kit). After extraction, clean up, and quantification, 500 ng of linear cassette was used to transform $S.$ $cerevisiae$ PDM. Yeast strains were transformed using the lithium acetate/polyethylene glycol/ssDNA method. Following transformation, cells were left to recover in YEG at 30° C. for 3 hours before plating on to YPD plates supplemented with 500 µg/mL G418 (Sigma, USA). Plates were incubated at 30° C. until colonies appeared.

Deletion mutant laboratory yeast strains for tor1Δ, dal80Δ, gzf3Δ, and ure2Δ were also obtained from a commercial source in order to complete some of the tests.

6. Asparagine and Acrylamide Reduction Studies

Whole wheat bread dough was prepared with the following ingredients: Whole wheat flour, Vital wheat gluten, salt vegetable oil, molasses, water and yeast (either a test strain or the control). The method followed closely the process of a 'no time dough' method. At time point 5 h samples were also heated in order to obtain acrylamide data (details are given below).

1. Chill liquid nitrogen dewar in −30° C. freezer and fill with liquid $N_2$.
2. In a 250-mL media bottle, dissolve L-asparagine in 50-mL of filtered water.
3. Determine the moisture/solids content of the yeast (either wet or dry) to be added to the dough recipe.
4. Have the calculated amount of yeast measured out in the 200-mL conical Falcon tube.
5. Determine the required amount of RO water by accounting for the moisture content brought in by the yeast to be added. Measure out the required amount of RO water by weight on a pan balance.
6. Resuspend the appropriate amount of yeast with ⅔ of the remaining RO water (30° C.). Use the remaining ⅓ for rinsing.
7. Determine weight of the mixing bowl.
8. Weigh out dry ingredients (flour, gluten, and salt) into KitchenAid mixing bowl. Stir the dry ingredients with a paddle for 20-30 sec. Switch paddle attachment to hook.
9. Add measured vegetable oil and molasses and L-asparagine solution to the mixing bowl. Mix at speed 2 until dough is of even consistency.
10. Set timer to 10 minutes.
11. Add yeast suspension to the mixing dough. Immediately start the timer and mixing at speed 2.

Time of Yeast Addition:

12. Rinse the Falcon tube with the remaining water and add rinse to the mixing bowl.
13. Continue to mix until the timer beeps after 10 minutes.
14. Take the final weight of mixing bowl+dough:
15. Immediately roll out the dough to ~1.0 cm thickness and use a circular cookie cutter to cut out the appropriate number of dough samples for the experiment.

Quickly remove 1 dough sample and break apart and then pour liquid nitrogen into the mortar to freeze the dough bits. This will be the "T=15 min" sample.

Store the frozen dough bits in a labeled 50-mL Falcon tube at −80° C. for further analysis.

16. Place the remaining dough samples onto a cooking sheet and incubate at 30° C.

17. Remove a dough sample at desired time point for experiment and break up into smaller pieces and freeze with liquid nitrogen.

Store the frozen pieces in a labeled 50-mL Falcon at −80° C.

18. For some experiments at T=5 hours remove an additional cookie and bake at 400° F. (204° C.) for 20 min and store at −80° C.

Liquid media preparations were made according to standard protocol and spiked with various amounts of asparagine. Equal cell numbers of each strain were inoculated into separate test tubes containing the sterile prepared media and samples were taken periodically, Asparagine concentration was determined using an enzymatic kit (Megazyme, K-AS-NAM) or by LC-MS/MS (described below).

7. Quantification of Asparagine and Acrylamide.

Previously prepared dough samples were treated with liquid nitrogen at time of preparation in order to halt asparaginase activity. Samples were then ground and stored at −80 degrees Celsius until analysis. Analysis of asparagine in dough samples was carried out via enzymatic analysis (K-ASNAM—Megazyme), following their extraction protocol for bakery products with the following amendments: Homogenized dough samples (2 g) were quickly weighed and transferred to 100 mL volumetric flasks. Approximately 90 mL of 80 degree Celsius MilliQ $H_2O$ was added in order to prevent any recurrence of enzymatic activity and samples were incubated in an 80 degree Celsius water bath for 20 minutes. Samples were then left to cool to room temperature, diluted to volume and an aliquot centrifuged down (RT, 4000×g, 15 min.) for analysis.

Acrylamide in laboratory prepared baked samples were analyzed with an ELISA procedure. Bread samples were reduced in a grinder which also ensured homogeneity. Samples were stored at −80 degrees Celsius until analysis. 2 g of sample homogenates were weighed out and extracted with water for 30 minutes. Samples were then filtered and centrifuged prior to solid phase extraction cleanup and acrylamide elution. Extracted analyte was then assayed via ELISA assay (Abraxis).

For Asparagine by LC-MS/MS, cell culture samples prepared in liquid media were analyzed using the following parameters. A 2×250 mm Aquasil column (Thermo) and binary mobile phase consisting of 12% MeOH and 1 mM ammonium formate, monitoring asparagine ion transitions 133.0→74.0 and 133.0→87.0 (MRM). An internal standard of isotopically labelled $^{13}C$—acrylamide (Cambridge Isotope Laboratories) was used at a concentration of 0.01 g/L, added directly to clarified cell culture supernatants.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Summary of FDA data on Acrylamide Concetrations in Foods (U.S. FDA 2004a, 2004b)

| Food Product | Acrylamide concentration (ppb) Weighted Average |
|---|---|
| Grain-Based Foods | |
| Untoasted bagels | 31.00 |
| Toasted bagels | 55.36 |
| Biscuits | 36.75 |
| Whole grain and wheat breads | 38.70 |
| All yeast breads | 30.80 |
| White breads | 10.82 |
| Toast | 213.00 |
| Brownies | 16.6 |
| Cake | 9.83 |
| Cereals, Ready-to-eat | 86.11 |
| Oat ring cereal | 174.07 |
| Corn flakes | 60.04 |
| Toasted wheat cereal | 737.67 |
| Cookies | 188.16 |
| Granola and energy bars | 55.93 |
| Corn and tortilla chips | 198.88 |
| Crackers (includes baby food) | 166.50 |
| Doughnuts | 18.47 |
| Pancakes | 15.25 |
| Pie | 21.81 |
| Popcorn | 180.40 |
| Cornbread | 8.13 |
| Toasted English muffin | 31.25 |
| Tortillas | 6.44 |
| Wheat-based snacks | 163.31 |
| Vegetable-Based Foods | |
| All French fries | 413.46 |
| Restaurant French fries | 350.46 |
| Home baked French fires | 648.27 |
| Potato chips | 466.09 |
| Other potato and sweet-potato snacks | 1337.50 |
| Black Olives, canned | 413.63 |
| Sweet potatoes, canned | 93.25 |
| Legumes, nuts and butters | |
| Roasted almonds | 320.25 |
| Peanut butter | 88.06 |
| Roasted peanuts | 27.13 |
| Baked beans | 76.50 |
| Sunflower seeds | 39.50 |
| Beverages | |
| Regular roast coffee (grounds) | 222.50 |
| Dark roast coffee (grounds) | 189.92 |
| Dry instant coffee | 360.33 |
| Coffee, brewed | 7.35 |
| Grain-based coffee substitutes (dry) | 4573 |
| Prune juice | 159.00 |
| Meats, poultry and fish | |
| Chicken nuggets/strips | 24.00 |
| Breaded fried fish | 8.53 |
| Dairy foods | Levels were low |
| Gravies and seasonings | Highly variable; mostly low |
| Candy, sweets, sugar syrups, cocoa | Highly variable; mostly low |
| Mixtures | |
| Chili con Carne | 130.25 |
| Pizza | 19.50 |
| Taco/Tostada | 26.75 |
| Plum-containing cooked baby food | 35.50 |
| Peach cobbler - baby food | 40.25 |
| Baby food with carrots | 54.14 |
| Baby food with green beans | 23.23 |
| Baby food - squash | 19.29 |
| Baby food - sweet potatoes | 77.44 |

TABLE 2

Table of sequences

SEQ ID

NO: 1    a *S. cerevisiae* Asp3p protein sequence
MRSLNTLLLSLFVAMSSGAPLLKIREEKNSSLPSIKIFGTGGTIASKGSTSATTAGYSVG
LTVNDLIEAVPSLAEKANLDYLQVSNVGSNSLNYTHLIPLYHGISEALASDDYAGAVVTH
GTDTMEETAFFLDLTINSEKPVCIAGAMRPATATSADGPMNLYQAVSIAASEKSLGRGTM
ITLNDRIASGFWTTKMNANSLDTFRADEQGYLGYFSNDDVEFYYPPVKPNGWQFFDISNL
TDPSEIPEVIILYSYQGLNPELIVKAVKDLGAKGIVLAGSGAGSWTATGSIVNEQLYEEY
GIPIVHSRRTADGTVPPDDAPEYAIGSGYLNPQKSRILLQLCLYSGYGMDQIRSVFSGVY
GG*

NO: 2    a *S. cerevisiae* ASP3 coding sequence
ATGAGATCTTTAAATACCCTTTTACTTTCTCTCTTTGTCGCAATGTCCAGTGGTGCTCCA
CTACTAAAAATTCGTGAAGAGAAGAATTCTTCTTTGCCATCAATCAAAATTTTTGGTACC
GGCGGTACTATCGCTTCCAAGGGTTCGACAAGTGCAACAACGGCGGGTTATAGCGTGGGA
TTAACCGTAAATGATTTAATAGAAGCCGTCCCATCTTTAGCTGAGAAGGCAAATCTGGAC
TATCTTCAAGTGTCTAACGTTGGTTCAAATTCTTTAAACTATACGCATCTGATCCCATTG
TATCACGGTATCTCCGAGGCACTAGCCTCTGATGACTACGCTGGTGCGGTTGTCACTCAT
GGGACCGACACTATGGAGGAGACAGCTTTCTTCTTAGATTTGACCATAAATTCAGAGAAG
CCAGTATGTATCGCAGGCGCTATGCGTCCAGCCACTGCCACGTCTGCTGATGGCCCAATG
AATTTATATCAAGCAGTGTCTATTGCTGCTTCTGAGAAATCACTGGGTCGTGGCACGATG
ATCACTCTAAACGATCGTATTGCCTCTGGGTTTTGGACAACGAAATGAATGCCAACTCT
TTAGATACATTCAGAGCGGATGAACAGGGATATTTAGGTTACTTTTCAAATGATGACGTG
GAGTTTTACTACCCACCAGTCAAGCCAAATGGATGGCAATTTTTTGACATTTCCAACCTC
ACAGACCCTTCGGAAATTCCAGAAGTCATTATTCTGTACTCCTATCAAGGCTTGAATCCT
GAGCTAATAGTAAAGGCCGTCAAGGACCTGGGCGCAAAAGGTATCGTGTTGGCGGGTTCT
GGAGCTGGTTCCTGGACTGCTACGGGTAGTATTGTAAACGAACAACTTTATGAAGAGTAT
GGTATACCAATTGTTCACAGCAGAAGAACAGCAGATGGTACAGTTCCTCCAGATGATGCC
CCAGAGTACGCCATTGGATCTGGCTACCTAAACCCTCAAAAATCGCGTATTTTGCTACAA
TTATGTTTGTACTCCGGCTACGGCATGGATCAGATTAGGTCTGTTTTTTCTGGCGTCTAC
GGTGGTTAA NO: 3    a *S. cerevisiae* Gap1p protein sequence
MSNTSSYEKNNPDNLKHNGITIDSEFLTQEPITIPSNGSAVSIDETGSGSKWQDFKDSFK
RVKPIEVDPNLSEAEKVAIITAQTPLKHHLKNRHLQMIAIGGAIGTGLLVGSGTALRTGG
PASLLIGWGSTGTMIYAMVMALGELAVIFPISGGFTTYATRFIDESFGYANNFNYMLQWL
VVLPLEIVSASITVNFWGTDPKYRDGFVALFWLAIVIINMFGVKGYGEAEFVFSFIKVIT
VVGFIILGIILNCGGGPTGGYIGGKYWHDPGAFAGDTPGAKFKGVCSVFVTAAFSFAGSE
LVGLAASESVEPRKSVPKAAKQVFWRITLFYILSLLMIGLLVPYNDKSLIGASSVDAAAS
PFVIAIKTHGIKGLPSVVNVVILIAVLSVGNSAIYACSRTMVALAEQRFLPEIFSYVDRK
GRPLVGIAVTSAFGLIAFVAASKKEGEVFNWLLALSGLSSLFTWGGICICHIRFRKALAA
QGRGLDELSFKSPTGVWGSYWGLFMVIIMFIAQFYVAVFPVGDSPSAEGFFEAYLSFPLV
MVMYIGHKIYKRNWKLFIPAEKMDIDTGRREVDLDLLKQEIAEEKAIMATKPRWYRIWNF
WC*

NO: 4    the *S. cerevisiae* GAP1 coding sequence
ATGAGTAATACTTCTTCGTACGAGAAGAATAATCCAGATAATCTGAAACACAATGGTATT
ACCATAGATTCTGAGTTTCTAACTCAGGAGCCAATAACCATTCCCTCAAATGGCTCCGCT
GTTTCTATTGACGAAACAGGTTCAGGGTCCAAATGGCAAGACTTTAAAGATTCTTTCAAA
AGGGTAAAACCTATTGAAGTTGATCCTAATCTTTCAGAAGCTGAAAAGTGGCTATCATC
ACTGCCCAAACTCCATTGAAGCACCACTTGAAGAATAGACATTTGCAAATGATTGCCATC
GGTGGTGCCATCGGTACTGGTCTGCTGGTTGGGTCAGGTACTGCACTAAGAACAGGTGGT
CCCGCTTCGCTACTGATTGGATGGGGGTCTACAGGTACCATGATTTACGCTATGGTTATG
GCTCTGGGTGAGTTGGCTGTTATCTTCCCTATTTCGGGTGGGTTCACCACGTACGCTACC
AGATTTATTGATGAGTCCTTTGGTTACGCTAATAATTTCAATTATATGTTACAATGGTTG
GTTGTGCTACCATTGGAAATTGTCTCTGCATCTATTACTGTAAATTTCTGGGGTACAGAT
CCAAAGTATAGAGATGGGTTTGTTGCGTTGTTTTGGCTTGCAATTGTTATCATCAATATG
TTTGGTGTCAAAGGTTATGGTGAAGCAGAATTCGTCTTTTCATTTATCAAGGTCATCACT
GTTGTTGGGTTCATCATCTTAGGTATCATTCTAAACTGTGGTGGTGGTCCAACAGGTGGT
TACATTGGGGGCAAGTACTGGCATGATCCTGGTGCCTTTGCTGGTGACACTCCAGGTGCT
AAATTCAAAGGTGTTTGTTCTGTCTTCGTCACCGCTGCCTTTTCTTTTGCCGGTTCAGAA
TTGGTTGGTCTTGCTGCCAGTGAATCCGTAGAGCCTAGAAAGTCCGTTCCTAAGGCTGCT
AAACAAGTTTTCTGGAGAATCACCCTATTTTATATTCTGTCGCTATTAATGATTGGTCTT
TTAGTCCCATACAACGATAAAAGTTTGATTGGTGCCTCCTCTGTGGATGCTGCTGCTTCA
CCCTTCGTCATTGCCATTAAGACTCACGGTATCAAGGGTTTGCCAAGTGTTGTCAACGTC
GTTATCTTGATTGCCGTGTTATCTGTCGGTAACTCTGCCATTTATGCATGTTCCAGAACA
ATGGTTGCCCTAGCTGAACAGAGATTTCTGCCAGAAATCTTTTCCTACGTTGACCGTAAG
GGTAGACCATTGGTGGGAATTGCTGTCACATCTGCATTCGGTCTTATTGCGTTTGTTGCC
GCCTCCAAAAAGGAAGGTGAAGTTTTCAACTGGTTACTAGCCTTGTCTGGGTTGTCATCT
CTATTCACATGGGGTGGTATCTGTATTTGTCACATTCGTTTCAGAAAGGCATTGGCCGCC
CAAGGAAGAGGCTTGGATGAATTGTCTTTCAAGTCTCCTACCGGTGTTTGGGGTTCCTAC
TGGGGGTTATTTATGGTTATTATTATGTTCATTGCCCAATTCTACGTTGCTGTATTCCCC
GTGGGAGATTCTCCAAGTGCGGAAGGTTTCTTCGAAGCTTATCTATCCTTCCCACTTGTT
ATGGTTATGTACATCGGACACAAGATCTATAAGAGGAATTGGAAGCTTTTCATCCCAGCA
GAAAAGATGGACATTGATACGGGTAGAAGAGAAGTCGATTTAGATTTGTTGAAACAAGAA
ATTGCAGAAGAAAAGGCAATTATGGCCACAAAGCCAAGATGGTATAGAATCTGGAATTTC
TGGTGTTAA TABLE 2-continued Table of sequences

SEQ ID

NO: 5     the *S. cerevisiae* Agp3p protein sequence
MAVLNLKRETVDIEETAKKDIKPYFASNVEAVDIDEDPDVSRYDPQTGVKRALKNRHISL
LALGGVIGPGCLVGAGNALNKGGPLALLLGFSIIGIIAFSVMESIGEMITLYPSGGGFTT
LARRFHSDALPAVCGYAYVVVFFAVLANEYNTLSSILQFWGPQVPLYGYILIFWFAFEIF
QLVGVGLFGETEYWLAWLKIVGLVAYYIFSIVYISGDIRNRPAFGFHYWNSPGALSHGFK
GIAIVFVFCSTFYSGTESVALAATESKNPGKAVPLAVRQTLWRILVVYIGIAVFYGATVP
FDDPNLSASTKVLKSPIAIAISRAGWAGGAHLVNAFILITCISAINGSLYIGSRTLTHLA
HEGLAPKILAWTDRRGVPIPAITVFNALGLISLMNVSVGAANAYSYIVNLSGVGVFIVWG
VISYTHLRIRKAWVAQGRSIEELPYEALFYPWTPVLSLAANIFLALIQGWSYFVPFDAGN
FVDAYILLPVGILLYIGICVFKSNHFRTVDLRSINLDEGRRKDMEADLSDQESSLASSET
MKDYKSATFFRYLSNIFT*

NO: 6     the *S. cerevisiae* AGP3 coding sequence
ATGGCAGTCCTTAACTTGAAACGTGAAACTGTCGACATTGAAGAGACAGCGAAGAAAGAT
ATCAAACCTTATTTTGCTTCGAATGTTGAAGCGGTTGATATTGATGAAGATCCCGATGTT
TCAAGATACGATCCCCAGACAGGAGTGAAAAGGGCGCTCAAAAATAGGCATATCTCATTG
CTAGCTTTGGGTGGTGTTATTGGCCCAGGTTGTCTTGTTGGTGCAGGAAACGCACTCAAC
AAAGGTGGGCCACTTGCTTTACTTTTAGGCTTTAGTATTATTGGGATCATTGCTTTCTCA
GTGATGGAATCTATAGGTGAAATGATCACTTTATATCCCTCGGGCGGTGGATTTACCACT
TTGGCTCGAAGATTTCATAGCGATGCACTGCCTGCAGTTTGCGGTTATGCTTACGTTGTT
GTGTTCTTCGCAGTTTTGGCAAATGAGTACAACACTCTCTCCTCCATACTACAGTTTTGG
GGCCCACAAGTCCCTCTATATGGTTACATCTTGATATTCTGGTTTGCATTTGAAATTTTT
CAACTAGTTGGCGTTGGTCTTTTTGGTGAAACGGAGTACTGGCTTGCTTGGTTGAAAATA
GTAGGATTAGTAGCCTATTATATTTTCTCGATTGTTTACATATCTGGGGATATTAGGAAT
AGACCAGCTTTCGGCTTTCATTATTGGAATAGTCCAGGTGCATTATCACATGGGTTTAAG
GGAATTGCGATAGTGTTTGTGTTTTGTTCGACCTTCTATTCTGGAACGGAATCAGTTGCC
TTGGCTGCAACGGAATCAAAAAACCCTGGGAAGGCTGTGCCACTTGCTGTTCGACAAACT
CTGTGGAGAATTTTAGTTGTTTATATTGGAATTGCTGTTTTCTATGGAGCAACTGTTCCG
TTTGACGACCCAAACCTCTCTGCTTCTACCAAAGTCCTAAAATCTCCCATTGCTATCGCC
ATATCTCGTGCTGGTTGGGCCGGCGGAGCTCATCTGGTTAATGCCTTCATTTTGATAACT
TGCATCTCCGCCATTAATGGGTCACTTTATATAGGGAGCAGAACCTTGACGCATTTAGCA
CATGAAGGCCTAGCTCCAAAAATTCTGGCTTGGACCGATCGAAGAGGCGTTCCCATCCCC
GCCATCACTGTTTTCAACGCCTTGGGCCTAATATCATTGATGAATGTGAGCGTTGGAGCT
GCAAATGCGTACTCTTATATCGTTAATCTTTCTGGTGTTGGCGTCTTTATTGTCTGGGGT
GTAATAAGTTATACGCACCTGAGAATAAGGAAGGCGTGGGTTGCTCAAGGAAGATCCATA
GAAGAGCTACCTTATGAAGCGCTATTTTATCCGTGGACGCCAGTACTTAGTCTGGCCGCT
AACATTTTTCTAGCACTCATCCAAGGATGGAGCTATTTCGTACCTTTTGATGCGGGCAAT
TTTGTTGATGCTTATATCCTTCTGCCTGTTGGAATTTTATTGTATATTGGCATATGTGTT
TTTAAGAGCAATCATTTTAGAACTGTTGATTTGCGGTCAATCAACCTAGACGAAGGACGA
AGAAAAGACATGGAGGCTGATCTTCTGATCAAGAGAGTAGCTTAGCATCTTCGGAAACG
ATGAAGGATTATAAAAGTGCAACTTTTTTCAGATACCTCAGCAACATTTTCACCTGA NO: 7     the *S. cerevisiae* Agp2p protein sequence
MTKERMTIDYENDGDPEYDKNKYKTITTRIKSIEPSEGWLEPSGSVGHINTIPEAGDVHV
DEHEDRGSSIDDDSRTYLLYFTETRRKLENRHVQLTATSGVIGTALFVAIGKALYRGGPA
SLLLAFALWCVPILCITVSTAEMVCFFPVSSPFLRLATKCVDDSLAVMASWNFWFLECVQ
IPFEIVSVNTIIHYWRDDYSAGIPLAVQVVLYLLISICAVKYYGEMEFWLASFKIILALG
LFTFTFITMLGGNPEHDRYGFRNYGESPFKKYFPDGNDVGKSSGYFQGFLACLIQASFTI
AGGEYISMLAGEVKRPRKVLPKAFKQVFVRLTFLFLGSCLCVGIVCSPNDPDLTAAINEA
RPGAGSSPYVIAMNNLKIRILPDIVNIALITAAFSAGNAYTYCSSRTFYGMALDGYAPKI
FTRCNRHGVPIYSVAISLVWALVSLLQLNSNSAVVLNWLINLITASQLINFVVLCIVYLF
FRRAYHVQQDSLPKLPFRSWGQPYTAIIGLVSCSAMILIQGYTVFFPKLWNTQDFLFSYL
MVFINIGIYVGYKFIWKRGKDHFKNPHEIDFSKELTEIENHEIESSFEKFQYYSKA*

NO: 8     the *S. cerevisiae* AGP2 coding sequence
ATGACAAAGGAACGTATGACCATCGACTACGAAAATGACGGTGATTTTGAGTACGATAAG
AATAAATACAAGACAATAACCACTCGAATAAAGAGTATCGAACCTAGTGAGGGATGGTTG
GAACCTTCTGGGTCAGTGGGTCACATAAACACGATACCCGAAGCGGGCGATGTTCACGTG
GATGAACATGAGGATAGAGGGTCTTCTATTGATGATGACTCAAGGACTTACCTGCTATAT
TTCACAGAAACTCGACGTAAACTAGAAAACAGGCACGTCCAGTTGATTGCTATTTCCGGT
GTCATTGGTACGGCGCTATTCGTGGCGATCGGAAAAGCTTTATACCGTGGAGGGCCCGCC
TCTTTATTATTGGCATTTGCTCTTTGGTGTGTTCCAATACTTTGCATTACTGTGTCTACA
GCGGAAATGGTCTGCTTTTTCCCTGTAAGTTCCCCCTTTTTGAGATTAGCAACGAAGTGC
GTTGACGATTCATTGGCTGTCATGGCTAGCTGGAATTTCTGGTTTCTTGAATGCGTACAG
ATCCCTTTCGAGATTGTTTCTGTTAATACAATTATACATTATTGGAGAGATGATTATTCA
GCTGGTATTCCGCTCGCCGTTCAAGTAGTTTTGTATCTGCTTATTTCCATTTGTGCAGTC
AAATATTACGGTGAAATGGAATTTTGGTTGGCTTCTTTCAAAATTATCCTTGCACTCGGC
CTATTTACATTCACGTTCATTACCATGTTGGGTGGAAATCCTGAACATGATCGTTACGGG
TTTCGTAATTATGGTGAAAGTCCATTCAAGAAATACTTTCCCGATGGCAATGATGTGGGG
AAGTCTTCGGGCTACTTCCAGGGGTTTCTCGCTTGCTTGATTCAGGCATCGTTTACCATA
GCTGGTGGCGAGTATATTTCTATGTTAGCGGGAGAGGTCAAACGACCAAGAAAAGTATTA
CCCAAGGCGTTTAAGCAGGTGTTTGTGAGATTAACATTTTTGTTTTTAGGGAGTTGTCTG
TGTGTTGGGATTGTTTGTTCGCCAAATGATCCTGACTTGACAGCAGCAATTAATGAAGCA
AGGCCTGGCGCCGGGTCTTCACCTTATGTCATTGCAATGAATAATCTGAAAATTAGAATA
TTACCTGACATTGTTAATATAGCTTTGATTACAGCCGCTTTTCTGCTGGTAACGCTTAC
ACTTATTGCTCATCCAGAACATTTATGGTATGGCATTAGATGGCTACGCGCCAAAAATC TABLE 2-continued Table of sequences

SEQ ID

```
TTCACTAGATGCAATAGGCATGGTGTGCCCATTTACTCTGTGGCCATATCTTTGGTATGG
GCTTTAGTGAGCCTTTTGCAACTGAATTCTAATAGTGCGGTCGTATTGAATTGGTTAATT
AACTTGATTACTGCCTCTCAATTGATTAATTTTGTCGTCCTTTGTATCGTCTATTTATTT
TTCAGAAGGGCTTACCACGTCCAACAAGATTCGTTACCCAAGTTGCCATTCCGTTCGTGG
GGTCAACCATACACTGCTATTATCGGCCTTGTTTCATGTTCCGCAATGATTTTAATACAG
GGCTACACCGTTTTCTTTCCCAAATTATGGAACACACAAGATTTTTTGTTTTCGTATTTA
ATGGTGTTTATCAACATCGGTATATATGTGGGCTACAAATTTATTTGGAAACGTGGTAAA
GATCACTTCAAAAACCCACATGAAATTGACTTTTCTAAAGAGCTAACAGAAATTGAAAAC
CATGAGATTGAAAGCTCCTTCGAAAAATTTCAATATTATAGCAAAGCATAA
```

NO: 9   the *S. cerevisiae* Gnp1p protein sequence
```
MTLGNRRHGRNNEGSSNMNMNRNDLDDVSHYEMKEIQPKEKQIGSIEPENEVEYFEKTVE
KTIENMEYEGEHHASYLRRFIDSFRRAEGSHANSPDSSNSNGTTPISTKDSSSQLDNELN
RKSSYITVDGIKQSPQEQEQKQENLKKSIKPRHTVMMSLGTGIGTGLLVGNSKVLNNAGP
GGLIIGYAIMGSCVYCIIQACGELAVIYSDLIGGFNTYPLFLVDPALGFSVAWLFCLQWL
CVCPLELVTASMTIKYWTTSVNPDVFVVIFYVLIVVINVFGAKGYAEADFFFNCCKILMI
VGFFILAIIIDCGGAGTDGYIGSKYWRDPGAFRGDTPIQRFKGVVATFVTAAFAFGMSEQ
LAMTASEQSNPRKAIPSAAKKMIYRILFVFLASLTLVGFLVPYTSDQLLGAAGSATKASP
YVIAVSSHGVRVVPHFINAVILLSVLSVANGAFYTSSRILMSLAKQGNAPKCFDYIDREG
RPAAAMLVSALFGVIAFCASSKKEEDVFTWLLAISGLSQLFTWITICLSHIRFRRAMKVQ
GRSLGEVGYKSQVGVWGSAYAVLMMVLALIAQFWVAIAPIGGGGKLSAQSFFENYLAMPI
WIALYIFYKVWKKDWSLFIPADKVDLVSHRNIFDEELLKQEDEEYKERLRNGPYWKRVLD
FWC*
```

NO: 10   the *S. cerevisiae* GNP1 coding sequence
```
ATGACGCTTGGTAATAGACGCCATGGGCGGAATAATGAGGGAAGCTCTAATATGAATATG
AATCGTAACGACCTTGACGATGTTTCCCATTACGAGATGAAGGAAATACAACCAAAGGAA
AAACAAATTGGCTCTATAGAACCGGAAAATGAAGTAGAATATTTTGAAAAAACAGTGGAA
AAAACCATTGAAAATATGGAATATGAAGGTGAACATCATGCATCTTACTTACGGAGGTTC
ATTGACTCGTTTAGAAGAGCGGAAGGCTCGCATGCAAATTCCCCAGACTCGAGCAACTCT
AATGGGACTACTCCTATATCCACAAAAGATTCCAGCTCTCAATTGGACAATGAGTTGAAT
CGGAAGAGCTCATACATCACTGTTGATGGTATTAAACAGTCACCACAAGAACAAGAACAG
AAACAAGAAAATTTGAAAAAGAGTATAAAGCCCCGTCATACGGTGATGATGTCCCTAGGG
ACTGGTATTGGTACTGGTTTGCTGGTCGGTAACTCCAAAGTTTTGAACAATGCAGGTCCG
GGTGGTTTGATCATTGGTTATGCTATTATGGGTAGTTGTGTTTACTGTATTATTCAAGCT
TGTGGTGAATTAGCGGTTATATACAGTGATTTGATTGGTGGATTTAATACATATCCTTTG
TTTTTGGTCGACCCTGCACTTGGCTTTTCTGTTGCTTGGCTTTTTTGCTTACAATGGCTA
TGTGTTTGTCCTCTAGAATTGGTCACTGGCATCCATGACTATCAAATATTGGACGACATCT
GTGAACCCGGATGTTTTCGTTGTTATCTTCTACGTACTAATCGTTGTTATCAACGTTTTT
GGAGCTAAGGGTTATGCAGAGGCAGATTTCTTCTTCAATTGTTGTAAAATTCTGATGATA
GTTGGATTTTTCATTCTCGCCATTATTATTGATTGTGGTGGTGCAGGTACCGATGGTTAC
ATAGGTAGCAAATATTGGCGTGATCCCGGAGCCTTCCGTGGTGATACACCCATCCAGAGG
TTCAAAGGTGTCGTTGCCACATTTGTCACAGCAGCGTTCGCCTTTGGTATGAGTGAACAG
CTGGCTATGACTGCCAGTGAACAATCCAATCCAAGAAAGGCTATTCCATCGGCGGCAAAG
AAAATGATTTATAGAATTCTGTTTGTGTTCTTGGCGTCTTTAACGTTAGTTGGTTTCCTT
GTACCTTACACCTCAGATCAATTGCTAGGGGCCGCAGGTTCAGCCTACTAAAGCGTCGCC
TACGTCATCGCTGTCTCCTCTCATGGTGTTCGTGTGCTTCCTCATTTCATAAACGCTGTC
ATCCTGTTGTCTGTTCTTTCCGTTGCTAACGGTGCCTTCTATACCAGTTCTCGTATTTTG
ATGTCGTTGGCCAAACAAGGTAATGCACCCAATGTTTCGATTACATCGATAGGGAAGGT
AGACCTGCTGCTGCTATGCTTGTCAGTGCATTATTTGGTGTCATTGCATTCTGTGCCTCA
TCTAAAAAGGAAGAGGACGTTTTCACCTGGTTGTTAGCAATCTCCGGTTTGTCTCAATTA
TTCACGTGGATTACCATTTGTTTGTCTCACATTAGGTTTAGAAGAGCTATGAAAGTGCAA
GGAAGGTCCTTAGGAGAGGTTGGTTATAAATCTCAAGTCGGTGTCTGGGGGTCGGCTTAC
GCTGTCCTTATGATGGTGTTAGCTTTAATCGCCCAATTTTGGGTTGCCATTGCCCCAATT
GGTGGAGGAGGTAAGTTAAGTGCCCAATCATTTTTTGAGAATTATTTGGCTATGCCAATC
TGGATTGCTTTATACATCTTTTACAAAGTTTGGAAAAAGATTGGAGTTTATTCATTCCC
GCTGATAAAGTAGACTTAGTTTCTCATAGAAACATCTTTGATGAAGAATTATTAAAACAA
GAAGATGAAGAATATAAAGAGAGATTAAGAAACGGACCATACTGGAAAAGAGTTCTTGAT
TTCTGGTGTTAA
```

NO: 11   the *S. cerevisiae* Agp1p protein sequence
```
MSSSKSLYELKDLKNSSTEIHATGQDNEIEYFETGSNDRPSSQPHLGYEQHNTSAVRRFF
DSFKRADQGPQDEVEATQMNDLTSAISPSSRQAQELEKNESSDNIGANTGHKSDSLKKTI
QPRHVLMIALGTGIGTGLLVGNGTALVHAGPAGLLIGYAIMGSILYCIIQACGEMALVYS
NLTGGYNAYPSFLVDDGFGFAVAWVYCLQWLCVCPLELVTASMTIKYWTTSVNPDVFVII
FYVLVITINIFGARGYAEAEFFFNCCKILMMTGFFILGIIIDVGGAGNDGFIGGKYWHDP
GAFNGKHAIDRFKGVAATLVTAAFAFGGSEFIAITTAEQSNPRKAIPGAAKQMIYRILFL
FLATIILLGFLVPYNSDQLLGSTGGGTKASPYVIAVASHGVRVVPHFINAVILLSVLSMA
NSSFYSSARLFLTLSEQGYAPKVFSYIDRAGRPLIAMGVSALFAVIAFCAASPKEEQVFT
WLLAISGLSQLFTWTAICLSHLRFRRRAMKVQGRSLGELGFKSQTGVWGSAYACIMMILIL
IAQFWVAIAPIGEGKLDAQAFFENYLAMPILIALYVGYKVWHKDWKLFIRADKIDLDSHR
QIFDEELIKQEDEEYRERLRNGPYWKRVVAFWC*
```

NO: 12   the *S. cerevisiae* AGP1 coding sequence
```
ATGTCGTCGTCGAAGTCTCTATACGAACTGAAAGACTTGAAAAATAGCTCCACAGAAATA
CATGCCACGGGGCAGGATAATGAAATTGAATATTTCGAAACAGGCTCCAATGACCGTCCA
```

TABLE 2-continued

Table of sequences

SEQ ID

```
            TCCTCACAACCTCATTTAGGTTACGAACAGCATAACACTTCTGCCGTGCGTAGGTTTTTC
            GACTCCTTTAAAAGAGCGGATCAGGGTCCACAGGATGAAGTAGAAGCAACACAAATGAAC
            GATCTTACGTCGGCTATCTCACCTTCTTCTAGACAGGCTCAAGAACTAGAAAAAAATGAA
            AGTTCGGACAACATAGGCGCTAATACAGGTCATAAGTCGGACTCGCTGAAGAAAACCATT
            CAGCCTAGACATGTTCTGATGATTGCGTTGGGTACGGGTATCGGTACTGGGTTATTGGTC
            GGTAACGGTACCGCGTTGGTTCATGCGGGTCCAGCTGGACTACTTATTGGTTACGCTATT
            ATGGGTTCTATCTTGTACTGTATTATTCAAGCATGTGGTGAAATGGCGCTAGTGTATAGT
            AACTTGACTGGTGGCTACAATGCATACCCCAGTTTCCTTGTGGATGATGGTTTTGGGTTT
            GCAGTCGCTTGGGTTTATTGTTTGCAATGGCTGTGTGTGTGCCTCTGGAATTGGTGACC
            GCATCCATGACTATCAAATATTGGACGACATCTGTGAACCCGGATGTGTTCGTCATTATT
            TTCTATGTTTTGGTGATTACTATTAATATTTTCGGTGCTCGTGGTTATGCAGAAGCTGAG
            TTCTTCTTCAACTGTTGCAAAATTTTGATGATGACTGGGTTCTTCATTCTTGGTATTATC
            ATCGATGTTGGTGGCGCTGGTAATGATGGTTTTATTGGTGGTAAATACTGGCACGATCCG
            GGCGCTTTCAATGGTAAACATGCCATTGACAGATTTAAAGGTGTTGCTGCAACATTAGTG
            ACTGCTGCTTTTGCCTTTGGTGGTTCAGAGTTTATTGCCATCACCACTGCAGAACAATCT
            AATCCAAGAAAGGCCATTCCAGGTGCGGCCAAACAAATGATCTACAGAATCTTATTCCTA
            TTCTTGGCTACCATTATTCTACTGGGTTTCTTGGTGCCATACAATTCCGATCAATTATTG
            GGTTCTACCGGTGGTGGTACTAAAGCCTCGCCATATGTCATTGCTGTTGCATCCCACGGT
            GTCCGTGTCGTCCCACACTTCATTAACGCCGTTATTCTACTTTCCGTGCTGTCCATGGCT
            AACTCCTCCTTCTACTCCAGTGCTCGTTTATTTTTAACTCTATCCGAGCAAGGTTACGCT
            CCTAAGGTTTTCTCCTACATCGACAGAGCCGGTAGACCATTGATTGCCATGGGTGTTTCT
            GCATTGTTTGCCGTTATTGCCTTCTGTGCTGCATCTCCCAAGGAAGAACAAGTTTTCACT
            TGGTTATTGGCCATTTCTGGTTTGTCTCAGCTTTTCACATGGACTGCCATTTGTTTATCC
            CATCTTAGATTTAGAAGAGCCATGAAAGTCCAAGGGAGATCTCTTGGAGAATTGGGTTTC
            AAATCTCAAACTGGTGTTTGGGGATCTGCCTACGCTTGCATTATGATGATTTTAATTCTT
            ATTGCCCAATTTTGGGTCGCTATCGCCCCCATTGGTGAAGGTAAGCTGGATGCACAAGCC
            TTTTTCGAAAACTACTTGGCTATGCCAATCTTGATTGCACTTTATGTCGGCTACAAGGTC
            TGGCACAAGGATTGGAAACTGTTCATCAGGGCAGACAAGATCGACCTAGATTCTCATAGA
            CAAATCTTTGATGAAGAATTAATCAAGCAAGAAGACGAAGAATATAGGGAACGTTTGAGG
            AACGGACCTTATTGGAAAAGGGTCGTTGCCTTCTGGTGTTAA
```

NO: 13    the S. cerevisiae Gat1p protein sequence
          MHVFFPLLFRPSPVLFIACAYIYIDIYIHCTRCTVVNITMSTNRVPNLDPDLNLNKEIWD
          LYSSAQKILPDSNRILNLSWRLHNRTSFHRINRIMQHSNSIMDFSASPFASGVNAAGPGN
          NDLDDTDTDNQQFFLSDMNLNGSSVFENVFDDDDDDDDVETHSIVHSDLLNDMDSASQRA
          SHNASGFPNFLDTSCSSSFDDHFIFTNNLPFLNNNSINNNHSHNSSHNNNSPSIANNTNA
          NTNTNTSASTNTNSPLLRRNPSPSIVKPGSRRNSSVRKKKPALKKIKSSTSVQSSATPPS
          NTSSNPDIKCSNCTTSTTPLWRKDPKGLPLCNACGLFLKLHGVTRPLSLKTDIIKKRQRS
          STKINNNITPPPSSSLNPGAAGKKKNYTASVAASKRKNSLNIVAPLKSQDIPIPKIASPS
          IPQYLRSNTRHHLSSSVPIEAETFSSFRPDMNMTMNMNLHNASTSSFNNEAFWKPLDSAI
          DHHSGDTNPNSNMNTTPNGNLSLDWLNLNL*

NO: 14    the S. cerevisiae GAT1 coding sequence
          ATGCACGTTTTCTTTCCTTTGCTTTTCCGCCCTTCCCCTGTTCTGTTCATCGCATGTGCA
          TATATATATATAGATATATATATACATTGTACACGGTGCACGGTAGTGAACATAACTATG
          AGCACGAACAGAGTCCCGAACCTCGACCCGGACTTGAATTTAAACAAAGAAATCTGGGAC
          CTGTACTCGAGCGCCCAGAAAATATTGCCCGATTCTAACCGTATTTTGAACCTTTCTTGG
          CGTTTTGCATAACCGCACGTCTTTCCATCGAATTAACCGCATAATGCAACATTCTAACTCT
          ATTATGGACTTCTCCGCCTCGCCCTTTGCCAGCGGCGTGAACGCCGCTGGCCCAGGCAAC
          AACGACCTCGATGACACCGATACTGATAACCAGCAATTCTTCCTTTCAGACATGAACCTC
          AACGGATCTTCTGTTTTTGAAAATGTGTTTGACGACGATGACGATGATGATGACGTGGAG
          ACGCACTCCATTGTGCACTCAGACCTGCTCAACGACATGGACAGCGCTTCCCAGCGTGCT
          TCACATAATGCTTCTGGTTTCCCTAATTTTCTGGACACTTCCTGCTCGTCCTCCTTCGAT
          GACCACTTTATTTTCACCAATAACTTACCATTTTTAAATAATAATAGCATTAATAATAAT
          CATAGTCATAATAGTAGTCATAATAATAACAGTCCCAGCATCGCCAATAATACAAACGCA
          AACACAAACACAAACACAAGTGCAAGTACAAACACCAATAGTCCTTTACTGAGAAGAAAC
          CCCTCCCCATCTATAGTGAAGCCTGGCTCGCGAAGAAATTCCTCCGTGAGGAAGAAGAAA
          CCTGCTTTGAAGAAGATCAAGTCTTCCACTTCTGTGCAATCTTCGGCTACTCCGCCTTCG
          AACACCTCATCCAATCCGGATATAAAATGCTCCAACTGCACAACCTCCACCACTCCGCTG
          TGGAGGAAGGACCCCAAGGGTCTTCCCCTGTGCAATGCTTGCGGCCTCTTCCTCAAGCTC
          CACGGCGTCACAAGGCCTCTGTCGTTGAAGACTGACATCATTAAGAAGAGACAGAGGTCG
          TCTACCAAGATAAACAACAATATAACGCCCCCTCCATCGTCGTCTCTCAATCCGGGAGCA
          GCAGGGAAAAAGAAAAACTATACAGCAAGTGTGGCAGCGTCCAAGAGGAAGAACTCACTG
          AACATTGTCGCACCTTTGAAGTCTCAGGACATACCCATTCCGAAGATTGCCTCACCTTCC
          ATCCCACAATACCTCCGCTCTAACACTCGCCACCACCTTTCGAGTTCCGTACCCATCGAG
          GCGGAAACGTTCTCCAGCTTTCGGCCTGATATGAATATGACTATGAACATGAACCTTCAC
          AACGCCTCAACCTCCTCCTTCAACAATGAAGCCTTCTGGAAGCCTTTGGACTCCGCAATA
          GATCATCATTCGGAGACACAAATCCAAACTCAAACATGAACACCACTCCAAATGGCAAT
          CTGAGCCTGGATTGGTTGAATCTGAATTTATAG NO: 15    the S. cerevisiae Ure2p protein sequence
          MMNNNGNQVSNLSNALRQVNIGNRNSNTTTDQSNINFEFSTGVNNNNNNSSSNNNNVQN
          NNSGRNGSQNNDNENNIKNTLEQHRQQQQAFSDMSHVEYSRITKFFQEQPLEGYTLFSHR
          SAPNGFKVAIVLSELGFHYNTIFLDFNLGEHRAPEFVSVNPNARVPALIDHGMDNLSIWE
          SGAILLHLVNKYYKETGNPLLWSDDLADQSQINAWLFFQTSGHAPMIGQALHFRYFHSQK TABLE 2-continued Table of sequences

SEQ ID

IASAVERYTDEVRRVYGVVEMALAERREALVMELDTENAAAYSAGTTPMSQSRFFDYPVW
LVGDKLTIADLAFVPWNNVVDRIGINIKIEFPEVYKWTKHMMRRPAVIKALRGE*

NO: 16　the *S. cerevisiae* URE2 coding sequence
ATGGATGAATAACAACGGCAACCAAGTGTCGAATCTCTCCAATGCGCTCCGTCAAGTAAAC
ATAGGAAACAGGAACAGTAATACAACCACCGATCAAAGTAATATAAATTTTGAATTTTCA
ACAGGTGTAAATAATAATAATAATAACAATAGCAGTAGTAATAACAATAATGTTCAAAAC
AATAACAGCGGCCGCAATGGTAGCCAAAATAATGATAACGAGAATAATATCAAGAATACC
TTAGAACAACATCGACAACAACAACAGGCATTTTCGGATATGAGTCACGTGGAGTATTCC
AGAATTACAAAATTTTTTCAAGAACAACCACTGGAGGGATATACCCTTTTCTCTCACAGG
TCTGCGCCTAATGGATTCAAAGTTGCTATAGTACTAAGTGAACTTGGATTTCATTATAAC
ACAATCTTCCTAGATTTCAATCTTGGCGAACATAGGGCCCCCGAATTTGTGTCTGTGAAC
CCTAATGCAAGAGTTCCAGCTTTAATCGATCATGGTATGGACAACTTGTCTATTTGGGAA
TCAGGGGCGATTTTATTACATTTGGTAAATAAATATTACAAAGAGACTGGTAATCCATTA
CTCTGGTCCGATGATTTAGCTGACCAATCACAAATCAACGCATGGTTGTTCTTCCAAACG
TCAGGGCATGCGCCAATGATTGGACAAGCTTTACATTTCAGATACTTCCATTCACAAAAG
ATAGCAAGTGCTGTAGAAAGATATACGGATGAGGTTAGAAGAGTTTACGGTGTAGTGGAG
ATGGCCTTGGCTGAACGTAGAGAAGCGCTGGTGATGGAATTAGACACGGAAAATGCGGCT
GCATACTCAGCTGGTACAACACCAATGTCACAAAGTCGTTTCTTTGATTATCCCGTATGG
CTTGTAGGAGATAAATTAACTATAGCAGATTTGGCCTTTGTCCCATGGAATAATGTCGTG
GATAGAATTGGCATTAATATCAAAATTGAATTTCCAGAAGTTTACAAATGGACGAAGCAT
ATGATGAGAAGACCCGCGGTCATCAAGGCATTGCGTGGTGAATGA NO: 17　the *S. cerevisiae* Tor1p protein sequence
MEPHEEQIWKSKLLKAANNDMDMDRNVPLAPNLNVNMNMKMNASRNGDEFGLTSSRFDGV
VIGSNGDVNFKPILEKIFRELTSDYKEERKLASISLFDLLVSLEHELSIEEFQAVSNDIN
NKILELVHTKKTSTRVGAVLSIDTLISFYAYTERLPNETSRLAGYLRGLIPSNDVEVMRL
AAKTLGKLAVPGGTYTSDFVEFEIKSCLEWLTASTEKNSFSSSKPDHAKHAALLIITALA
ENCPYLLYQYLNSILDNIWRALRDPHLVIRIDASITLAKCLSTLRNRDPQLTSQWVQRLA
TSCEYGFQVNTLECIHASLLVYKEILFLKDPFLNQVFDQMCLNCIAYENHKAKMIREKIY
QIVPLLASFNPQLFAGKYLHQIMDNYLEILTNAPANKIPHLKDDKPQILISIGDIAYEVG
PDIAPYVKQILDYIEHDLQTKFKFRKKFENEIFYCIGRLAVPLGPVLGKLLNRNILDLMF
KCPLSDYMQETFQILTERIPSLGPKINDELLNLVCSTLSGTPFIQPGSPMEIPSFSRERA
REWRNKNILQKTGESNDDNNDIKIIIQAFRMLKNIKSRFSLVEFVRIVALSYIEHTDPRV
RKLAALTSCEIYVKDNICKQTSLHSLNTVSEVLSKLLAITIADPLQDIRLEVLKNLNPCF
DPQLAQPDNLRLLFTALHDESFNIQSVAMELVGRLSSVNPAYVIPSIRKILLELLTKLKF
STSSREKEETASLLCTLIRSSKDVAKPYIEPLLNVLLPKFQDTSSTVASTALRTIGELSV
VGGEDMKIYLKDLFPLIIKTFQDQSNSFKREAALKALGQLAASSGYVIDPLLDYPELLGI
LVNILKTENSQNIRRQTVTLIGILGAIDPYRQKEREVTSTTDISTEQNAPPIDIALLMQG
MSPSNDEYYTTVVIHCLLKILKDPSLSSYHTAVIQAIMHIFQTLGLKCVSFLDQIIPTIL
DVMRTCSQSLLEFYFQQLCSLIIIVRQHIRPHVDSIFQAIKDFSSVAKLQITLVSVIEAI
SKALEGEFKRLVPLTLTLFLVILENDKSSDKVLSRRVLRLLESFGPNLEGYSHLITPKIV
QMAEFTSGNLQRSAIITIGKLAKDVDLFEMSSRIVHSLLRVLSSTTSDELSKVIMNTLSL
LLIQMGTSFAIFIPVINEVLMKKHIQHTIYDDLTNRILNNDVLPTKILEANTTDYKPAEQ
MEAADAGVAKLPINQSVLKSAWNSSQQRTKEDWQEWSKRLSIQLLKESPSHALRACSNLA
SMYYPLAKELFNTAFACVWTELYSQYQEDLIGSLCIALSSPLNPPEIHQTLLNLVEFMEH
DDKALPIPTQSLGEYAERCHAYAKALHYKEIKFIKEPENSTIESLISINNQLNQTDAAIG
ILKHAQQHHSLQLKETWFEKLERWEDALHAYNEREKAGDTSVSVTLGKMRSLHALGEWEQ
LSQLAARKWKVSKLQTKKLIAPLAAGAAWGLGEWDMLEQYISVMKPKSPDKEFFDAILYL
HKNDYDNASKHILNARDLLVTEISALINESYNRAYSVIVRTQIITEFEEIIKYKQLPPNS
EKKLHYQNLWTKRLLGCQKNVDLWQRVLRVRSLVIKPKQDLQIWIKFANLCRKSGRMRLA
NKALNMLLEGGNDPSLPNTFKAPPPVVYAQLKYIWATGAYKEALNHLIGFTSRLAHDLGL
DPNNMIAQSVKLSSASTAPYVEEYTKLLARCFLKQGEWRIATQPNWRNTNPDAILGSYLL
ATHFDKNWYKAWHNWALANFEVISMVQEETKLNGGKNDDDDDTAVNNDNVRIDGSILGSG
SLTINGNRYPLELIQRHVVPAIKGFFHSISLLETSCLQDTLRLLTLLFNFGGIKEVSQAM
YEGFNLMKIENWLEVLPQLISRIHQPDPTVSNSLLSLLSDLGKAHPQALVYPLTVAIKSE
SVSRQKAALSIIEKIRIHSPVLVNQAELVSHELIRVAVLWHELWYEGLEDASRQFFVEHN
IEKMFSTLEPLHKHLGNEPQTLSEVSFQKSFGRDLNDAYEWLNNYKKSKDINNLNQAWDI
YYNVFRKITRQIPQLQTLDLQHVSPQLLATHDLELAVPGTYFPGKPTIRIAKFEPLFSVI
SSKQRPRKFSIKGSDGKDYKYVLKGHEDIRQDSLVMQLFGLVNTLLKNDSECFKRHLDIQ
QYPAIPLSPKSGLLGWVPNSDTFHVLIREHRDAKKIPLNIEHWVMLQMAPDYENLTLLQK
IEVFTYALDNTKGQDLYKILWLKSRSSETWLERRTTYTRSLAVMSMTGYILGLGDRHPSN
LMLDRITGKVIHIDFGDCFEAAILREKYPEKVPFRLTRMLTYAMEVSGIEGSFRITCENV
MRVLRDNKESLMAILEAFALDPLIHWGFDLPPQKLTEQTGIPLPLINPSELLRKGAITVE
EAANMEAEQQNETKNARAMLVLRRITDKLTGNDIKRFNELDVPEQVDKLIQQATSIERLC
QHYIGWCPFW*

NO: 18　the *S. cerevisiae* TOR1 coding sequence
ATGGAACCGCATGAGGAGCAGATTTGGAAGAGTAAACTTTTGAAAGCGGCTAACAACGAT
ATGGACATGGATAGAAATGTGCCGTTGGCACCGAATCTGAATGTGAATATGAACATGAAA
ATGAATGCGAGCAGGAACGGGGATGAATTCGGTCTGACTTCTAGTAGGTTTGATGGAGTG
GTGATTGGCAGTAATGGGGATGTAAATTTTAAGCCCATTTTGGAGAAAATTTTCCGCGAA
TTAACCAGTGATTACAAGGAGGAACGAAAATTGGCCAGTATTTCATTATTTGATCTACTA
GTATCCTTGGAACATGAATTGTCGATAGAAGAGTTCCAAGCAGTTTCAAATGACATAAAC
AATAAGATTTTGGAGCTGGTCCATACAAAAAAAACGAGCACTAGGGTAGGGGCTGTTCTA
TCCATAGACACTTTGATTTCATTCTACGCATATACTGAAAGGTTGCCTAACGAAACTTCA

TABLE 2-continued

Table of sequences

SEQ ID

```
CGACTGGCTGGTTACCTTCGAGGGCTAATACCTTCTAATGATGTAGAGGTCATGAGACTC
GCTGCAAAGACTCTGGGCAAGTTAGCCGTTCCAGGAGGTACATATACCTCTGATTTCGTG
GAATTTGAGATAAAGTCTTGCTTAGAATGGCTTACTGCCTCCACGGAAAAGAATTCATTC
TCGAGTTCGAAGCCAGACCATGCTAAACATGCTGCGCTTCTGATTATAACAGCGTTGGCA
GAGAATTGTCCTTATTTACTCTACCAATACTTGAATTCCATACTAGATAACATTTGGAGA
GCACTAAGAGACCCACATTTGGTGATCAGAATTGATGCGTCCATTACATTGGCAAATGT
CTTTCCACCCTACGAAATAGGGATCCTCAGTTAACTAGCCAGTGGGTGCAGAGATTGGCT
ACAAGTTGTGAATACGGATTTCAAGTAAACACATTAGAATGCATCCATGCAAGTTTGTTG
GTTTATAAGGAAATCTTGTTTTTGAAGGATCCCTTTTTGAATCAAGTGTTCGACCAAATG
TGTCTAAATTGCATAGCTTATGAAAATCATAAAGCGAAATGATTAGAGAAAAGATTTAC
CAGATTGTTCCCCTATTAGCATCGTTCAATCCTCAATTATTTGCTGGCAAATATTTGCAC
CAAATTATGGACAACTATTTAGAGATTTTAACCAATGCTCCAGCAAATAAAATACCACAT
CTCAAAGATGACAAACCACAGATTTTAATATCGATTGGTGATATTGCATATGAAGTCGGG
CCCGATATCGCACCTTATGTGAAACAAATTCTTGATTATATTGAACATGATTTACAGACG
AAATTCAAATTCAGAAGAAATTTGAAAATGAAATTTTCTACTGCATCGGAAGATTGGCA
GTTCCCTTGGGCCCCGTTCTAGGTAAATTATTAAACAGAAATATACTGGACCTGATGTTC
AAATGCCCTCTTTCCGACTATATGCAGGAAACGTTTCAAATTCTGACTGAGAGAATACCA
TCACTAGGCCCCAAAATAAATGACGAGTTGCTTAACCTAGTCTGTTCAACCTTATCTGGA
ACACCATTTATCCAGCCAGGGTCACCAATGGAGATACCATCGTTTTCGAGAGAAAGAGCA
AGAGAATGGAGAAATAAAAACATCCTACAGAAAACTGGTGAAAGTAACGATGATAATAAT
GATATAAAAATCATTATACAAGCTTTTAGAATGTTAAAAAATATCAAAAGCAGATTTTCG
TTGGTGGAATTCGTGAGAATTGTTGCACTTTCTTACATTGAGCATACAGATCCCAGAGTA
AGGAAACTAGCTGCGTTGACATCTTGTGAAATTTACGTCAAGGATAACATCTGCAAACAA
ACATCACTACACTCTCTGAACACTGTATCTGAAGTGTTATCAAAGCTTCTAGCCATTACG
ATTGCGGACCCTTTACAAGATATCCGTTTAGAAGTTTTAAAGAATCTTAATCCATGTTTC
GATCCCCAGTTGGCACAACCAGATAATTTGAGACTCTTGTTTACTGCACTGCACGATGAG
TCGTTCAATATTCAGTCAGTAGCAATGGAGCTTGTCGGTAGGTTGTCTTCCGTAAACCCT
GCATACGTCATCCCATCGATAAGAAAAATACTACTGGAACTGCTAACAAAATTAAAATTC
TCAACTTCTTCTCGAGAAAAGGAAGAAACTGCCAGTTTGTTATGTACTCTTATCAGGTCG
AGTAAAGATGTTGCGAAACCTTATATCGAACCTCTTTTAAATGTTCTTTTACCAAAATTC
CAAGATACCTCTTCAACGGTTGCATCAACTGCACTGAGAACTATAGGTGAGCTATCTGTT
GTAGGGGGCGAAGATATGAAGATATATCTTAAGGATTTGTTTCCTTTAATTATCAAACA
TTTCAGGATCAATCAAACTCTTTCAAGAGAGAAGCTGCACTTAAGGCCCTTGGTCAACTT
GCAGCCTCATCTGGTTACGTGATAGATCCTTTACTCGACTATCCCGAATTATTGGGTATA
TTGGTGAATATATTGAAGACAGAAAACTCTCAAAATATTAGGAGACAAACAGTCACTTTG
ATAGGTATACTGGGAGCTATCGACCCATATCGCCAAAAAGAACGTGAGGTTACCTCTACT
ACCGATATATCTACAGAACAGAACGCCCCGCCTATCGACATTGCTCTTCTCATGCAGGGC
ATGTCTCCTTCGAATGATGAGTATTATACCACTGTTGTCATTCACTGCCTGCTAAAAATC
CTAAAAGATCCATCCCTATCATCTTACCACACTGCCGTGATCCAAGCGATTATGCATATT
TTTCAAACCCTTGGTCTAAAATGTGTTTCATTCTTGGACCAGATCATCCCAACTATTTTG
GACGTAATGCGTACATGCTCTCAGTCACTATTAGAATTTTACTTCCAACAGCTTTGCTCT
TTGATTATTATCGTAAGGCAACACATAAGACCTCATGTCGATTCTATATTCCAGGCTATC
AAAGATTTTTCTTCGGTTGCTAAGCTACAAATAACGCTTGTAAGTGTTATTGAAGCAATA
TCAAAGGCTCTGGAGGGTGAATTCAAAAGATTGGTCCCTCTTACTCTGACCTTGTTCCTT
GTAATTTTGGAGAATGACAAGTCTAGTGACAAGGTCCTCTCCAGAAGGGTATTGAGACTG
TTAGAATCGTTTGGTCCTAACTTAGAAGGTTATTCGCATTTGATTACACCCAAGATAGTT
CAAATGGCAGAATTCACCAGCGGGAACCTACAAAGGTCTGCAATAATTACTATTGGCAAA
CTGGCCAAGGATGTTGACCTTTTTGAGATGTCCTCAAGAATTGTTCACTCTTTACTTAGG
GTACTAAGTTCAACAACGAGTGACGAACTCTCAAAAGTCATTATGAATACTTTAAGTCTA
CTGCTAATACAAATGGGCACATCCTTTGCTATCTTCATCCCTGTCATTAATGAAGTTTTA
ATGAAGAAACATATTCAACACACAATATATGATGACTTGACAAACAGAATATTAAACAAT
GATGTTTTACCCACAAAAATTCTTGAAGCAAATACAACGGATTATAAGCCCGCGGAACAA
ATGGAGGCAGCAGATGCTGGGGTCGCAAAATTACCTATAAACCAATCAGTTTTGAAAAGT
GCATGGAATTCTAGCCAACAAAGAACTAAAGAAGATTGGCAGGAATGGAGCAAACGTCTA
TCCATTCAATTATTAAAAGAGTCACCCTCCCATGCTCTAAGAGCTTGTTCAAATCTTGCA
AGCATGTATTATCCACTAGCCAAAGAACTTTTTAATACCGCATTCGCATGTGTTTGGACC
GAACTTTATAGCCAATATCAAGAAGATTTAATTGGGTCATTATGTATAGCCTTATCTTCT
CCCTTAAATCCACCAGAAATACATCAAACATTGTTAAACCTGGTAGAATTTATGGAACAC
GATGACAAGGCATTACCAATACCAACTCAAAGCCTGGGCGAGTATGCTGAAAGATGTCAC
GCCTATGCCAAAGCGCTACATTATAAAGAGATTAAATTTATTAAAGAGCCTGAGAACTCA
ACTATTGAATCATTGATCAGCATTAACAACCAGCTGAATCAAACGGATGCTGCAATTGGT
ATATTAAAGCATGCCCAACAACATCATTCACTTCAATTAAAGGAGACATGGTTTGAAAAA
TTAGAGCGTTGGGAAGATGCACTACATGCTTATAATGAACGTGAAAAGGCAGGTGATACT
TCCGTGAGCGTTACACTCGGTAAGATGAGATCCCTTCATGCCCTTGGCGAATGGGAACAG
TTGTCGCAATTGGCAGCTAGAAAGTGGAAAGTTTCGAAGCTACAAACTAAGAAGCTAATA
GCTCCCTTGGCAGCTGGTGCTGCGTGGGGGTTGGGAGAGTGGGATATGCTTGAGCAATAT
ATCAGCGTTATGAAACTAAATCTCCAGATAAGGAATTTTTTGATGCAATTTTATACTTG
CACAAGAATGATTACGACAATGTCAGTAAGCATATATTAAACGCCAGAGATTTGCTTGTG
ACTGAAATTCCGCGTTGATCAATGAAAGTTATAATAGAGCATATAGCGTTATTGTTAGA
ACTCAAATAATAACAGAGTTTGAGGAAATCATCAAGTATAAACAATTGCCACCTAATTCC
GAGAAAAAACTTCACTATCAAAATCTTTGGACAAAAAGACTGCTGGGCTGCCAAAAAAT
GTCGATTTATGGCAAAGAGTGCTTAGAGTAAGATCATTGGTAATAAAGCCCAAGCAAGAC
CTGCAAATATGGATAAAATTTGCAAATTTGTCAGAAAATCTGGTAGAATGAGGCTAGCA
AATAAGGCATTGAATATGCTACTAGAAGGAGGCAACGATCCTAGTTTACCAAATACGTTC
AAAGCTCCTCCCCCAGTTGTTTACGCGCAACTAAAATATATTTGGGCTACAGGAGCTTAT
AAAGAAGCATTAAACCACTTGATAGGATTTACATCCAGGTTAGCGCATGATCTTGGTTTG
```

| SEQ ID | | |
|---|---|---|
| | | GATCCGAATAATATGATCGCGCAAAGTGTCAAACTCTCAAGTGCAAGTACTGCTCCGTAT<br>GTTGAGGAATACACAAAATTATTAGCTCGATGTTTTTTAAAGCAAGGTGAGTGGAGAATA<br>GCAACACAACCGAACTGGAGAAACACAAATCCGGATGCAATTCTTGGTTCTTATCTATTG<br>GCTACACATTTCGATAAAAATTGGTACAAGGCATGGCATAATTGGGCCTTAGCTAATTTT<br>GAAGTAATATCCATGGTTCAGGAAGAGACTAAGCTCAACGGAGGTAAGAATGATGATGAT<br>GATGACACGGCAGTTAATAATGATAATGTGCGGATTGACGGTAGTATCCTAGGAAGTGGT<br>TCTTTGACTATTAATGGCAACAGATACCCGCTAGAGCTTATTCAAAGACATGTTGTTCCA<br>GCGATCAAGGGCTTTTTTCATTCAATATCTCTATTAGAAACAAGTTGTTTGCAAGACACG<br>TTGAGGTTATTGACTCTTTTATTTAACTTTGGTGGTATTAAAGAAGTCTCACAAGCCATG<br>TATGAAGGCTTCAATTTGATGAAAATAGAGAACTGGCTTGAAGTCTTACCACAGTTGATC<br>TCTCGTATACATCAGCCAGATCCTACGGTGAGTAATTCCCTTTTGTCGTTGCTTTCTGAT<br>TTAGGGAAAGCTCATCCACAAGCTCTCGTGTATCCTTTAACTGTCGCGATCAAGTCTGAA<br>TCTGTTTCAAGACAAAAAGCGGCTCTTTCAATAATAGAGAAAATTAGGATTCATAGTCCA<br>GTCCTGGTAAACCAGGCAGAATTAGTTAGTCACGAGTTGATCAGAGTAGCCGTTCTATGG<br>CACGAATTATGGTATGAAGGACTGGAAGATGCGAGCCGCCAATTTTTCGTTGAACATAAC<br>ATAGAAAAAATGTTTTCTACTTTAGAACCTTTACATAAACACTTAGGCAATGAGCCTCAA<br>ACGTTAAGTGAGGTATCGTTTCAGAAATCATTTGGTAGAGATTTGAACGATGCCTACGAA<br>TGGTTGAATAACTACAAAAAGTCAAAAGACATCAATAATTTGAACCAAGCTTGGGATATT<br>TATTATAACGTCTTCAGAAAAATAACACGTCAAATACCACAGTTACAAACCTTAGACTTA<br>CAGCATGTTTCTCCCCAGCTTCTGGCTACTCATGATCTCGAATTGGCTGTTCCTGGGACA<br>TATTTCCCAGGAAAACCTACCATTAGAATAGCGAAGTTTGACCATTATTTTCTGTGATC<br>TCTTCGAAGCAAAGGCCAAGAAAATTCTCCATCAAGGGTAGCGACGGTAAAGATTATAAA<br>TACGTTTTAAAGGGACATGAAGATATAAGACAAGATAGCCTTGTTATGCAATTATTTGGT<br>CTAGTTAACACTTTGTTGAAGAATGATTCAGAGTGTTTCAAGAGACATTTGGATATCCAA<br>CAATACCCGGCTATTCCATTGTCGCCTAAATCTGGTTTACTAGGATGGGTACCAAATAGT<br>GACACATTCCACGTTTTGATCAGAGAACACCGTGATGCCAAAAAAATTCCGTTGAACATT<br>GAACATTGGGTTATGTTACAAATGGCCCCCGATTATGAGAATTTGACTCTTTTACAAAAA<br>ATTGAAGTATTCACGTACGCTTTAGATAATACAAAAGGCCAAGACCTTTATAAAATATTA<br>TGGTTAAAGAGTAGGTCGTCAGAGACATGGCTAGAACGTAGAACAACTTATACGAGATCT<br>TTAGCAGTTATGTCCATGACTGGTTATATTCTGGGACTAGGTGATCGCCATCCAAGCAAC<br>CTGATGCTAGATAGAATCACCGGTAAAGTTATCCACATTGATTTCGGCGATTGTTTTGAA<br>GCTGCCATCTTAAGAGAAAGTATCCAGAAAAGTGCCATTTAGACTAACTAGGATGTTA<br>ACATACGCAATGGAAGTTAGTGGAATTGAAGGCAGTTTCCGAATTACTTGTGAAAATGTC<br>ATGAGAGTCTTAAGAGATAATAAAGAATCATTAATGGCGATCTTGGAAGCTTTTGCGCTT<br>GATCCTTTGATCCATTGGGGATTTGATTTACCGCCACAAAAACTTACTGAGCAAACTGGA<br>ATTCCTTTGCCGTTGATTAATCCTAGTGAATTATTAAGGAAGGGGGCAATTACTGTCGAA<br>GAAGCGGCAAATATGGAAGCAGAACAACAAAATGAGACCAAAAACGCCAGAGCAATGCTT<br>GTTTTGAGACGTATTACAGATAAATTAACGGGCAATGATATCAAGAGGTTCAATGAATTA<br>GACGTCCCTGAGCAGGTTGATAAACTGATCCAACAAGCCACTTCTATTGAAAGGTTATGT<br>CAACATTATATTGGATGGTGCCCATTCTGGTGA |
| NO: 19 | the S. cerevisiae Dal80p protein sequence | MVLSDSLKLPSPTLSAAAGVDDCDGEDHPTCQNCFTVKTPLWRRDEHGTVLCNACGLFLK<br>LHGEPRPISLKTDTIKSRNRKKLNNNNVNTNANTHSNDPNKIFKRKKRLLTTGGGSLPTN<br>NPKVSILEKFMVSGSIKPLLKPKETVPNTKECSTQRGKFSLDPCEPSGKNYLYQINGSDI<br>YTSNIELTRLPNLSTLLEPSPFSDSAVPEIELTWKLHNEEEVIKLKTKISELELVTDLYK<br>KHIFQLNEKCKQLEVELHSRASVQSHPQH* |
| NO: 20 | the S. cerevisiae DAL80 coding sequence | ATGGTGCTTAGTGATTCGTTGAAGCTGCCCTCGCCTACACTTTCAGCTGCTGCTGGAGTG<br>GATGATTGTGACGGAGAGGACCACCCCACGTGCCAGAATTGTTTCACTGTCAAAACGCCC<br>CTATGGAGAAGAGATGAACACGGTACTGTTCTCTGTAATGCATGTGGCCTCTTCCTGAAG<br>TTGCACGGGGAACCAAGGCCTATCAGCTTGAAGACGGACACCATTAAGTCAAGAAATAGG<br>AAAAAGCTGAATAACAACAATGTGAACACTAATGCCAATACCCATTCTAACGACCCAAAT<br>AAAATATTCAAGAGAAAGAAGAGACTGCTTACAACTGGTGGTGTTCATTACCTACGAAT<br>AATCCGAAGGTTTCTATTCTGGAAAAGTTTATGGTGAGCGGGTCCATTAAGCCACTGTTA<br>AAACCAAAGGAAACCGTTCCCAACACAAAGGAGTGCTCCACGCAGCGGGGAAAATTTTCT<br>TTGGACCCCTGCGAACCTAGTGGGAAAAACTACCTCTATCAGATCAACGGTTCAGATATA<br>TACACGTCAAATATAGAGCTGACAAGGCTGCCTAATTTGTCAACATTATTAGAACCCTCA<br>CCTTTTTCAGATTCCGCTGTACCAGAAATAGAACTAACTTGGAAGCTACATAATGAGGAG<br>GAGGTAATCAAATTGAAGACCAAGATAAGCGAATTGGAGTTGTGACAGACCTATACAAA<br>AAGCACATATTCCAACTGAACGAAAAATGCAAGCAACTGGAAGTGGAACTACACTCCAGA<br>GCTTCAGTACAATCTCACCCCACAACATTAA |
| NO: 21 | the S. cerevisiae Gzf3p protein sequence | MASQATTLRGYNIRKRDNVFEPKSSENLNSLNQSEEEGHIGRWPPLGYEAVSAEQKSAVQ<br>LRESQAGASISNNMNFPKANDKSFSTSTAGRMSPDTNSLHHILPKNQVKNNGQTMDANCNN<br>NVSNDANVPVCKNCLTSTTPLWRRDEHGAMLCNACGLFLKLHGKPRPISLKTDVIKSRNR<br>KSNTNHAHNLDNFRNQTLIAELKGDCNTESSGRKANRVTSEDKKKKSSQLLMGTSSTAKI<br>SKKKPKTESKERSDSHLSATKLEVLMSGDCSRPNLKPKLPKQDTAIYQEKLLTFPSYTDVK<br>EYSNSAHQSAFIKERSQFNAASFPLNASHSVTSKTGADSPQLPHLSMLLGSLSSTSISNN<br>GSEIVSNCNNGIASTAATLAPTSSRTTDSNPSEVPNQIRSTMSSPDIISAKRNDPAPLSF<br>HMASINDMLETRDRAISNVKTETTPPHFIPFLQSSKAPCISKANSQSISNSVSSSDVSGR<br>KFENHPAKDLGDQLSTKLHKEEEIIKLKTRINELELVTDLYRRHINELDGKCRALEERLQ<br>RTVKQEGNKGG* |

TABLE 2-continued

Table of sequences

SEQ ID

NO: 22  the *S. cerevisiae* GZF3 coding sequence
ATGGCATCGCAGGCTACAACTCTTCGAGGCTATAACATTAGAAAACGAGATAATGTATTT
GAACCAAAATCAAGTGAAAACCTCAACAGCTTAAATCAAAGCGAAGAAGAAGGGCATATT
GGGAGATGGCCACCTTTAGGTTATGAAGCAGTATCTGCCGAGCAAAAATCGGCAGTTCAA
TTGCGTGAATCGCAAGCAGGAGCGTCAATAAGCAACAATATGAATTTTAAGGCGAATGAC
AAGTCTTTTTCCACATCTACTGCTGGAAGAATGAGTCCGGATACGAATTCATTACACCAT
ATATTACCTAAAAATCAAGTTAAGAATAATGGACAAACAATGGATGCCAATTGCAATAAT
AACGTATCCAATGATGCTAATGTTCCTGTTTGTAAGAACTGTTTAACCTCTACAACACCA
TTATGGAAGAGATGAGCATGGAGCTATGCTTTGTAATGCGTGTGGTCTCTTTTTAAAG
CTTCATGGGAAACCCAGGCCAATTAGTTTGAAAACTGATGTAATAAAGTCTCGAAATAGG
AAAAGTAATACAAATCATGCACATAATCTGGACAACTTTCGGAATCAGACGCTGATTGCA
GAGCTTAAGGGTGATTGTAATATAGAATCAAGCGGTCGCAAAGCTAACAGAGTAACATCT
GAAGATAAAAGAAAAAAAGTTCGCAACTTTTAATGGGAACTATCATCTACTGCGAAGATA
TCCAAGAAGCCAAAAACGGAGTCTAAGGAAAGAAGCGATTCTCACCTATCAGCAACAAAA
TTAGAGGTACTGATGTCGGGAGATTGTTCGAGACCAAACTTAAAGCCTAAACTGCCCAAA
CAAGATACTGCTATATACCAAGAGAAGTTACTTACGTTCCCAAGTTATACGGACGTTAAA
GAGTATTCAAATTCTGCACACCAATCTGCTTTTATCAAAGAACGGTCGCAATTCAACGCA
GCCTCTTTCCCCCTCAATGCTTCACATTCAGTAACATCAAAAACAGGCGCAGATTCTCCT
CAATTACCTCACTTATCAATGCTGCTTGGAAGCTTGAGCAGTACTTCAATATCAAATAAC
GGAAGTGAAATAGTGTCCAATTGCAATAATGGTATTGCCTCTACCGCCGCAACTCTGGCA
CCCACTTCTTCACGGACGACTGACTCTAATCCATCCGAGGTACCGAATCAAATTAGATCG
ACGATGTCTTCCCCAGATATAATATCTGCTAAGCGTAACGACCCAGCCCCTTTATCTTTC
CACATGGCTTCTATTAACGACATGCTTGAGACGAGAGATCGTGCGATTAGCAACGTGAAA
ACCGAGACGACACCGCCTCATTTCATACCGTTTCTACAATCTTCTAAAGCTCCCTGTATA
TCCAAAGCAAATTCACAATCCATCTCAAATAGTGTTTCTAGTTCTGATGTTTCTGGACGA
AAATTTGAAAATCACCCAGCTAAAGATTTAGGTGATCAGTTATCCACTAAATTGCACAAA
GAAGAAGAAATTATAAAGCTCAAAACTAGAATAAATGAGTTAGAACTTGTTACAGATTTA
TATAGGAGACATATCAATGAATTAGACGGGAAATGTCGAGCTCTTGAGGAACGTTTGCAA
AGGACAGTAAAACAAGAAGGGAATAAAGGAGGATAG NO: 23  the sequence of a portion of the upstream region of the
ASP3 gene, ending at the ASP3 start codon ATG. Putative
NCR element GATAA(G) boxes are in bold and underlined
ATATGGCCGCAACCGAAATAGTTAGGTGTGGCAGCCGTACATATGGAAGCCGGGCGATGG
CTCCGCCACGTGCAAAGTGCAGGAGCTTTGGAAAGAGCGTGCATATAGTGATGAAAACAG
AGAGCACGGTTGCGAACGGAGGGTCTCACAATGTCTCAAAGGATAAATCTCTTGGTTTGC
GGGCCGCATACAAGATATGATTGTAGTTTTTTCAATGGCTCTACTGTCCCACTGCTGTAC
AACAGAAAATGAGAGATCAGAGAAATAGTATTCCGGAAGCCAGTGGTGTTTACTTATTAG
TTTTTTGACGCCACTGCGCGAGTTGCTGCCTAGCTGTTCCTTGGCCAACGCATATTGGAA
CTTCATTCGACTGATATGCTTACTCAGAGGTCCATTACTTCAAGAATTGTCTCACCTATC
GGGATTGGCGTTTGTACAAGAAGAAACTTTCATCACCTTTGTTTCGCCACCAAATGAAAA
AAAAAACTTGCATGGCTTAGGTGGTTCTTTGTCAGAAATATCTTCTAAGGATCAAGAGTC
TTACGTGATTCTAATCCCTTGGCAAGTCAGATCTCAAATATGCTCACTCGCAGATGAGTA
GCAATGAATGCGACCAAGTGACTAGTGACTGGTGACGACATGAGCCAAGCTGGAACCAGC
AGCTTTCACGTCGGCTTATAGCTCTCTATGGGGCAATCAACCACTCATAGTGACTGAAGA
TCTTTTTAATATAATTACATTGCTAAAAACGTCATACCGCCTTGTGAGCACGATAAACAG
CATATGCATTGAGCCTTGTTATTCTTCGGAACTGGGGATAGTAAAATGCGACCCGCTTAG
GATGATCAAGCTATCTTTGGGACGGAGTTTTGTCATGGGAGTGGTCATCCTACTGGTGAT
GCTTCAACATTTGATTTACTAAATTTTGAAATCGGCCGCAGAATAAAACTATTATGTCCA
AACAATTGATGGTCGAACCAACGTTAAGGGTTTCAAGTATTGAATTGAACTTTTATGAGT
TCTATAATTTCGTTGCGCAAATTCAACTAAACCACCAATATCCCCCCTACAACGCTACAC
TTTATACCGATAGAGGAATAACGCATAGAGCCTTCGTAGAATTCTTCAACTCGTACGTGA
TGGGGATTCTAAACCTATCGTCATGTCGCTGTACAAGGCTGCTGCCTGCTTTCAAATTCC
CAATTTTACCATGTCCGTTTCGCTGAGCCGAATCGTCACACAAGGTAATTAGTTCTGGGT
ATCGCTTCAGTATAGCACTGGTTTTTTCCTTGTAAAACCACAGTCTAACAATTAAATGAA
GCTTTTCGAAGAAATTAGACCATGTTAGACTGAAAGCAAAGACTCCGGCCCGTTCTGAGG
TAAGTTCAATGAAATTGGACAGTTTCTTTTCAAGGTTAGGTTTTGTGTTCGAAAAAAATA
GATTACCGCACCTCCTTTCCAAACCCCATGAGTTTCCATTAAGGAAGAGCAACGTCAATA
ATACCACCTTTTGCAGATGTGATTCAACTCAAGATGCTGTAATCTTTCCCTTCTGACCCT
AGATCACCTCATGATATCCTTTTGAGGCAATTAAAGCTGCAGTGTAAACTGTTGAATATC
TTTTTGAAACCAAAAAAAAGGACGTTCCACACTTGGCTGCTTTCTTGATAAGCAGATCT
TTACTTGGAGATCTCGCTTAGTCCTCCGAAGGGTAAACCCCGTCTCTTATCTTTAAAAAA
ATGTATCAGACCCTTCAGCACGTGACAGACAGCAAACTACCAGTCGACGAGGATGCTTTT
CCGAAAGTCATGACACAAGGGAAGGACTGTAAGATCGATATCGGCGCAGTCTTATCGGAT
GTTCCAAGTCCTTGTCTCTTTCATTATCTGCTTGCTATCGCAAAAAAAAAAAATCAATT
TGTTTAATATCAACACATAATGTACAAGAACAAATCATGACATACAAAAGCCATATAAGA
TGAGTCTTCAAGCAGCACCAAGAGGCCTGAGGCAGAGCAAATGTTGGCTCGCT
ATTCTTTTGTAAGCAATCTGGTACTCACCAACCTCCAACT NO: 24  the sequence of a portion of the upstream region of the
GAP1 gene, ending at the GAP1 start codon ATG. Putative
NCR element GATAA(G) boxes are in bold and underlined
ACATCATGTTTTGCTTAGTAGACTCTTGCGGGCGTTCCATCCGTGTGAAATACATCATTT
ACACCTCGCTCTGGGTCAAGTAATCAAAAAATACCTCGTCGAATATCTTCGACAAATCTG
TCGCTTGGTTTATGTTTGACCTGATGTATATAAAATCATCACTACCCAATTTAGAGAACA
CATTGCGTTGCCCGGCCGGCAAAAAATCCTGGGCCAAAAGTTAAAAGAAACTTTCTCATA TABLE 2-continued Table of sequences

SEQ ID

CTCACTCTGAAGTTGTACTATTACGAAGCACTAAAGCATTGATAGATAAATCAACACAGA
ACATACATGATTAAATTAGACACAGCTCTCTGTATTTTTTACTGTTTGAACTAAGGTTCT
AATACTTACACATTCTTTTCAACCCATCAGATGGTGTCTTGCCCCTGCTTACGTAACCTA
CAACAATAGATTAGACACACCAGTGCCAAGGACAATATGTTGCGTTCTGACTAGTCGAAG
TATCATTACGCTGTGCAGATCGACCTGACACCAGACACAAAGGAGAATAGGGGCAGCATG
AGTTCCGTCGGCGACTCATTCCGACCTTCCACAGGTCCGTTGATTACTTTTTCACTGATC
CGGTGGAATCTATGGTTGTTTTTTCATCATGATATCTGTTTTAGGACTTTTTTTTTCAG
CCGATCGCTTATCTGCTCACTAGAATCGTAATCAGTGATATTTTTATTAATAATTATTAT
TTATTTTTTTTATACCATTTCCTTTTGATAAGGGGTCGTTGGTGCCGTGCCGCTATCAG
GCAGCCTCACTAATCTACCCATTGACCTCATGCAGCAAAGTCACATCGCCCATATCTCTC
GAGTGCGATAACGGGGAACTTGATTTGGTAACTGATAAGATTGTTAAATGTCAGTTTGGA
TGCTTTTTCTTACGTCCGATTAGCTTATCTTCTGGAGCAACCGGCCATTTACCTCCTCAT
AGTAAATTAAACATGATAAGCGCATAGTTGGGGCAACACACCTTTCTTCCGGAATTCGCT
CTGGATGAGACATATAAAGATGAAGGTGAAGTCCACTTAAATGAATGTCAATGAGACGAT
GTTTTTTCTCCTAGATTGATTTTTGAATTCCTTGTATACAAAGTCTTGTTTTCTTATTGT
CCTCAACAAAACAAAAGTAGAAAAGAACAGACCAAGGACAGCAACATTTATAAGAAACAA
AAAAAAGAAATAAAAA

NO: 25  the sequence of a portion of the upstream region of the
AGP1 gene, ending at the AGP1 start codon ATG. Putative
NCR element GATAA(G) boxes are in bold and underlined
AGGAAAACATATTAGCATAAATCGTCATTGCTGAAAGAGCGCCTTTACCTCAACCTACCA
TGGCAAACATAACAGAAAACATAAAAAAATTATCCTAGAGCCCAATGTTCCATGAAAAGA
GCTGTGGCAAGGACAGAAACAAAAAAAAATCAAGAACTCAACATTACCTATATAATTTT
TGTTTTCTCCCATTTTCAAAGTCATTTGTTTTCCATTTTGCAAAGCAATTATTATATCAA
TAAGCCTTTTGATGACTTTACCTAGCACTCTTTCAAATAGAATCTTCTTACGAAGGTGTG
CATTCTCCCTTTTATACCTCGGCGGCTTCACTCGGCGGCTAACCCCTTATTTCCTCATTT
CCTCGGCGGCTAAAAAGGGACTTTGGAGAAATCTTGCATCCGTGCCTCCCACGGCATTTT
TTTTTGGTTTCTTTTTTTCCTTGACCGGCATAATAGAAGAAAAAAAAAAGCGCGCCGTTC
TTCAGTGCCGCTTGAGGGTGCCGTCTAAGCGGCACTGATCTGCTGCAAAAAGCTGCAACT
TTGCCGTTGATGGCACTCCCAGTGGCACCATCGCACTAAATAACGGTCTCATCGAGTCAT
AGATAAGCAGGTTGCAGTATCCGGCCAACTTTCAACTCCCCCACGTCCAGCGGATTGCTG
CTCCTTAGTAGTCCACAGTTCTTAAGTTGCGCTGCGAGGCTCTTTTTTTAGTGCCTTCTA
GCCATTTCTTCCAGCTTGGCAGTGGTTATCTCTTTCACTGAACCGCAAATCAATCCT**GAT
AA**GACGGCTAAGATGCATAGGATAGGTCGGCTATACGTGTGTCTTGCGCTATCTTCCCCT
CGTCCGCTAACAAGACTCATATCCTTCGTGATTAGTTTCTTTTTGTTATTTTCCTCGTAA
TACTCATTTGTTTTACATACATATATAAGTGCTTTGTCTTTGATGGTCTGCCCACAACAA
TGTAGAACAAGTTTATTATGTAATCTTTATAGAAGAAGCACGCTAATATAGACAAAGATA
GCTTCGCACA NO: 26  the sequence of a portion of the upstream region of the
GAT1 gene, ending at the GAT1 start codon ATG. Putative
NCR element GATAA(G) boxes are in bold and underlined
TCTTTACGTTAGGGGGTGAGAGAGGGAGGGGGGTGCCTTTAATGTATATATACGTAAGAT
ATATATATATATGTATATATATGGAAATGTATTCACAACTTTACATGTGCATTAACCACA
AGTACTGCGTACGTTCAAGATTACAGCAATGCGTTTTATTAATTTTTCAAGCATTTTTCA
CGTAGAGAGGAACAAAGTTTACTGAAAAGAAAAGAGGTAGAGAAAAACAGAAAAATTTTT
TTTTTCTGTTTTTCCTGCCTCTTTTCTTTGTTTGATTCAATATGGTCGACCGGGTAAACC
CCTGATAAAACGATACCAAAGCCGGGTCACCTAACTTATGGCCAAATGCGACCGGTCCCG
CTTTCCGATTTTAGCCGGCGAAGACGTACTTGGCGCCATAATCAAAACCTAGCTTGCCCA
ATACTTCTGAGTTCTACGTGGTGCAAAAATATTTTTTTTTTTTGAAAAACCTACCCTAT
TTCATTATAGATGCATCCATCAGTATTACGGTGTCCTCACACAACCCTGTCTCTGCACAA
CGTAATACCTCCTTTTCCCGTCTGCTAGCTCTCATTTCGCGGTAATCCAACTTCAACCAG
CAACCCGGATCTTCTATACGCAGTCCGGTGTGTGGGTGCATGACTGATTGGTCCGGCC**GA
TAACAGGTGTGCTTGCACCCAGTGCCCAACGTCAACAAAGCAGGAACAACGGGCTGATAA**
GGGAGAAGATAAGATAAGATAAGATAACAAATCATTGCGTCCGACCACAGGCCGACACAT
AGCAGAACGATGTGAAGCAGCGCAGCATAGTGTTAGTGCCGGTGCAGCTACCGCTGGTAT
TAACAGCCACCACAATACAGAGCAACAATAATAACAGCACTATGAGTCGCACACTTGCGG
TGCCCGGCCCAGCCACATATATATAGGTGTGTGCCACTCCCGGCCCCGGTATTAGC NO: 27  the sequence of a portion of the upstream region of the
DAL80 gene, ending at the DAL80 start codon ATG. Putative NCR
element GATAA(G) boxes are in bold and underlined
TCACCCTTGTTTATCTATCCTACCTTTTCTTCTTGCGTACGTGCCTCTCAATGCGTCGTG
TGAATTATCAGTGACCGGTCGTGCCTATAATGTCCTGCTAATTTCCCACTAAATCTTTCC
CCATGGCGTATTCATCGTTATGTTTGTGTCTTTTGTTCAACCCAAAGGGCTGTAGCAATC
TTCACCCGTTTGTCGTTGATAACGAGTTTCCACCTTATCACTTATCACTAGTGCTAATCA
AACAGCAAAGAATGCTTGATAGAAACCGATCCTGGGCTTATCTCGCTGCATTGTGGCGGC
ATCCCTGGACTGTAATCAGCAAGTGTTGCTTAGTATATATATACATCCAGCGTCAGCTTG
AATTTGGATACAGTTACTGTTTTTTCGATTTTCTCTTGGTTATTCTTTCTGAGACAGTAG
TAATTTTGTATTACTGAGCGGGATATTGTTTATCTGCCGTCATACTATATTACATTATAT
TATATCATATTATATATAAGAGAA NO: 28  the sequence of a portion of the upstream region of the
GZF3 gene, ending at the GZF3 start codon ATG. Putative
NCR element GATAA(G) boxes are in bold and underlined TABLE 2-continued Table of sequences

SEQ ID

```
GAAAAAAAAGGTGAAGTATTATGTAAATTTTTGTAAAGTAAAA
CACTATGCTGTTGAACGAAATCTTTCATTGAAAATATTGTTATTC
ATTCGTGATAGCTGCCCCTTTCTGAGTTTGAACTTAATATTTCAA
TTACGCTACTTCAAGTTTCAATGAGATATTATTCTGTCATCTTTCT
CGTCGTTCCTAGTGATTAACGTTACTAAAATTACTGATCCT
AAATAGCGGGCGAACAGAGTGAAAATTTTCTTATCTTCGCTT
ATCTGCGCTTATCAATCCTAATCAGTGAAAAATAAGATATAG
GCTTGATAATAAGGTAGTTTGAAAGAGAACATATTGCAAGCG
GTTGAAGCTATAATACTAGATATACGAATATCATTTCGGGTAT
TTGTACTGTGCTCTACAATTCTACTGGTAATATTA
```

NO: 29  a S. cerevisiae Dip5p protein sequence
```
MKMPLKKMFTSTSPRNSSSLDSDHDAYYSKQNPDNFPVKEQEIYNIDLEENNVSSRSSTS
TSPSARDDSFAVPDGKDENTRLRKDLKARHISMIAIGGSLGTGLLIGTGTALLTGGPVAM
LIAYAFVGLLVFYTMACLGEMASYIPLDGFTSYASRYVDPALGFAIGYTYLFKYFILPPN
QLTAAALVIQYWISRDRVNPGVWITIFLVVIVAINVVGVKFFGEFEFWLSSFKVMVMLGL
ILLLFIIMLGGGPNHDRLGFRYWRDPGAFKEYSTAITGGKGKFVSFVAVFVYSLFSYTGI
ELTGIVCSEAENPRKSVPKAIKLTVYRIIVFYLCTVFLLGMCVAYNDPRLLSTKGKSMSA
AASPFVVAIQNSGIEVLPHIFNACVLVFVFSACNSDLYVSSRNLYALAIDGKAPKIFAKT
SRWGVPYNALILSVLFCGLAYMNVSSGSAKIFNYFVNVVSMFGILSWITILIVYIYFDKA
CRAQGIDKSKFAYVAPGQRYGAYFALFFCILIALIKNFTVFLGHKFDYKTFITGYIGLPV
YIISWAGYKLIYKTKVIKSTDVDLYTFKEIYDREEEEGRMKDQEKEERLKSNGKNMEWFY
EKFLGNIF*
```

NO: 30  a S. cerevisiae DIP5 coding sequence
```
ATGAAGATGCCTCTAAAGAAGATGTTTACCAGCACGTCTCCTCGTAACTCTTCTTCTCTT
GACAGTGATCATGACGCTTACTATTCGAAACAAAATCCTGACAATTTCCCTGTAAAGGAG
CAAGAAATCTATAACATTGACCTGGAAGAAAACAATGTGTCCTCTCGTTCATCCACCTCT
ACATCACCTTCAGCAAGGGACGACTCTTTCGCAGTTCCAGATGGTAAAGACGAAAACACG
CGGTTGAGGAAAGATTTAAAGGCAAGACATATTTCTATGATCGCCATTGGTGGTTCATTA
GGTACAGGTCTGCTTATAGGTACAGGTACCGCCTTATTGACGGGTGGTCCGGTTGCGATG
TTAATTGCATATGCCTTTGTCGGCCTTTTAGTCTTTTACACCATGGCCTGTCTTGGTGAA
ATGGCTTCTTACATTCCATTGGATGGTTTTACAAGTTATGCCTCACGTTACGTGGATCCT
GCATTAGGTTTTGCTATTGGTATACTTACCTTTTCAAATATTTCATCTTACCTCCCAAC
CAACTTACTGCTGCTGCTTTGGTCATTCAATATTGGATCAGCAGAGACCGTGTTAACCCT
GGTGTGTGGATTACTATATTCTTGGTTGTTATTGTCGCTATCAATGTCGTCGGTGTAAAA
TTCTTTGGTGAATTTGAATTTTGGTTGTCCAGTTTCAAAGTCATGGTAATGTTGGGTCTA
ATCCTGTTACTATTTATTATTATGCTTGGTGGAGGTCCTAACCATGACCGCTAGGGTTT
AGATACTGGCGTGATCCTGGTGCGTTCAAAGAATATTCGACGGCTATCACTGGTGGTAAA
GGTAAATTTGTTTCGTTCGTTGCTGTTTTCGTTTACAGTCTTTTCAGTTACACGGGTATT
GAATTGACAGGTATCGTTTGTTCTGAAGCTGAGAATCCAAGAAAAAGTGTTCCAAAGGCA
ATTAAATTGACAGTTTACCGTATCATTGTTTTTTTACCTATGCACCGTTTTCCTTTTGGGT
ATGTGCGTTGCATACAATGACCCTCGTTTACTTTCCACAAAAGGTAAGAGTATGTCTGCT
GCGGCATCTCCATTCGTGGTTGCCATTCAAAACTCAGGTATTGAAGTCTTACCTCATATC
TTCAATGCTTGTGTCTTGGTTTTCGTTTTCAGTGCTTGTAACTCAGATTTGTACGTTTCT
TCCAGAAATTTATATGCGTTGGCAATTGATGGTAAAGCGCCAAAGATCTTCGCTAAGACA
AGTAGATGGGGTGTTCCTTACAATGCTTTAATACTCTCCGTGCTGTTTTGTGGCTTGGCG
TACATGAATGTGTCTTCAGGATCAGCAAAGATTTTCAACTACTTTGTTAACGTTGTTTCT
ATGTTCGGAATCTTGAGTTGGATCACCATTTTAATTGTTTACATCTACTTCGATAAAGCC
TGCCGTGCTCAAGGGATTGACAAATCAAAATTTGCTTATGTCGCTCCTGGCCAACGTTAT
GGTGCTTATTTTGCTTTATTCTTCTGCATTTTGATTGCTTTAATCAAAAACTTCACTGTT
TTCCTAGGTCATAAATTTGATTATAAAACATTCATCACCGGGTATATTGGCCTGCCTGTC
TATATCATTTCTTGGGCTGGTTACAAATTGATATACAAAACCAAAGTGATAAAGTCTACC
GACGTGGATTTGTACACATTTAAGGAAATATACGATAGAGAAGAAGAAGAGGGAAGAATG
AAGGACCAAGAAAAGGAAGAGCGTTTAAAAAGTAACGGTAAAAATATGGAGTGGTTCTAT
GAAAAATTTTTGGGTAATATCTTCTAG
```

NO: 31  a S. cerevisiae Gln3p protein sequence
```
MQDDPENSKLYDLLNSHLDVHGRSNEEPRQTGDSRSQSSGNTGENEEDIAFASGLNGGTF
DSMLEALPDDLYFTDFVSPFTAAATTSVTTKTVKDTTPATNHMDDDIAMFDSLATTQPID
IAASNQQNGEIAQLWDFNVDQFNMTPSNSSGSATISAPNSFTSDIPQYNHGSLGNSVSKS
SLFPYNSSTSNSNINQPSINNNSNTNAQSHHSFNIYKLQNNNSSSAMNITNNNSNNSN
IQHPFLKKSDSIGLSSSNTTNSVRKNSLIKPMSSTSLANFKRAASVSSSISNMEPSGQNK
KPLIQCFNCKTFKTPLWRRSPEGNTLCNACGLFQKLHGTMRPLSLKSDVIKKRISKKRAK
QTDPNIAQNTPSAPATASTSVTTTNAKPIRSRKKSLQQNSLSRVIPEEIIRDNIGNTNNI
LNVRGGYNFNSVPSPVLMNSQSYNSSNANFNGASNANLNSNNLMRHNSNTVTPNFRRSS
RRSSTSSNTSSSSKSSSRVVPILPKPSPNSANSQQFNMNMNLMNTTNNVSAGNSVASSP
RIISSANFNSNSPLQQNLLSNSFQRQGMNIPRRKMSRNASYSSSFMAASLQQLHEQQQVD
VNSNTNTNSNRQNWNSSNSVSTNSRSSNFVSQKPNFDIFNTPVDSPSVSRPSSRKSHTSL
LSQQLQNSESNSFISNHKFNNRLSSDSTSPIKYEADVSAGGKISEDNSTKGSSKESSAIA
DELDWLKFGI*
```

NO: 32  a S. cerevisiae GLN3 coding sequence
```
ATGCAAGACGACCCCGAAAATTCGAAGCTGTACGACCTGCTGAATAGTCATCTGGACGTG
CATGGTCGAAGTAATGAAGAGCCGAGACAAACTGGTGACAGTAGGAGCCAGAGTAGTGGC
AACACCGGTGAAAACGAGGAGGATATAGCATTTGCCAGTGGATTAAACGGCGGCACATTC
```

TABLE 2-continued

Table of sequences

SEQ ID

```
GACTCAATGCTGGAGGCACTGCCCGATGATTTATATTTTACGGACTTCGTGTCTCCTTTT
ACAGCAGCTGCCACGACCAGCGTGACTACTAAGACGGTCAAGGACACCACACCAGCTACC
AATCATATGGATGATGATATTGCGATGTTTGATTCACTTGCCACAACTCAGCCCATCGAC
ATAGCCGCATCCAACCAACAAAATGGTGAAATTGCACAACTTTGGGACTTTAACGTGGAC
CAATTCAACATGACGCCCAGCAACTCGAGCGGTTCAGCTACTATTAGTGCTCCTAACAGC
TTTACTTCCGACATACCGCAATACAACCACGGTTCCCTCGGCAACAGCGTCTCCAAATCC
TCACTGTTCCCGTATAATTCCAGCACGTCCAACAGCAACATCAACCAGCCATCTATCAAT
AACAACTCAAATACTAATGCGCAGTCCCACCATTCCTTCAACATCTACAAACTACAAAAC
AACAACTCATCTTCATCCGCTATGAACATTACCAATAATAATAATAGCAACAATAGTAAT
ATCCAGCATCCTTTTCTGAAGAAGAGCGATTCGATAGGATTATCTTCATCCAACACAACA
AATTCTGTAAGAAAAAACTCACTTATCAAGCCAATGTCGTCCACGTCCCTGGCCAATTTC
AAAAGAGCTGCCTCAGTATCTTCCAGTATATCCAATATGGAACCATCAGGACAAAATAAA
AAACCTCTGATACAATGTTTCAATTGTAAAACTTTCAAGCACCCGCTTTGGAGGAGAAGC
CCAGAGGGGAATACTCTTTGCAATGCCTGCGGTCTTTTCCAGAAATTACATGGTACCATG
AGGCCATTATCCTTAAAATCGGACGTTATCAAAAGAGGATTTCAAGAAGAGAGCCAAA
CAAACGGACCCAAACATTGCACAAAATACTCCAAGTGCACCTGCAACTGCCTCAACTTCA
GTAACCACTACAAATGCTAAACCCATACGATCGAGGAAAAAATCACTACAACAAAACTCT
TTATCTAGAGTGATACCTGAAGAAATCATTAGAGACAACATCGGTAATACTAATAATATC
CTTAATGTAAATAGGGGAGGCTATAACTTCAACTCAGTCCCCTCCCCGGTCCTCATGAAC
AGCCAATCGTATAATAGTAGTAACGCAAATTTTAATGGAGCAAGCAATGCAAATTTGAAT
TCTAATAACTTAATGCGTCACAATTCGAACACTGTTACTCCTAATTTTAGAAGGTCTTCA
AGACGAAGTAGTACTTCATCGAACACCTCAAGTTCCAGTAAATCTTCATCCAGATCTGTT
GTTCCGATATTACCAAAACCTTCACCTAATAGCGCTAATTCACAGCAGTTCAACATGAAC
ATGAACCTAATGAACACAACAAATAATGTAAGTGCAGGAAATAGTGTCGCATCCTCACCA
AGAATTATATCGTCCGCAAACTTTAACTCAAATAGTCCTCTACAGCAGAATCTATTATCA
AATTCTTTCCAACGTCAAGGAATGAATATACCAAGAAGAAAGATGTCGCGCAATGCATCG
TACTCCTCATCGTTTATGGCTGCGTCTTTGCAACAACTGCACGAACAGCAACAAGTGGAC
GTGAATTCCAACACAAACACGAATTCGAATAGACAGAATTGGAATTCAAGCAATAGCGTT
TCAACAAATTCAAGATCATCAAATTTTGTCTCTCAAAAGCCAAATTTTGATATTTTTAAT
ACTCCTGTAGATTCACCGAGTGTCTCAAGACCTTCTTCAAGAAAATCACATACCTCATTG
TTATCACAACAATTGCAGAACTCGGAGTCGAATTCGTTTATCTCAAATCACAAATTTAAC
AATAGATTATCAAGTGACTCTACTTCACCTATAAAATATGAAGCAGATGTGAGTGCAGGC
GGAAAGATCAGTGAGGATAATTCCACAAAAGGATCTTCTAAAGAAAGTTCAGCAATTGCT
GACGAATTGGATTGGTTAAAATTTGGTATATGA
```

NO: 33 a *S. cerevisiae* Tor2p protein sequence
```
MNKYINKYTTPPNLLSLRQRAEGKHRTRKKLTHKSHSHDDEMSTTSNTDSNHNGPNDSGR
VITGSAGHIGKISFVDSELDTTFSTLNLIFDKLKSDVPQERASGANELSTTLTSLAREVS
AEQFQRFSNSLNNKIFELIHGFTSSEKIGGILAVDTLISFYLSTEELPNQTSRLANYLRV
LIPSSDIEVMRLAANTLGRLTVPGGTLTSDFVEFEVRTCIDWLTLTADNNSSSSKLEYRR
HAALLIIKALADNSPYLLYPYVNSILDNIWVPLRDAKLIIRLDAAVALGKCLTIIQDRDP
ALGKQWFQRLFQGCTHGLSLNTNDSVHATLLVFRELLSLKAPYLRDKYDDIYKSTMKYKE
YKFDVIRREVYAILPLLAAFDPAIFTKKYLDRIMVHYLRYLKNIDMNAANNSDKPFILVS
IGDIAFEVGSSISPYMTLILDNIREGLRTKFKVRKQFEKDLEYCIGKLACALGPAFAKHL
NKDLLNLMLNCPMSDHMQETLMILNEKIPSLESTVNSRILNLLSISLSGEKFIQSNQYDF
NNQFSIEKARKSRNQSFMKKTGESNDDITDAQILIQCFKMLQLIHHQYSLTEFVRLITIS
YIEHEDSSVRKLAALTSCDLFIKDDICKQTSVHALHSVSEVLSKLLMIAITDPVAEIRLE
ILQHLGSNFDPQLAQPDNLRLLFMALNDEIFGIQLEAIKIIGRLSSVNPAYVVPSLRKTL
LELLTQLKFSNMPKKKEESATLLCTLINSSDEVAKPYIDPILDVILPKCQDASSAVASTA
LKVLGELSVVGGKEMTRYLKELMPLIINTFQDQSNSFKRDAALTTLGQLAASSGYVVGPL
LDYPELLGILINILKTENNPHIRRGTVRLIGILGALDPYKHREIEVTSNSKSSVEQNAPS
IDIALLMQGVSPSNDEYYPTVVIHNLMKILNDPSLSIHHTAAIQAIMHIFQNLGLRCVSF
LDQIIPGIILVMRSCPPSQLDFYFQQLGSLISIVKQHIRPHVEKIYGVIREFFPIIKLQI
TIISVIESISKALEGEFKRFVPETLTFFLDILENDQSNKRIVPIRILKSLVTFGPNLEDY
SHLIMPIVVRMTEYSAGSLKKISIITLGRLAKNINLSEMSSRIVQALVRILNNGDRELTK
ATMNTLSLLLLQLGTDFVVFVPVINKALLRNRIQHSVYDQLVNKLLNNECLPTNIIFDKE
NEVPERKNYEDEMQVTKLPVNQNILKNAWYCSQQKTEDWQEWIRRLSIQLLKESPSACL
RSCSSLVSVYYPLARELFNASFSSCWVELQTSYQEDLIQALCKALSSSENPPEIYQMLLN
LVEFMEHDDKPLPIPIHTLGKYAQKCHAFAKALHYKEVEFLEEPKNSTIEALISINNQLH
QTDSAIGILKHAQQHNELQLKETWYEKLQRWEDALAAYNEKEAAGEDSVEVMMGKLRSLY
ALGEWEELSKLASEKWGTAKPEVKKAMAPLAAGAAWGLEQWDEIAQYTSVMKSQSPDKEF
YDAILCLHRNNFKKAEVHIFNARDLLVTELSALVNESYNRAYNVVVRAQIIAELEEIIKY
KKLPQNSDKRLTMRETWNTRLLGCQKNIDVWQRILRVRSLVIKPKEDAQVRIKFANLCRK
SGRMALAKKVLNTLLEETDDPDHPNTAKASPPVVYAQLKYLWATGLQDEALKQLINFTSR
MAHDLGLDPNNMIAQSVPQQSKRVPRHVEDYTKLLARCFLKQGEWRVCLQPKWRLSNPDS
ILGSYLLATHFDNTWYKAWHNWALANFEVISMLTSVSKKKQEGSDASSVTDINEFDNGMI
GVNTFDAKEVHYSSNLIHRHVIPAIKGFFHSISLSESSSLQDALRLLTLWFTFGGIPEAT
QAMHEGFNLIQIGTWLEVLPQLISRIHQPNQIVSRSLLSLLSDLGKAHPQALVYPLMVAI
KSESLSRQKAALSIIEKMRIHSPVLVDQAELVSHELIRMAVLWHEQWYEGLDDASRQFFG
EHNTEKMFAALEPLYEMLKRGPETLREISFQNSFGRDLNDAYEWLMNYKKSKDVSNLQA
WDIYYNVFRKIGKQLPQLQTLELQHVSPKLLSAHDLELAVPGTRASGGKPIVKISKFEPV
FSVISSKQRPRKFCIKGSDGKDYKYVLKGHEDIRQDSLVMQLFGLVNTLLQNDAECFRRH
LDIQQYPAIPLSPKSGLLGWVPNSDTFHVLIREHREAKKIPLNIEHWVMLQMAPDYDNLT
LLQKVEVFTYALNNTEGQDLYKVLWLKSRSSETWLERRTTYTRSLAVMSMTGYILGLGDR
HPSNLMLDRITGKVIHIDEGDCFEAAILREKFPEKVPFRLTRMLTYAMEVSGIEGSFRIT
CENVMKVLRDNKGSLMAILEAFAFDPLINWGFDLPTKKIEEETGIQLPVMNANELLSNGA
```

TABLE 2-continued

Table of sequences

| SEQ ID | |
|---|---|
| | ITEEEVQRVENEHKNAIRNARAMLVLKRITDKLTGNDIRRFNDLDVPEQVDKLIQQATSV<br>ENLCQHYIGWCPFW* |
| NO: 34 | a *S. cerevisiae* TOR2 coding sequence<br>ATGAATAAATACATTAACAAATACACCACGCCACCTAACTTATTGTCTTTACGACAAAGG<br>GCCGAAGGCAAACACAGAACAAGAAAGAAACTTACACACAAATCGCACTCCCACGATGAT<br>GAGATGTCAACTACTTCAAACACAGATTCCAATCACAATGGGCCCAATGACTCTGGTAGA<br>GTGATCACTGGTTCTGCTGGTCATATTGGTAAAATATCCTTTGTAGATTCAGAACTAGAT<br>ACAACATTTTCTACTTTAAATTTGATTTTTGATAAACTTAAAAGCGATGTGCCACAAGAA<br>CGAGCCTCTGGCGCTAATGAATTAAGCACTACTTTGACCTCATTAGCAAGGGAAGTATCT<br>GCTGAGCAATTTCAAAGGTTTAGCAACAGTTTAAACAATAAGATATTTGAACTTATTCAC<br>GGGTTTACTTCAAGTGAGAAGATAGGTGGTATTCTTGCTGTTGATACTCTGATCTCATTC<br>TACCTGAGTACAGAGGAGCTGCCAAACCAAACTTCAAGACTGGCGAACTATTTACGTGTT<br>TTAATTCCATCCAGTGACATTGAAGTTATGAGATTAGCGGCTAACACCTTAGGTAGATTG<br>ACCGTGCCAGGTGGTACATTAACATCAGATTTCGTCGAATTTGAGGTCAGAACTTGCATT<br>GATTGGCTTACTCTGACAGCAGATAATAACTCATCGAGCTCTAAGTTGGAATACAGGAGA<br>CATGCTGCGCTATTAATCATAAAGGCATTAGCAGACAATTCACCCTATCTTTTATACCCT<br>TACGTTAACTCTATCTTAGACAATATTTGGGTGCCATTAAGGGATGCAAAGTTAATTATA<br>CGATTAGATGCCGCAGTGGCATTGGGTAAATGTCTTACTATTATTCAGGATAGAGACCCT<br>GCTTTGGGAAAACAGTGGTTTCAAAGATTATTTCAAGGTTGTACACATGGCTTAAGTCTC<br>AATACGAATGATTCAGTGCATGCTACTCTGTTGGTATTTCGAGAATTACTCAGCTTGAAA<br>GCACCTTATCTCAGGGATAAATATGATGATATTTACAAATCTACTATGAAGTACAAGGAA<br>TATAAATTTGATGTTATAAGGAGAGAAGTTTATGCTATTTTACCTCTTTTAGCTGCTTTT<br>GACCCTGCCATTTTCACAAAGAAATATCTCGATAGGATAATGGTTCATTATTTAAGATAT<br>TTGAAGAACATCGATATGAATGCTGCAAATAATTCGGATAAACCTTTTATATTAGTTTCT<br>ATAGGTGATATTGCATTTGAAGTTGGTTCGAGCATTTCACCCTATATGACACTTATTCTG<br>GATAATATTAGGGAAGGCTTAAGAACGAAATTCAAAGTTAGAAAACAATTCGAGAAGGAT<br>TTATTTTATTGCATTGGTAAATTAGCTTGTGCTTTGGGCCCAGCTTTTGCTAAGCACTTG<br>AACAAAGATCTTCTTAATTTGATGTTAAACTGTCCAATGTCCGACCATATGCAGGAGACT<br>TTAATGATCCTTAACGAGAAAATACCCTCTTTGGAATCTACCGTTAATTCGAGGATACTA<br>AATTTACTGTCGATATCCTTATCTGGTGAAAAATTTATTCAATCAAACCAATACGATTTT<br>AATAATCAATTTTCCATTGAAAAGGCTCGTAAATCAAGAAACCAAAGTTTCATGAAAAAA<br>ACTGGTGAATCTAATGACGATATTACAGATGCCCAAATTTTGATTCAGTGTTTTAAAATG<br>CTGCAACTAATTCATCATCAATATTCCTTGACGGAGTTTGTTAGGCTTATAACCATTTCT<br>TACATTGAGCATGAGGATTCGTCTGTCAGAAAATTGGCAGCATTAACGTCGTGTGATTTA<br>TTTATCAAAGACGATATATGTAAACAAACATCAGTTCATGCTTTACACTCGGTTTCTGAA<br>GTGCTAAGTAAGCTATTAATGATCGCAATAACTGATCCGGTTGCAGAAATTAGATTGGAA<br>ATTCTTCAGCATTTGGGGTCAAATTTTGATCCTCAATTGGCCACCAGACAATTTCAGC<br>CTACTTTTCATGGCGCTGAACGATGAGATTTTTGGTATTCAATTGGAAGCTATCAAAATA<br>ATAGGCAGATTGAGTTCTGTCAACCCCGCTTATGTAGTTCCTTCTTTGAGGAAAACTTTA<br>CTGGAACTATTAACGCAATTGAAGTTCTCAAATATGCCAAAAAAAAAGGAGGAAAGTGCA<br>ACTCTATTATGTACGCTGATAAATTCCAGCGATGAAGTAGCGAAACCTTATATTGATCCT<br>ATTCTAGACGTCATTCTTCCTAAATGCCAGGATGCTTCATCTGCCGTAGCATCCACCGCT<br>TTAAAGGTTTTGGGTGAACTATCTGTTGTTGGAGGAAAAGAAATGACGCGTTACTTAAAG<br>GAATTGATGCCATTGATCATTAACACATTTCAGGACCAATCAAACTCTTTTAAAAGAGAT<br>GCCGCCTTAACAACATTAGGACAGCTGGCTGCTTCCTCTGGTTATGTTGTTGGCCCTTTA<br>CTAGACTACCCAGAGTTACTTGGCATTTTGATAAATATTCTTAAGACTGAAAACAACCCT<br>CATATCAGGCGTGGAACTGTTCGTTTGATTGGTATATTAGGCGCTCTTGATCCATATAAG<br>CACAGAGAAATAGAAGTCACATCAAACTCAAAGAGTTCAGTAGAGCAAAATGCTCCTTCA<br>ATCGACATCGCATTGCTAATGCAAGGGGTATCTCCATCCAACGATGAATATTACCCCACT<br>GTAGTTATCCACAATCTGATGAAGATATTGAATGATCCATCGTTGTCAATCCATCACACG<br>GCTGCTATTCAAGCTATTATCCATATTTTTCAAAACCTTGGTTTACGATGTGTCTCCTTT<br>TTGGATCAAATTATTCCAGGTATCATTTTAGTCATGCGTTCATGCCCGCCGTCCCAACTT<br>GACTTTTATTTTCAGCAACTGGGATCTCTCATCTCAATTGTCAAGCAACATATTAGGCCC<br>CATGTCGAGAAAATTTATGGTGTGATCAGGGAGTTTTTCCCGATCATTAAACTACAAATC<br>ACAATTATTCTGTCATAGAATCGATATCTAAGGCTCTGGAAGGTGAGTTTAAAAGATTT<br>GTTCCCGAGACTCTAACCTTTTTCCTTGATATTCTTGAGAACGACCAGTCTAATAAAAGG<br>ATCGTTCCGATTCGTATATTAAAATCTTTGGTTACTTTTGGGCCGAATCTAGAAGACTAT<br>TCCCATTTGATTATGCCTATCGTTGTTAGAATGACTGAGTATTCTGCTGGAAGTCTAAAG<br>AAAATCTCCATTATAACTTTGGGTAGATTAGCAAAGAATATCAACCTCTCTGAAATGTCA<br>TCAAGAATTGTTCAGGCGTTGGTAAGAATTTTGAATAATGGGGATAGAGAACTAACAAAA<br>GCAACCATGAATACGCTAAGTTTGCTCCTTTTACAACTAGGTACCGACTTTGTGGTCTTT<br>GTGCCAGTGATTAACAAGGCGTTATTGAGGAATAGGATTCAGCATTCAGTGTACGATCAA<br>CTGGTTAATAAATTACTGAACAATGAATGCTTGCCAACAAATATCATATTTGACAAGGAG<br>AACGAAGTACCTGAAAGGAAAAATTATGAAGACGAAATGCAAGTAACGAAATTACCGGTA<br>AACCAAAATATCCTAAAGAATGCATGGTATTGTTCTCAACAGAAGACCAAAGAAGATTGG<br>CAAGAATGGATAAGAAGGCTATCTATTCAGCTTCTAAAGGAATCACCTTCAGCTTGTCTA<br>CGATCCTGTTCGAGTTTAGTCAGCGTTTATTATCCGTTGGCGAGAGAATTGTTTAATGCT<br>TCATTCTCAAGTTGCTGGGTTGAGCTTCAAACGTCATACCAAGAGGATTTGATTCAAGCA<br>TTATGCAAGGCTTTATCATCCTCTGAAAACCCACCCGAGATTTATCAAATGTTGTTAAAT<br>TTAGTGGAATTTATGGAGCACGATGACAAACCATTGCCTATCCCAATCCATACATTACGT<br>AAGTATGCCCAAAAATGTCATGCTTTTGCGAAGGCACTACATTACAAAGAGGTAGAATTC<br>TTAGAGAGCCGAAAAATTCAACAATCGAGGCATTGATTAGCATTAATAATCAACTTCAC<br>CAAACTGATTCTGCTATTGGTATTTTGAAGCATGCGCAACAACACAATGAATTGCAGCTG<br>AAGGAAACTTGGTATGAAAAACTTCAACGTTGGGAGGATGCTCTTGCAGCATATAATGAG<br>AAGGAGGCAGCAGGAGAAGATTCGGTTGAAGTGATGATGGGAAAATTAAGATCGTTATAT |

TABLE 2-continued

Table of sequences

| SEQ ID | |
|---|---|
| | GCCCTTGGAGAGTGGGAAGAGCTTTCTAAATTGGCATCTGAAAAGTGGGGCACGGCAAAA<br>CCCGAAGTGAAGAAGGCAATGGCGCCTTTGGCTGCCGGCGCTGCCTGGGGTTTGGAGCAA<br>TGGGATGAAATAGCCCAGTATACTAGCGTCATGAAATCGCAGTCTCCAGATAAAGAATTC<br>TATGATGCAATTTTATGTTTGCATAGGAATAATTTTAAGAAGGCGGAAGTTCACATCTTT<br>AATGCAAGGGATCTTCTAGTTACTGAATTGTCAGCTCTTGTTAATGAAAGCTACAATAGA<br>GCATATAATGTTGTTGTTAGAGCGCAGATTATAGCAGAGTTGGAGGAAATCATCAAATAT<br>AAGAAGTTGCCACAAAATTCAGATAAACGTCTAACTATGAGAGAAACTTGGAATACCAGA<br>TTACTGGGCTGTCAAAAAAATATTGATGTGTGGCAAAGAATTCTGCGTGTCAGATCATTG<br>GTGATAAAGCCAAAGGAGGATGCTCAAGTGAGGATTAAGTTTGCCAACTTATGCAGAAAA<br>TCGGGTAGGATGGCGCTAGCTAAAAAAGTCTTAAATACATTGCTTGAAGAAACAGATGAC<br>CCAGATCATCCTAATACTGCTAAGGCATCCCCTCCAGTTGTTTATGCACAACTGAAGTAC<br>TTGTGGGCTACGGGGTTGCAAGATGAGGCTTTGAAGCAATTAATTAATTTCACATCTAGA<br>ATGGCTCATGATTTAGGTTTGGATCCAAATAATATGATAGCTCAAAGCGTTCCTCAACAA<br>AGCAAAAGAGTCCCTCGTCACGTTGAAGATTATACTAAGCTTTTAGCTCGTTGTTTCTTG<br>AAGCAAGGAGAATGGAGAGTTTGCTTACAGCCTAAATGGAGATTGAGCAATCCAGATTCG<br>ATCCTAGGCTCCTATTTGCTCGCTACACATTTTGACAACACATGGTACAAAGCGTGGCAT<br>AACTGGGCACTGGCCAATTTTGAAGTCATTTCTATGCTAACATCTGTCTCTAAAAAGAAA<br>CAGGAAGGAAGTGATGCTTCCTCGGTAACTGATATTAATGAGTTTGATAATGGCATGATC<br>GGCGTCAATACATTTGATGCTAAGGAAGTTCATTACTCTTCTAATTTAATACACAGGCAC<br>GTAATTCCAGCAATTAAGGGTTTTTTTCATTCCATTTCTTTATCAGAATCAAGCTCTCTT<br>CAAGATGCATTAAGGTTATTAACTTTATGGTTTACTTTTGGTGGTATTCCAGAAGCAACC<br>CAAGCTATGCACGAGGGTTTCAACCTAATCCAAATAGGCACATGGTTAGAAGTGTTGCCA<br>CAGTTAATTTCTAGAATTCATCAACCCAATCAATTGTTAGTAGGTCATTACTCTCCCTA<br>TTATCTGATCTAGGTAAGGCTCATCCGCAGGCATTAGTGTACCCCTTAATGGTTGCGATT<br>AAATCCGAATCTCTCTCACGACAGAAAGCAGCTTTGTCCATCATAGAAAAGATGAGAATA<br>CATAGTCCAGTTTTGGTCGACCAGGCTGAACTTGTCAGCCACGAATTGATACGTATGGCG<br>GTGCTTTGGCATGAGCAATGGTATGAGGGTCTGGATGACGCCAGTAGGCAGTTTTTTGGA<br>GAACATAATACCGAAAAAATGTTTGCTGCTTTAGAGCCTCTGTACGAAATGCTGAAGAGA<br>GGACCGGAAACTTTGAGGGAAATATCGTTCCAAAATTCTTTTGGTAGGGACTTGAATGAC<br>GCTTACGAATGGCTGATGAATTACAAAAAATCTAAAGATGTTAGTAATTTAAACCAAGCG<br>TGGGACATTTACTATAATGTTTTCAGGAAAATTGGTAAACAGTTGCCACAATTACAAACT<br>CTTGAACTACAACATGTGTCGCCAAAACTACTATCTGCGCATGATTTGGAATTGGCTGTC<br>CCCGGGACCCGTGCAAGTGGTGGAAAACCAATTGTTAAAATATCTAAATTCGAGCCAGTA<br>TTTTCAGTAATCTCATCCAAACAAAGACCGAGAAAGTTTTGTATCAAGGGTAGTGATGGT<br>AAAGATTATAAGTATGTGTTGAAAGGACATGAAGACATTAGACAGGATAGCTTGGTCATG<br>CAATTATTCGGACTAGTTAACACGCTTTTGCAAAATGACGCTGAGTGCTTTAGAAGGCAT<br>CTAGATATCCAGCAATATCCAGCAATCCCATTATCTCCGAAGTCTGGGTTACTGGGTTGG<br>GTACCGAATAGTGACACGTTCCATGTATTAATTAGGGAGCATAGAGAAGCCAAAAAAATT<br>CCTTTAAACATTGAGCATTGGGTCATGTTACAAATGGCACCTGATTATGACAATTTAACG<br>TTGTTGCAGAAAGTAGAAGTCTTCACTTACGCCCTAAATAATACGGAGGGACAAGATCTT<br>TATAAGGTGTTATGGCTGAAGAGTAGGTCATCGGAAACGTGGTTGGAGCGTAGAACTACT<br>TACACTCGATCGCTAGCCGTGATGTCCATGACCGGTTATATATTGGGGTTAGGTGACCGC<br>CACCCTAGTAATTTGATGTTGGATAGAATCACTGGGAAAGTCATTCATATTGATTTTGGT<br>GATTGTTTCGAGGCTGCTATATTAAGAGAAAAATTCCCCGAAAAAGTACCTTTTAGATTA<br>ACTAGAATGTTAACATATGCAATGGAAGTGAGTGGAATTGAAGGTAGCTTCCGTATTACT<br>TGTGAGAATGTTATGAAGGTACTTAGAGATAACAAGGGTTCATTAATGGCAATCCTTGAA<br>GCTTTTGCTTTCGATCCTTTGATCAATTGGGGTTTTGACTTACCAACAAAGAAAATTGAG<br>GAAGAAACGGGCATTCAACTTCCCGTGATGAATGCCAATGAGCTATTGAGTAATGGGGCT<br>ATTACCGAAGAAGAAGTTCAAAGGGTGGAAAACGAGCACAAGAATGCCATTCGAAATGCA<br>AGGGCCATGTTGGTATTGAAGCGCATTACTGACAAATTAACGGGGAACGATATAAGAAGG<br>TTTAATGACTTGGACGTTCCAGAACAAGTGGATAAACTAATCCAACAAGCCACATCAGTG<br>GAAAACCTATGCCAACATTATATCGGTTGGTGTCCATTCTGGTAG |
| NO: 35 | the sequence of a portion of the upstream region of the DIP5 gene, ending at the DIP5 start codon ATG. Putative NCR element GATAA(G) boxes are in bold and underlined<br>AGCTCTCTTATCAATTATGTAAGTGCTTGTATACTATTTACCTAAGATAA<br>GAAAAAAAAAGCAATTCAAAATTAAGCTTATCTTGACAGCGGGGCTGGT<br>TTGTTTCTAGAAGACAAAAGTGGGGAATCATTTTTACGTAACTCCCCCT<br>GATAAGAAGGACTCACATCCTTATAGGTACGATAAAGAATGGTTGTATCT<br>TTCCTATTTTCGAAATCGTTATCTTATATAGTTGAACTACTACGGTTAA<br>AAAGCTTAAGCCTCAGCCCTCTTAGTCAAACTTCTTTTTTGAAGGCACCA<br>GGGTGCATAAAAGTGCGTCTATTGTTTCCCAGTGGAACTCTGTTGAGATA<br>GCGATGTTTGTTTTTTTTTCACTTAACGGCAACCAATACCGATAGCGACG<br>TCGCTGGCAGTGTAGAGTGGCCGTACGGCGTCGCTAGATGGCACGGCACT<br>GATTGCGGCGGGAGTCGCTAGGCGGTGATGCATTTCCGCACAGGGACCAG<br>AGGAAGCTTCCCAGGCGGTGACAGTAAGTGAACTCATTATCATGTCTTCT<br>CCAAAAACATTCGTGACATCTAGTCATGCTCCTCGCAATTCACTCCGATTG<br>GTATAGCTTTTTCGGTAGTTTTAGCTACTATGCTTAGGGGAAAGAGGAGA<br>AACCGTACCGTCAGTCTCAGTCAAAAAATTTTGATATTCAATCTGATAGC<br>AAAGTTGGAACTTGGGGTTATCTGGCCCTTTTTTGTTATCATATTCGTAT<br>ACCCAACAACATATCGGTTCCACCGGTCCTTTTTATATATAAAAGACGAT<br>GTGTAGATGCACTCGAGTATTCTTGGAGAACGTAACTTGTATTGAGCTAG<br>AGTGCTGGATAAAGTACCACATACTAACGTTCTTTTATAGAGCCAAACAT<br>AATTCTTTTGCACTTTCAATATAAGGTACAAGTGAAACACAGGAAAAAAA<br>GAACTAACTCTAAGTA |

TABLE 2-continued

Table of sequences

SEQ ID

NO: 36 the sequence of a portion of the upstream region of the TOR2 gene, ending at the TOR2 start codon ATG. Putative NCR element GATAA(G) boxes are in bold and underlined
AAAGTCGGAGAACCTGACTGAAAATTCATGAATCTCTTCATTTCTATAGC
CTTTCCTCTATGCATTTGTATTATATATTTATTACCGTCATTTTTTACAT
ACTGCTGCATTTTGGCGCCAGTGATAAGTGGCAAACAATTCGACGGAATC
GTGGTAATTATACCACGTTACTCTATAACATCATGATATTGCAATTAATC
AAACATACATTTAATCTTAATGCTATTAGCTTACTACAACTCTTTTCTTT
AAGTTATATCGTATATTTCTTGGGCGATGTCAGAATATTTACCCGGATAT
TCCTTTTTAAGCACTGAATATGTTTGAATAGAGACTGACATATATGGCAG
CAATTAAAATTGGAAGAAATGTAATGACAGTAGGAAAGACCAATTTTTAT
CATCGTGACACCAATCACTTCCTTAACTGAGCTTTACTTGTATTTATTTA
CAGGTAGATTAGGAGCAGTAGAAAGGGAAAATATACCGGGTGCATAAAGA
GCATAGTCATTAAGATcAAATAGTTATCTTTCTCAAAGAGATTTCTGATC
TTTACTTTCCCCATATGAAAAA

REFERENCES

Amrein, T. M., Schonbachler, B., Escher, F., Amado, R., 2004. Acrylamide in gingerbread: critical factors for formation and possible ways for reduction. Journal of Agricultural and Food Chemistry 52, 4282-4288.

Becaiski, A., Lau, B. P. Y., Lewis, D., Seaman, S. W., 2003. Acrylamide in foods: occurrence, sources and modeling. Journal of Agricultural and Food Chemistry 51, 802-808.

Brathen, E., Kita, A., Knutsen, S. H., Wicklund, T., 2005. Addition of glycine reduces the content of acrylamide in cereal and potato products. Journal of Agricultural and Food Chemistry 53, 3259-3264.

Claus, A., Schreiter, P., Weber, A., Graeff, S., Hermann, W., Claupein, W., Schieber, A., Carle, R., 2006. Influence of agronomic factors and extraction rate on the acrylamide contents in yeast-leavened breads. Journal of Agricultural and Food Chemistry 54, 8968-8976.

Claus, A., Mongili, M., Weisz, G., Schieber, A., Carle, R., 2007. Impact of formulation and technological factors on the acrylamide content of wheat bread and bread rolls. Journal of Cereal Science 47, 546-554.

Cooper, T. G., 1982. In The Molecular Biology of the Yeast Saccharomyces: Metabolism and Gene Expression, eds Strathern J. N., Jones E. W., Borach J. (Cold Spring Harbour Laboratory, Cold Spring Harbor, N.Y.), pp 39-99.

Fink, M., Andersson, R., Rosen, J., Aman, P., 2006. Effect of added asparagine and glycine on acrylamide content in yeast-leavened bread. Cereal Chemistry 83, 218-222.

Fredriksson, H., Tallying, J., Rosen, J., Aman, P., 2004. Fermentation reduces free asparagine in dough and acrylamide content in bread. Cereal Chemistry 81, 650-653.

Gietz, R. D., Schiestl, R. N., 1995. Transforming Yeast with DNA. Methods in Molecular and Cellular Biology. Vol 5, #5, 255-269.

Gokmen, V., Senyuva, H. Z., 2007. Acrylamide formation is prevented by divalent cations during the Maillard reaction. Food Chemistry 103, 196-203.

International Agency on Research on Cancer, 1994. IARC Monographs on the Evaluation of Carcinogenic Risks to Humans. Some Industrial Chemicals, vol. 60. Acrylamid, Lyon, France, IARC 1994, pp. 389-433.

Mustafa, A., Andersson, R., Rosen, J., Kamal-Eldin, A., Aman, P., 2005. Factors influencing acylamide content and color in rye crisp bread. Journal of Agricultural and Food Chemistry 53, 5985-5989.

Negritto, M. T., Wu, X., Kuo, T., Chu, S., Bailis, A. M., 1997. Influence of DNA sequence identity on efficiency of targeted gene replacement. Mol Cell Biol 17, 278-286.

Rice, J. M., 2005. The carcinogenicity of acrylamide. Mutation Research 580, 3-20.

Rothstein, R., 1991. Targeting, disruption, replacement, and allele rescue: integrative DNA transformation in yeast. Methods Enzymol. 194, 281-301.

Simon, J. R., Moore, P. D., 1987. Homologous recombination between single-stranded DNA and chromosolmal genes in Saccharomyces cerevisiae. Mol Cell Biochem 7, 2329-2334.

Surdyk, N., Rosen, J., Andersson, R., Aman, P., 2004. Effects of asparagine, fructose and baking conditions on acrylamide content in yeast-leavened wheat bread. Journal of Agricultural and Food Chemistry 52, 2047-2051.

Wilson, K. M., Rimm, E. B., Thompson, K. M., Mucci, L. A., 2006. Dietary acrylamide and cancer risk in humans: a review. Journal fur Verbraucherschutz und Lebensmittelsicherheit 1, 19-27. Cited in Claus, A., Carle, R., Schieber, A., 2008. Acrylamide in cereal products: a review. Journal of Cereal Science 47, 118-133.

Winzeler E A, Shoemaker D D, Astromoff A, Liang H, Anderson K, Andre B, Bangham R, Benito R, Boeke J D, Bussey H, Chu A M, Connelly C, Davis K, Dietrich F, Dow S W, El Bakkoury M, Foury F, Friend S H, Gentalen E, Giaever G, Hegemann J H, Jones T, Laub M, Liao H, Liebundguth N, Lockhart D J, Lucau-Danila A, Lussier M, M'Rabet N, Menard P, Mittmann M, Pai C, Rebischung C, Revuelta J L, Riles L, Roberts C J, Ross-MacDonald P, Scherens B, Snyder M, Sookhai-Mahadeo S, Storms R K, Véronneau S, Voet M, Volckaert G, Ward T R, Wysocki R, Yen G S, Yu K, Zimmermann K, Philippsen P, Johnston M, Davis R W., 1999. Functional characterization of the S. cerevisiae genome by gene deletion and parallel analysis. Science 285, 901-906.

Yaylayan, V. A., Wnorowski, A., Locas Perez, C., 2003. Why asparagine needs carbohydrates to generate acrylamide. Journal of Agricultural and Food Chemistry 51, 1753-1757.

Wickner, R. B., 1994. [URE3] as an altered URE2 protein: evidence for a prion analog in Saccharomyces cerevisiae. Science 264(5158), 566-9.

Wickner, R. B., Masison, D. C., Edskes, H. K., 1995. [PSI] and [URE3] as yeast prions. Yeast 11(16), 1671-85

The invention claimed is:

1. A microorganism transformed with at least two nucleic acid molecules, wherein the two nucleic acid molecules are from at least two of the following:
    (a) a nucleic acid molecule to reduce nitrogen catabolite repression;
    (b) a nucleic acid molecule to overexpress a gene encoding an extracellular protein involved in asparagine degradation; and
    (c) a nucleic acid molecule to overexpress a gene encoding a protein involved in asparagine transport.

2. The microorganism of claim 1, wherein the nucleic acid molecule of (b) encodes a cell-wall asparaginase.

3. The microorganism of claim 2, wherein the asparaginase is encoded by ASP3 or wherein the asparaginase is Asp3p.

4. The microorganism of claim 1, wherein the nucleic acid molecule of (c) encodes an amino acid transporter.

5. The microorganism of claim 4, wherein the amino acid transporter is encoded by GAP1, AGP1, GNP1, DIP5, AGP2 or AGP3 or is Gap1p, Agp1p, Gnp1p, Dip5p Agp2p or Agp3p.

6. The microorganism of claim 1, wherein the nucleic acid molecule of (a) modifies the activity of a regulatory factor of nitrogen catabolite repression.

7. The microorganism of claim 6, wherein the regulatory factor is encoded by URE2, GAT1, TOR1, TOR2, DAL80, GLN3 or GZF3 or is Ure2p, Gat1p, Tor1p, Tor2p, Dal80p, Gln3p or Gzf3p.

8. The microorganism of claim 6, wherein the nucleic acid molecule of (a) comprises a URE2 deletion cassette or encodes.

9. The microorganism of claim 1, wherein the microorganism is yeast.

10. The microorganism of claim 1, wherein at least one of the nucleic acid molecules is operatively linked to a constitutively active promoter.

11. The microorganism of claim 1 transformed with a first and a second nucleic acid molecule, wherein the first nucleic acid molecule encodes Asp3p and the second nucleic acid molecule encodes Gap1p or Gat1p.

12. A method for reducing asparagine during food preparation or processing or for reducing acrylamide in a food product comprising a) transforming a microorganism with at least two nucleic acid molecules, wherein the two nucleic acid molecules are from at least two of the following:
    (i) a nucleic add molecule to reduce nitrogen catabolite repression;
    (ii) a nucleic acid molecule to overexpress a gene encoding an extracellular protein involved in asparagine degradation; and
    (iii) a nucleic acid molecule to overexpress a gene encoding a protein involved in asparagine transport;
b) adding the microorganism to food under the preparation or processing conditions;
wherein the microorganism reduces nitrogen catabolite repression and/or overexpresses the gene encoding the extracellular protein involved in asparagine degradation and/or the gene encoding the protein involved in asparagine transport thereby reducing asparagine during the food preparation or processing or reducing acrylamide in the food product.

13. The method of claim 12, wherein the nucleic acid molecule of a) (ii) encodes a cell-wall asparaginase.

14. The method of claim 13, wherein the asparaginase is encoded by ASP3 or wherein the asparaginase is Asp3p.

15. The method of claim 12, wherein the nucleic acid molecule of a) (iii) encodes an amino acid transporter.

16. The method of claim 15, wherein the amino acid transporter is encoded by GAP1, AGP1, GNP1, DIP5, AGP2 or AGP3 or is Gap1p, Agp1p, Gnp1p, Dip5p Agp2p or Agp3p.

17. The method of claim 12, wherein the nucleic acid of a) (i) encodes a protein that modifies the activity of a regulatory factor of nitrogen catabolite repression in the microorganism.

18. The method of claim 17, wherein the regulatory factor is encoded by URE2, GAT1, TOR1, TOR2, DAL80, GLN3 or GZF3 or is Ure2p, Gat1p, Tor1p, Tor2p, Dal80p, Gln3p or Gzf3p.

19. The method of claim 17, wherein the nucleic acid of a) (i) comprises a URE2 deletion cassette.

20. The method of claim 12, wherein the microorganism is yeast.

21. The method of claim 12, wherein at least one of the nucleic acid molecules is operatively linked to a constitutively active promoter.

22. The method of claim 12, wherein the food product is a vegetable-based food product, a beverage, a bakery product, a grain product, a fruit, legume, dairy or meat product.

\* \* \* \* \*

SEQUENCE LISTING

<160> NUMBER OF SEQ ID NOS: 36

<210> SEQ ID NO 1
<211> LENGTH: 362
<212> TYPE: PRT
<213> ORGANISM: Saccharomyces cerevisiae

<400> SEQUENCE: 1

Met Arg Ser Leu Asn Thr Leu Leu Ser Leu Phe Val Ala Met Ser
1               5                   10                  15

Ser Gly Ala Pro Leu Leu Lys Ile Arg Glu Glu Lys Asn Ser Ser Leu
            20                  25                  30

Pro Ser Ile Lys Ile Phe Gly Thr Gly Thr Ile Ala Ser Lys Gly
        35                  40                  45

Ser Thr Ser Ala Thr Thr Ala Gly Tyr Ser Val Gly Leu Thr Val Asn
    50                  55                  60

Asp Leu Ile Glu Ala Val Pro Ser Leu Ala Glu Lys Ala Asn Leu Asp
65                  70                  75                  80

Tyr Leu Gln Val Ser Asn Val Gly Ser Asn Ser Leu Asn Tyr Thr His
                85                  90                  95

Leu Ile Pro Leu Tyr His Gly Ile Ser Glu Ala Leu Ala Ser Asp Asp
            100                 105                 110

Tyr Ala Gly Ala Val Val Thr His Gly Thr Asp Thr Met Glu Glu Thr
        115                 120                 125

Ala Phe Phe Leu Asp Leu Thr Ile Asn Ser Glu Lys Pro Val Cys Ile
130                 135                 140

Ala Gly Ala Met Arg Pro Ala Thr Ala Thr Ser Ala Asp Gly Pro Met
145                 150                 155                 160

Asn Leu Tyr Gln Ala Val Ser Ile Ala Ala Ser Glu Lys Ser Leu Gly
                165                 170                 175

Arg Gly Thr Met Ile Thr Leu Asn Asp Arg Ile Ala Ser Gly Phe Trp
            180                 185                 190

Thr Thr Lys Met Asn Ala Asn Ser Leu Asp Thr Phe Arg Ala Asp Glu
        195                 200                 205

Gln Gly Tyr Leu Gly Tyr Phe Ser Asn Asp Asp Val Glu Phe Tyr Tyr
    210                 215                 220

Pro Pro Val Lys Pro Asn Gly Trp Gln Phe Phe Asp Ile Ser Asn Leu
225                 230                 235                 240

Thr Asp Pro Ser Glu Ile Pro Glu Val Ile Ile Leu Tyr Ser Tyr Gln
                245                 250                 255

Gly Leu Asn Pro Glu Leu Ile Val Lys Ala Val Lys Asp Leu Gly Ala
            260                 265                 270

Lys Gly Ile Val Leu Ala Gly Ser Gly Ala Gly Ser Trp Thr Ala Thr
        275                 280                 285

Gly Ser Ile Val Asn Glu Gln Leu Tyr Glu Glu Tyr Gly Ile Pro Ile
    290                 295                 300

Val His Ser Arg Arg Thr Ala Asp Gly Thr Val Pro Pro Asp Asp Ala
305                 310                 315                 320

Pro Glu Tyr Ala Ile Gly Ser Gly Tyr Leu Asn Pro Gln Lys Ser Arg
                325                 330                 335

Ile Leu Leu Gln Leu Cys Leu Tyr Ser Gly Tyr Gly Met Asp Gln Ile
            340                 345                 350

Arg Ser Val Phe Ser Gly Val Tyr Gly Gly
        355                 360

<210> SEQ ID NO 2
<211> LENGTH: 1089
<212> TYPE: DNA
<213> ORGANISM: Saccharomyces cerevisiae

<400> SEQUENCE: 2

```
atgagatctt taaataccct tttactttct ctctttgtcg caatgtccag tggtgctcca      60
ctactaaaaa ttcgtgaaga gaagaattct tctttgccat caatcaaaat ttttggtacc    120
ggcggtacta tcgcttccaa gggttcgaca agtgcaacaa cggcgggtta tagcgtggga    180
ttaaccgtaa atgatttaat agaagccgtc ccatctttag ctgagaaggc aaatctggac    240
tatcttcaag tgtctaacgt tggttcaaat tctttaaact atacgcatct gatcccattg    300
tatcacggta tctccgaggc actagcctct gatgactacg ctggtgcggt tgtcactcat    360
gggaccgaca ctatggagga gacagctttc ttcttagatt tgaccataaa ttcagagaag    420
ccagtatgta tcgcaggcgc tatgcgtcca gccactgcca gtctgctga tggcccaatg    480
aatttatatc aagcagtgtc tattgctgct tctgagaaat cactgggtcg tggcacgatg    540
atcactctaa acgatcgtat tgcctctggg ttttggacaa cgaaaatgaa tgccaactct    600
ttagatacat tcagagcgga tgaacaggga tatttaggtt acttttcaaa tgatgacgtg    660
gagttttact acccaccagt caagccaaat ggatggcaat tttttgacat ttccaacctc    720
acagacccct cggaaattcc agaagtcatt attctgtact cctatcaagg cttgaatcct    780
gagctaatag taaaggccgt caaggacctg gcgcaaaag gtatcgtgtt ggcgggttct    840
ggagctggtt cctggactgc tacgggtagt attgtaaacg aacaacttta tgaagagtat    900
ggtataccaa ttgttcacag cagaagaaca gcagatggta cagttcctcc agatgatgcc    960
ccagagtacg ccattggatc tggctaccta aaccctcaaa aatcgcgtat tttgctacaa   1020
ttatgtttgt actccggcta cggcatggat cagattaggt ctgttttttc tggcgtctac   1080
ggtggttaa                                                             1089
```

<210> SEQ ID NO 3
<211> LENGTH: 602
<212> TYPE: PRT
<213> ORGANISM: Saccharomyces cerevisiae

<400> SEQUENCE: 3

```
Met Ser Asn Thr Ser Ser Tyr Glu Lys Asn Asn Pro Asp Asn Leu Lys
1               5                   10                  15

His Asn Gly Ile Thr Ile Asp Ser Glu Phe Leu Thr Gln Glu Pro Ile
            20                  25                  30

Thr Ile Pro Ser Asn Gly Ser Ala Val Ser Ile Asp Glu Thr Gly Ser
        35                  40                  45

Gly Ser Lys Trp Gln Asp Phe Lys Asp Ser Phe Lys Arg Val Lys Pro
    50                  55                  60

Ile Glu Val Asp Pro Asn Leu Ser Glu Ala Lys Val Ala Ile Ile
65                  70                  75                  80

Thr Ala Gln Thr Pro Leu Lys His His Leu Lys Asn Arg His Leu Gln
                85                  90                  95

Met Ile Ala Ile Gly Gly Ala Ile Gly Thr Gly Leu Leu Val Gly Ser
            100                 105                 110

Gly Thr Ala Leu Arg Thr Gly Gly Pro Ala Ser Leu Leu Ile Gly Trp
        115                 120                 125

Gly Ser Thr Gly Thr Met Ile Tyr Ala Met Val Met Ala Leu Gly Glu
```

-continued

```
            130                 135                 140
Leu Ala Val Ile Phe Pro Ile Ser Gly Gly Phe Thr Thr Tyr Ala Thr
145                 150                 155                 160

Arg Phe Ile Asp Glu Ser Phe Gly Tyr Ala Asn Asn Phe Asn Tyr Met
                165                 170                 175

Leu Gln Trp Leu Val Val Leu Pro Leu Glu Ile Val Ser Ala Ser Ile
            180                 185                 190

Thr Val Asn Phe Trp Gly Thr Asp Pro Lys Tyr Arg Asp Gly Phe Val
        195                 200                 205

Ala Leu Phe Trp Leu Ala Ile Val Ile Asn Met Phe Gly Val Lys
    210                 215                 220

Gly Tyr Gly Glu Ala Glu Phe Val Phe Ser Phe Ile Lys Val Ile Thr
225                 230                 235                 240

Val Val Gly Phe Ile Ile Leu Gly Ile Ile Leu Asn Cys Gly Gly Gly
                245                 250                 255

Pro Thr Gly Gly Tyr Ile Gly Gly Lys Tyr Trp His Asp Pro Gly Ala
                260                 265                 270

Phe Ala Gly Asp Thr Pro Gly Ala Lys Phe Lys Gly Val Cys Ser Val
            275                 280                 285

Phe Val Thr Ala Ala Phe Ser Phe Ala Gly Ser Glu Leu Val Gly Leu
        290                 295                 300

Ala Ala Ser Glu Ser Val Glu Pro Arg Lys Ser Val Pro Lys Ala Ala
305                 310                 315                 320

Lys Gln Val Phe Trp Arg Ile Thr Leu Phe Tyr Ile Leu Ser Leu Leu
                325                 330                 335

Met Ile Gly Leu Leu Val Pro Tyr Asn Asp Lys Ser Leu Ile Gly Ala
                340                 345                 350

Ser Ser Val Asp Ala Ala Ser Pro Phe Val Ile Ala Ile Lys Thr
        355                 360                 365

His Gly Ile Lys Gly Leu Pro Ser Val Asn Val Val Ile Leu Ile
    370                 375                 380

Ala Val Leu Ser Val Gly Asn Ser Ala Ile Tyr Ala Cys Ser Arg Thr
385                 390                 395                 400

Met Val Ala Leu Ala Glu Gln Arg Phe Leu Pro Glu Ile Phe Ser Tyr
                405                 410                 415

Val Asp Arg Lys Gly Arg Pro Leu Val Gly Ile Ala Val Thr Ser Ala
                420                 425                 430

Phe Gly Leu Ile Ala Phe Val Ala Ala Ser Lys Lys Glu Gly Glu Val
            435                 440                 445

Phe Asn Trp Leu Leu Ala Leu Ser Gly Leu Ser Ser Leu Phe Thr Trp
    450                 455                 460

Gly Gly Ile Cys Ile Cys His Ile Arg Phe Arg Lys Ala Leu Ala Ala
465                 470                 475                 480

Gln Gly Arg Gly Leu Asp Glu Leu Ser Phe Lys Ser Pro Thr Gly Val
                485                 490                 495

Trp Gly Ser Tyr Trp Gly Leu Phe Met Val Ile Met Phe Ile Ala
            500                 505                 510

Gln Phe Tyr Val Ala Val Phe Pro Val Gly Asp Ser Pro Ser Ala Glu
        515                 520                 525

Gly Phe Phe Glu Ala Tyr Leu Ser Phe Pro Leu Val Met Val Met Tyr
    530                 535                 540

Ile Gly His Lys Ile Tyr Lys Arg Asn Trp Lys Leu Phe Ile Pro Ala
545                 550                 555                 560
```

```
Glu Lys Met Asp Ile Asp Thr Gly Arg Arg Glu Val Asp Leu Asp Leu
            565                 570                 575

Leu Lys Gln Glu Ile Ala Glu Glu Lys Ala Ile Met Ala Thr Lys Pro
        580                 585                 590

Arg Trp Tyr Arg Ile Trp Asn Phe Trp Cys
        595                 600

<210> SEQ ID NO 4
<211> LENGTH: 1809
<212> TYPE: DNA
<213> ORGANISM: Saccharomyces cerevisiae

<400> SEQUENCE: 4
atgagtaata cttcttcgta cgagaagaat aatccagata atctgaaaca caatggtatt     60
accatagatt ctgagtttct aactcaggag ccaataacca ttccctcaaa tggctccgct    120
gtttctattg acgaaacagg ttcagggtcc aaatggcaag actttaaaga ttctttcaaa    180
agggtaaaac ctattgaagt tgatcctaat ctttcagaag ctgaaaaagt ggctatcatc    240
actgcccaaa ctccattgaa gcaccacttg aagaatagac atttgcaaat gattgccatc    300
ggtggtgcca tcggtactgg tctgctggtt gggtcaggta ctgcactaag aacaggtggt    360
cccgcttcgc tactgattgg atggggtct acaggtacca tgatttacgc tatggttatg    420
gctctgggtg agttggctgt tatcttccct atttcgggtg ggtcaccac gtacgctacc    480 agatttattg atgagtcctt tggttacgct aataatttca attatatgtt acaatggttg    540
gttgtgctac cattggaaat tgtctctgca tctattactg taaatttctg gggtacagat    600
ccaaagtata gagatgggtt tgttgcgttg ttttggcttg caattgttat catcaatatg    660
tttggtgtca aaggttatgg tgaagcagaa ttcgtctttt catttatcaa ggtcatcact    720
gttgttgggt tcatcatctt aggtatcatt ctaaactgtg gtggtggtcc aacaggtggt    780
tacattgggg gcaagtactg gcatgatcct ggtgcctttg ctggtgacac tccaggtgct    840
aaattcaaag gtgtttgttc tgtcttcgtc accgctgcct tttcttttgc cggttcagaa    900
ttggttggtc ttgctgccag tgaatccgta gagcctagaa agtccgttcc taaggctgct    960
aaacaagttt tctggagaat caccctattt tatattctgt cgctattaat gattggtctt   1020
ttagtcccat acaacgataa aagtttgatt ggtgcctcct ctgtggatgc tgctgcttca   1080
cccttcgtca ttgccattaa gactcacggt atcaagggtt gccaagtgt tgtcaacgtc   1140 gttatcttga ttgccgtgtt atctgtcggt aactctgcca tttatgcatg ttccagaaca   1200
atggttgccc tagctgaaca gagatttctg ccagaaatct tttcctacgt tgaccgtaag   1260
ggtagaccat ggtgggaat tgctgtcaca tctgcattcg gtcttattgc gtttgttgcc   1320
gcctccaaaa aggaaggtga agttttcaac tggttactag ccttgtctgg ttgtcatct   1380 ctattcacat ggggtggtat ctgtatttgt cacattcgtt tcagaaaggc attggccgcc   1440
caaggaagag gcttggatga attgtctttc aagtctccta ccggtgtttg gggttcctac   1500
tgggggttat ttatggttat tattatgttc attgcccaat tctacgttgc tgtattcccc   1560
gtgggagatt ctccaagtgc ggaaggtttc ttcgaagctt atctatcctt cccacttgtt   1620
atggttatgt acatcggaca aagatctat aagaggaatt ggaagctttt catcccagca   1680
gaaaagatgg acattgatac gggtagaaga gaagtcgatt tagatttgtt gaaacaagaa   1740
attgcagaag aaaaggcaat tatggccaca aagccaagat ggtatagaat ctggaatttc   1800
tggtgttaa                                                           1809
```

<210> SEQ ID NO 5
<211> LENGTH: 558
<212> TYPE: PRT
<213> ORGANISM: Saccharomyces cerevisiae

<400> SEQUENCE: 5

```
Met Ala Val Leu Asn Leu Lys Arg Glu Thr Val Asp Ile Glu Glu Thr
1               5                   10                  15

Ala Lys Lys Asp Ile Lys Pro Tyr Phe Ala Ser Asn Val Glu Ala Val
            20                  25                  30

Asp Ile Asp Glu Asp Pro Asp Val Ser Arg Tyr Asp Pro Gln Thr Gly
        35                  40                  45

Val Lys Arg Ala Leu Lys Asn Arg His Ile Ser Leu Leu Ala Leu Gly
    50                  55                  60

Gly Val Ile Gly Pro Gly Cys Leu Val Gly Ala Gly Asn Ala Leu Asn
65                  70                  75                  80

Lys Gly Gly Pro Leu Ala Leu Leu Leu Gly Phe Ser Ile Ile Gly Ile
                85                  90                  95

Ile Ala Phe Ser Val Met Glu Ser Ile Gly Glu Met Ile Thr Leu Tyr
            100                 105                 110

Pro Ser Gly Gly Gly Phe Thr Thr Leu Ala Arg Arg Phe His Ser Asp
        115                 120                 125

Ala Leu Pro Ala Val Cys Gly Tyr Ala Tyr Val Val Val Phe Phe Ala
    130                 135                 140

Val Leu Ala Asn Glu Tyr Asn Thr Leu Ser Ser Ile Leu Gln Phe Trp
145                 150                 155                 160

Gly Pro Gln Val Pro Leu Tyr Gly Tyr Ile Leu Ile Phe Trp Phe Ala
                165                 170                 175

Phe Glu Ile Phe Gln Leu Val Gly Val Gly Leu Phe Gly Glu Thr Glu
            180                 185                 190

Tyr Trp Leu Ala Trp Leu Lys Ile Val Gly Leu Val Ala Tyr Tyr Ile
        195                 200                 205

Phe Ser Ile Val Tyr Ile Ser Gly Asp Ile Arg Asn Arg Pro Ala Phe
    210                 215                 220

Gly Phe His Tyr Trp Asn Ser Pro Gly Ala Leu Ser His Gly Phe Lys
225                 230                 235                 240

Gly Ile Ala Ile Val Phe Val Phe Cys Ser Thr Phe Tyr Ser Gly Thr
                245                 250                 255

Glu Ser Val Ala Leu Ala Ala Thr Glu Ser Lys Asn Pro Gly Lys Ala
            260                 265                 270

Val Pro Leu Ala Val Arg Gln Thr Leu Trp Arg Ile Leu Val Val Tyr
        275                 280                 285

Ile Gly Ile Ala Val Phe Tyr Gly Ala Thr Val Pro Phe Asp Asp Pro
    290                 295                 300

Asn Leu Ser Ala Ser Thr Lys Val Leu Lys Ser Pro Ile Ala Ile Ala
305                 310                 315                 320

Ile Ser Arg Ala Gly Trp Ala Gly Gly Ala His Leu Val Asn Ala Phe
                325                 330                 335

Ile Leu Ile Thr Cys Ile Ser Ala Ile Asn Gly Ser Leu Tyr Ile Gly
            340                 345                 350

Ser Arg Thr Leu Thr His Leu Ala His Glu Gly Leu Ala Pro Lys Ile
        355                 360                 365

Leu Ala Trp Thr Asp Arg Arg Gly Val Pro Ile Pro Ala Ile Thr Val
```

```
                370              375              380
Phe Asn Ala Leu Gly Leu Ile Ser Leu Met Asn Val Ser Val Gly Ala
385              390              395              400

Ala Asn Ala Tyr Ser Tyr Ile Val Asn Leu Ser Gly Val Gly Val Phe
                405              410              415

Ile Val Trp Gly Val Ile Ser Tyr Thr His Leu Arg Ile Arg Lys Ala
            420              425              430

Trp Val Ala Gln Gly Arg Ser Ile Glu Glu Leu Pro Tyr Glu Ala Leu
                435              440              445

Phe Tyr Pro Trp Thr Pro Val Leu Ser Leu Ala Ala Asn Ile Phe Leu
450              455              460

Ala Leu Ile Gln Gly Trp Ser Tyr Phe Val Pro Phe Asp Ala Gly Asn
465              470              475              480

Phe Val Asp Ala Tyr Ile Leu Leu Pro Val Gly Ile Leu Leu Tyr Ile
                485              490              495

Gly Ile Cys Val Phe Lys Ser Asn His Phe Arg Thr Val Asp Leu Arg
                500              505              510

Ser Ile Asn Leu Asp Glu Gly Arg Arg Lys Asp Met Glu Ala Asp Leu
            515              520              525

Ser Asp Gln Glu Ser Ser Leu Ala Ser Ser Glu Thr Met Lys Asp Tyr
530              535              540

Lys Ser Ala Thr Phe Phe Arg Tyr Leu Ser Asn Ile Phe Thr
545              550              555

<210> SEQ ID NO 6
<211> LENGTH: 1677
<212> TYPE: DNA
<213> ORGANISM: Saccharomyces cerevisiae

<400> SEQUENCE: 6
atggcagtcc ttaacttgaa acgtgaaact gtcgacattg aagagacagc gaagaaagat      60
atcaaacctt attttgcttc gaatgttgaa gcggttgata ttgatgaaga tcccgatgtt     120
tcaagatacg atccccagac aggagtgaaa agggcgctca aaaataggca tatctcattg     180
ctagctttgg gtggtgttat tggcccaggt tgtcttgttg gtgcaggaaa cgcactcaac     240
aaaggtgggc cacttgcttt acttttaggc tttagtatta ttgggatcat tgctttctca     300
gtgatggaat ctataggtga aatgatcact ttatatccct cgggcggtgg atttaccact     360
ttggctcgaa gatttcatag cgatgcactg cctgcagttt gcggttatgc ttacgttgtt     420
gtgttcttcg cagtttggc aaatgagtac aacactctct cctccatact acagttttgg     480
ggcccacaag tccctctata tggttacatc ttgatattct ggtttgcatt tgaaattttt     540
caactagttg gcgttggtct ttttggtgaa acggagtact ggcttgcttg gttgaaaata     600
gtaggattag tagcctatta tattttctcg attgtttaca tatctgggga tattaggaat     660
agaccagctt tcggctttca ttattggaat agtccaggtg cattatcaca tgggtttaag     720
ggaattgcga tagtgtttgt gttttgttcg accttctatt ctggaacgga atcagttgcc     780
ttggctgcaa cggaatcaaa aaaccctggg aaggctgtgc cacttgctgt tcgacaaact     840
ctgtggagaa tttagttgt ttatattgga attgctgttt tctatggagc aactgttccg     900
tttgacgacc caaacctctc tgcttctacc aaagtcctaa atctcccat gctatcgcc     960 atatctcgtg ctggttgggc cggcggagct catctggtta atgccttcat tttgataact    1020
tgcatctccg ccattaatgg gtcactttat ataggagca gaaccttgac gcatttagca    1080
```

```
catgaaggcc tagctccaaa aattctggct tggaccgatc gaagaggcgt tcccatcccc  1140
gccatcactg ttttcaacgc cttgggccta atatcattga tgaatgtgag cgttggagct  1200
gcaaatgcgt actcttatat cgttaatctt tctggtgttg gcgtctttat tgtctggggt  1260
gtaataagtt atacgcacct gagaataagg aaggcgtggg ttgctcaagg aagatccata  1320
gaagagctac cttatgaagc gctattttat ccgtggacgc cagtacttag tctggccgct  1380
aacatttttc tagcactcat ccaaggatgg agctatttcg tacctttga tgcgggcaat  1440 tttgttgatg cttatatcct tctgcctgtt ggaattttat tgtatattgg catatgtgtt  1500
tttaagagca atcattttag aactgttgat ttgcggtcaa tcaacctaga cgaaggacga  1560
agaaaagaca tggaggctga tctttctgat caagagagta gcttagcatc ttcggaaacg  1620
atgaaggatt ataaaagtgc aacttttttc agatacctca gcaacatttt cacctga     1677
```

<210> SEQ ID NO 7
<211> LENGTH: 596
<212> TYPE: PRT
<213> ORGANISM: Saccharomyces cerevisiae

<400> SEQUENCE: 7

```
Met Thr Lys Glu Arg Met Thr Ile Asp Tyr Glu Asn Asp Gly Asp Phe
 1               5                  10                  15

Glu Tyr Asp Lys Asn Lys Tyr Lys Thr Ile Thr Arg Ile Lys Ser
                20                  25                  30

Ile Glu Pro Ser Glu Gly Trp Leu Glu Pro Ser Gly Ser Val Gly His
            35                  40                  45

Ile Asn Thr Ile Pro Glu Ala Gly Asp Val His Val Asp Glu His Glu
        50                  55                  60

Asp Arg Gly Ser Ser Ile Asp Asp Ser Arg Thr Tyr Leu Leu Tyr
 65                 70                  75                  80

Phe Thr Glu Thr Arg Arg Lys Leu Glu Asn Arg His Val Gln Leu Ile
                85                  90                  95

Ala Ile Ser Gly Val Ile Gly Thr Ala Leu Phe Val Ala Ile Gly Lys
           100                 105                 110

Ala Leu Tyr Arg Gly Gly Pro Ala Ser Leu Leu Leu Ala Phe Ala Leu
           115                 120                 125

Trp Cys Val Pro Ile Leu Cys Ile Thr Val Ser Thr Ala Glu Met Val
130                 135                 140

Cys Phe Phe Pro Val Ser Ser Pro Phe Leu Arg Leu Ala Thr Lys Cys
145                 150                 155                 160

Val Asp Asp Ser Leu Ala Val Met Ala Ser Trp Asn Phe Trp Phe Leu
                165                 170                 175

Glu Cys Val Gln Ile Pro Phe Glu Ile Val Ser Val Asn Thr Ile Ile
           180                 185                 190

His Tyr Trp Arg Asp Asp Tyr Ser Ala Gly Ile Pro Leu Ala Val Gln
           195                 200                 205

Val Val Leu Tyr Leu Leu Ile Ser Ile Cys Ala Val Lys Tyr Tyr Gly
           210                 215                 220

Glu Met Glu Phe Trp Leu Ala Ser Phe Lys Ile Ile Leu Ala Leu Gly
225                 230                 235                 240

Leu Phe Thr Phe Thr Phe Ile Thr Met Leu Gly Gly Asn Pro Glu His
                245                 250                 255

Asp Arg Tyr Gly Phe Arg Asn Tyr Gly Glu Ser Pro Phe Lys Lys Tyr
           260                 265                 270
```

Phe Pro Asp Gly Asn Asp Val Gly Lys Ser Ser Gly Tyr Phe Gln Gly
            275                 280                 285

Phe Leu Ala Cys Leu Ile Gln Ala Ser Phe Thr Ile Ala Gly Gly Glu
        290                 295                 300

Tyr Ile Ser Met Leu Ala Gly Glu Val Lys Arg Pro Arg Lys Val Leu
305                 310                 315                 320

Pro Lys Ala Phe Lys Gln Val Phe Val Arg Leu Thr Phe Leu Phe Leu
                325                 330                 335

Gly Ser Cys Leu Cys Val Gly Ile Val Cys Ser Pro Asn Asp Pro Asp
            340                 345                 350

Leu Thr Ala Ala Ile Asn Glu Ala Arg Pro Gly Ala Gly Ser Ser Pro
        355                 360                 365

Tyr Val Ile Ala Met Asn Asn Leu Lys Ile Arg Ile Leu Pro Asp Ile
370                 375                 380

Val Asn Ile Ala Leu Ile Thr Ala Ala Phe Ser Ala Gly Asn Ala Tyr
385                 390                 395                 400

Thr Tyr Cys Ser Ser Arg Thr Phe Tyr Gly Met Ala Leu Asp Gly Tyr
                405                 410                 415

Ala Pro Lys Ile Phe Thr Arg Cys Asn Arg His Gly Val Pro Ile Tyr
            420                 425                 430

Ser Val Ala Ile Ser Leu Val Trp Ala Leu Val Ser Leu Leu Gln Leu
        435                 440                 445

Asn Ser Asn Ser Ala Val Val Leu Asn Trp Leu Ile Asn Leu Ile Thr
450                 455                 460

Ala Ser Gln Leu Ile Asn Phe Val Val Leu Cys Ile Val Tyr Leu Phe
465                 470                 475                 480

Phe Arg Arg Ala Tyr His Val Gln Gln Asp Ser Leu Pro Lys Leu Pro
                485                 490                 495

Phe Arg Ser Trp Gly Gln Pro Tyr Thr Ala Ile Ile Gly Leu Val Ser
            500                 505                 510

Cys Ser Ala Met Ile Leu Ile Gln Gly Tyr Thr Val Phe Phe Pro Lys
        515                 520                 525

Leu Trp Asn Thr Gln Asp Phe Leu Phe Ser Tyr Leu Met Val Phe Ile
530                 535                 540

Asn Ile Gly Ile Tyr Val Gly Tyr Lys Phe Ile Trp Lys Arg Gly Lys
545                 550                 555                 560

Asp His Phe Lys Asn Pro His Glu Ile Asp Phe Ser Lys Glu Leu Thr
                565                 570                 575

Glu Ile Glu Asn His Glu Ile Glu Ser Ser Phe Glu Lys Phe Gln Tyr
            580                 585                 590

Tyr Ser Lys Ala
        595

<210> SEQ ID NO 8
<211> LENGTH: 1791
<212> TYPE: DNA
<213> ORGANISM: Saccharomyces cerevisiae

<400> SEQUENCE: 8
atgacaaagg aacgtatgac catcgactac gaaaatgacg gtgatttgta gtacgataag      60
aataaataca agacaataac cactcgaata aagagtatcg aacctagtga gggatggttg     120
gaaccttctg ggtcagtggg tcacataaac acgatacccg aagcgggcga tgttcacgtg     180
gatgaacatg aggatagagg gtcttctatt gatgatgact caaggactta cctgctatat     240

-continued

```
ttcacagaaa ctcgacgtaa actagaaaac aggcacgtcc agttgattgc tatttccggt      300
gtcattggta cggcgctatt cgtgcgatc ggaaaagctt tataccgtgg agggcccgcc       360
tctttattat tggcatttgc tctttggtgt gttccaatac tttgcattac tgtgtctaca     420
gcggaaatgg tctgcttttt ccctgtaagt tccccctttt tgagattagc aacgaagtgc     480
gttgacgatt cattggctgt catggctagc tggaatttct ggtttcttga atgcgtacag     540
atcccttcg agattgtttc tgttaataca attatacatt attggagaga tgattattca      600
gctggtattc cgctcgccgt tcaagtagtt ttgtatctgc ttatttccat ttgtgcagtc     660
aaatattacg gtgaaatgga attttggttg cttctttca aaattatcct tgcactcggc      720
ctatttacat tcacgttcat taccatgttg ggtggaaatc ctgaacatga tcgttacggg    780
tttcgtaatt atggtgaaag tccattcaag aaatactttc ccgatggcaa tgatgtgggg    840
aagtcttcgg gctacttcca ggggtttctc gcttgcttga ttcaggcatc gtttaccata    900
gctggtggcg agtatatttc tatgttagcg ggagaggtca aacgaccaag aaaagtatta    960
cccaaggcgt ttaagcaggt gtttgtgaga ttaacatttt tgttttagg gagttgtctg     1020
tgtgttggga ttgtttgttc gccaaatgat cctgacttga cagcagcaat taatgaagca    1080
aggcctggcc ccgggtcttc acttatgtc attgcaatga ataatctgaa aattagaata    1140
ttacctgaca ttgttaatat agctttgatt acagccgcct tttctgctgg taacgcttac   1200
acttattgct catccagaac attttatggt atggcattag atggctacgc gccaaaaatc   1260
ttcactagat gcaataggca tggtgtgccc atttactctg tggccatatc tttggtatgg   1320
gctttagtga gccttttgca actgaattct aatagtgcgg tcgtattgaa ttggttaatt   1380
aacttgatta ctgcctctca attgattaat tttgtcgtcc tttgtatcgt ctatttattt   1440
ttcagaaggg cttaccacgt ccaacaagat tcgttaccca agttgccatt ccgttcgtgg   1500
ggtcaaccat acactgctat atcggcctt gtttcatgtt ccgcaatgat tttaatacag   1560
ggctacaccg ttttctttcc caaattatgg aacacacaag attttttgtt ttcgtattta   1620
atggtgttta tcaacatcgg tatatatgtg gctacaaat ttatttggaa acgtggtaaa    1680
gatcacttca aaaacccaca tgaaattgac ttttctaaag agctaacaga aattgaaaac   1740
catgagattg aaagctcctt cgaaaaattt caatattata gcaaagcata a             1791
```

<210> SEQ ID NO 9
<211> LENGTH: 663
<212> TYPE: PRT
<213> ORGANISM: Saccharomyces cerevisiae

<400> SEQUENCE: 9

```
Met Thr Leu Gly Asn Arg Arg His Gly Arg Asn Asn Glu Gly Ser Ser
1               5                   10                  15

Asn Met Asn Met Asn Arg Asn Asp Leu Asp Asp Val Ser His Tyr Glu
            20                  25                  30

Met Lys Glu Ile Gln Pro Lys Glu Lys Gln Ile Gly Ser Ile Glu Pro
        35                  40                  45

Glu Asn Glu Val Glu Tyr Phe Glu Lys Thr Val Glu Lys Thr Ile Glu
    50                  55                  60

Asn Met Glu Tyr Glu Gly Glu His His Ala Ser Tyr Leu Arg Arg Phe
65                  70                  75                  80

Ile Asp Ser Phe Arg Arg Ala Glu Gly Ser His Ala Asn Ser Pro Asp
                85                  90                  95

Ser Ser Asn Ser Asn Gly Thr Thr Pro Ile Ser Thr Lys Asp Ser Ser
```

```
            100                 105                 110
Ser Gln Leu Asp Asn Glu Leu Asn Arg Lys Ser Tyr Ile Thr Val
            115                 120                 125

Asp Gly Ile Lys Gln Ser Pro Gln Glu Gln Glu Lys Gln Glu Asn
            130                 135                 140

Leu Lys Lys Ser Ile Lys Pro Arg His Thr Val Met Met Ser Leu Gly
145                 150                 155                 160

Thr Gly Ile Gly Thr Gly Leu Leu Val Gly Asn Ser Lys Val Leu Asn
                    165                 170                 175

Asn Ala Gly Pro Gly Gly Leu Ile Ile Gly Tyr Ala Ile Met Gly Ser
                    180                 185                 190

Cys Val Tyr Cys Ile Ile Gln Ala Cys Gly Glu Leu Ala Val Ile Tyr
            195                 200                 205

Ser Asp Leu Ile Gly Gly Phe Asn Thr Tyr Pro Leu Phe Leu Val Asp
            210                 215                 220

Pro Ala Leu Gly Phe Ser Val Ala Trp Leu Phe Cys Leu Gln Trp Leu
225                 230                 235                 240

Cys Val Cys Pro Leu Glu Leu Val Thr Ala Ser Met Thr Ile Lys Tyr
                    245                 250                 255

Trp Thr Thr Ser Val Asn Pro Asp Val Phe Val Ile Phe Tyr Val
            260                 265                 270

Leu Ile Val Val Ile Asn Val Phe Gly Ala Lys Gly Tyr Ala Glu Ala
                    275                 280                 285

Asp Phe Phe Phe Asn Cys Cys Lys Ile Leu Met Ile Val Gly Phe Phe
            290                 295                 300

Ile Leu Ala Ile Ile Ile Asp Cys Gly Gly Ala Gly Thr Asp Gly Tyr
305                 310                 315                 320

Ile Gly Ser Lys Tyr Trp Arg Asp Pro Gly Ala Phe Arg Gly Asp Thr
                    325                 330                 335

Pro Ile Gln Arg Phe Lys Gly Val Val Ala Thr Phe Val Thr Ala Ala
                    340                 345                 350

Phe Ala Phe Gly Met Ser Glu Gln Leu Ala Met Thr Ala Ser Glu Gln
            355                 360                 365

Ser Asn Pro Arg Lys Ala Ile Pro Ser Ala Ala Lys Lys Met Ile Tyr
            370                 375                 380

Arg Ile Leu Phe Val Phe Leu Ala Ser Leu Thr Leu Val Gly Phe Leu
385                 390                 395                 400

Val Pro Tyr Thr Ser Asp Gln Leu Leu Gly Ala Ala Gly Ser Ala Thr
                    405                 410                 415

Lys Ala Ser Pro Tyr Val Ile Ala Val Ser Ser His Gly Val Arg Val
                    420                 425                 430

Val Pro His Phe Ile Asn Ala Val Ile Leu Leu Ser Val Leu Ser Val
            435                 440                 445

Ala Asn Gly Ala Phe Tyr Thr Ser Ser Arg Ile Leu Met Ser Leu Ala
            450                 455                 460

Lys Gln Gly Asn Ala Pro Lys Cys Phe Asp Tyr Ile Asp Arg Glu Gly
465                 470                 475                 480

Arg Pro Ala Ala Ala Met Leu Val Ser Ala Leu Phe Gly Val Ile Ala
                    485                 490                 495

Phe Cys Ala Ser Ser Lys Lys Glu Glu Asp Val Phe Thr Trp Leu Leu
            500                 505                 510

Ala Ile Ser Gly Leu Ser Gln Leu Phe Thr Trp Ile Thr Ile Cys Leu
            515                 520                 525
```

```
Ser His Ile Arg Phe Arg Arg Ala Met Lys Val Gln Gly Arg Ser Leu
        530                 535                 540

Gly Glu Val Gly Tyr Lys Ser Gln Val Gly Val Trp Gly Ser Ala Tyr
545                 550                 555                 560

Ala Val Leu Met Met Val Leu Ala Leu Ile Ala Gln Phe Trp Val Ala
                565                 570                 575

Ile Ala Pro Ile Gly Gly Gly Lys Leu Ser Ala Gln Ser Phe Phe
            580                 585                 590

Glu Asn Tyr Leu Ala Met Pro Ile Trp Ile Ala Leu Tyr Ile Phe Tyr
            595                 600                 605

Lys Val Trp Lys Lys Asp Trp Ser Leu Phe Ile Pro Ala Asp Lys Val
        610                 615                 620

Asp Leu Val Ser His Arg Asn Ile Phe Asp Glu Glu Leu Leu Lys Gln
625                 630                 635                 640

Glu Asp Glu Glu Tyr Lys Glu Arg Leu Arg Asn Gly Pro Tyr Trp Lys
                645                 650                 655

Arg Val Leu Asp Phe Trp Cys
            660

<210> SEQ ID NO 10
<211> LENGTH: 1992
<212> TYPE: DNA
<213> ORGANISM: Saccharomyces cerevisiae

<400> SEQUENCE: 10
atgacgcttg gtaatagacg ccatgggcgg aataatgagg gaagctctaa tatgaatatg    60
aatcgtaacg accttgacga tgtttcccat tacgagatga aggaaatata accaaaggaa   120
aaacaaattg ctctataga accggaaaat gaagtagaat attttgaaaa acagtggaa    180 aaaccattg aaatatgga atatgaaggt gaacatcatg catcttactt acggaggttc    240
attgactcgt ttagaagagc ggaaggctcg catgcaaatt ccccagactc gagcaactct    300
aatgggacta ctcctatatc cacaaaagat tccagctctc aattggacaa tgagttgaat    360
cggaagagct catacatcac tgttgatggt attaaacagt caccacaaga caagaacag    420 aaacaagaaa atttgaaaaa gagtataaag ccccgtcata cggtgatgat gtccctaggg    480
actggtattg gtactggttt gctggtcggt aactccaaag ttttgaacaa tgcaggtccg    540 ggtggttttga tcattggtta tgctattatg ggtagttgtg tttactgtat tattcaagct    600
tgtggtgaat tagcggttat atacagtgat ttgattggtg gatttaatac atatcctttg    660
tttttggtcg accctgcact tggcttttct gttgcttggc ttttttgctt acaatggcta    720 tgtgttttgtc ctctagaatt ggtcactgca tccatgacta tcaaatatatg gacgacatct    780 gtgaacccgg atgttttcgt tgttatcttc tacgtactaa tcgttgttat caacgttttt    840
ggagctaagg ttatgcaga ggcagatttc ttcttcaatt gttgtaaaat tctgatgata    900
gttggatttt tcattctcgc cattattatt gattgtggtg gtgcaggtac cgatggttac    960
ataggtagca atattggcg tgatcccgga gccttccgtg gtgatacacc catccagagg   1020
ttcaaaggtg tcgttgccac atttgtcaca gcagcgttcg cctttggtat gagtgaacag   1080
ctggctatga ctgccagtga acaatccaat ccaagaaagg ctattccatc ggcggcaaag   1140
aaaatgattt tagaattct gtttgtgttc ttggcgtctt taacgttagt tggtttcctt   1200
gtaccttaca cctcagatca attgctaggg ccgcaggtt cagccactaa agcgtcgccc   1260
tacgtcatcg ctgtctcctc tcatggtgtt cgtgtggttc ctcatttcat aaacgctgtc   1320
```

| | |
|---|---|
| atcctgttgt ctgttctttc cgttgctaac ggtgccttct ataccagttc tcgtattttg | 1380 |
| atgtcgttgg ccaaacaagg taatgcaccc aaatgtttcg attacatcga tagggaaggt | 1440 |
| agacctgctg ctgctatgct tgtcagtgca ttatttggtg tcattgcatt ctgtgcctca | 1500 |
| tctaaaaagg aagaggacgt tttcacctgg ttgttagcaa tctccggttt gtctcaatta | 1560 |
| ttcacgtgga ttaccatttg tttgtctcac attaggttta aagagctat gaaagtgcaa | 1620 |
| ggaaggtcct taggagaggt tggttataaa tctcaagtcg gtgtctgggg gtcggcttac | 1680 |
| gctgtcctta tgatggtgtt agctttaatc gcccaatttt gggttgccat tgccccaatt | 1740 |
| ggtggaggag gtaagttaag tgcccaatca ttttttgaga attatttggc tatgccaatc | 1800 |
| tggattgctt tatacatctt ttacaaagtt tggaaaaaag attggagttt attcattccc | 1860 |
| gctgataaag tagacttagt ttctcataga aacatctttg atgaagaatt attaaaacaa | 1920 |
| gaagatgaag aatataaaga gagattaaga aacggaccat actggaaaag agttcttgat | 1980 |
| ttctggtgtt aa | 1992 |

<210> SEQ ID NO 11
<211> LENGTH: 633
<212> TYPE: PRT
<213> ORGANISM: Saccharomyces cerevisiae

<400> SEQUENCE: 11

```
Met Ser Ser Ser Lys Ser Leu Tyr Glu Leu Lys Asp Leu Lys Asn Ser
1               5                   10                  15

Ser Thr Glu Ile His Ala Thr Gly Gln Asp Asn Glu Ile Glu Tyr Phe
            20                  25                  30

Glu Thr Gly Ser Asn Asp Arg Pro Ser Ser Gln Pro His Leu Gly Tyr
        35                  40                  45

Glu Gln His Asn Thr Ser Ala Val Arg Arg Phe Phe Asp Ser Phe Lys
    50                  55                  60

Arg Ala Asp Gln Gly Pro Gln Asp Glu Val Glu Ala Thr Gln Met Asn
65                  70                  75                  80

Asp Leu Thr Ser Ala Ile Ser Pro Ser Ser Arg Gln Ala Gln Glu Leu
                85                  90                  95

Glu Lys Asn Glu Ser Ser Asp Asn Ile Gly Ala Asn Thr Gly His Lys
            100                 105                 110

Ser Asp Ser Leu Lys Lys Thr Ile Gln Pro Arg His Val Leu Met Ile
        115                 120                 125

Ala Leu Gly Thr Gly Ile Gly Thr Gly Leu Leu Val Gly Asn Gly Thr
    130                 135                 140

Ala Leu Val His Ala Gly Pro Ala Gly Leu Leu Ile Gly Tyr Ala Ile
145                 150                 155                 160

Met Gly Ser Ile Leu Tyr Cys Ile Ile Gln Ala Cys Gly Glu Met Ala
                165                 170                 175

Leu Val Tyr Ser Asn Leu Thr Gly Gly Tyr Asn Ala Tyr Pro Ser Phe
            180                 185                 190

Leu Val Asp Asp Gly Phe Gly Phe Ala Val Ala Trp Val Tyr Cys Leu
        195                 200                 205

Gln Trp Leu Cys Val Cys Pro Leu Glu Leu Val Thr Ala Ser Met Thr
    210                 215                 220

Ile Lys Tyr Trp Thr Thr Ser Val Asn Pro Asp Val Phe Val Ile Ile
225                 230                 235                 240

Phe Tyr Val Leu Val Ile Thr Ile Asn Ile Phe Gly Ala Arg Gly Tyr
```

```
                245                 250                 255
Ala Glu Ala Glu Phe Phe Asn Cys Cys Lys Ile Leu Met Met Thr
            260                 265                 270

Gly Phe Phe Ile Leu Gly Ile Ile Asp Val Gly Ala Gly Asn
        275                 280                 285

Asp Gly Phe Ile Gly Gly Lys Tyr Trp His Asp Pro Gly Ala Phe Asn
    290                 295                 300

Gly Lys His Ala Ile Asp Arg Phe Lys Gly Val Ala Ala Thr Leu Val
305                 310                 315                 320

Thr Ala Ala Phe Ala Phe Gly Gly Ser Glu Phe Ile Ala Ile Thr Thr
                325                 330                 335

Ala Glu Gln Ser Asn Pro Arg Lys Ala Ile Pro Gly Ala Ala Lys Gln
            340                 345                 350

Met Ile Tyr Arg Ile Leu Phe Leu Phe Leu Ala Thr Ile Ile Leu Leu
        355                 360                 365

Gly Phe Leu Val Pro Tyr Asn Ser Asp Gln Leu Leu Gly Ser Thr Gly
    370                 375                 380

Gly Gly Thr Lys Ala Ser Pro Tyr Val Ile Ala Val Ala Ser His Gly
385                 390                 395                 400

Val Arg Val Val Pro His Phe Ile Asn Ala Val Ile Leu Leu Ser Val
                405                 410                 415

Leu Ser Met Ala Asn Ser Ser Phe Tyr Ser Ser Ala Arg Leu Phe Leu
            420                 425                 430

Thr Leu Ser Glu Gln Gly Tyr Ala Pro Lys Val Phe Ser Tyr Ile Asp
        435                 440                 445

Arg Ala Gly Arg Pro Leu Ile Ala Met Gly Val Ser Ala Leu Phe Ala
    450                 455                 460

Val Ile Ala Phe Cys Ala Ala Ser Pro Lys Glu Gln Val Phe Thr
465                 470                 475                 480

Trp Leu Leu Ala Ile Ser Gly Leu Ser Gln Leu Phe Thr Trp Thr Ala
                485                 490                 495

Ile Cys Leu Ser His Leu Arg Phe Arg Arg Ala Met Lys Val Gln Gly
            500                 505                 510

Arg Ser Leu Gly Glu Leu Gly Phe Lys Ser Gln Thr Gly Val Trp Gly
        515                 520                 525

Ser Ala Tyr Ala Cys Ile Met Met Ile Leu Ile Leu Ile Ala Gln Phe
    530                 535                 540

Trp Val Ala Ile Ala Pro Ile Gly Glu Gly Lys Leu Asp Ala Gln Ala
545                 550                 555                 560

Phe Phe Glu Asn Tyr Leu Ala Met Pro Ile Leu Ile Ala Leu Tyr Val
                565                 570                 575

Gly Tyr Lys Val Trp His Lys Asp Trp Lys Leu Phe Ile Arg Ala Asp
            580                 585                 590

Lys Ile Asp Leu Asp Ser His Arg Gln Ile Phe Asp Glu Glu Leu Ile
        595                 600                 605

Lys Gln Glu Asp Glu Glu Tyr Arg Glu Arg Leu Arg Asn Gly Pro Tyr
    610                 615                 620

Trp Lys Arg Val Val Ala Phe Trp Cys
625                 630

<210> SEQ ID NO 12
<211> LENGTH: 1902
<212> TYPE: DNA
<213> ORGANISM: Saccharomyces cerevisiae
```

<400> SEQUENCE: 12

```
atgtcgtcgt cgaagtctct atacgaactg aaagacttga aaaatagctc cacagaaata      60
catgccacgg ggcaggataa tgaaattgaa tatttcgaaa caggctccaa tgaccgtcca     120
tcctcacaac ctcatttagg ttacgaacag cataacactt ctgccgtgcg taggttttc     180
gactccttta aaagagcgga tcagggtcca caggatgaag tagaagcaac acaaatgaac     240
gatcttacgt cggctatctc accttcttct agacaggctc aagaactaga aaaaatgaa     300
agttcggaca acataggcgc taatacaggt cataagtcgg actcgctgaa gaaaaccatt     360
cagcctagac atgttctgat gattgcgttg ggtacgggta tcggtactgg gttattggtc     420
ggtaacggta ccgcgttggt tcatgcgggt ccagctggac tacttattgg ttacgctatt     480
atgggttcta tcttgtactg tattattcaa gcatgtggtg aaatggcgct agtgtatagt     540
aacttgactg gtggctacaa tgcataccccc agtttccttg tggatgatgg ttttgggttt     600
gcagtcgctt gggtttattg tttgcaatgg ctgtgtgtgt gtcctctgga attggtgacc     660
gcatccatga ctatcaaata ttggacgaca tctgtgaacc cggatgtgtt cgtcattatt     720
ttctatgttt tggtgattac tattaatatt ttcggtgctc gtggttatgc agaagctgag     780
ttcttcttca actgttgcaa aattttgatg atgactgggt tcttcattct tggtattatc     840
atcgatgttg gtgcgctgg taatgatggt tttattggtg gtaaatactg gcacgatccg     900
ggcgctttca atggtaaaca tgccattgac agatttaaag gtgttgctgc aacattagtg     960
actgctgctt ttgcctttgg tggttcagag tttattgcca tcaccactgc agaacaatct    1020
aatccaagaa aggccattcc aggtgcggcc aaacaaatga tctacagaat cttattccta    1080
ttcttggcta ccattattct actgggtttc ttggtgccat acaattccga tcaattattg    1140
ggttctaccg gtggtggtac taaagcctcg ccatatgtca ttgctgttgc atcccacggt    1200
gtccgtgtcg tcccacactt cattaacgcc gttattctac tttccgtgct gtccatggct    1260
aactcctcct tctactccag tgctcgttta tttttaactc tatccgagca aggttacgct    1320
cctaaggttt tctcctacat cgacagagcc ggtagaccat tgattgccat gggtgttct    1380
gcattgtttg ccgttattgc cttctgtgct gcatctccca aggaagaaca agttttcact    1440
tggttattgg ccattctgg tttgtctcag cttttcacat ggactgccat tgtttatcc    1500
catcttagat ttagaagagc catgaaagtc caagggagt ctcttggaga attgggtttc    1560
aaatctcaaa ctggtgtttg gggatctgcc tacgcttgca ttatgatgat tttaattctt    1620
attgcccaat tttgggtcgc tatcgccccc attggtgaag taagctgga tgcacaagcc    1680
ttttttcgaaa actacttggc tatgccaatc ttgattgcac tttatgtcgg ctacaaggtc    1740
tggcacaagg attggaaact gttcatcagg gcagacaaga tcgacctaga ttctcataga    1800
caaatctttg atgaagaatt aatcaagcaa gaagacgaag aatatagga acgtttgagg    1860
aacggacctt attggaaaag ggtcgttgcc ttctggtgtt aa                       1902
```

<210> SEQ ID NO 13
<211> LENGTH: 510
<212> TYPE: PRT
<213> ORGANISM: Saccharomyces cerevisiae

<400> SEQUENCE: 13

```
Met His Val Phe Phe Pro Leu Leu Phe Arg Pro Ser Pro Val Leu Phe
1               5                   10                  15

Ile Ala Cys Ala Tyr Ile Tyr Ile Asp Ile Tyr Ile His Cys Thr Arg
```

```
                20                  25                  30
Cys Thr Val Val Asn Ile Thr Met Ser Thr Asn Arg Val Pro Asn Leu
                35                  40                  45
Asp Pro Asp Leu Asn Leu Asn Lys Glu Ile Trp Asp Leu Tyr Ser Ser
 50                  55                  60
Ala Gln Lys Ile Leu Pro Asp Ser Asn Arg Ile Leu Asn Leu Ser Trp
 65                  70                  75                  80
Arg Leu His Asn Arg Thr Ser Phe His Arg Ile Asn Arg Ile Met Gln
                 85                  90                  95
His Ser Asn Ser Ile Met Asp Phe Ser Ala Ser Pro Phe Ala Ser Gly
                100                 105                 110
Val Asn Ala Ala Gly Pro Gly Asn Asn Asp Leu Asp Asp Thr Asp Thr
                115                 120                 125
Asp Asn Gln Gln Phe Phe Leu Ser Asp Met Asn Leu Asn Gly Ser Ser
                130                 135                 140
Val Phe Glu Asn Val Phe Asp Asp Asp Asp Asp Asp Asp Asp Val Glu
145                 150                 155                 160
Thr His Ser Ile Val His Ser Asp Leu Leu Asn Asp Met Asp Ser Ala
                165                 170                 175
Ser Gln Arg Ala Ser His Asn Ala Ser Gly Phe Pro Asn Phe Leu Asp
                180                 185                 190
Thr Ser Cys Ser Ser Ser Phe Asp Asp His Phe Ile Phe Thr Asn Asn
                195                 200                 205
Leu Pro Phe Leu Asn Asn Asn Ser Ile Asn Asn Asn His Ser His Asn
                210                 215                 220
Ser Ser His Asn Asn Asn Ser Pro Ser Ile Ala Asn Asn Thr Asn Ala
225                 230                 235                 240
Asn Thr Asn Thr Asn Thr Ser Ala Ser Thr Asn Thr Asn Ser Pro Leu
                245                 250                 255
Leu Arg Arg Asn Pro Ser Pro Ser Ile Val Lys Pro Gly Ser Arg Arg
                260                 265                 270
Asn Ser Ser Val Arg Lys Lys Lys Pro Ala Leu Lys Lys Ile Lys Ser
                275                 280                 285
Ser Thr Ser Val Gln Ser Ser Ala Thr Pro Pro Ser Asn Thr Ser Ser
                290                 295                 300
Asn Pro Asp Ile Lys Cys Ser Asn Cys Thr Thr Ser Thr Thr Pro Leu
305                 310                 315                 320
Trp Arg Lys Asp Pro Lys Gly Leu Pro Leu Cys Asn Ala Cys Gly Leu
                325                 330                 335
Phe Leu Lys Leu His Gly Val Thr Arg Pro Leu Ser Leu Lys Thr Asp
                340                 345                 350
Ile Ile Lys Lys Arg Gln Arg Ser Thr Lys Ile Asn Asn Asn Ile
                355                 360                 365
Thr Pro Pro Pro Ser Ser Leu Asn Pro Gly Ala Ala Gly Lys Lys
                370                 375                 380
Lys Asn Tyr Thr Ala Ser Val Ala Ala Ser Lys Arg Lys Asn Ser Leu
385                 390                 395                 400
Asn Ile Val Ala Pro Leu Lys Ser Gln Asp Ile Pro Ile Pro Lys Ile
                405                 410                 415
Ala Ser Pro Ser Ile Pro Gln Tyr Leu Arg Ser Asn Thr Arg His His
                420                 425                 430
Leu Ser Ser Ser Val Pro Ile Glu Ala Glu Thr Phe Ser Ser Phe Arg
                435                 440                 445
```

```
Pro Asp Met Asn Met Thr Met Asn Met Asn Leu His Asn Ala Ser Thr
    450                 455                 460

Ser Ser Phe Asn Asn Glu Ala Phe Trp Lys Pro Leu Asp Ser Ala Ile
465                 470                 475                 480

Asp His His Ser Gly Asp Thr Asn Pro Asn Ser Asn Met Asn Thr Thr
                485                 490                 495

Pro Asn Gly Asn Leu Ser Leu Asp Trp Leu Asn Leu Asn Leu
            500                 505                 510

<210> SEQ ID NO 14
<211> LENGTH: 1533
<212> TYPE: DNA
<213> ORGANISM: Saccharomyces cerevisiae

<400> SEQUENCE: 14
atgcacgttt tctttccttt gcttttccgc ccttcccctg ttctgttcat cgcatgtgca      60
tatatatata tagatatata tatacattgt acacggtgca cggtagtgaa cataactatg     120
agcacgaaca gagtcccgaa cctcgacccg gacttgaatt taaacaaaga aatctgggac     180
ctgtactcga gcgcccagaa atattgccc gattctaacc gtattttgaa cctttcttgg     240
cgtttgcata accgcacgtc tttccatcga attaaccgca taatgcaaca ttctaactct     300
attatggact tctccgcctc gcccttttgcc agcggcgtga acgccgctgg cccaggcaac     360
aacgacctcg atgacaccga tactgataac cagcaattct tcctttcaga catgaacctc     420
aacggatctt ctgttttga aaatgtgttt gacgacgatg acgatgatga tgacgtggag     480
acgcactcca ttgtgcactc agacctgctc aacgacatgg acagcgcttc ccagcgtgct     540
tcacataatg cttctggttt ccctaatttt ctggacactt cctgctcgtc ctccttcgat     600
gaccacttta ttttcaccaa taacttacca tttttaaata ataatagcat taataataat     660
catagtcata atagtagtca taataataac agtcccagca tcgccaataa tacaaacgca     720
aacacaaaca caaacacaag tgcaagtaca aacaccaata gtcctttact gagaagaaac     780
ccctccccat ctatagtgaa gcctggctcg cgaagaaatt cctccgtgag gaagaagaaa     840
cctgctttga agaagatcaa gtcttccact tctgtgcaat cttcggctac tccgccttcg     900
aacacctcat ccaatccgga tataaaatgc tccaactgca caacctccac cactccgctg     960
tggaggaagg accccaaggg tcttcccctg tgcaatgctt gcggcctctt cctcaagctc    1020
cacggcgtca aaggcctctc gtcgttgaag actgacatca ttaagaagag acagaggtcg    1080
tctaccaaga taaacaacaa tataacgccc cctccatcgt cgtctctcaa tccgggagca    1140
gcagggaaaa agaaaaacta tacagcaagt gtggcagcgt ccaagaggaa gaactcactg    1200
aacattgtcg caccctttgaa gtctcaggac atacccattc cgaagattgc ctcacccttcc   1260 atcccacaat acctccgctc taacactcgc caccacccttt cgagttccgt acccatcgag    1320
gcggaaacgt tctccagctt tcggcctgat atgaatatga ctatgaacat gaaccttcac    1380
aacgcctcaa cctcctcctt caacaatgaa gccttctgga gcctttggaa ctccgcaata    1440
gatcatcatt ctggagacac aaatccaaac tcaaacatga acaccactcc aaatggcaat    1500
ctgagcctgg attggttgaa tctgaattta tag                                 1533

<210> SEQ ID NO 15
<211> LENGTH: 354
<212> TYPE: PRT
<213> ORGANISM: Saccharomyces cerevisiae
```

<400> SEQUENCE: 15

```
Met Met Asn Asn Gly Asn Gln Val Ser Asn Leu Ser Asn Ala Leu
1               5                   10                  15

Arg Gln Val Asn Ile Gly Asn Arg Asn Ser Asn Thr Thr Thr Asp Gln
            20                  25                  30

Ser Asn Ile Asn Phe Glu Phe Ser Thr Gly Val Asn Asn Asn Asn
            35                  40                  45

Asn Asn Ser Ser Asn Asn Asn Val Gln Asn Asn Asn Ser Gly
    50                  55                  60

Arg Asn Gly Ser Gln Asn Asn Asp Asn Glu Asn Asn Ile Lys Asn Thr
65                  70                  75                  80

Leu Glu Gln His Arg Gln Gln Gln Ala Phe Ser Asp Met Ser His
                85                  90                  95

Val Glu Tyr Ser Arg Ile Thr Lys Phe Phe Gln Glu Gln Pro Leu Glu
            100                 105                 110

Gly Tyr Thr Leu Phe Ser His Arg Ser Ala Pro Asn Gly Phe Lys Val
            115                 120                 125

Ala Ile Val Leu Ser Glu Leu Gly Phe His Tyr Asn Thr Ile Phe Leu
130                 135                 140

Asp Phe Asn Leu Gly Glu His Arg Ala Pro Glu Phe Val Ser Val Asn
145                 150                 155                 160

Pro Asn Ala Arg Val Pro Ala Leu Ile Asp His Gly Met Asp Asn Leu
                165                 170                 175

Ser Ile Trp Glu Ser Gly Ala Ile Leu Leu His Leu Val Asn Lys Tyr
                180                 185                 190

Tyr Lys Glu Thr Gly Asn Pro Leu Leu Trp Ser Asp Asp Leu Ala Asp
            195                 200                 205

Gln Ser Gln Ile Asn Ala Trp Leu Phe Phe Gln Thr Ser Gly His Ala
    210                 215                 220

Pro Met Ile Gly Gln Ala Leu His Phe Arg Tyr Phe His Ser Gln Lys
225                 230                 235                 240

Ile Ala Ser Ala Val Glu Arg Tyr Thr Asp Glu Val Arg Arg Val Tyr
                245                 250                 255

Gly Val Val Glu Met Ala Leu Ala Glu Arg Arg Glu Ala Leu Val Met
            260                 265                 270

Glu Leu Asp Thr Glu Asn Ala Ala Ala Tyr Ser Ala Gly Thr Thr Pro
            275                 280                 285

Met Ser Gln Ser Arg Phe Phe Asp Tyr Pro Val Trp Leu Val Gly Asp
290                 295                 300

Lys Leu Thr Ile Ala Asp Leu Ala Phe Val Pro Trp Asn Asn Val Val
305                 310                 315                 320

Asp Arg Ile Gly Ile Asn Ile Lys Ile Glu Phe Pro Glu Val Tyr Lys
                325                 330                 335

Trp Thr Lys His Met Met Arg Arg Pro Ala Val Ile Lys Ala Leu Arg
                340                 345                 350

Gly Glu
```

<210> SEQ ID NO 16
<211> LENGTH: 1065
<212> TYPE: DNA
<213> ORGANISM: Saccharomyces cerevisiae

<400> SEQUENCE: 16

```
atgatgaata acaacggcaa ccaagtgtcg aatctctcca atgcgctccg tcaagtaaac      60
```

```
ataggaaaca ggaacagtaa tacaaccacc gatcaaagta atataaattt tgaattttca    120
acaggtgtaa ataataataa taataacaat agcagtagta ataacaataa tgttcaaaac    180
aataacagcg gccgcaatgg tagccaaaat aatgataacg agaataatat caagaatacc    240
ttagaacaac atcgacaaca acaacaggca ttttcggata tgagtcacgt ggagtattcc    300
agaattacaa aatttttca agaacaacca ctggagggat atacccttt ctctcacagg    360
tctgcgccta atggattcaa agttgctata gtactaagtg aacttggatt tcattataac    420
acaatcttcc tagatttcaa tcttggcgaa catagggccc ccgaatttgt gtctgtgaac    480
cctaatgcaa gagttccagc tttaatcgat catggtatgg acaacttgtc tatttgggaa    540
tcagggcga ttttattaca tttggtaaat aaatattaca aagagactgg taatccatta    600
ctctggtccg atgatttagc tgaccaatca caaatcaacg catggttgtt cttccaaacg    660
tcagggcatg cgccaatgat tggacaagct ttacatttca gatacttcca ttcacaaaag    720
atagcaagtg ctgtagaaag atatacggat gaggttagaa gagtttacgg tgtagtggag    780
atggccttgg ctgaacgtag agaagcgctg gtgatggaat tagacacgga aaatgcggct    840
gcatactcag ctggtacaac accaatgtca caaagtcgtt tctttgatta tcccgtatgg    900
cttgtaggag ataaattaac tatagcagat ttggcctttg tcccatggaa taatgtcgtg    960
gatagaattg gcattaatat caaaattgaa tttccagaag tttacaaatg gacgaagcat   1020
atgatgagaa gacccgcggt catcaaggca ttgcgtggtg aatga                   1065
```

<210> SEQ ID NO 17
<211> LENGTH: 2470
<212> TYPE: PRT
<213> ORGANISM: Saccharomyces cerevisiae

<400> SEQUENCE: 17

```
Met Glu Pro His Glu Glu Gln Ile Trp Lys Ser Lys Leu Leu Lys Ala
1               5                   10                  15

Ala Asn Asn Asp Met Asp Met Asp Arg Asn Val Pro Leu Ala Pro Asn
            20                  25                  30

Leu Asn Val Asn Met Asn Met Lys Met Asn Ala Ser Arg Asn Gly Asp
        35                  40                  45

Glu Phe Gly Leu Thr Ser Ser Arg Phe Asp Gly Val Val Ile Gly Ser
    50                  55                  60

Asn Gly Asp Val Asn Phe Lys Pro Ile Leu Glu Lys Ile Phe Arg Glu
65                  70                  75                  80

Leu Thr Ser Asp Tyr Lys Glu Arg Lys Leu Ala Ser Ile Ser Leu
                85                  90                  95

Phe Asp Leu Leu Val Ser Leu Glu His Glu Leu Ser Ile Glu Glu Phe
            100                 105                 110

Gln Ala Val Ser Asn Asp Ile Asn Asn Lys Ile Leu Glu Leu Val His
        115                 120                 125

Thr Lys Lys Thr Ser Thr Arg Val Gly Ala Val Leu Ser Ile Asp Thr
    130                 135                 140

Leu Ile Ser Phe Tyr Ala Tyr Thr Glu Arg Leu Pro Asn Glu Thr Ser
145                 150                 155                 160

Arg Leu Ala Gly Tyr Leu Arg Gly Leu Ile Pro Ser Asn Asp Val Glu
                165                 170                 175

Val Met Arg Leu Ala Ala Lys Thr Leu Gly Lys Leu Ala Val Pro Gly
            180                 185                 190
```

```
Gly Thr Tyr Thr Ser Asp Phe Val Glu Phe Glu Ile Lys Ser Cys Leu
            195                 200                 205

Glu Trp Leu Thr Ala Ser Thr Glu Lys Asn Ser Phe Ser Ser Ser Lys
210                 215                 220

Pro Asp His Ala Lys His Ala Ala Leu Leu Ile Ile Thr Ala Leu Ala
225                 230                 235                 240

Glu Asn Cys Pro Tyr Leu Leu Tyr Gln Tyr Leu Asn Ser Ile Leu Asp
                245                 250                 255

Asn Ile Trp Arg Ala Leu Arg Asp Pro His Leu Val Ile Arg Ile Asp
            260                 265                 270

Ala Ser Ile Thr Leu Ala Lys Cys Leu Ser Thr Leu Arg Asn Arg Asp
        275                 280                 285

Pro Gln Leu Thr Ser Gln Trp Val Gln Arg Leu Ala Thr Ser Cys Glu
    290                 295                 300

Tyr Gly Phe Gln Val Asn Thr Leu Glu Cys Ile His Ala Ser Leu Leu
305                 310                 315                 320

Val Tyr Lys Glu Ile Leu Phe Leu Lys Asp Pro Phe Leu Asn Gln Val
                325                 330                 335

Phe Asp Gln Met Cys Leu Asn Cys Ile Ala Tyr Glu Asn His Lys Ala
            340                 345                 350

Lys Met Ile Arg Glu Lys Ile Tyr Gln Ile Val Pro Leu Leu Ala Ser
        355                 360                 365

Phe Asn Pro Gln Leu Phe Ala Gly Lys Tyr Leu His Gln Ile Met Asp
    370                 375                 380

Asn Tyr Leu Glu Ile Leu Thr Asn Ala Pro Ala Asn Lys Ile Pro His
385                 390                 395                 400

Leu Lys Asp Asp Lys Pro Gln Ile Leu Ile Ser Ile Gly Asp Ile Ala
                405                 410                 415

Tyr Glu Val Gly Pro Asp Ile Ala Pro Tyr Val Lys Gln Ile Leu Asp
            420                 425                 430

Tyr Ile Glu His Asp Leu Gln Thr Lys Phe Lys Phe Arg Lys Lys Phe
        435                 440                 445

Glu Asn Glu Ile Phe Tyr Cys Ile Gly Arg Leu Ala Val Pro Leu Gly
    450                 455                 460

Pro Val Leu Gly Lys Leu Leu Asn Arg Asn Ile Leu Asp Leu Met Phe
465                 470                 475                 480

Lys Cys Pro Leu Ser Asp Tyr Met Gln Glu Thr Phe Gln Ile Leu Thr
                485                 490                 495

Glu Arg Ile Pro Ser Leu Gly Pro Lys Ile Asn Asp Glu Leu Leu Asn
            500                 505                 510

Leu Val Cys Ser Thr Leu Ser Gly Thr Pro Phe Ile Gln Pro Gly Ser
        515                 520                 525

Pro Met Glu Ile Pro Ser Phe Ser Arg Glu Arg Ala Arg Glu Trp Arg
    530                 535                 540

Asn Lys Asn Ile Leu Gln Lys Thr Gly Glu Ser Asn Asp Asn Asn
545                 550                 555                 560

Asp Ile Lys Ile Ile Ile Gln Ala Phe Arg Met Leu Lys Asn Ile Lys
                565                 570                 575

Ser Arg Phe Ser Leu Val Glu Phe Val Arg Ile Val Ala Leu Ser Tyr
            580                 585                 590

Ile Glu His Thr Asp Pro Arg Val Arg Lys Leu Ala Ala Leu Thr Ser
        595                 600                 605

Cys Glu Ile Tyr Val Lys Asp Asn Ile Cys Lys Gln Thr Ser Leu His
```

```
                610                 615                 620
Ser Leu Asn Thr Val Ser Glu Val Leu Ser Lys Leu Leu Ala Ile Thr
625                 630                 635                 640

Ile Ala Asp Pro Leu Gln Asp Ile Arg Leu Glu Val Leu Lys Asn Leu
                645                 650                 655

Asn Pro Cys Phe Asp Pro Gln Leu Ala Gln Pro Asp Asn Leu Arg Leu
                660                 665                 670

Leu Phe Thr Ala Leu His Asp Glu Ser Phe Asn Ile Gln Ser Val Ala
                675                 680                 685

Met Glu Leu Val Gly Arg Leu Ser Ser Val Asn Pro Ala Tyr Val Ile
                690                 695                 700

Pro Ser Ile Arg Lys Ile Leu Glu Leu Leu Thr Lys Leu Lys Phe
705                 710                 715                 720

Ser Thr Ser Ser Arg Glu Lys Glu Glu Thr Ala Ser Leu Leu Cys Thr
                725                 730                 735

Leu Ile Arg Ser Ser Lys Asp Val Ala Lys Pro Tyr Ile Glu Pro Leu
                740                 745                 750

Leu Asn Val Leu Leu Pro Lys Phe Gln Asp Thr Ser Ser Thr Val Ala
                755                 760                 765

Ser Thr Ala Leu Arg Thr Ile Gly Glu Leu Ser Val Val Gly Gly Glu
                770                 775                 780

Asp Met Lys Ile Tyr Leu Lys Asp Leu Phe Pro Leu Ile Ile Lys Thr
785                 790                 795                 800

Phe Gln Asp Gln Ser Asn Ser Phe Lys Arg Glu Ala Ala Leu Lys Ala
                805                 810                 815

Leu Gly Gln Leu Ala Ala Ser Ser Gly Tyr Val Ile Asp Pro Leu Leu
                820                 825                 830

Asp Tyr Pro Glu Leu Leu Gly Ile Leu Val Asn Ile Leu Lys Thr Glu
                835                 840                 845

Asn Ser Gln Asn Ile Arg Arg Gln Thr Val Thr Leu Ile Gly Ile Leu
                850                 855                 860

Gly Ala Ile Asp Pro Tyr Arg Gln Lys Glu Arg Glu Val Thr Ser Thr
865                 870                 875                 880

Thr Asp Ile Ser Thr Glu Gln Asn Ala Pro Pro Ile Asp Ile Ala Leu
                885                 890                 895

Leu Met Gln Gly Met Ser Pro Ser Asn Asp Glu Tyr Tyr Thr Thr Val
                900                 905                 910

Val Ile His Cys Leu Leu Lys Ile Leu Lys Asp Pro Ser Leu Ser Ser
                915                 920                 925

Tyr His Thr Ala Val Ile Gln Ala Ile Met His Ile Phe Gln Thr Leu
                930                 935                 940

Gly Leu Lys Cys Val Ser Phe Leu Asp Gln Ile Ile Pro Thr Ile Leu
945                 950                 955                 960

Asp Val Met Arg Thr Cys Ser Gln Ser Leu Leu Glu Phe Tyr Phe Gln
                965                 970                 975

Gln Leu Cys Ser Leu Ile Ile Val Arg Gln His Ile Arg Pro His
                980                 985                 990

Val Asp Ser Ile Phe Gln Ala Ile Lys Asp Phe Ser Ser Val Ala Lys
                995                 1000                1005

Leu Gln Ile Thr Leu Val Ser Val Ile Glu Ala Ile Ser Lys Ala
                1010                1015                1020

Leu Glu Gly Glu Phe Lys Arg Leu Val Pro Leu Thr Leu Thr Leu
                1025                1030                1035
```

```
Phe Leu Val Ile Leu Glu Asn Asp Lys Ser Ser Asp Lys Val Leu
    1040                1045                1050

Ser Arg Arg Val Leu Arg Leu Leu Glu Ser Phe Gly Pro Asn Leu
    1055                1060                1065

Glu Gly Tyr Ser His Leu Ile Thr Pro Lys Ile Val Gln Met Ala
    1070                1075                1080

Glu Phe Thr Ser Gly Asn Leu Gln Arg Ser Ala Ile Ile Thr Ile
    1085                1090                1095

Gly Lys Leu Ala Lys Asp Val Asp Leu Phe Glu Met Ser Ser Arg
    1100                1105                1110

Ile Val His Ser Leu Leu Arg Val Leu Ser Ser Thr Thr Ser Asp
    1115                1120                1125

Glu Leu Ser Lys Val Ile Met Asn Thr Leu Ser Leu Leu Leu Ile
    1130                1135                1140

Gln Met Gly Thr Ser Phe Ala Ile Phe Ile Pro Val Ile Asn Glu
    1145                1150                1155

Val Leu Met Lys Lys His Ile Gln His Thr Ile Tyr Asp Asp Leu
    1160                1165                1170

Thr Asn Arg Ile Leu Asn Asn Asp Val Leu Pro Thr Lys Ile Leu
    1175                1180                1185

Glu Ala Asn Thr Thr Asp Tyr Lys Pro Ala Glu Gln Met Glu Ala
    1190                1195                1200

Ala Asp Ala Gly Val Ala Lys Leu Pro Ile Asn Gln Ser Val Leu
    1205                1210                1215

Lys Ser Ala Trp Asn Ser Ser Gln Gln Arg Thr Lys Glu Asp Trp
    1220                1225                1230

Gln Glu Trp Ser Lys Arg Leu Ser Ile Gln Leu Leu Lys Glu Ser
    1235                1240                1245

Pro Ser His Ala Leu Arg Ala Cys Ser Asn Leu Ala Ser Met Tyr
    1250                1255                1260

Tyr Pro Leu Ala Lys Glu Leu Phe Asn Thr Ala Phe Ala Cys Val
    1265                1270                1275

Trp Thr Glu Leu Tyr Ser Gln Tyr Gln Glu Asp Leu Ile Gly Ser
    1280                1285                1290

Leu Cys Ile Ala Leu Ser Ser Pro Leu Asn Pro Glu Ile His
    1295                1300                1305

Gln Thr Leu Leu Asn Leu Val Glu Phe Met Glu His Asp Asp Lys
    1310                1315                1320

Ala Leu Pro Ile Pro Thr Gln Ser Leu Gly Glu Tyr Ala Glu Arg
    1325                1330                1335

Cys His Ala Tyr Ala Lys Ala Leu His Tyr Lys Glu Ile Lys Phe
    1340                1345                1350

Ile Lys Glu Pro Glu Asn Ser Thr Ile Glu Ser Leu Ile Ser Ile
    1355                1360                1365

Asn Asn Gln Leu Asn Gln Thr Asp Ala Ala Ile Gly Ile Leu Lys
    1370                1375                1380

His Ala Gln Gln His His Ser Leu Gln Leu Lys Glu Thr Trp Phe
    1385                1390                1395

Glu Lys Leu Glu Arg Trp Glu Asp Ala Leu His Ala Tyr Asn Glu
    1400                1405                1410

Arg Glu Lys Ala Gly Asp Thr Ser Val Ser Val Thr Leu Gly Lys
    1415                1420                1425
```

```
Met Arg Ser Leu His Ala Leu Gly Glu Trp Glu Gln Leu Ser Gln
1430                1435                1440

Leu Ala Ala Arg Lys Trp Lys Val Ser Lys Leu Gln Thr Lys Lys
1445                1450                1455

Leu Ile Ala Pro Leu Ala Ala Gly Ala Ala Trp Gly Leu Gly Glu
1460                1465                1470

Trp Asp Met Leu Glu Gln Tyr Ile Ser Val Met Lys Pro Lys Ser
1475                1480                1485

Pro Asp Lys Glu Phe Phe Asp Ala Ile Leu Tyr Leu His Lys Asn
1490                1495                1500

Asp Tyr Asp Asn Ala Ser Lys His Ile Leu Asn Ala Arg Asp Leu
1505                1510                1515

Leu Val Thr Glu Ile Ser Ala Leu Ile Asn Glu Ser Tyr Asn Arg
1520                1525                1530

Ala Tyr Ser Val Ile Val Arg Thr Gln Ile Ile Thr Glu Phe Glu
1535                1540                1545

Glu Ile Ile Lys Tyr Lys Gln Leu Pro Pro Asn Ser Glu Lys Lys
1550                1555                1560

Leu His Tyr Gln Asn Leu Trp Thr Lys Arg Leu Leu Gly Cys Gln
1565                1570                1575

Lys Asn Val Asp Leu Trp Gln Arg Val Leu Arg Val Arg Ser Leu
1580                1585                1590

Val Ile Lys Pro Lys Gln Asp Leu Gln Ile Trp Ile Lys Phe Ala
1595                1600                1605

Asn Leu Cys Arg Lys Ser Gly Arg Met Arg Leu Ala Asn Lys Ala
1610                1615                1620

Leu Asn Met Leu Leu Glu Gly Gly Asn Asp Pro Ser Leu Pro Asn
1625                1630                1635

Thr Phe Lys Ala Pro Pro Val Val Tyr Ala Gln Leu Lys Tyr
1640                1645                1650

Ile Trp Ala Thr Gly Ala Tyr Lys Glu Ala Leu Asn His Leu Ile
1655                1660                1665

Gly Phe Thr Ser Arg Leu Ala His Asp Leu Gly Leu Asp Pro Asn
1670                1675                1680

Asn Met Ile Ala Gln Ser Val Lys Leu Ser Ser Ala Ser Thr Ala
1685                1690                1695

Pro Tyr Val Glu Glu Tyr Thr Lys Leu Leu Ala Arg Cys Phe Leu
1700                1705                1710

Lys Gln Gly Glu Trp Arg Ile Ala Thr Gln Pro Asn Trp Arg Asn
1715                1720                1725

Thr Asn Pro Asp Ala Ile Leu Gly Ser Tyr Leu Leu Ala Thr His
1730                1735                1740

Phe Asp Lys Asn Trp Tyr Lys Ala Trp His Asn Trp Ala Leu Ala
1745                1750                1755

Asn Phe Glu Val Ile Ser Met Val Gln Glu Glu Thr Lys Leu Asn
1760                1765                1770

Gly Gly Lys Asn Asp Asp Asp Asp Thr Ala Val Asn Asn Asp
1775                1780                1785

Asn Val Arg Ile Asp Gly Ser Ile Leu Gly Ser Gly Ser Leu Thr
1790                1795                1800

Ile Asn Gly Asn Arg Tyr Pro Leu Glu Leu Ile Gln Arg His Val
1805                1810                1815

Val Pro Ala Ile Lys Gly Phe Phe His Ser Ile Ser Leu Leu Glu
```

```
                 1820                1825                 1830
Thr Ser Cys Leu Gln Asp Thr Leu Arg Leu Leu Thr Leu Leu Phe
    1835                1840                 1845

Asn Phe Gly Gly Ile Lys Glu Val Ser Gln Ala Met Tyr Glu Gly
    1850                1855                 1860

Phe Asn Leu Met Lys Ile Glu Asn Trp Leu Glu Val Leu Pro Gln
    1865                1870                 1875

Leu Ile Ser Arg Ile His Gln Pro Asp Pro Thr Val Ser Asn Ser
    1880                1885                 1890

Leu Leu Ser Leu Leu Ser Asp Leu Gly Lys Ala His Pro Gln Ala
    1895                1900                 1905

Leu Val Tyr Pro Leu Thr Val Ala Ile Lys Ser Glu Ser Val Ser
    1910                1915                 1920

Arg Gln Lys Ala Ala Leu Ser Ile Ile Glu Lys Ile Arg Ile His
    1925                1930                 1935

Ser Pro Val Leu Val Asn Gln Ala Glu Leu Val Ser His Glu Leu
    1940                1945                 1950

Ile Arg Val Ala Val Leu Trp His Glu Leu Trp Tyr Glu Gly Leu
    1955                1960                 1965

Glu Asp Ala Ser Arg Gln Phe Phe Val Glu His Asn Ile Glu Lys
    1970                1975                 1980

Met Phe Ser Thr Leu Glu Pro Leu His Lys His Leu Gly Asn Glu
    1985                1990                 1995

Pro Gln Thr Leu Ser Glu Val Ser Phe Gln Lys Ser Phe Gly Arg
    2000                2005                 2010

Asp Leu Asn Asp Ala Tyr Glu Trp Leu Asn Asn Tyr Lys Lys Ser
    2015                2020                 2025

Lys Asp Ile Asn Asn Leu Asn Gln Ala Trp Asp Ile Tyr Tyr Asn
    2030                2035                 2040

Val Phe Arg Lys Ile Thr Arg Gln Ile Pro Gln Leu Gln Thr Leu
    2045                2050                 2055

Asp Leu Gln His Val Ser Pro Gln Leu Leu Ala Thr His Asp Leu
    2060                2065                 2070

Glu Leu Ala Val Pro Gly Thr Tyr Phe Pro Gly Lys Pro Thr Ile
    2075                2080                 2085

Arg Ile Ala Lys Phe Glu Pro Leu Phe Ser Val Ile Ser Ser Lys
    2090                2095                 2100

Gln Arg Pro Arg Lys Phe Ser Ile Lys Gly Ser Asp Gly Lys Asp
    2105                2110                 2115

Tyr Lys Tyr Val Leu Lys Gly His Glu Asp Ile Arg Gln Asp Ser
    2120                2125                 2130

Leu Val Met Gln Leu Phe Gly Leu Val Asn Thr Leu Leu Lys Asn
    2135                2140                 2145

Asp Ser Glu Cys Phe Lys Arg His Leu Asp Ile Gln Gln Tyr Pro
    2150                2155                 2160

Ala Ile Pro Leu Ser Pro Lys Ser Gly Leu Leu Gly Trp Val Pro
    2165                2170                 2175

Asn Ser Asp Thr Phe His Val Leu Ile Arg Glu His Arg Asp Ala
    2180                2185                 2190

Lys Lys Ile Pro Leu Asn Ile Glu His Trp Val Met Leu Gln Met
    2195                2200                 2205

Ala Pro Asp Tyr Glu Asn Leu Thr Leu Leu Gln Lys Ile Glu Val
    2210                2215                 2220
```

```
Phe Thr Tyr Ala Leu Asp Asn Thr Lys Gly Gln Asp Leu Tyr Lys
    2225                2230                2235

Ile Leu Trp Leu Lys Ser Arg Ser Ser Glu Thr Trp Leu Glu Arg
    2240                2245                2250

Arg Thr Thr Tyr Thr Arg Ser Leu Ala Val Met Ser Met Thr Gly
    2255                2260                2265

Tyr Ile Leu Gly Leu Gly Asp Arg His Pro Ser Asn Leu Met Leu
    2270                2275                2280

Asp Arg Ile Thr Gly Lys Val Ile His Ile Asp Phe Gly Asp Cys
    2285                2290                2295

Phe Glu Ala Ala Ile Leu Arg Glu Lys Tyr Pro Glu Lys Val Pro
    2300                2305                2310

Phe Arg Leu Thr Arg Met Leu Thr Tyr Ala Met Glu Val Ser Gly
    2315                2320                2325

Ile Glu Gly Ser Phe Arg Ile Thr Cys Glu Asn Val Met Arg Val
    2330                2335                2340

Leu Arg Asp Asn Lys Glu Ser Leu Met Ala Ile Leu Glu Ala Phe
    2345                2350                2355

Ala Leu Asp Pro Leu Ile His Trp Gly Phe Asp Leu Pro Pro Gln
    2360                2365                2370

Lys Leu Thr Glu Gln Thr Gly Ile Pro Leu Pro Leu Ile Asn Pro
    2375                2380                2385

Ser Glu Leu Leu Arg Lys Gly Ala Ile Thr Val Glu Glu Ala Ala
    2390                2395                2400

Asn Met Glu Ala Glu Gln Gln Asn Glu Thr Lys Asn Ala Arg Ala
    2405                2410                2415

Met Leu Val Leu Arg Arg Ile Thr Asp Lys Leu Thr Gly Asn Asp
    2420                2425                2430

Ile Lys Arg Phe Asn Glu Leu Asp Val Pro Glu Gln Val Asp Lys
    2435                2440                2445

Leu Ile Gln Gln Ala Thr Ser Ile Glu Arg Leu Cys Gln His Tyr
    2450                2455                2460

Ile Gly Trp Cys Pro Phe Trp
    2465                2470

<210> SEQ ID NO 18
<211> LENGTH: 7413
<212> TYPE: DNA
<213> ORGANISM: Saccharomyces cerevisiae

<400> SEQUENCE: 18
atggaaccgc atgaggagca gatttggaag agtaaacttt tgaaagcggc taacaacgat      60
atggacatgg atagaaatgt gccgttggca ccgaatctga atgtgaatat gaacatgaaa     120
atgaatgcga gcaggaacgg ggatgaattc ggtctgactt ctagtaggtt tgatggagtg     180
gtgattggca gtaatgggga tgtaaatttt aagcccattt tggagaaaat tttccgcgaa     240
ttaaccagtg attacaagga ggaacgaaaa ttggccagta tttcattatt tgatctacta     300
gtatccttgg aacatgaatt gtcgataaa gagttccaag cagtttcaaa tgacataaac     360
aataagattt tggagctggt ccatacaaaa aaaacgagca ctagggtagg ggctgttcta     420
tccatagaca ctttgatttc attctacgca tatactgaaa ggttgcctaa cgaaacttca     480
cgactggctg ttaccttcg agggctaata ccttctaatg atgtagaggt catgagactc     540
gctgcaaaga ctctgggcaa gttagccgtt ccaggaggta catataccct tgatttcgtg     600
```

```
gaatttgaga taaagtcttg cttagaatgg cttactgcct ccacggaaaa gaattcattc    660
tcgagttcga agccagacca tgctaaacat gctgcgcttc tgattataac agcgttggca    720
gagaattgtc cttatttact ctaccaatac ttgaattcca tactagataa catttggaga    780
gcactaagag acccacattt ggtgatcaga attgatgcgt ccattacatt ggccaaatgt    840
ctttccaccc tacgaaatag ggatcctcag ttaactagcc agtgggtgca gagattggct    900
acaagttgtg aatacggatt tcaagtaaac acattagaat gcatccatgc aagtttgttg    960
gtttataagg aaatcttgtt tttgaaggat ccctttttga atcaagtgtt cgaccaaatg   1020
tgtctaaatt gcatagctta tgaaaatcat aaagcgaaaa tgattagaga aaagatttac   1080
cagattgttc ccctattagc atcgttcaat cctcaattat ttgctggcaa atatttgcac   1140
caaattatgg acaactattt agagatttta accaatgctc cagcaaataa aataccacat   1200
ctcaaagatg acaaaccaca gattttaata tcgattggtg atattgcata tgaagtcggg   1260
cccgatatcg caccttatgt gaaacaaatt cttgattata ttgaacatga tttacagacg   1320
aaattcaaat tcagaaagaa atttgaaaat gaaattttct actgcatcgg aagattggca   1380
gttcccttgg gccccgttct aggtaaatta ttaaacagaa atatactgga cctgatgttc   1440
aaatgccctc tttccgacta tatgcaggaa acgtttcaaa ttctgactga gagaatacca   1500
tcactaggcc ccaaaataaa tgacgagttg cttaacctag tctgttcaac cttatctgga   1560
acaccattta tccagccagg gtcaccaatg gagataccat cgttttcgag agaaagagca   1620
agagaatgga gaaataaaaa catcctacag aaaactggtg aaagtaacga tgataataat   1680
gatataaaaa tcattataca agcttttaga atgttaaaaa atatcaaaag cagattttcg   1740
ttggtggaat tcgtgagaat tgttgcactt tcttacattg agcatacaga tcccagagta   1800
aggaaactag ctgcgttgac atcttgtgaa atttacgtca aggataacat ctgcaaacaa   1860
acatcactac actctctgaa cactgtatct gaagtgttat caaagcttct agccattacg   1920
attgcggacc ctttacaaga tatccgttta gaagttttaa agaatcttaa tccatgtttc   1980
gatccccagt tggcacaacc agataaattg agactcttgt ttactgcact gcacgatgag   2040
tcgttcaata ttcagtcagt agcaatggag cttgtcggta ggttgtcttc cgtaaacccc   2100
gcatacgtca tcccatcgat aagaaaaata ctactggaac tgctaacaaa attaaaattc   2160
tcaacttctt ctcgagaaaa ggaagaaact gccagtttgt tatgtactct tatcaggtcg   2220
agtaaagatg ttgcgaaacc ttatatcgaa cctcttttaa atgttctttt accaaaattc   2280
caagatacct cttcaacggt tgcatcaact gcactgagaa ctataggtga gctatctgtt   2340
gtaggggcg aagatatgaa gatatatctt aaggatttgt ttccttaat tatcaaaaca    2400
tttcaggatc aatcaaactc tttcaagaga gaagctgcac ttaaggccct tggtcaactt   2460
gcagcctcat ctggttacgt gatagatcct ttactcgact atcccgaatt attgggtata   2520
ttggtgaata tattgaagac agaaaactct caaaatatta ggagacaaac agtcactttg   2580
ataggtatac tgggagctat cgacccatat cgccaaaaag aacgtgaggt tacctctact   2640
accgatatat ctacagaaca gaacgccccg cctatcgaca ttgctcttct catgcagggc   2700
atgtctcctt cgaatgatga gtattatacc actgttgtca ttcactgcct gctaaaaatc   2760
ctaaaagatc catccctatc atcttaccac actgccgtga tccaagcgat tatgcatatt   2820
tttcaaaccc ttggtctaaa atgtgtttca ttcttggacc agatcatccc aactattttg   2880
gacgtaatgc gtacatgctc tcagtcacta ttagaatttt acttccaaca gctttgctct   2940
```

-continued

```
ttgattatta tcgtaaggca acacataaga cctcatgtcg attctatatt ccaggctatc   3000
aaagattttt cttcggttgc taagctacaa ataacgcttg taagtgttat tgaagcaata   3060
tcaaaggctc tggagggtga attcaaaaga ttggtccctc ttactctgac cttgttcctt   3120
gtaattttgg agaatgacaa gtctagtgac aaggtcctct ccagaagggt attgagactg   3180
ttagaatcgt ttggtcctaa cttagaaggt tattcgcatt tgattacacc aagatagtt    3240
caaatggcag aattcaccag cgggaaccta caaaggtctg caataattac tattggcaaa   3300
ctggccaagg atgttgacct ttttgagatg tcctcaagaa ttgttcactc tttacttagg   3360
gtactaagtt caacaacgag tgacgaactc tcaaaagtca ttatgaatac tttaagtcta   3420
ctgctaatac aaatgggcac atcctttgct atcttcatcc ctgtcattaa tgaagtttta   3480
atgaagaaac atattcaaca cacaatatat gatgacttga caaacagaat attaaacaat   3540
gatgttttac ccacaaaaat tcttgaagca atacaacgg attataagcc cgcggaacaa    3600
atggaggcag cagatgctgg ggtcgcaaaa ttacctataa accatcagt tttgaaaagt    3660
gcatggaatt ctagccaaca aagaactaaa gaagattggc aggaatggag caaacgtcta   3720
tccattcaat tattaaaaga gtcaccctcc catgctctaa gagcttgttc aaatcttgca   3780
agcatgtatt atccactagc caaagaactt tttaataccg cattcgcatg tgtttggacc   3840
gaactttata gccaatatca agaagattta attgggtcat tatgtatagc cttatcttct   3900
cccttaaatc caccagaaat acatcaaaca ttgttaaacc tggtagaatt tatggaacac   3960
gatgacaagg cattaccaat accaactcaa agcctgggcg agtatgctga aagatgtcac   4020
gcctatgcca aagcgctaca ttataaagag attaaattta ttaaagagcc tgagaactca   4080
actattgaat cattgatcag cattaacaac cagctgaatc aaacggatgc tgcaattggt   4140
atattaaagc atgcccaaca acatcattca cttcaattaa aggagacatg gtttgaaaaa   4200
ttagagcgtt gggaagatgc actacatgct tataatgaac gtgaaaaggc aggtgatact   4260
tccgtgagcg ttacactcgg taagatgaga tcccttcatg cccttggcga atgggaacag   4320
ttgtcgcaat tggcagctag aaaagtggaaa gtttcgaagc tacaaactaa gaagctaata   4380
gctcccttgg cagctggtgc tgcgtggggg ttggagagt gggatatgct tgagcaatat    4440
atcagcgtta tgaaacctaa atctccagat aaggaatttt ttgatgcaat tttatacttg   4500
cacaagaatg attacgacaa tgctagtaag catatattaa acgccagaga tttgcttgtg   4560
actgaaattt ccgcgttgat caatgaaagt tataatagag catatagcgt tattgttaga   4620
actcaaataa taacagagtt tgaggaaatc atcaagtata aacaattgcc acctaattcc   4680
gagaaaaaac ttcactatca aaatctttgg acaaaaagac tgctgggctg ccaaaaaaat   4740
gtcgatttat ggcaaagagt gcttagagta agatcattgg taataaagcc caagcaagac   4800
ctgcaaatat ggataaaatt tgcaaatttg tgcagaaaat ctggtagaat gaggctagca   4860
aataaggcat tgaatatgct actagaagga ggcaacgatc ctagtttacc aaatacgttc   4920
aaagctcctc ccccagttgt ttacgcgcaa ctaaatatata tttgggctac aggagcttat   4980
aaagaagcat taaaccactt gataggattt acatccaggt tagcgcatga tcttggtttg   5040
gatccgaata atatgatcgc gcaaagtgtc aaactctcaa gtgcaagtac tgctccgtat   5100
gttgaggaat acacaaaatt attagctcga tgttttttaa agcaaggtga gtggagaata   5160
gcaacacaac cgaactggag aaacacaaat ccggatgcaa ttcttggttc ttatctattg   5220
gctacacatt tcgataaaaa ttggtacaag gcatggcata attgggcctt agctaatttt   5280
gaagtaatat ccatggttca ggaagagact aagctcaacg gaggtaagaa tgatgatgat   5340
```

```
gatgacacgg cagttaataa tgataatgtg cggattgacg gtagtatcct aggaagtggt    5400
tctttgacta ttaatggcaa cagatacccg ctagagctta ttcaaagaca tgttgttcca    5460
gcgatcaagg gcttttttca ttcaatatct ctattagaaa caagttgttt gcaagacacg    5520
ttgaggttat tgactctttt atttaacttt ggtggtatta agaagtctc acaagccatg     5580 tatgaaggct tcaatttgat gaaaatagag aactggcttg aagtcttacc acagttgatc    5640
tctcgtatac atcagccaga tcctacggtg agtaattccc ttttgtcgtt gctttctgat    5700
ttagggaaag ctcatccaca agctctcgtg tatcctttaa ctgtcgcgat caagtctgaa    5760
tctgtttcaa gacaaaaagc ggctcttttca ataatagaga aaattaggat tcatagtcca   5820
gtcctggtaa accaggcaga attagttagt cacgagttga tcagagtagc cgttctatgg    5880
cacgaattat ggtatgaagg actggaagat gcgagccgcc aattttttcgt tgaacataac   5940 atagaaaaaa tgttttctac tttagaacct ttacataaac acttaggcaa tgagcctcaa    6000
acgttaagtg aggtatcgtt tcagaaatca tttggtagag atttgaacga tgcctacgaa    6060
tggttgaata actacaaaaa gtcaaaagac atcaataatt tgaaccaagc ttgggatatt    6120
tattataacg tcttcagaaa aataacacgt caaataccac agttacaaac cttagactta    6180
cagcatgttt ctccccagct tctggctact catgatctcg aattggctgt tcctgggaca    6240
tatttcccag gaaaacctac cattagaata gcgaagtttg agccattatt ttctgtgatc    6300
tcttcgaagc aaaggccaag aaaattctcc atcaagggta gcgacggtaa agattataaa    6360
tacgttttaa agggacatga agatataaga caagatagcc ttgttatgca attatttggt    6420
ctagttaaca ctttgttgaa gaatgattca gagtgtttca agagacattt ggatatccaa    6480
caatacccgg ctattccatt gtcgcctaaa tctggtttac taggatgggt accaaatagt    6540
gacacattcc acgttttgat cagagaacac cgtgatgcca aaaaaattcc gttgaacatt    6600
gaacattggg ttatgttaca aatggccccc gattatgaga atttgactct tttacaaaaa    6660
attgaagtat tcacgtacgc tttagataat acaaaaggcc aagacctta taaaatatta     6720 tggttaaaga gtaggtcgtc agagacatgg ctagaacgta gaacaactta tacgagatct    6780
ttagcagtta tgtccatgac tggttatatt ctgggactag gtgatcgcca tccaagcaac    6840
ctgatgctag atagaatcac cggtaaagtt atccacattg atttcggcga ttgttttgaa    6900
gctgccatct aagagaaaaa gtatccagaa aaagtgccat ttagactaac taggatgtta    6960
acatacgcaa tggaagttag tggaattgaa ggcagtttcc gaattacttg tgaaaatgtc    7020
atgagagtct taagagataa taagaatca ttaatggcga tcttggaagc ttttgcgctt     7080
gatcctttga tccattgggg atttgattta ccgccacaaa aacttactga gcaaactgga    7140
attcctttgc cgttgattaa tcctagtgaa ttattaagga aggggcaat tactgtcgaa     7200 gaagcggcaa atatggaagc agaacaacaa aatgagacca aaaacgccag agcaatgctt    7260
gttttgagac gtattacaga taattaacg ggcaatgata tcaagaggtt caatgaatta    7320
gacgtccctg agcaggttga taaactgatc caacaagcca cttctattga aaggttatgt    7380
caacattata ttggatggtg cccattctgg tga                                7413
```

<210> SEQ ID NO 19
<211> LENGTH: 269
<212> TYPE: PRT
<213> ORGANISM: Saccharomyces cerevisiae

<400> SEQUENCE: 19

```
Met Val Leu Ser Asp Ser Leu Lys Leu Pro Ser Thr Leu Ser Ala
1               5                   10                  15

Ala Ala Gly Val Asp Asp Cys Asp Gly Glu Asp His Pro Thr Cys Gln
            20                  25                  30

Asn Cys Phe Thr Val Lys Thr Pro Leu Trp Arg Arg Asp Glu His Gly
        35                  40                  45

Thr Val Leu Cys Asn Ala Cys Gly Leu Phe Leu Lys Leu His Gly Glu
    50                  55                  60

Pro Arg Pro Ile Ser Leu Lys Thr Asp Thr Ile Lys Ser Arg Asn Arg
65              70                  75                  80

Lys Lys Leu Asn Asn Asn Val Asn Thr Asn Ala Asn Thr His Ser
                85                  90                  95

Asn Asp Pro Asn Lys Ile Phe Lys Arg Lys Arg Leu Leu Thr Thr
            100                 105                 110

Gly Gly Gly Ser Leu Pro Thr Asn Asn Pro Lys Val Ser Ile Leu Glu
            115                 120                 125

Lys Phe Met Val Ser Gly Ser Ile Lys Pro Leu Leu Lys Pro Lys Glu
    130                 135                 140

Thr Val Pro Asn Thr Lys Glu Cys Ser Thr Gln Arg Gly Lys Phe Ser
145                 150                 155                 160

Leu Asp Pro Cys Glu Pro Ser Gly Lys Asn Tyr Leu Tyr Gln Ile Asn
                165                 170                 175

Gly Ser Asp Ile Tyr Thr Ser Asn Ile Glu Leu Thr Arg Leu Pro Asn
            180                 185                 190

Leu Ser Thr Leu Leu Glu Pro Ser Pro Phe Ser Asp Ser Ala Val Pro
    195                 200                 205

Glu Ile Glu Leu Thr Trp Lys Leu His Asn Glu Glu Val Ile Lys
210                 215                 220

Leu Lys Thr Lys Ile Ser Glu Leu Glu Leu Val Thr Asp Leu Tyr Lys
225                 230                 235                 240

Lys His Ile Phe Gln Leu Asn Glu Lys Cys Lys Gln Leu Glu Val Glu
                245                 250                 255

Leu His Ser Arg Ala Ser Val Gln Ser His Pro Gln His
            260                 265
```

<210> SEQ ID NO 20
<211> LENGTH: 810
<212> TYPE: DNA
<213> ORGANISM: Saccharomyces cerevisiae

<400> SEQUENCE: 20

```
atggtgctta gtgattcgtt gaagctgccc tcgcctacac tttcagctgc tgctggagtg      60
gatgattgtg acgagagga ccaccccacg tgccagaatt gtttcactgt caaaacgccc     120
ctatggagaa gagatgaaca cggtactgtt ctctgtaatg catgtggcct cttcctgaag     180
ttgcacgggg aaccaaggcc tatcagcttg aagacggaca ccattaagtc aagaaatagg     240
aaaaagctga ataacaacaa tgtgaacact aatgccaata cccattctaa cgacccaaat     300
aaatattca agagaaagaa gagactgctt acaactggtg gtggttcatt acctacgaat     360
aatccgaagg tttctattct ggaaaagttt atggtgagcg gtccattaa gccactgtta     420
aaaccaaagg aaaccgttcc aacacaaag gagtgctcca cgcagcgggg aaaattttct     480
ttggacccct gcgaacctag tgggaaaaac tacctctatc agatcaacgg ttcagatata     540
tacacgtcaa atatagagct gacaaggctg cctaatttgt caacattatt agaaccctca     600
```

```
cctttttcag attccgctgt accagaaata gaactaactt ggaagctaca taatgaggag      660
gaggtaatca aattgaagac caagataagc gaattggagt tggtgacaga cctatacaaa      720
aagcacatat tccaactgaa cgaaaaatgc aagcaactgg aagtggaact acactccaga      780
gcttcagtac aatctcaccc acaacattaa                                       810
```

<210> SEQ ID NO 21
<211> LENGTH: 551
<212> TYPE: PRT
<213> ORGANISM: Saccharomyces cerevisiae

<400> SEQUENCE: 21

```
Met Ala Ser Gln Ala Thr Thr Leu Arg Gly Tyr Asn Ile Arg Lys Arg
1               5                   10                  15

Asp Asn Val Phe Glu Pro Lys Ser Ser Glu Asn Leu Asn Ser Leu Asn
            20                  25                  30

Gln Ser Glu Glu Glu Gly His Ile Gly Arg Trp Pro Pro Leu Gly Tyr
        35                  40                  45

Glu Ala Val Ser Ala Glu Gln Lys Ser Ala Val Gln Leu Arg Glu Ser
    50                  55                  60

Gln Ala Gly Ala Ser Ile Ser Asn Asn Met Asn Phe Lys Ala Asn Asp
65                  70                  75                  80

Lys Ser Phe Ser Thr Ser Thr Ala Gly Arg Met Ser Pro Asp Thr Asn
                85                  90                  95

Ser Leu His His Ile Leu Pro Lys Asn Gln Val Lys Asn Asn Gly Gln
            100                 105                 110

Thr Met Asp Ala Asn Cys Asn Asn Val Ser Asn Asp Ala Asn Val
        115                 120                 125

Pro Val Cys Lys Asn Cys Leu Thr Ser Thr Thr Pro Leu Trp Arg Arg
    130                 135                 140

Asp Glu His Gly Ala Met Leu Cys Asn Ala Cys Gly Leu Phe Leu Lys
145                 150                 155                 160

Leu His Gly Lys Pro Arg Pro Ile Ser Leu Lys Thr Asp Val Ile Lys
                165                 170                 175

Ser Arg Asn Arg Lys Ser Asn Thr Asn His Ala His Asn Leu Asp Asn
            180                 185                 190

Phe Arg Asn Gln Thr Leu Ile Ala Glu Leu Lys Gly Asp Cys Asn Ile
        195                 200                 205

Glu Ser Ser Gly Arg Lys Ala Asn Arg Val Thr Ser Glu Asp Lys Lys
    210                 215                 220

Lys Lys Ser Ser Gln Leu Leu Met Gly Thr Ser Ser Thr Ala Lys Ile
225                 230                 235                 240

Ser Lys Lys Pro Lys Thr Glu Ser Lys Glu Arg Ser Asp Ser His Leu
                245                 250                 255

Ser Ala Thr Lys Leu Glu Val Leu Met Ser Gly Asp Cys Ser Arg Pro
            260                 265                 270

Asn Leu Lys Pro Lys Leu Pro Lys Gln Asp Thr Ala Ile Tyr Gln Glu
        275                 280                 285

Lys Leu Leu Thr Phe Pro Ser Tyr Thr Asp Val Lys Glu Tyr Ser Asn
    290                 295                 300

Ser Ala His Gln Ser Ala Phe Ile Lys Glu Arg Ser Gln Phe Asn Ala
305                 310                 315                 320

Ala Ser Phe Pro Leu Asn Ala Ser His Ser Val Thr Ser Lys Thr Gly
                325                 330                 335
```

```
Ala Asp Ser Pro Gln Leu Pro His Leu Ser Met Leu Leu Gly Ser Leu
            340                 345                 350

Ser Ser Thr Ser Ile Ser Asn Asn Gly Ser Glu Ile Val Ser Asn Cys
        355                 360                 365

Asn Asn Gly Ile Ala Ser Thr Ala Ala Thr Leu Ala Pro Thr Ser Ser
    370                 375                 380

Arg Thr Thr Asp Ser Asn Pro Ser Glu Val Pro Asn Gln Ile Arg Ser
385                 390                 395                 400

Thr Met Ser Ser Pro Asp Ile Ile Ser Ala Lys Arg Asn Asp Pro Ala
                405                 410                 415

Pro Leu Ser Phe His Met Ala Ser Ile Asn Asp Met Leu Glu Thr Arg
            420                 425                 430

Asp Arg Ala Ile Ser Asn Val Lys Thr Glu Thr Thr Pro Pro His Phe
        435                 440                 445

Ile Pro Phe Leu Gln Ser Ser Lys Ala Pro Cys Ile Ser Lys Ala Asn
    450                 455                 460

Ser Gln Ser Ile Ser Asn Ser Val Ser Ser Asp Val Ser Gly Arg
465                 470                 475                 480

Lys Phe Glu Asn His Pro Ala Lys Asp Leu Gly Asp Gln Leu Ser Thr
                485                 490                 495

Lys Leu His Lys Glu Glu Ile Ile Lys Leu Lys Thr Arg Ile Asn
            500                 505                 510

Glu Leu Glu Leu Val Thr Asp Leu Tyr Arg Arg His Ile Asn Glu Leu
        515                 520                 525

Asp Gly Lys Cys Arg Ala Leu Glu Glu Arg Leu Gln Arg Thr Val Lys
    530                 535                 540

Gln Glu Gly Asn Lys Gly Gly
545                 550

<210> SEQ ID NO 22
<211> LENGTH: 1656
<212> TYPE: DNA
<213> ORGANISM: Saccharomyces cerevisiae

<400> SEQUENCE: 22
atggcatcgc aggctacaac tcttcgaggc tataacatta gaaacgaga taatgtattt      60 gaaccaaaat caagtgaaaa cctcaacagc ttaaatcaaa gcgaagaaga agggcatatt     120
gggagatggc cacctttagg ttatgaagca gtatctgccg agcaaaaatc ggcagttcaa     180
ttgcgtgaat cgcaagcagg agcgtcaata agcaacaata tgaattttaa ggcgaatgac     240
aagtcttttt ccacatctac tgctggaaga atgagtccgg atacgaattc attacaccat     300
atattaccta aaaatcaagt taagaataat ggacaaacaa tggatgccaa ttgcaataat     360
aacgtatcca atgatgctaa tgttcctgtt tgtaagaact gtttaacctc tacaacacca     420
ttatggagaa gagatgagca tggagctatg ctttgtaatg cgtgtggtct cttttaaag     480 cttcatggga aacccaggcc aattagtttg aaaactgatg taataaagtc tcgaaatagg     540
aaaagtaata caaatcatgc acataatctg acaactttc ggaatcagac gctgattgca     600
gagcttaagg gtgattgtaa tatagaatca agcggtcgca aagctaacag agtaacatct     660
gaagataaaa agaaaaaaag ttcgcaactt ttaatgggaa catcatctac tgcgaagata     720
tccaagaagc caaaaacgga gtctaaggaa agaagcgatt ctcacctatc agcaacaaaa     780
ttagaggtac tgatgtcggg agattgttcg agaccaaact aaagcctaa actgcccaaa     840 caagatactg ctatatacca agagaagtta cttacgttcc caagttatac ggacgttaaa     900
```

```
gagtattcaa attctgcaca ccaatctgct tttatcaaag aacgtcgca attcaacgca      960
gcctctttcc ccctcaatgc ttcacattca gtaacatcaa aaacaggcgc agattctcct     1020
caattacctc actatcaat gctgcttgga agcttgagca gtacttcaat atcaaataac     1080
ggaagtgaaa tagtgtccaa ttgcaataat ggtattgcct ctaccgccgc aactctggca     1140
cccacttctt cacggacgac tgactctaat ccatccgagg taccgaatca aattagatcg     1200
acgatgtctt ccccagatat aatatctgct aagcgtaacg acccagcccc tttatctttc     1260
cacatggctt ctattaacga catgcttgag acgagagatc gtgcgattag caacgtgaaa     1320
accgagacga caccgcctca tttcataccg tttctacaat cttctaaagc tccctgtata     1380
tccaaagcaa attcacaatc catctcaaat agtgtttcta gttctgatgt ttctggacga     1440
aaatttgaaa atcacccagc taagattta ggtgatcagt tatccactaa attgcacaaa     1500
gaagaagaaa ttataaagct caaaactaga ataaatgagt tagaacttgt tacagattta     1560
tataggagac atatcaatga attagacggg aaatgtcgag ctcttgagga acgtttgcaa     1620
aggacagtaa aacaagaagg gaataaagga ggatag                              1656
```

<210> SEQ ID NO 23
<211> LENGTH: 2073
<212> TYPE: DNA
<213> ORGANISM: Saccharomyces cerevisiae

<400> SEQUENCE: 23

```
atatggccgc aaccgaaata gttaggtgtg gcagccgtac atatggaagc cgggcgatgg       60
ctccgccacg tgcaaagtgc aggagctttg gaaagagcgt gcatatagtg atgaaaacag     120
agagcacggt tgcgaacgga gggtctcaca atgtctcaaa ggataaatct cttggttttgc    180
gggccgcata caagatatga ttgtagtttt ttcaatggct ctactgtccc actgctgtac     240
aacagaaaat gagagatcag agaaatagta ttccggaagc cagtggtgtt tacttattag     300
tttttttgacg ccactgcgcg agttgctgcc tagctgttcc ttggccaacg catattggaa    360
cttcattcga ctgatatgct tactcagagg tccattactt caagaattgt ctcacctatc     420
gggattggcg tttgtacaag aagaaacttt catcaccttt gtttcgccac caatgaaaa      480
aaaaaacttg catggcttag gtggttcttt gtcagaaata tcttctaagg atcaagagtc     540
ttacgtgatt ctaatccctt ggcaagtcag atctcaaata tgctcactcg cagatgagta     600
gcaatgaatg cgaccaagtg actagtgact ggtgacgaca tgagccaagc tggaaccagc     660
agctttcacg tcggcttata gctctctatg gggcaatcaa ccactcatag tgactgaaga     720
tcttttttaat ataattacat tgctaaaaac gtcataccgc cttgtgagca cgataaacag    780
catatgcatt gagccttgtt attcttcgga actggggata gtaaaatgcg acccgcttag     840
gatgatcaag ctatctttgg gacggagttt tgtcatggga gtggtcatcc tactggtgat     900
gcttcaacat ttgatttact aaattttgaa atcggccgca gaataaaact attatgtcca     960
aacaattgat ggtcgaacca acgttaaggg tttcaagtat tgaattgaac ttttatgagt    1020
tctataattt cgttgcgcaa attcaactaa accaccaata tccccctac aacgctacac     1080
tttataccga tagaggaata acgcatagag ccttcgtaga attcttcaac tcgtacgtga    1140
tgggattct aaacctatcg tcatgtcgct gtacaaggct gctgcctgct ttcaaattcc     1200
caatttacc atgtccgttt cgctgagccg aatcgtcaca caaggtaatt agttctgggt     1260
atcgcttcag tatagcactg gttttttcct tgtaaaacca cagtctaaca attaaatgaa     1320
```

```
gcttttcgaa gaaattagac catgttagac tgaaagcaaa gactccggcc cgttctgagg    1380
taagttcaat gaaattggac agtttctttt caaggttagg ttttgtgttc gaaaaaaata    1440
gattaccgca cctcctttcc aaacccatg agtttccatt aaggaagagc aacgtcaata     1500
ataccacctt ttgcagatgt gattcaactc aagatgctgt aatctttccc ttctgaccct    1560 agatcaccctc atgatatcct tttgaggcaa ttaaagctgc agtgtaaact gttgaatatc   1620
tttttgaaac caaaaaaaag gacgttccac acttggctgc tttcttgata agcgagatct    1680
ttacttggag atctcgctta gtcctccgaa gggtaaaccc cgtctcttat ctttaaaaaa    1740
atgtatcaga cccttcagca cgtgacagac agcaaactac cagtcgacga ggatgctttt   1800
ccgaaagtca tgacacaagg gaaggactgt aagatcgata tcggcgcagt cttatcggat    1860
gttccaagtc cttgtctctt tcattatctg cttgctatcg caaaaaaaaa aaaatcaatt    1920
tgtttaatat caacacataa tgtacaagaa caaatcatga catacaaaag ccatataaga    1980
tgagtcttca agcagcacca agaggcctga ggcagagcaa atgttggctc gctattcttt    2040
tgtaagcaat ctggtactca ccaacctcca act                                 2073

<210> SEQ ID NO 24
<211> LENGTH: 1216
<212> TYPE: DNA
<213> ORGANISM: Saccharomyces cerevisiae

<400> SEQUENCE: 24
acatcatgtt ttgcttagta gactcttgcg ggcgttccat ccgtgtgaaa tacatcattt     60
acacctcgct ctgggtcaag taatcaaaaa ataccctcgtc gaatatcttc gacaaatctg   120
tcgcttggtt tatgtttgac ctgatgtata taaaatcatc actacccaat ttagagaaca    180
cattgcgttg cccggccggc aaaaaatcct gggccaaaag ttaaagaaa ctttctcata     240 ctcactctga agttgtacta ttacgaagca ctaaagcatt gatagataaa tcaacacaga    300
acatacatga ttaaattaga cacagctctc tgtatttttt actgtttgaa ctaaggttct    360
aatacttaca cattctttc aacccatcag atggtgtctt gccctgctt acgtaaccta     420 caacaataga ttagacacac cagtgccaag gacaatatgt tgcgttctga ctagtcgaag    480
tatcattacg ctgtgcagat cgacctgaca ccagacacaa aggagaatag gggcagcatg    540
agttccgtcg cgactcatt ccgaccttcc acaggtccgt tgattacttt ttcactgatc    600
cggtggaatc tatggttgtt tttttcatca tgatatctgt tttaggactt tttttttcag    660
ccgatcgctt atctgctcac tagaatcgta atcagtgata ttttattaa taattattat     720 ttattttttt ttataccatt ccttttgat aaggggtcgt tggtgccgtg ccgctatcag     780
gcagcctcac taatctaccc attgacctca tgcagcaaag tcacatcgcc catatctctc    840
gagtgcgata acggggaact tgatttggta actgataaga ttgttaaatg tcagtttgga    900 tgcttttttct tacgtccgat tagcttatct tctggagcaa ccggccattt acctcctcat   960
agtaaattaa acatgataag cgcatagttg gggcaacaca cctttcttcc ggaattcgct   1020
ctggatgaga catataaaga tgaaggtgaa gtccacttaa atgaatgtca atgagacgat   1080
gtttttcctc ctagattgat ttttgaattc cttgtataca aagtcttgtt ttcttattgt   1140
cctcaacaaa acaaagtag aaaagaacag accaaggaca gcaacattta taagaaacaa   1200
aaaaaagaaa taaaaa                                                   1216

<210> SEQ ID NO 25
<211> LENGTH: 1030
```

```
<212> TYPE: DNA
<213> ORGANISM: Saccharomyces cerevisiae

<400> SEQUENCE: 25
aggaaaacat attagcataa atcgtcattg ctgaaagagc gcctttacct caacctacca      60
tggcaaacat aacagaaaac ataaaaaaat tatcctagag cccaatgttc catgaaaaga     120
gctgtggcaa ggacagaaac aaaaaaaaaa tcaagaactc aacattacct atataatttt     180
tgttttctcc cattttcaaa gtcatttgtt ttccattttg caaagcaatt attatatcaa     240
taagccttt tgatgactta cctagcactc tttcaaatag aatcttctta cgaaggtgtg      300
cattctccct tttatacctc ggcggcttca ctcggcggct aaccccttat ttcctcattt     360
cctcggcggc taaaaaggga ctttggagaa atcttgcatc cgtgcctccc acggcatttt     420
tttttggttt ctttttttcc ttgaccggca taatagaaga aaaaaaaaag cgcgccgttc     480
ttcagtgccg cttgagggtg ccgtctaagc ggcactgatc tgctgcaaaa agctgcaact     540
tgccgttga tggcactccc agtggcacca tcgcactaaa taacggtctc atcgagtcat      600
agataagcag gttgcagtat ccggccaact ttcaactccc ccacgtccag cggattgctg     660
ctccttagta gtccacagtt cttaagttgc gctgcgaggc tctttttta gtgccttcta     720
gccatttctt ccagcttggc agtggttatc tctttcactg aaccgcaaat caatcctgat     780
aagacggcta agatgcatag gataggtcgg ctatacgtgt gtcttgcgct atcttcccct     840
cgtccgctaa caagactcat atccttcgtg attagtttct ttttgttatt ttcctcgtaa     900
tactcatttg ttttacatac atatataagt gctttgtctt tgatggtctg cccacaacaa     960
tgtagaacaa gtttattatg taatctttat agaagaagca cgctaatata gacaaagata    1020
gcttcgcaca                                                           1030

<210> SEQ ID NO 26
<211> LENGTH: 956
<212> TYPE: DNA
<213> ORGANISM: Saccharomyces cerevisiae

<400> SEQUENCE: 26
tctttacgtt aggggtgag agagggaggg gggtgccttt aatgtatata tacgtaagat       60
atatatatat atgtatatat atggaaatgt attcacaact ttacatgtgc attaaccaca     120
agtactgcgt acgttcaaga ttacagcaat gcgttttatt aattttttcaa gcattttcca    180
cgtagagagg aacaaagttt actgaaaaga aagaggtag agaaaaacag aaaaattttt      240
tttttctgtt tttcctgcct ctttttcttg tttgattcaa tatggtcgac cgggtaaacc     300
cctgataaaa cgataccaaa gccgggtcac ctaacttatg gccaaatgcg accggtcccg     360
cttttccgatt ttagccggcg aagacgtact tggcgccata atcaaaacct agcttgccca    420
atacttctga gttctacgtg gtgcaaaaat atttttttt ttttgaaaaa cctaccctat      480
ttcattatag atgcatccat cagtattacg gtgtcctcac acaaccctgt ctctgcacaa     540
cgtaatacct ccttttcccg tctgctagct ctcatttcgc ggtaatccaa cttcaaccag     600
caacccggat cttctatacg cagtccggtg tgtgggtgca tgactgattg gtccggccga    660
taacaggtgt gcttgcaccc agtgcccaac gtcaacaaag caggaacaac gggctgataa    720
gggagaagat aagataagat aagataacaa atcattgcgt ccgaccacag gccgacacat    780
agcagaacga tgtgaagcag cgcagcatag tgttagtgcc ggtgcagcta ccgctggtat    840
taacagccac cacaatacag agcaacaata ataacagcac tatgagtcgc acacttgcgg    900
```

```
tgcccggccc agccacatat ataggtgt gtgccactcc cggccccggt attagc      956
```

<210> SEQ ID NO 27
<211> LENGTH: 504
<212> TYPE: DNA
<213> ORGANISM: Saccharomyces cerevisiae

<400> SEQUENCE: 27

```
tcacccttgt ttatctatcc tacctttct tcttgcgtac gtgcctctca atgcgtcgtg   60
tgaattatca gtgaccggtc gtgcctataa tgtcctgcta atttcccact aaatctttcc  120
ccatggcgta ttcatcgtta tgtttgtgtc ttttgttcaa cccaaagggc tgtagcaatc  180
ttcacccgtt tgtcgttgat aacgagtttc caccttatca cttatcacta gtgctaatca  240
aacagcaaag aatgcttgat agaaaccgat cctgggctta tctcgctgca ttgtggcggc  300
atccctggac tgtaatcagc aagtgttgct tagtatatat atacatccag cgtcagcttg  360
aatttggata cagttactgt tttttcgatt ttctcttggt tattctttct gagacagtag  420
taattttgta ttactgagcg ggatattgtt tatctgccgt catactatat tacattatat  480
tatatcatat tatatataag agaa                                        504
```

<210> SEQ ID NO 28
<211> LENGTH: 424
<212> TYPE: DNA
<213> ORGANISM: Saccharomyces cerevisiae

<400> SEQUENCE: 28

```
gaaaaaaaag gtgaagtatt atgtaaattt ttgtaaagta aaacactatg ctgttgaacg   60
aaatctttca ttgaaaatat tgttattcat tcgtgatagc tgccccttc tgagtttgaa   120
cttaatattt caattacgct acttcaagtt tcaatgagat attattctgt catctttctc  180
gtcgttccta gtgattaacg ttactaaaat tactgatcct aaatagcggg cgaacagagt  240
gaaaattttc ttatcttcgc ttatctgcgc ttatcaatcc taatcagtga aaataagat   300
ataggcttga taataaggta gtttgaaaga gaacatattg caagcggttg aagctataat  360
actagatata cgaatatcat ttcgggtatt tgtactgtgc tctacaattc tactggtaat  420
atta                                                              424
```

<210> SEQ ID NO 29
<211> LENGTH: 608
<212> TYPE: PRT
<213> ORGANISM: Saccharomyces cerevisiae

<400> SEQUENCE: 29

```
Met Lys Met Pro Leu Lys Lys Met Phe Thr Ser Thr Ser Pro Arg Asn
1               5                   10                  15

Ser Ser Ser Leu Asp Ser Asp His Asp Ala Tyr Tyr Ser Lys Gln Asn
            20                  25                  30

Pro Asp Asn Phe Pro Val Lys Glu Gln Glu Ile Tyr Asn Ile Asp Leu
        35                  40                  45

Glu Glu Asn Asn Val Ser Ser Arg Ser Thr Ser Thr Ser Pro Ser
    50                  55                  60

Ala Arg Asp Asp Ser Phe Ala Val Pro Asp Gly Lys Asp Glu Asn Thr
65                  70                  75                  80

Arg Leu Arg Lys Asp Leu Lys Ala Arg His Ile Ser Met Ile Ala Ile
                85                  90                  95

Gly Gly Ser Leu Gly Thr Gly Leu Leu Ile Gly Thr Gly Thr Ala Leu
```

```
                100                 105                 110
Leu Thr Gly Gly Pro Val Ala Met Leu Ile Ala Tyr Ala Phe Val Gly
            115                 120                 125

Leu Leu Val Phe Tyr Thr Met Ala Cys Leu Gly Glu Met Ala Ser Tyr
        130                 135                 140

Ile Pro Leu Asp Gly Phe Thr Ser Tyr Ala Ser Arg Tyr Val Asp Pro
145                 150                 155                 160

Ala Leu Gly Phe Ala Ile Gly Tyr Thr Tyr Leu Phe Lys Tyr Phe Ile
                165                 170                 175

Leu Pro Pro Asn Gln Leu Thr Ala Ala Ala Leu Val Ile Gln Tyr Trp
            180                 185                 190

Ile Ser Arg Asp Arg Val Asn Pro Gly Val Trp Ile Thr Ile Phe Leu
        195                 200                 205

Val Val Ile Val Ala Ile Asn Val Val Gly Val Lys Phe Phe Gly Glu
210                 215                 220

Phe Glu Phe Trp Leu Ser Ser Phe Lys Val Met Val Met Leu Gly Leu
225                 230                 235                 240

Ile Leu Leu Leu Phe Ile Ile Met Leu Gly Gly Pro Asn His Asp
                245                 250                 255

Arg Leu Gly Phe Arg Tyr Trp Arg Asp Pro Gly Ala Phe Lys Glu Tyr
                260                 265                 270

Ser Thr Ala Ile Thr Gly Gly Lys Gly Lys Phe Val Ser Phe Val Ala
            275                 280                 285

Val Phe Val Tyr Ser Leu Phe Ser Tyr Thr Gly Ile Glu Leu Thr Gly
        290                 295                 300

Ile Val Cys Ser Glu Ala Glu Asn Pro Arg Lys Ser Val Pro Lys Ala
305                 310                 315                 320

Ile Lys Leu Thr Val Tyr Arg Ile Ile Val Phe Tyr Leu Cys Thr Val
                325                 330                 335

Phe Leu Leu Gly Met Cys Val Ala Tyr Asn Asp Pro Arg Leu Leu Ser
                340                 345                 350

Thr Lys Gly Lys Ser Met Ser Ala Ala Ala Ser Pro Phe Val Val Ala
            355                 360                 365

Ile Gln Asn Ser Gly Ile Glu Val Leu Pro His Ile Phe Asn Ala Cys
        370                 375                 380

Val Leu Val Phe Val Phe Ser Ala Cys Asn Ser Asp Leu Tyr Val Ser
385                 390                 395                 400

Ser Arg Asn Leu Tyr Ala Leu Ala Ile Asp Gly Lys Ala Pro Lys Ile
                405                 410                 415

Phe Ala Lys Thr Ser Arg Trp Gly Val Pro Tyr Asn Ala Leu Ile Leu
                420                 425                 430

Ser Val Leu Phe Cys Gly Leu Ala Tyr Met Asn Val Ser Ser Gly Ser
            435                 440                 445

Ala Lys Ile Phe Asn Tyr Phe Val Asn Val Val Ser Met Phe Gly Ile
        450                 455                 460

Leu Ser Trp Ile Thr Ile Leu Ile Val Tyr Ile Tyr Phe Asp Lys Ala
465                 470                 475                 480

Cys Arg Ala Gln Gly Ile Asp Lys Ser Lys Phe Ala Tyr Val Ala Pro
                485                 490                 495

Gly Gln Arg Tyr Gly Ala Tyr Phe Ala Leu Phe Phe Cys Ile Leu Ile
                500                 505                 510

Ala Leu Ile Lys Asn Phe Thr Val Phe Leu Gly His Lys Phe Asp Tyr
            515                 520                 525
```

```
Lys Thr Phe Ile Thr Gly Tyr Ile Gly Leu Pro Val Tyr Ile Ile Ser
    530                 535                 540

Trp Ala Gly Tyr Lys Leu Ile Tyr Lys Thr Lys Val Ile Lys Ser Thr
545                 550                 555                 560

Asp Val Asp Leu Tyr Thr Phe Lys Glu Ile Tyr Asp Arg Glu Glu Glu
                565                 570                 575

Glu Gly Arg Met Lys Asp Gln Glu Lys Glu Glu Arg Leu Lys Ser Asn
                580                 585                 590

Gly Lys Asn Met Glu Trp Phe Tyr Glu Lys Phe Leu Gly Asn Ile Phe
                595                 600                 605
```

<210> SEQ ID NO 30
<211> LENGTH: 1827
<212> TYPE: DNA
<213> ORGANISM: Saccharomyces cerevisiae

<400> SEQUENCE: 30

| | | |
|---|---|---|
| atgaagatgc ctctaaagaa gatgtttacc agcacgtctc ctcgtaactc ttcttctctt | 60 |
| gacagtgatc atgacgctta ctattcgaaa caaaatcctg acaatttccc tgtaaaggag | 120 |
| caagaaatct ataacattga cctggaagaa acaatgtgt cctctcgttc atccacctct | 180 |
| acatcacctt cagcaaggga cgactctttc gcagttccag atggtaaaga cgaaaacacg | 240 |
| cggttgagga aagatttaaa ggcaagacat atttctatga tcgccattgg tggttcatta | 300 |
| ggtacaggtc tgcttatagg tacaggtacc gccttattga cgggtggtcc ggttgcgatg | 360 |
| ttaattgcat atgcctttgt cggcctttta gtcttttaca ccatggcctg tcttggtgaa | 420 |
| atggcttctt acattccatt ggatggtttt acaagttatg cctcacgtta cgtggatcct | 480 |
| gcattaggtt ttgctattgg ttatacttac cttttcaaat atttcatctt acctcccaac | 540 |
| caacttactg ctgctgcttt ggtcattcaa tattggatca gcagagaccg tgttaaccct | 600 |
| ggtgtgtgga ttactatatt cttggttgtt attgtcgcta tcaatgtcgt cggtgtaaaa | 660 |
| ttctttggtg aatttgaatt ttggttgtcc agtttcaaag tcatggtaat gttgggtcta | 720 |
| atcctgttac tatttattat tatgcttggt ggaggtccta accatgaccg cctagggttt | 780 |
| agatactggc gtgatcctgg tgcgttcaaa gaatattcga cggctatcac tggtggtaaa | 840 |
| ggtaaatttg tttcgttcgt tgctgttttc gtttacagtc ttttcagtta cacgggtatt | 900 |
| gaattgacag gtatcgtttg ttctgaagct gagaatccaa gaaaaagtgt tccaaaggca | 960 |
| attaaattga cagtttaccg tatcattgtt ttttacctat gcaccgtttt cctttgggt | 1020 |
| atgtgcgttg catacaatga ccctcgttta cttccacaa aaggtaagag tatgtctgct | 1080 |
| gcggcatctc cattcgtggt tgccattcaa aactcaggta ttgaagtctt acctcatatc | 1140 |
| ttcaatgctt gtgtcttggt tttcgttttc agtgcttgta actcagattt gtacgtttct | 1200 |
| tccagaaatt tatatgcgtt ggcaattgat ggtaaagcgc caaagatctt cgctaagaca | 1260 |
| agtagatggg gtgttcctta caatgcttta atactctccg tgctgttttg tggcttggcg | 1320 |
| tacatgaatg tgtcttcagg atcagcaaag attttcaact actttgttaa cgttgtttct | 1380 |
| atgttcggaa tcttgagttg gatcaccatt ttaattgttt acatctactt cgataaagcc | 1440 |
| tgccgtgctc aagggattga caaatcaaaa tttgcttatg tcgctcctgg ccaacgttat | 1500 |
| ggtgcttatt tgctttatt cttctgcatt ttgattgctt taatcaaaaa cttcactgtt | 1560 |
| ttcctaggtc ataaatttga ttataaaaca ttcatcaccg gtatattgg cctgcctgtc | 1620 |
| tatatcattt cttgggctgg ttacaaattg atatacaaaa ccaaagtgat aaagtctacc | 1680 |

-continued

```
gacgtggatt tgtacacatt taaggaaata tacgatagag aagaagaaga gggaagaatg    1740
aaggaccaag aaaaggaaga gcgtttaaaa agtaacggta aaaatatgga gtggttctat    1800
gaaaaatttt tgggtaatat cttctag                                        1827
```

<210> SEQ ID NO 31
<211> LENGTH: 730
<212> TYPE: PRT
<213> ORGANISM: Saccharomyces cerevisiae

<400> SEQUENCE: 31

```
Met Gln Asp Asp Pro Glu Asn Ser Lys Leu Tyr Asp Leu Leu Asn Ser
1               5                   10                  15

His Leu Asp Val His Gly Arg Ser Asn Glu Glu Pro Arg Gln Thr Gly
            20                  25                  30

Asp Ser Arg Ser Gln Ser Ser Gly Asn Thr Gly Glu Asn Glu Glu Asp
        35                  40                  45

Ile Ala Phe Ala Ser Gly Leu Asn Gly Gly Thr Phe Asp Ser Met Leu
    50                  55                  60

Glu Ala Leu Pro Asp Asp Leu Tyr Phe Thr Asp Phe Val Ser Pro Phe
65                  70                  75                  80

Thr Ala Ala Ala Thr Thr Ser Val Thr Thr Lys Thr Val Lys Asp Thr
                85                  90                  95

Thr Pro Ala Thr Asn His Met Asp Asp Ile Ala Met Phe Asp Ser
            100                 105                 110

Leu Ala Thr Thr Gln Pro Ile Asp Ile Ala Ala Ser Asn Gln Gln Asn
        115                 120                 125

Gly Glu Ile Ala Gln Leu Trp Asp Phe Asn Val Asp Gln Phe Asn Met
    130                 135                 140

Thr Pro Ser Asn Ser Ser Gly Ser Ala Thr Ile Ser Ala Pro Asn Ser
145                 150                 155                 160

Phe Thr Ser Asp Ile Pro Gln Tyr Asn His Gly Ser Leu Gly Asn Ser
                165                 170                 175

Val Ser Lys Ser Ser Leu Phe Pro Tyr Asn Ser Ser Thr Ser Asn Ser
            180                 185                 190

Asn Ile Asn Gln Pro Ser Ile Asn Asn Ser Asn Thr Asn Ala Gln
        195                 200                 205

Ser His His Ser Phe Asn Ile Tyr Lys Leu Gln Asn Asn Ser Ser
    210                 215                 220

Ser Ser Ala Met Asn Ile Thr Asn Asn Asn Ser Asn Asn Ser Asn
225                 230                 235                 240

Ile Gln His Pro Phe Leu Lys Lys Ser Asp Ser Ile Gly Leu Ser Ser
                245                 250                 255

Ser Asn Thr Thr Asn Ser Val Arg Lys Asn Ser Leu Ile Lys Pro Met
            260                 265                 270

Ser Ser Thr Ser Leu Ala Asn Phe Lys Arg Ala Ala Ser Val Ser Ser
        275                 280                 285

Ser Ile Ser Asn Met Glu Pro Ser Gly Gln Asn Lys Lys Pro Leu Ile
    290                 295                 300

Gln Cys Phe Asn Cys Lys Thr Phe Lys Thr Pro Leu Trp Arg Arg Ser
305                 310                 315                 320

Pro Glu Gly Asn Thr Leu Cys Asn Ala Cys Gly Leu Phe Gln Lys Leu
                325                 330                 335

His Gly Thr Met Arg Pro Leu Ser Leu Lys Ser Asp Val Ile Lys Lys
```

```
                340                 345                 350
Arg Ile Ser Lys Lys Arg Ala Lys Gln Thr Asp Pro Asn Ile Ala Gln
            355                 360                 365

Asn Thr Pro Ser Ala Pro Ala Thr Ala Ser Thr Ser Val Thr Thr Thr
370                 375                 380

Asn Ala Lys Pro Ile Arg Ser Arg Lys Lys Ser Leu Gln Gln Asn Ser
385                 390                 395                 400

Leu Ser Arg Val Ile Pro Glu Glu Ile Ile Arg Asp Asn Ile Gly Asn
                405                 410                 415

Thr Asn Asn Ile Leu Asn Val Asn Arg Gly Gly Tyr Asn Phe Asn Ser
            420                 425                 430

Val Pro Ser Pro Val Leu Met Asn Ser Gln Ser Tyr Asn Ser Ser Asn
        435                 440                 445

Ala Asn Phe Asn Gly Ala Ser Asn Ala Asn Leu Asn Ser Asn Asn Leu
    450                 455                 460

Met Arg His Asn Ser Asn Thr Val Thr Pro Asn Phe Arg Arg Ser Ser
465                 470                 475                 480

Arg Arg Ser Ser Thr Ser Ser Asn Thr Ser Ser Ser Lys Ser Ser
                485                 490                 495

Ser Arg Ser Val Val Pro Ile Leu Pro Lys Pro Ser Pro Asn Ser Ala
            500                 505                 510

Asn Ser Gln Gln Phe Asn Met Asn Met Asn Leu Met Asn Thr Thr Asn
        515                 520                 525

Asn Val Ser Ala Gly Asn Ser Val Ala Ser Ser Pro Arg Ile Ile Ser
    530                 535                 540

Ser Ala Asn Phe Asn Ser Asn Ser Pro Leu Gln Gln Asn Leu Leu Ser
545                 550                 555                 560

Asn Ser Phe Gln Arg Gln Gly Met Asn Ile Pro Arg Arg Lys Met Ser
                565                 570                 575

Arg Asn Ala Ser Tyr Ser Ser Ser Phe Met Ala Ala Ser Leu Gln Gln
            580                 585                 590

Leu His Glu Gln Gln Gln Val Asp Val Asn Ser Asn Thr Asn Thr Asn
        595                 600                 605

Ser Asn Arg Gln Asn Trp Asn Ser Ser Asn Ser Val Ser Thr Asn Ser
    610                 615                 620

Arg Ser Ser Asn Phe Val Ser Gln Lys Pro Asn Phe Asp Ile Phe Asn
625                 630                 635                 640

Thr Pro Val Asp Ser Pro Ser Val Ser Arg Pro Ser Ser Arg Lys Ser
                645                 650                 655

His Thr Ser Leu Leu Ser Gln Gln Leu Gln Asn Ser Glu Ser Asn Ser
            660                 665                 670

Phe Ile Ser Asn His Lys Phe Asn Asn Arg Leu Ser Ser Asp Ser Thr
        675                 680                 685

Ser Pro Ile Lys Tyr Glu Ala Asp Val Ser Ala Gly Gly Lys Ile Ser
    690                 695                 700

Glu Asp Asn Ser Thr Lys Gly Ser Ser Lys Glu Ser Ser Ala Ile Ala
705                 710                 715                 720

Asp Glu Leu Asp Trp Leu Lys Phe Gly Ile
                725                 730

<210> SEQ ID NO 32
<211> LENGTH: 2193
<212> TYPE: DNA
<213> ORGANISM: Saccharomyces cerevisiae
```

<400> SEQUENCE: 32

```
atgcaagacg accccgaaaa ttcgaagctg tacgacctgc tgaatagtca tctggacgtg      60
catggtcgaa gtaatgaaga gccgagacaa actggtgaca gtaggagcca gagtagtggc     120
aacaccggtg aaaacgagga ggatatagca tttgccagtg gattaaacgg cggcacattc     180
gactcaatgc tggaggcact gcccgatgat ttatatttta cggacttcgt gtctcctttt     240
acagcagctg ccacgaccag cgtgactact aagacggtca aggacaccac accagctacc     300
aatcatatgg atgatgatat tgcgatgttt gattcacttg ccacaactca gcccatcgac     360
atagccgcat ccaaccaaca aaatggtgaa attgcacaac tttgggactt taacgtggac     420
caattcaaca tgacgcccag caactcgagc ggttcagcta ctattagtgc tcctaacagc     480
tttacttccg ataccgca atacaaccac ggttccctcg caacagcgt ctccaaatcc       540
tcactgttcc cgtataattc cagcacgtcc aacagcaaca tcaaccagcc atctatcaat     600
aacaactcaa atactaatgc gcagtcccac cattccttca acatctacaa actacaaaac     660
aacaactcat cttcatccgc tatgaacatt accaataata ataatagcaa caatagtaat     720
atccagcatc cttttctgaa gaagagcgat tcgataggat tatcttcatc caacacaaca     780
aattctgtaa gaaaaaactc acttatcaag ccaatgtcgt ccacgtccct ggccaatttc     840
aaaagagctg cctcagtatc ttccagtata tccaatatgg aaccatcagg acaaaataaa     900
aaacctctga tacaatgttt caattgtaaa actttcaaga caccgctttg gaggagaagc     960
ccagagggga atactctttg caatgcctgc ggtcttttcc agaaattaca tggtaccatg    1020
aggccattat ccttaaaatc ggacgttatc aaaaagagga tttcaagaa gagagccaaa    1080
caaacggacc caaacattgc acaaaatact ccaagtgcac ctgcaactgc ctcaacttca    1140
gtaaccacta caaatgctaa acccatacga tcgaggaaaa aatcactaca caaaactct     1200
ttatctagag tgatacctga agaaatcatt agagacaaca tcggtaatac taataatatc    1260
cttaatgtaa atagggggagg ctataacttc aactcagtcc cctccccggt cctcatgaac    1320
agccaatcgt ataatagtag taacgcaaat tttaatggag caagcaatgc aaatttgaat    1380
tctaataact taatgcgtca caattcgaac actgttactc ctaatttag aaggtcttca     1440
agacgaagta gtacttcatc gaacaccctca agttccagta atcttcatc cagatctgtt    1500
gttccgatat taccaaaacc ttcacctaat agcgctaatt cacagcagtt caacatgaac    1560
atgaacctaa tgaacacaac aaataatgta agtgcaggaa atagtgtcgc atcctcacca    1620
agaattatat cgtccgcaaa ctttaactca aatagtcctc tacagcagaa tctattatca    1680
aattctttcc aacgtcaagg aatgaatata ccaagaagaa agatgtcgcg caatgcatcg    1740
tactcctcat cgtttatggc tgcgtctttg caacaactgc acgaacagca acaagtggac    1800
gtgaattcca acacaaacac gaattcgaat agacagaatt ggaattcaag caatagcgtt    1860
tcaacaaatt caagatcatc aaattttgtc tctcaaaagc caaattttga tattttaat    1920
actcctgtag attcaccgag tgtctcaaga ccttcttcaa gaaaatcaca tacctcattg    1980
ttatcacaac aattgcagaa ctcggagtcg aattcgttta tctcaaatca caaatttaac    2040
aatagattat caagtgactc tacttcacct ataaaatatg aagcagatgt gagtgcaggc    2100
ggaaagatca gtgaggataa ttccacaaaa ggatcttcta agaaagttc agcaattgct    2160
gacgaattgg attggttaaa atttggtata tga                                 2193
```

<210> SEQ ID NO 33

<211> LENGTH: 2474
<212> TYPE: PRT
<213> ORGANISM: Saccharomyces cerevisiae

<400> SEQUENCE: 33

```
Met Asn Lys Tyr Ile Asn Lys Tyr Thr Thr Pro Pro Asn Leu Leu Ser
1               5                   10                  15

Leu Arg Gln Arg Ala Glu Gly Lys His Arg Thr Arg Lys Lys Leu Thr
            20                  25                  30

His Lys Ser His Ser His Asp Asp Glu Met Ser Thr Thr Ser Asn Thr
        35                  40                  45

Asp Ser Asn His Asn Gly Pro Asn Asp Ser Gly Arg Val Ile Thr Gly
    50                  55                  60

Ser Ala Gly His Ile Gly Lys Ile Ser Phe Val Asp Ser Glu Leu Asp
65                  70                  75                  80

Thr Thr Phe Ser Thr Leu Asn Leu Ile Phe Asp Lys Leu Lys Ser Asp
                85                  90                  95

Val Pro Gln Glu Arg Ala Ser Gly Ala Asn Glu Leu Ser Thr Thr Leu
            100                 105                 110

Thr Ser Leu Ala Arg Glu Val Ser Ala Glu Gln Phe Gln Arg Phe Ser
        115                 120                 125

Asn Ser Leu Asn Asn Lys Ile Phe Glu Leu Ile His Gly Phe Thr Ser
    130                 135                 140

Ser Glu Lys Ile Gly Gly Ile Leu Ala Val Asp Thr Leu Ile Ser Phe
145                 150                 155                 160

Tyr Leu Ser Thr Glu Glu Leu Pro Asn Gln Thr Ser Arg Leu Ala Asn
                165                 170                 175

Tyr Leu Arg Val Leu Ile Pro Ser Ser Asp Ile Glu Val Met Arg Leu
            180                 185                 190

Ala Ala Asn Thr Leu Gly Arg Leu Thr Val Pro Gly Gly Thr Leu Thr
        195                 200                 205

Ser Asp Phe Val Glu Phe Glu Val Arg Thr Cys Ile Asp Trp Leu Thr
    210                 215                 220

Leu Thr Ala Asp Asn Asn Ser Ser Ser Ser Lys Leu Glu Tyr Arg Arg
225                 230                 235                 240

His Ala Ala Leu Leu Ile Ile Lys Ala Leu Ala Asp Asn Ser Pro Tyr
                245                 250                 255

Leu Leu Tyr Pro Tyr Val Asn Ser Ile Leu Asp Asn Ile Trp Val Pro
            260                 265                 270

Leu Arg Asp Ala Lys Leu Ile Ile Arg Leu Asp Ala Ala Val Ala Leu
        275                 280                 285

Gly Lys Cys Leu Thr Ile Ile Gln Asp Arg Asp Pro Ala Leu Gly Lys
    290                 295                 300

Gln Trp Phe Gln Arg Leu Phe Gln Gly Cys Thr His Gly Leu Ser Leu
305                 310                 315                 320

Asn Thr Asn Asp Ser Val His Ala Thr Leu Leu Val Phe Arg Glu Leu
                325                 330                 335

Leu Ser Leu Lys Ala Pro Tyr Leu Arg Asp Lys Tyr Asp Asp Ile Tyr
            340                 345                 350

Lys Ser Thr Met Lys Tyr Lys Glu Tyr Lys Phe Asp Val Ile Arg Arg
        355                 360                 365

Glu Val Tyr Ala Ile Leu Pro Leu Leu Ala Ala Phe Asp Pro Ala Ile
    370                 375                 380

Phe Thr Lys Lys Tyr Leu Asp Arg Ile Met Val His Tyr Leu Arg Tyr
```

```
                385                 390                 395                 400
Leu Lys Asn Ile Asp Met Asn Ala Ala Asn Asn Ser Asp Lys Pro Phe
                    405                 410                 415

Ile Leu Val Ser Ile Gly Asp Ile Ala Phe Glu Val Gly Ser Ser Ile
            420                 425                 430

Ser Pro Tyr Met Thr Leu Ile Leu Asp Asn Ile Arg Glu Gly Leu Arg
                435                 440                 445

Thr Lys Phe Lys Val Arg Lys Gln Phe Glu Lys Asp Leu Phe Tyr Cys
        450                 455                 460

Ile Gly Lys Leu Ala Cys Ala Leu Gly Pro Ala Phe Ala Lys His Leu
465                 470                 475                 480

Asn Lys Asp Leu Leu Asn Leu Met Leu Asn Cys Pro Met Ser Asp His
                485                 490                 495

Met Gln Glu Thr Leu Met Ile Leu Asn Glu Lys Ile Pro Ser Leu Glu
                500                 505                 510

Ser Thr Val Asn Ser Arg Ile Leu Asn Leu Leu Ser Ile Ser Leu Ser
            515                 520                 525

Gly Glu Lys Phe Ile Gln Ser Asn Gln Tyr Asp Phe Asn Asn Gln Phe
        530                 535                 540

Ser Ile Glu Lys Ala Arg Lys Ser Arg Asn Gln Ser Phe Met Lys Lys
545                 550                 555                 560

Thr Gly Glu Ser Asn Asp Asp Ile Thr Asp Ala Gln Ile Leu Ile Gln
                565                 570                 575

Cys Phe Lys Met Leu Gln Leu Ile His His Gln Tyr Ser Leu Thr Glu
                580                 585                 590

Phe Val Arg Leu Ile Thr Ile Ser Tyr Ile Glu His Glu Asp Ser Ser
            595                 600                 605

Val Arg Lys Leu Ala Ala Leu Thr Ser Cys Asp Leu Phe Ile Lys Asp
        610                 615                 620

Asp Ile Cys Lys Gln Thr Ser Val His Ala Leu His Ser Val Ser Glu
625                 630                 635                 640

Val Leu Ser Lys Leu Leu Met Ile Ala Ile Thr Asp Pro Val Ala Glu
                645                 650                 655

Ile Arg Leu Glu Ile Leu Gln His Leu Gly Ser Asn Phe Asp Pro Gln
                660                 665                 670

Leu Ala Gln Pro Asp Asn Leu Arg Leu Leu Phe Met Ala Leu Asn Asp
            675                 680                 685

Glu Ile Phe Gly Ile Gln Leu Glu Ala Ile Lys Ile Ile Gly Arg Leu
        690                 695                 700

Ser Ser Val Asn Pro Ala Tyr Val Val Pro Ser Leu Arg Lys Thr Leu
705                 710                 715                 720

Leu Glu Leu Leu Thr Gln Leu Lys Phe Ser Asn Met Pro Lys Lys Lys
                725                 730                 735

Glu Glu Ser Ala Thr Leu Leu Cys Thr Leu Ile Asn Ser Ser Asp Glu
                740                 745                 750

Val Ala Lys Pro Tyr Ile Asp Pro Ile Leu Asp Val Ile Leu Pro Lys
            755                 760                 765

Cys Gln Asp Ala Ser Ser Ala Val Ala Ser Thr Ala Leu Lys Val Leu
        770                 775                 780

Gly Glu Leu Ser Val Val Gly Gly Lys Glu Met Thr Arg Tyr Leu Lys
785                 790                 795                 800

Glu Leu Met Pro Leu Ile Ile Asn Thr Phe Gln Asp Gln Ser Asn Ser
                805                 810                 815
```

-continued

Phe Lys Arg Asp Ala Ala Leu Thr Thr Leu Gly Gln Leu Ala Ala Ser
           820                 825                 830

Ser Gly Tyr Val Val Gly Pro Leu Asp Tyr Pro Glu Leu Leu Gly
           835                 840                 845

Ile Leu Ile Asn Ile Leu Lys Thr Glu Asn Asn Pro His Ile Arg Arg
           850                 855                 860

Gly Thr Val Arg Leu Ile Gly Ile Leu Gly Ala Leu Asp Pro Tyr Lys
865                 870                 875                 880

His Arg Glu Ile Glu Val Thr Ser Asn Ser Lys Ser Val Glu Gln
                885                 890                 895

Asn Ala Pro Ser Ile Asp Ile Ala Leu Leu Met Gln Gly Val Ser Pro
           900                 905                 910

Ser Asn Asp Glu Tyr Tyr Pro Thr Val Val Ile His Asn Leu Met Lys
           915                 920                 925

Ile Leu Asn Asp Pro Ser Leu Ser Ile His Thr Ala Ala Ile Gln
           930                 935                 940

Ala Ile Met His Ile Phe Gln Asn Leu Gly Leu Arg Cys Val Ser Phe
945                 950                 955                 960

Leu Asp Gln Ile Ile Pro Gly Ile Ile Leu Val Met Arg Ser Cys Pro
                965                 970                 975

Pro Ser Gln Leu Asp Phe Tyr Phe Gln Leu Gly Ser Leu Ile Ser
           980                 985                 990

Ile Val Lys Gln His Ile Arg Pro His Val Glu Lys Ile Tyr Gly Val
           995                 1000                1005

Ile Arg Glu Phe Phe Pro Ile Ile Lys Leu Gln Ile Thr Ile Ile
           1010                1015                1020

Ser Val Ile Glu Ser Ile Ser Lys Ala Leu Glu Gly Glu Phe Lys
           1025                1030                1035

Arg Phe Val Pro Glu Thr Leu Thr Phe Phe Leu Asp Ile Leu Glu
           1040                1045                1050

Asn Asp Gln Ser Asn Lys Arg Ile Val Pro Ile Arg Ile Leu Lys
           1055                1060                1065

Ser Leu Val Thr Phe Gly Pro Asn Leu Glu Asp Tyr Ser His Leu
           1070                1075                1080

Ile Met Pro Ile Val Val Arg Met Thr Glu Tyr Ser Ala Gly Ser
           1085                1090                1095

Leu Lys Lys Ile Ser Ile Ile Thr Leu Gly Arg Leu Ala Lys Asn
           1100                1105                1110

Ile Asn Leu Ser Glu Met Ser Ser Arg Ile Val Gln Ala Leu Val
           1115                1120                1125

Arg Ile Leu Asn Asn Gly Asp Arg Glu Leu Thr Lys Ala Thr Met
           1130                1135                1140

Asn Thr Leu Ser Leu Leu Leu Leu Gln Leu Gly Thr Asp Phe Val
           1145                1150                1155

Val Phe Val Pro Val Ile Asn Lys Ala Leu Leu Arg Asn Arg Ile
           1160                1165                1170

Gln His Ser Val Tyr Asp Gln Leu Val Asn Lys Leu Leu Asn Asn
           1175                1180                1185

Glu Cys Leu Pro Thr Asn Ile Ile Phe Asp Lys Glu Asn Glu Val
           1190                1195                1200

Pro Glu Arg Lys Asn Tyr Glu Asp Glu Met Gln Val Thr Lys Leu
           1205                1210                1215

-continued

```
Pro Val Asn Gln Asn Ile Leu Lys Asn Ala Trp Tyr Cys Ser Gln
1220                1225                1230

Gln Lys Thr Lys Glu Asp Trp Gln Glu Trp Ile Arg Arg Leu Ser
    1235                1240                1245

Ile Gln Leu Leu Lys Glu Ser Pro Ser Ala Cys Leu Arg Ser Cys
    1250                1255                1260

Ser Ser Leu Val Ser Val Tyr Tyr Pro Leu Ala Arg Glu Leu Phe
    1265                1270                1275

Asn Ala Ser Phe Ser Ser Cys Trp Val Glu Leu Gln Thr Ser Tyr
    1280                1285                1290

Gln Glu Asp Leu Ile Gln Ala Leu Cys Lys Ala Leu Ser Ser Ser
    1295                1300                1305

Glu Asn Pro Pro Glu Ile Tyr Gln Met Leu Leu Asn Leu Val Glu
    1310                1315                1320

Phe Met Glu His Asp Asp Lys Pro Leu Pro Ile Pro Ile His Thr
    1325                1330                1335

Leu Gly Lys Tyr Ala Gln Lys Cys His Ala Phe Ala Lys Ala Leu
    1340                1345                1350

His Tyr Lys Glu Val Glu Phe Leu Glu Glu Pro Lys Asn Ser Thr
    1355                1360                1365

Ile Glu Ala Leu Ile Ser Ile Asn Asn Gln Leu His Gln Thr Asp
    1370                1375                1380

Ser Ala Ile Gly Ile Leu Lys His Ala Gln Gln His Asn Glu Leu
    1385                1390                1395

Gln Leu Lys Glu Thr Trp Tyr Glu Lys Leu Gln Arg Trp Glu Asp
    1400                1405                1410

Ala Leu Ala Ala Tyr Asn Glu Lys Glu Ala Ala Gly Glu Asp Ser
    1415                1420                1425

Val Glu Val Met Met Gly Lys Leu Arg Ser Leu Tyr Ala Leu Gly
    1430                1435                1440

Glu Trp Glu Glu Leu Ser Lys Leu Ala Ser Glu Lys Trp Gly Thr
    1445                1450                1455

Ala Lys Pro Glu Val Lys Lys Ala Met Ala Pro Leu Ala Ala Gly
    1460                1465                1470

Ala Ala Trp Gly Leu Glu Gln Trp Asp Glu Ile Ala Gln Tyr Thr
    1475                1480                1485

Ser Val Met Lys Ser Gln Ser Pro Asp Lys Glu Phe Tyr Asp Ala
    1490                1495                1500

Ile Leu Cys Leu His Arg Asn Asn Phe Lys Lys Ala Glu Val His
    1505                1510                1515

Ile Phe Asn Ala Arg Asp Leu Leu Val Thr Glu Leu Ser Ala Leu
    1520                1525                1530

Val Asn Glu Ser Tyr Asn Arg Ala Tyr Asn Val Val Arg Ala
    1535                1540                1545

Gln Ile Ile Ala Glu Leu Glu Glu Ile Ile Lys Tyr Lys Lys Leu
    1550                1555                1560

Pro Gln Asn Ser Asp Lys Arg Leu Thr Met Arg Glu Thr Trp Asn
    1565                1570                1575

Thr Arg Leu Leu Gly Cys Gln Lys Asn Ile Asp Val Trp Gln Arg
    1580                1585                1590

Ile Leu Arg Val Arg Ser Leu Val Ile Lys Pro Lys Glu Asp Ala
    1595                1600                1605

Gln Val Arg Ile Lys Phe Ala Asn Leu Cys Arg Lys Ser Gly Arg
```

-continued

```
            1610                1615                1620
Met Ala Leu Ala Lys Lys Val Leu Asn Thr Leu Leu Glu Glu Thr
            1625                1630                1635
Asp Asp Pro Asp His Pro Asn Thr Ala Lys Ala Ser Pro Pro Val
            1640                1645                1650
Val Tyr Ala Gln Leu Lys Tyr Leu Trp Ala Thr Gly Leu Gln Asp
            1655                1660                1665
Glu Ala Leu Lys Gln Leu Ile Asn Phe Thr Ser Arg Met Ala His
            1670                1675                1680
Asp Leu Gly Leu Asp Pro Asn Asn Met Ile Ala Gln Ser Val Pro
            1685                1690                1695
Gln Gln Ser Lys Arg Val Pro Arg His Val Glu Asp Tyr Thr Lys
            1700                1705                1710
Leu Leu Ala Arg Cys Phe Leu Lys Gln Gly Glu Trp Arg Val Cys
            1715                1720                1725
Leu Gln Pro Lys Trp Arg Leu Ser Asn Pro Asp Ser Ile Leu Gly
            1730                1735                1740
Ser Tyr Leu Leu Ala Thr His Phe Asp Asn Thr Trp Tyr Lys Ala
            1745                1750                1755
Trp His Asn Trp Ala Leu Ala Asn Phe Glu Val Ile Ser Met Leu
            1760                1765                1770
Thr Ser Val Ser Lys Lys Lys Gln Glu Gly Ser Asp Ala Ser Ser
            1775                1780                1785
Val Thr Asp Ile Asn Glu Phe Asp Asn Gly Met Ile Gly Val Asn
            1790                1795                1800
Thr Phe Asp Ala Lys Glu Val His Tyr Ser Ser Asn Leu Ile His
            1805                1810                1815
Arg His Val Ile Pro Ala Ile Lys Gly Phe Phe His Ser Ile Ser
            1820                1825                1830
Leu Ser Glu Ser Ser Ser Leu Gln Asp Ala Leu Arg Leu Leu Thr
            1835                1840                1845
Leu Trp Phe Thr Phe Gly Gly Ile Pro Glu Ala Thr Gln Ala Met
            1850                1855                1860
His Glu Gly Phe Asn Leu Ile Gln Ile Gly Thr Trp Leu Glu Val
            1865                1870                1875
Leu Pro Gln Leu Ile Ser Arg Ile His Gln Pro Asn Gln Ile Val
            1880                1885                1890
Ser Arg Ser Leu Leu Ser Leu Leu Ser Asp Leu Gly Lys Ala His
            1895                1900                1905
Pro Gln Ala Leu Val Tyr Pro Leu Met Val Ala Ile Lys Ser Glu
            1910                1915                1920
Ser Leu Ser Arg Gln Lys Ala Ala Leu Ser Ile Ile Glu Lys Met
            1925                1930                1935
Arg Ile His Ser Pro Val Leu Val Asp Gln Ala Glu Leu Val Ser
            1940                1945                1950
His Glu Leu Ile Arg Met Ala Val Leu Trp His Glu Gln Trp Tyr
            1955                1960                1965
Glu Gly Leu Asp Asp Ala Ser Arg Gln Phe Phe Gly Glu His Asn
            1970                1975                1980
Thr Glu Lys Met Phe Ala Ala Leu Glu Pro Leu Tyr Glu Met Leu
            1985                1990                1995
Lys Arg Gly Pro Glu Thr Leu Arg Glu Ile Ser Phe Gln Asn Ser
            2000                2005                2010
```

```
Phe Gly Arg Asp Leu Asn Asp Ala Tyr Glu Trp Leu Met Asn Tyr
    2015                2020                2025

Lys Lys Ser Lys Asp Val Ser Asn Leu Asn Gln Ala Trp Asp Ile
    2030                2035                2040

Tyr Tyr Asn Val Phe Arg Lys Ile Gly Lys Gln Leu Pro Gln Leu
    2045                2050                2055

Gln Thr Leu Glu Leu Gln His Val Ser Pro Lys Leu Leu Ser Ala
    2060                2065                2070

His Asp Leu Glu Leu Ala Val Pro Gly Thr Arg Ala Ser Gly Gly
    2075                2080                2085

Lys Pro Ile Val Lys Ile Ser Lys Phe Glu Pro Val Phe Ser Val
    2090                2095                2100

Ile Ser Ser Lys Gln Arg Pro Arg Lys Phe Cys Ile Lys Gly Ser
    2105                2110                2115

Asp Gly Lys Asp Tyr Lys Tyr Val Leu Lys Gly His Glu Asp Ile
    2120                2125                2130

Arg Gln Asp Ser Leu Val Met Gln Leu Phe Gly Leu Val Asn Thr
    2135                2140                2145

Leu Leu Gln Asn Asp Ala Glu Cys Phe Arg Arg His Leu Asp Ile
    2150                2155                2160

Gln Gln Tyr Pro Ala Ile Pro Leu Ser Pro Lys Ser Gly Leu Leu
    2165                2170                2175

Gly Trp Val Pro Asn Ser Asp Thr Phe His Val Leu Ile Arg Glu
    2180                2185                2190

His Arg Glu Ala Lys Lys Ile Pro Leu Asn Ile Glu His Trp Val
    2195                2200                2205

Met Leu Gln Met Ala Pro Asp Tyr Asp Asn Leu Thr Leu Leu Gln
    2210                2215                2220

Lys Val Glu Val Phe Thr Tyr Ala Leu Asn Asn Thr Glu Gly Gln
    2225                2230                2235

Asp Leu Tyr Lys Val Leu Trp Leu Lys Ser Arg Ser Ser Glu Thr
    2240                2245                2250

Trp Leu Glu Arg Arg Thr Thr Tyr Thr Arg Ser Leu Ala Val Met
    2255                2260                2265

Ser Met Thr Gly Tyr Ile Leu Gly Leu Gly Asp Arg His Pro Ser
    2270                2275                2280

Asn Leu Met Leu Asp Arg Ile Thr Gly Lys Val Ile His Ile Asp
    2285                2290                2295

Phe Gly Asp Cys Phe Glu Ala Ala Ile Leu Arg Glu Lys Phe Pro
    2300                2305                2310

Glu Lys Val Pro Phe Arg Leu Thr Arg Met Leu Thr Tyr Ala Met
    2315                2320                2325

Glu Val Ser Gly Ile Glu Gly Ser Phe Arg Ile Thr Cys Glu Asn
    2330                2335                2340

Val Met Lys Val Leu Arg Asp Asn Lys Gly Ser Leu Met Ala Ile
    2345                2350                2355

Leu Glu Ala Phe Ala Phe Asp Pro Leu Ile Asn Trp Gly Phe Asp
    2360                2365                2370

Leu Pro Thr Lys Lys Ile Glu Glu Thr Gly Ile Gln Leu Pro
    2375                2380                2385

Val Met Asn Ala Asn Glu Leu Leu Ser Asn Gly Ala Ile Thr Glu
    2390                2395                2400
```

```
Glu Glu Val Gln Arg Val Glu Asn Glu His Lys Asn Ala Ile Arg
    2405                2410                2415

Asn Ala Arg Ala Met Leu Val Leu Lys Arg Ile Thr Asp Lys Leu
    2420                2425                2430

Thr Gly Asn Asp Ile Arg Arg Phe Asn Asp Leu Asp Val Pro Glu
    2435                2440                2445

Gln Val Asp Lys Leu Ile Gln Gln Ala Thr Ser Val Glu Asn Leu
    2450                2455                2460

Cys Gln His Tyr Ile Gly Trp Cys Pro Phe Trp
    2465                2470
```

<210> SEQ ID NO 34
<211> LENGTH: 7425
<212> TYPE: DNA
<213> ORGANISM: Saccharomyces cerevisiae

<400> SEQUENCE: 34

| | | | | | |
|---|---|---|---|---|---|
| atgaataaat | acattaacaa | atacaccacg | ccacctaact | tattgtcttt | acgacaaagg | 60 |
| gccgaaggca | aacacagaac | aagaaagaaa | cttacacaca | aatcgcactc | ccacgatgat | 120 |
| gagatgtcaa | ctacttcaaa | cacagattcc | aatcacaatg | ggcccaatga | ctctggtaga | 180 |
| gtgatcactg | gttctgctgg | tcatattggt | aaaatatcct | ttgtagattc | agaactagat | 240 |
| acaacatttt | ctactttaaa | tttgattttt | gataaactta | aaagcgatgt | gccacaagaa | 300 |
| cgagcctctg | gcgctaatga | attaagcact | actttgacct | cattagcaag | ggaagtatct | 360 |
| gctgagcaat | ttcaaaggtt | tagcaacagt | ttaaacaata | agatatttga | acttattcac | 420 |
| gggtttactt | caagtgagaa | gataggtggt | attcttgctg | ttgatactct | gatctcattc | 480 |
| tacctgagta | cagaggagct | gccaaaccaa | acttcaagac | tggcgaacta | tttacgtgtt | 540 |
| ttaattccat | ccagtgacat | tgaagttatg | agattagcgg | ctaacacctt | aggtagattg | 600 |
| accgtgccag | gtggtacatt | aacatcagat | ttcgtcgaat | tgaggtcag | aacttgcatt | 660 |
| gattggctta | ctctgacagc | agataataac | tcatcgagct | ctaagttgga | atacaggaga | 720 |
| catgctgcgc | tattaatcat | aaaggcatta | gcagacaatt | caccctatct | tttatacct | 780 |
| tacgttaact | ctatcttaga | caatatttgg | gtgccattaa | gggatgcaaa | gttaattata | 840 |
| cgattagatg | ccgcagtggc | attgggtaaa | tgtcttacta | ttattcagga | tagagaccct | 900 |
| gctttgggaa | aacagtggtt | tcaaagatta | tttcaaggtt | gtacacatgg | cttaagtctc | 960 |
| aatacgaatg | attcagtgca | tgctactctg | ttggtatttc | gagaattact | cagcttgaaa | 1020 |
| gcaccttatc | tcagggataa | atatgatgat | atttacaaat | ctactatgaa | gtacaaggaa | 1080 |
| tataaatttg | atgttataag | gagagaagtt | tatgctattt | tacctctttt | agctgctttt | 1140 |
| gaccctgcca | ttttcacaaa | gaatatctc | gataggataa | tggttcatta | tttaagatat | 1200 |
| ttgaagaaca | tcgatatgaa | tgctgcaaat | aattcggata | aaccttttat | attagtttct | 1260 |
| ataggtgata | ttgcatttga | agttggttcg | agcatttcac | cctatatgac | acttattctg | 1320 |
| gataatatta | gggaaggctt | aagaacgaaa | ttcaaagtta | gaaacaatt | cgagaaggat | 1380 |
| ttattttatt | gcattggtaa | attagcttgt | gctttgggcc | cagcttttgc | taagcacttg | 1440 |
| aacaaagatc | ttcttaatt | gatgttaaac | tgtccaatgt | ccgaccatat | gcaggagact | 1500 |
| ttaatgatcc | ttaacgagaa | ataccctct | ttggaatcta | ccgttaattc | gaggatacta | 1560 |
| aatttactgt | cgatatcctt | atctggtgaa | aaattattc | aatcaaacca | atacgatttt | 1620 |
| aataatcaat | tttccattga | aaaggctcgt | aaatcaagaa | accaaagttt | catgaaaaaa | 1680 |

```
actggtgaat ctaatgacga tattacagat gcccaaattt tgattcagtg tttaaaatg    1740
ctgcaactaa ttcatcatca atattccttg acggagtttg ttaggcttat aaccatttct    1800
tacattgagc atgaggattc gtctgtcaga aaattggcag cattaacgtc gtgtgattta    1860
tttatcaaag acgatatatg taaacaaaca tcagttcatg ctttacactc ggtttctgaa    1920
gtgctaagta agctattaat gatcgcaata actgatccgg ttgcagaaat tagattggaa    1980
attcttcagc atttggggtc aaattttgat cctcaattgg cccaaccaga caatttacgc    2040
ctacttttca tggcgctgaa cgatgagatt tttggtattc aattggaagc tatcaaaata    2100
ataggcagat tgagttctgt caaccccgct tatgtagttc cttctttgag gaaaacttta    2160
ctggaactat taacgcaatt gaagttctca aatatgccaa aaaaaaagga ggaaagtgca    2220
actctattat gtacgctgat aaattccagc gatgaagtag cgaaaccta tattgatcct    2280
attctagacg tcattcttcc taaatgccag gatgcttcat ctgccgtagc atccaccgct    2340
ttaaaggttt tgggtgaact atctgttgtt ggaggaaaag aaatgacgcg ttacttaaag    2400
gaattgatgc cattgatcat taacacattt caggaccaat caaactcttt taaaagagat    2460
gccgccttaa caacattagg acagctggct gcttcctctg gttatgttgt tggcccttta    2520
ctagactacc cagagttact tggcattttg ataaatattc ttaagactga aaacaaccct    2580
catatcaggc gtggaactgt tcgtttgatt ggtatattag gcgctcttga tccatataag    2640
cacagagaaa tagaagtcac atcaaactca aagagttcag tagagcaaaa tgctccttca    2700
atcgacatcg cattgctaat gcaaggggta tctccatcca acgatgaata ttaccccact    2760
gtagttatcc acaatctgat gaagatattg aatgatccat cgttgtcaat ccatcacacg    2820
gctgctattc aagctattat gcatattttt caaaaccttg gtttacgatg tgtctccttt    2880
ttggatcaaa ttattccagg tatcatttta gtcatgcgtt catgcccgcc gtcccaactt    2940
gactttatt ttcagcaact gggatctctc atctcaattg tcaagcaaca tattaggccc    3000
catgtcgaga aaatttatgg tgtgatcagg gagttttcc cgatcattaa actacaaatc    3060
acaattattt ctgtcataga atcgatatct aaggctctgg aaggtgagtt taaaagattt    3120
gttcccgaga ctctaacctt tttccttgat attcttgaga acgaccagtc taataaaagg    3180
atcgttccga ttcgtatatt aaaatctttg gttacttttg ggccgaatct agaagactat    3240
tcccatttga ttatgcctat cgttgttaga atgactgagt attctgctgg aagtctaaag    3300
aaaatctcca ttataacttt gggtagatta gcaaagaata tcaacctctc tgaaatgtca    3360
tcaagaattg ttcaggcgtt ggtaagaatt ttgaataatg gggatagaga actaacaaaa    3420
gcaaccatga atacgctaag tttgctcctt ttacaactag gtaccgactt tgtggtcttt    3480
gtgccagtga ttaacaaggc gttattgagg aataggattc agcattcagt gtacgatcaa    3540
ctggttaata aattactgaa caatgaatgc ttgccaacaa atatcatatt tgacaaggag    3600
aacgaagtac ctgaaaggaa aaattatgaa gacgaaatgc aagtaacgaa attaccggta    3660
aaccaaaata tcctaaagaa tgcatggtat tgttctcaac agaagaccaa agaagattgg    3720
caagaatgga taagaaggct atctattcag cttctaaagg aatcaccttc agcttgtcta    3780
cgatcctgtt cgagtttagt cagcgtttat tatccgttgg cgagagaatt gtttaatgct    3840
tcattctcaa gttgctgggt tgagcttcaa acgtcatacc aagaggattt gattcaagca    3900
ttatgcaagg ctttatcatc ctctgaaaac ccacccgaga tttatcaaat gttgttaaat    3960
ttagtggaat ttatggagca cgatgacaaa ccattgccta tcccaatcca tacattaggt    4020
aagtatgccc aaaaatgtca tgcttttgcg aaggcactac attacaaaga ggtagaattc    4080
```

```
ttagaagagc cgaaaaattc aacaatcgag gcattgatta gcattaataa tcaacttcac    4140
caaactgatt ctgctattgg tattttgaag catgcgcaac aacacaatga attgcagctg    4200
aaggaaactt ggtatgaaaa acttcaacgt tgggaggatg ctcttgcagc atataatgag    4260
aaggaggcag caggagaaga ttcggttgaa gtgatgatgg gaaaattaag atcgttatat    4320
gcccttggag agtgggaaga gctttctaaa ttggcatctg aaaagtgggg cacggcaaaa    4380
cccgaagtga agaaggcaat ggcgcctttg gctgccggcg ctgcctgggg tttggagcaa    4440
tgggatgaaa tagcccagta tactagcgtc atgaaatcgc agtctccaga taaagaattc    4500
tatgatgcaa ttttatgttt gcataggaat aattttaaga aggcggaagt tcacatcttt    4560
aatgcaaggg atcttctagt tactgaattg tcagctcttg ttaatgaaag ctacaataga    4620
gcatataatg ttgttgttag agcgcagatt atagcagagt tggaggaaat catcaaatat    4680
aagaagttgc cacaaaattc agataaacgt ctaactatga gagaaacttg gaataccaga    4740
ttactgggct gtcaaaaaaa tattgatgtg tggcaaagaa ttctgcgtgt cagatcattg    4800
gtgataaagc caaaggagga tgctcaagtg aggattaagt ttgccaactt atgcagaaaa    4860
tcgggtagga tggcgctagc taaaaaagtc ttaaatacat tgcttgaaga aacagatgac    4920
ccagatcatc ctaatactgc taaggcatcc cctccagttg tttatgcaca actgaagtac    4980
ttgtgggcta cggggttgca agatgaggct ttgaagcaat taattaattt cacatctaga    5040
atggctcatg atttaggttt ggatccaaat aatatgatag ctcaaagcgt tcctcaacaa    5100
agcaaaagag tccctcgtca cgttgaagat tatactaagc ttttagctcg ttgtttcttg    5160
aagcaaggag aatggagagt tgcttacag cctaaatgga gattgagcaa tccagattcg    5220
atcctaggct cctatttgct cgctacacat tttgacaaca catggtacaa agcgtggcat    5280
aactgggcac tggccaattt tgaagtcatt tctatgctaa catctgtctc taaaaagaaa    5340
caggaaggaa gtgatgcttc ctcggtaact gatattaatg agtttgataa tggcatgatc    5400
ggcgtcaata catttgatgc taaggaagtt cattactctt ctaatttaat acacaggcac    5460
gtaattccag caattaaggg tttttttcat tccatttctt tatcagaatc aagctctctt    5520
caagatgcat taaggttatt aactttatgg tttacttttg gtggtattcc agaagcaacc    5580
caagctatgc acgagggttt caacctaatc caaataggca catggttaga agtgttgcca    5640
cagttaattt ctagaattca tcaacccaat caaattgtta gtaggtcatt actctcccta    5700
ttatctgatc taggtaaggc tcatccgcag gcattagtgt accccttaat ggttgcgatt    5760
aaatccgaat ctctctcacg acagaaagca gctttgtcca tcatagaaaa gatgagaata    5820
catagtccag ttttggtcga ccaggctgaa cttgtcagcc acgaattgat acgtatggcg    5880
gtgctttggc atgagcaatg gtatgagggt ctggatgacg ccagtaggca gttttttgga    5940
gaacataata ccgaaaaaat gtttgctgct ttagagcctc tgtacgaaat gctgaagaga    6000
ggaccggaaa ctttgaggga aatatcgttc caaaattctt ttggtaggga cttgaatgac    6060
gcttacgaat ggctgatgaa ttacaaaaaa tctaaagatg ttagtaattt aaaccaagcg    6120
tgggacattt actataatgt tttcaggaaa attggtaaac agttgccaca attcaaaact    6180
cttgaactac aacatgtgtc gccaaaacta ctatctgcgc atgatttgga attggctgtc    6240
cccgggaccc gtgcaagtgg tggaaaacca attgttaaaa tatctaaatt cgagccagta    6300
ttttcagtaa tctcatccaa acaaagaccg agaaagtttt gtatcaaggg tagtgatggt    6360
aaagattata agtatgtgtt gaaaggacat gaagacatta gacaggatag cttggtcatg    6420
```

```
caattattcg gactagttaa cacgcttttg caaaatgacg ctgagtgctt tagaaggcat    6480
ctagatatcc agcaatatcc agcaatccca ttatctccga agtctgggtt actgggttgg    6540
gtaccgaata gtgacacgtt ccatgtatta attagggagc atagagaagc caaaaaaatt    6600
cctttaaaca ttgagcattg ggtcatgtta caaatggcac ctgattatga caatttaacg    6660
ttgttgcaga agtagaagt cttcacttac gccctaaata atacggaggg acaagatctt    6720
tataaggtgt tatggctgaa gagtaggtca tcggaaacgt ggttggagcg tagaactact    6780
tacactcgat cgctagccgt gatgtccatg accggttata tattggggtt aggtgaccgc    6840
caccctagta atttgatgtt ggatagaatc actgggaaag tcattcatat tgattttggt    6900
gattgtttcg aggctgctat attaagagaa aaattccccg aaaagtacc ttttagatta    6960 actagaatgt taacatatgc aatgaagtg agtggaattg aaggtagctt ccgtattact    7020
tgtgagaatg ttatgaaggt acttagagat aacaagggtt cattaatggc aatccttgaa    7080
gcttttgctt tcgatccttt gatcaattgg ggttttgact taccaacaaa gaaaattgag    7140
gaagaaacgg gcattcaact tcccgtgatg aatgccaatg agctattgag taatgggggct   7200 attaccgaag aagaagttca aagggtggaa aacgagcaca agaatgccat tcgaaatgca    7260
agggccatgt tggtattgaa gcgcattact gacaaattaa cggggaacga tataagaagg    7320
tttaatgact tggacgttcc agaacaagtg gataaactaa tccaacaagc cacatcagtg    7380
gaaaacctat gccaacatta tatccggttgg tgtccattct ggtag                    7425

<210> SEQ ID NO 35
<211> LENGTH: 966
<212> TYPE: DNA
<213> ORGANISM: Saccharomyces cerevisiae

<400> SEQUENCE: 35
agctctctta tcaattatgt aagtgcttgt atactatta cctaagataa gaaaaaaaaa     60
agcaattcaa aattaagctt atcttgacag cggggctggt ttgtttctag aagacaaaaa   120
gtggggaatc attttacgt aactccccct gataagaagg actcacatcc ttataggtac    180
gataaagaat ggttgtatct ttcctatttt tcgaaatcgt tatcttatat agttgaacta   240
ctacggttaa aaagcttaag cctcagccct cttagtcaaa cttcttttt gaaggcacca    300 gggtgcataa aagtgcgtct attgtttccc agtggaactc tgttgagata gcgatgtttg   360 ttttttttc acttaacggc aaccaatacc gatagcgacg tcgctggcag tgtagagtgg    420
ccgtacggcg tcgctagatg gcacggcact gattgcggcg ggagtcgcta ggcggtgatg   480
catttccgca cagggaccag aggaagcttc ccaggcggtg acagtaagtg aactcattat    540
catgtcttct ccaaaacatt cgtgacatct agtcatgctc ctcgcaattc actccgattg    600
gtatagcttt tcggtagtt ttagctacta tgcttagggg aaagaggaga aaccgtaccg    660
tcagtctcag tcaaaaaatt ttgatattca atctgatagc aaagttggaa cttggggtta    720 tctggcccctt ttttgttatc atattcgtat acccaacaac atatcggttc caccggtcct   780
ttttatatat aaaagacgat gtgtagatgc actcgagtat tcttggagaa cgtaacttgt   840
attgagctag agtgctggat aaagtaccac atactaacgt tctttttatag agccaaacat    900 aattcttttg cactttcaat ataaggtaca agtgaaacac aggaaaaaaa gaactaactc    960
taagta                                                                966

<210> SEQ ID NO 36
<211> LENGTH: 572
```

```
<212> TYPE: DNA
<213> ORGANISM: Saccharomyces cerevisiae

<400> SEQUENCE: 36
aaagtcggag aacctgactg aaaattcatg aatctcttca tttctatagc ctttcctcta      60
tgcatttgta ttatatattt attaccgtca tttttttacat actgctgcat tttggcgcca    120
gtgataagtg gcaaacaatt cgacggaatc gtggtaatta taccacgtta ctctataaca    180
tcatgatatt gcaattaatc aaacatacat ttaatcttaa tgctattagc ttactacaac    240
tcttttcttt aagttatatc gtatatttct tgggcgatgt cagaatattt acccggatat    300 tccttttttaa gcactgaata tgtttgaata gagactgaca tatatggcag caattaaaat   360
tggaagaaat gtaatgacag taggaaagac caatttttat catcgtgaca ccaatcactt    420
ccttaactga gctttacttg tatttattta caggtagatt aggagcagta gaaagggaaa    480 ataccgggg tgcataaaga gcatagtcat taagatcaaa tagttatctt tctcaaagag     540
atttctgatc tttactttcc ccatatgaaa aa                                   572
```